United States Patent
Link et al.

(10) Patent No.: US 6,583,180 B2
(45) Date of Patent: Jun. 24, 2003

(54) GLUCOCORTICOID RECEPTOR MODULATORS

(75) Inventors: James T. Link, Chicago, IL (US); Bryan K. Sorensen, Waukegan, IL (US); Jyoti R. Patel, Libertyville, IL (US); David L. Arendsen, Libertyville, IL (US); Gaoquan Li, Park City, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/072,548

(22) Filed: Feb. 8, 2002

(65) Prior Publication Data

US 2002/0156311 A1 Oct. 24, 2002

Related U.S. Application Data

(60) Provisional application No. 60/268,787, filed on Feb. 14, 2001.

(51) Int. Cl.$^7$ .................. A61K 31/18; A61K 31/47; A61K 31/35; A61K 31/135
(52) U.S. Cl. .................. 514/603; 560/13; 560/27; 560/43; 560/44; 562/437; 562/457; 564/86; 564/87; 564/373
(58) Field of Search ................ 560/27, 43, 44, 560/13; 562/437, 457; 514/533, 535, 539, 563, 564, 566, 239.2, 309, 331, 427, 456, 524, 603, 646; 544/160; 546/142, 232, 235; 548/560; 549/362; 556/422, 413; 558/413; 564/86, 87, 373

(56) References Cited

U.S. PATENT DOCUMENTS

| | | | | | |
|---|---|---|---|---|---|
| 3,660,374 A | * | 5/1972 | Weaver et al. | ............... | 260/207 |
| 3,763,141 A | * | 10/1973 | Weaver et al. | ............... | 260/207 |
| 3,816,388 A | * | 6/1974 | Weaver et al. | ............... | 260/152 |
| 5,929,058 A | | 7/1999 | Deisher | ................... | 514/239.5 |
| 6,166,013 A | | 12/2000 | Coghlan et al. | ............ | 514/169 |
| 6,197,223 B1 | * | 3/2001 | Weaver et al. | ............... | 252/582 |

FOREIGN PATENT DOCUMENTS

| WO | 99/63976 | 12/1999 |
|---|---|---|
| WO | 00/07972 | 2/2000 |

OTHER PUBLICATIONS

E. Fujita et al., "Terpenoids. Part XXVIII. Total Synthesis of Enmein," J. Chem. Soc., Perkin Transactions I, (1994) 1: 165–177.

S. W. Elmore et al., "Nonsterodial Selective Glucocorticoid Modulators: The Effect of C–5 Alkyl Substitution on the Transcriptional Activation/Repression Profile of 2,5–Dihydro–10–methoxy–2,2,4–trimethyl–1H–[1]benzopyrano[3,4–f]quinolines," Journal of Medicinal Chemistry, (2001) 44: 4481–4491.

C.F. Bigge et al., "Synthesis and Pharmacological Evaluation of 4a–Phenanthrenamine Derivatives Acting at the Phencyclidine Binding Site of the N–Methyl–D–asparate Receptor Complex," J. med. Chem. (1993) 36: 1977–1995.

Friedman et al., "Phosphoenolpyruvate Carboxykinase (GTP) Gene Transcription and Hyperglycemia Are Regulated by Glucocorticoids in Genetically Obese db/db Transgenic Mice," J. Biol. Chem. (1997) vol. 272, Issue 50, p. 31475–31481.

M. J. Coghlan et al., "Synthesis and Characterization of Non–Steroidal Ligands for the Glucocorticoid Receptor . . . " J. Med. Chem. (2001) 44: 2879–2885.

Argaud et al., "Regulation of Rat Liver Glucose–6– Phosphatase Gene Expression in Different Nutritional and Hormonal States", Diabetes (1996) 45: 1563–1571.

R.W. Hanson and Y. M. Patel, "Phosphoenolpyruvate Carboxykinase (GTP): The Gene and the Enzyme," Adv. Enzymol. (1994) vol 69, p 203–281.

De Feo et al., "Contribution of cortisol to glucose counter regulation in humans," American Journal of Physiology (1989) 257: E35–E42.

Miguel Beato, "Gene Regulation by Steroid Hormones," Cell, vol 56, (1989) 335–344.

J. Solomon et al., "Effetcs of Adrenalectomy on Body Weight and Hyperglycemia in Five Month Old Ob/Ob Mice," Hormone and Metabolic Research, (1977) 9:152–156.

(List continued on next page.)

*Primary Examiner*—Peter O'Sullivan
(74) *Attorney, Agent, or Firm*—Christopher P. Rogers

(57) ABSTRACT

Compounds of formula (I)

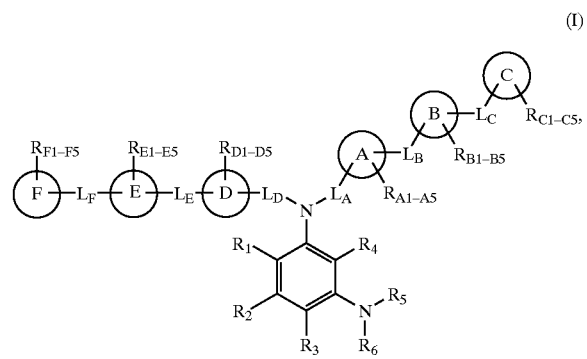

or pharmaceutically acceptable salts thereof are novel glucocorticoid receptor modulators and are useful for treating type II diabetes in a mammal.

75 Claims, No Drawings

OTHER PUBLICATIONS

Patrick Boyle, "Cushing's disease, glucocorticoid excess, glucocorticoid deficiency and diabetes," Diabetes Reviews, vol. 1, No. 3, Fall 1993, p. 301–308.

D. P. Rooney et al., "The Effect of Cortisol on Glucose/Glucose–6–Phosphate Cycle Activity and Insulin Action," J. Clinical Endocrinology and Metabolism, vol. 77, No. 5 (1984) 1180–1183.

P. Naeser, "Effects of Adrenalectomy on the Obese–Hyperglycemic Syndrome in Mice," Diabetologia, (1973) 9: 376–379.

Dinneen et al., "Metabolic Effects of the Nocturnal Rise in Cortisol on Carbohydrate Metabolism in Normal Humans," J. Clin. Invest, (1993) 92: 2283–2290.

Keith R. Yamamoto, "Steroid Receptor Regulated Transcription of Specific Genes and Gene Networks," Ann. Rev. Genet. (1985) 19:209–252.

J. H. Exton et al., "The Hormonal Control of Hepatic Gluconeogensis," Recent Progress in Hormone Research, vol. 26, (1970) 411–457.

R. A. DeFronzo, "Pathogensis of type 2 diabetes: metabolic and molecular implications for identifying diabetes genes," Diabetes Reviews, vol 5, No. 3 (1997) 177–259.

Naomi Karus–Friedmann, "Hormonal Regulation of Hepatic Gluconeogenesis," Physiological Reviews, vol. 64, No. 1 (1984) 170–259.

* cited by examiner

GLUCOCORTICOID RECEPTOR MODULATORS

This application claims priority to the provisional application Ser. No. 60/268,787 filed on Feb. 14, 2001.

FIELD OF THE INVENTION

The present invention relates to non-steroidal compounds which are selective modulators of steroid receptors, in particular, the glucocorticoid receptor. In particular, the present invention is directed to compounds and methods for using such compounds to treat mammals requiring glucocorticoid receptor modulation.

BACKGROUND OF THE INVENTION

Glucocorticoids are lipid soluble hormones synthesized in the adrenal cortex (Neville and O'Hare, The Adrenal Gland, James, Ed. New York, Raven, 1–65, (1979)). These molecules readily pass through cell membranes and enter the cytoplasm of target tissues, where they bind to glucocorticoid receptors sequestered in the cytoplasm by complexation with heat shock proteins. Upon binding of the hormone to its receptor, the receptor undergoes a conformational change which results in dissociation of heat shock proteins, and translocation of the ligand bound glucocorticoid receptor into the nucleus where it can either initiate or repress specific gene transcription. Transcriptional activation occurs when the ligand bound receptor complex homodimerizes, and the homodimeric receptor ligand complex binds to chromosomal deoxyribonucleic acid (DNA) at sequence specific sites in the promoter region of regulated genes (Beato, Cell, 56, 335–344 (1989); and Yamamato, Annu. Rev. Genet., 19, 209–215 (1989)). Excesses or deficiencies of these ligands can have profound physiological consequences. As an example, glucocorticoid excess results in Cushing's Syndrome, while glucocorticoid insufficiency results in Addison's Disease.

Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist.

Type II diabetes (also referred to as non insulin-dependent Diabetes Mellitus) is a debilitating disease characterized by an abnormal elevation of blood glucose levels driven by three factors: increased hepatic glucose production, inadequate clearance of glucose via insulin mediated pathways, and decreased uptake of circulating glucose by tissues (DeFronzo, Diabetes Review 5(3), 177–269, (1997)). Administration of agents that decrease hepatic glucose production are a fundamental approach to controlling blood glucose (De Feo et al., Am. J. Physiol. 257, E35–E42 (1989); Rooney, et al., J. Clin. Endocrinol. Metab. 77, 1180–1183 (1994); and Dinneen et al., J. Clin. Invest.,92, 2283–2290 (1993)). Glucocorticoids have been shown to have major influences on glucose production. Glucocorticoid excess aggravates established diabetes while glucocorticoid deficiency reduces blood glucose and improves glucose control in diabetic mice (Boyle, Diabetes Review, 1(3), 301–308, (1993); Naeser, Diabetologia, 9, 376–379 (1973); and Solomon et al., Horm, Metab. Res., 9, 152–156 (1977)). The underlying mechanism responsible for these effects is the glucocorticoid-induced upregulation of key hepatic enzymes required for gluconeogenesis (Exton et al., Recent Prog. Horm. Res., 26, 411–457 (1970); and Kraus-Friedmann, Physiol. Rev., 64, 170–259 (1984)).

Among the genes that glucocorticoids up-regulate are several genes that play key roles in gluconeogenesis and glycogenolysis, particularly phosphoenolpyruvyl carboxykinase (PEPCK) and glucose-6-phosphatase (Hanson and Patel, Adv. Enzymol., Meister, Ed. New York, John Wiley and Sons, Inc., 203–281 (1994); and Argaud et al., Diabetes 45, 1563–1571 (1996)). Mifepristone (RU486), a potent GR antagonist reduces messenger ribonucleic acid (mRNA), levels of PEPCK and glucose-6-phosphate in the liver, and causes a 50% reduction of plasma glucose levels in obese diabetic db/db transgenic mice (Friedman et al., J. Biol. Chem. 272(50), 31475–31481 (1997)). While steroid-based GR antagonists have been useful in demonstrating efficacy for in vivo glucose lowering effects, the utility of such agents is limited due to side effects resulting from potent cross-reactivity with other steroid receptors, in particular progesterone receptor (PR) and mineralocorticoid receptor (MR). U.S. Pat. No. 5,929,058 discloses a method for treating type II diabetes by administering a combination of steroidal-agents that exhibit mineralcorticoid receptor agonist activity and glucocorticoid receptor antagonist activity. Pharmaceutical agents that function as glucocorticoid receptor (GR) antagonists represent a novel approach to controlling type II diabetes.

Other examples of proteins that interact with the glucocorticoid receptor are the transcription factors AP-1 and NFκ-B. Such interactions result in inhibition of AP-1- and NFκ-B- mediated transcription and are believed to be responsible for some of the anti-inflammatory activity of endogenously administered glucocorticoids. In addition, glucocorticoids may also exert physiologic effects independent of nuclear transcription.

Glucocorticoid selective non-steroidal agents that antagonize functional activity mediated by the glucocorticoid receptor may be useful for treating mammals suffering from type II diabetes and for treating symptoms of type II diabetes including hyperglycemia, inadequate glucose clearance, obesity, hyperinsulinemia, hypertriglyceridemia and high circulating glucocorticoid levels. In addition to diabetes, glucocorticoid receptor modulators are useful to treat diseases such as obesity, Syndrome X, Cushing's Syndrome, Addison's disease, inflammatory diseases such as asthma, rhinitis and arthritis, allergy, autoimmune disease, immunodeficiency, anorexia, cachexia, bone loss or bone frailty, and wound healing.

U.S. Pat. No. 5,929,058 discloses a method for treating type II diabetes by administering a combination of steroidal-agents that exhibit mineralcorticoid receptor agonist activity and glucocorticoid receptor antagonist activity.

Although there are glucocorticoid receptor therapies in the art, there is a continuing need for and a continuing search in this field of art for selective glucocorticoid receptor therapies. Thus, the identification of non-steroidal compounds which have specificity for one or more steroid receptors, but which have reduced or no cross-reactivity for other steroid or intracellular receptors, is of significant value in this field.

SUMMARY OF THE INVENTION

In its principle embodiment, the present invention discloses compounds of formula (I) that are useful as glucocorticoid receptor modulators:

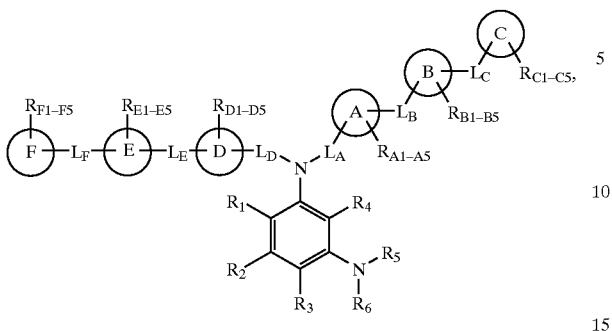

(I)

or a pharmaceutically acceptable salt or prodrug thereof, wherein $L_A$ is a covalent bond or $C(X_{A1})(X_{A2})$;

$L_D$ is a covalent bond or $C(X_{D1})(X_{D2})$;

$X_{A1}$ is selected from the group consisting of hydrogen, alkoxy, alkoxycarbonyl, alkoxyalkyl, alkyl, alkylcarbonyl, cyano, halogen, hydroxy, hydroxyalkyl, nitro and $(NR_{10}R_{11})$carbonyl;

$X_{A2}$ is selected from the group consisting of hydrogen and alkyl;

or $X_{A1}$ and $X_{A2}$ together are oxo;

$X_{D1}$ is selected from the group consisting of hydrogen, alkoxy, alkoxycarbonyl, alkoxyalkyl, alkyl, alkylcarbonyl, cyano, halogen, hydroxy, hydroxyalkyl, nitro and $(NR_{10}R_{11})$carbonyl;

$X_{D2}$ is selected from the group consisting of hydrogen and alkyl;

or $X_{D1}$ and $X_{D2}$ together are oxo;

$L_B$ is absent or selected from the group consisting of a covalent bond, alkenylene, alkylene, alkynylene, —(CH$_2$)$_m$C(O)(CH$_2$)$_n$—, —(CH$_2$)$_m$C(O)(CH$_2$)$_n$CH=CH—, —(CH$_2$)$_m$C(O)(CH$_2$)$_n$C≡C—, —(CH$_2$)$_m$CH(OH)(CH$_2$)$_n$—, —(CH$_2$)$_m$CH(OH)(CH$_2$)$_n$CH$_2$CH=CH—, —(CH$_2$)$_m$CH(OH)(CH$_2$)$_n$CH$_2$C≡C—, —(CH$_2$)$_m$O(CH$_2$)$_n$—, —(CH$_2$)$_m$O(CH$_2$)$_n$CH$_2$CH=CH—, —(CH$_2$)$_m$O(CH$_2$)$_n$CH$_2$C≡C—, —(CH$_2$)$_m$S(CH$_2$)$_n$—, —(CH$_2$)$_m$S(O)(CH$_2$)$_n$—, —(CH$_2$)$_m$S(O)$_2$(CH$_2$)$_n$—, —(CH$_2$)$_m$N(R$_7$)(CH$_2$)$_n$—, —(CH$_2$)$_m$N(R$_7$)C(CH$_2$)$_n$—, —(CH$_2$)$_m$C(O)N(R$_7$)(CH$_2$)$_n$—, —O(CH$_2$)$_m$C(O)N(R$_7$)(CH$_2$)$_n$—, —(CH$_2$)$_m$C(O)O(CH$_2$)$_n$—, —O(CH$_2$)$_m$C(O)(CH$_2$)$_n$—, —(CH$_2$)$_m$N(R$_7$)S(O)$_2$(CH$_2$)$_n$—, —(CH$_2$)$_m$S(O)$_2$N(R$_7$)(CH$_2$)$_n$—, —(CH$_2$)$_m$S(O)$_2$O(CH$_2$)$_n$— and —(CH$_2$)$_m$OS(O)$_2$(CH$_2$)$_n$— wherein each group is inserted as drawn with the left end attached to A and the right end attached to B;

m is an integer of 0–6;

n is an integer of 0–6;

$L_C$ is absent or selected from the group consisting of a covalent bond, alkenylene, alkylene, alkynylene, —(CH$_2$)$_p$C(O)(CH$_2$)$_q$—, —(CH$_2$)$_p$C(O)(CH$_2$)$_q$CH=CH—, —(CH$_2$)$_p$C(O)(CH$_2$)$_q$C≡C—, —(CH$_2$)$_p$CH(OH)(CH$_2$)$_q$—, —(CH$_2$)$_p$CH(OH)(CH$_2$)$_q$CH$_2$CH=CH—, —(CH$_2$)$_p$CH(OH)(CH$_2$)$_q$CH$_2$C≡C—, —(CH$_2$)$_p$O(CH$_2$)$_q$—, —(CH$_2$)$_p$O(CH$_2$)$_q$CH$_2$CH=CH—, —(CH$_2$)$_p$O(CH$_2$)$_q$CH$_2$C≡C—, —(CH$_2$)$_p$S(CH$_2$)$_q$—, —(CH$_2$)$_p$S(O)(CH$_2$)$_q$—, —(CH$_2$S(O)$_2$(CH$_2$)$_q$—, —(CH$_2$)$_p$N(R$_7$)(CH$_2$)$_q$—, —(CH$_2$)$_p$N(R$_7$)C(O)(CH$_2$)$_q$—, —(CH$_2$)$_p$C(O)N(R$_7$)(CH$_2$)$_q$—, —O(CH$_2$)$_p$C(O)N(R$_7$)(CH$_2$)$_q$—, —(CH$_2$)$_p$C(O)O(CH$_2$)$_q$—, —O(CH$_2$)$_p$C(O)(CH$_2$)$_q$—, —(CH$_2$)$_p$N(R$_7$)S(O)$_2$(CH$_2$)$_q$—, —(CH$_2$)$_p$S(O)$_2$N(R$_7$)(CH$_2$)$_q$—, —(CH$_2$)$_p$S(O)$_2$O(CH$_2$)$_q$— and —(CH$_2$)$_p$OS(O)$_2$(CH$_2$)$_q$— wherein each group is inserted as drawn with the left end attached to B and the right end attached to C;

p is an integer of 0–6;

q is an integer of 0–6;

$L_E$ is absent or selected from the group consisting of a covalent bond, alkenylene, alkylene, alkynylene, —(CH$_2$)$_r$C(O)(CH$_2$)$_s$—, —(CH$_2$)$_r$C(O)(CH$_2$)$_s$CH=CH—, —(CH$_2$)$_r$C(O)(CH$_2$)$_s$C≡C—, —(CH$_2$)$_r$CH(OH)(CH$_2$)$_s$—, —(CH$_2$)$_r$CH(OH)(CH$_2$)$_s$CH$_2$CH=CH—, —(CH$_2$)$_r$CH(OH)(CH$_2$)$_s$CH$_2$C≡C—, —(CH$_2$)$_r$O(CH$_2$)$_s$—, —(CH$_2$)$_r$O(CH$_2$)$_s$CH$_2$CH=CH—, —(CH$_2$)$_r$O(CH$_2$)$_s$CH$_2$C≡C—, —(CH$_2$)$_r$S(CH$_2$)$_s$—, —(CH$_2$)$_r$S(O)(CH$_2$)$_s$—, —(CH$_2$)$_r$S(O)$_2$(CH$_2$)$_s$—, —(CH$_2$)$_r$N(R$_7$)(CH$_2$)$_s$—, —(CH$_2$)$_r$N(R$_7$)C(O)(CH$_2$)$_s$—, —(CH$_2$)$_r$C(O)N(R$_7$)(CH$_2$)$_s$—, —O(CH$_2$)$_r$C(O)N(R$_7$)(CH$_2$)$_s$—, —(CH$_2$)$_r$C(O)O(CH$_2$)$_s$—, —O(CH$_2$)$_r$C(O)(CH$_2$)$_s$—, —(CH$_2$)$_r$N(R$_7$)S(O)$_2$(CH$_2$)$_s$—, —(CH$_2$)$_r$S(O)$_2$N(R$_7$)(CH$_2$)$_s$—, —(CH$_s$)$_r$S(O)$_2$O(CH$_2$)$_s$— and —(CH$_2$)$_r$OS(O)$_2$(CH$_2$)$_s$— wherein each group is inserted as drawn with the left end attached to D and the right end attached to E;

r is an integer of 0–6;

s is an integer of 0–6;

$L_F$ is absent or selected from the group consisting of a covalent bond, alkenylene, alkylene, alkynylene, —(CH$_2$)$_u$C(O)(CH$_2$)$_v$—, —(CH$_2$)$_u$C(O)(CH$_2$)$_v$CH=CH—, —(CH$_2$)$_u$C(O)(CH$_2$)$_v$C≡C—, —(CH$_2$)$_u$CH(OH)(CH$_2$)$_v$—, —(CH$_2$)$_u$CH(OH)(CH$_2$)$_v$CH$_2$CH=CH—, —(CH$_2$)$_u$CH(OH)(CH$_2$)$_v$CH$_2$C≡C—, —(CH$_2$)$_u$O(CH$_2$)$_v$—, —(CH$_2$)$_u$O(CH$_2$)$_v$CH$_2$CH=CH—, —(CH$_2$)$_u$O(CH$_2$)$_v$CH$_2$C≡C—, —(CH$_2$)$_u$S(CH$_2$)$_v$—, —(CH$_2$)$_u$S(O)(CH$_2$)$_v$—, —(CH$_2$)$_u$S(O)$_2$(CH$_2$)$_v$—, —(CH$_2$)$_u$N(R$_7$)(CH$_2$)$_v$—, —(CH$_2$)$_u$N(R$_7$)C(O)(CH$_2$)$_v$—, —(CH$_2$)$_u$C(O)N(R$_7$)(CH$_2$)$_v$—, —O(CH$_2$)$_u$C(O)N(R$_7$)(CH$_2$)$_v$—, —(CH$_2$)$_u$C(O)O(CH$_2$)$_v$—, —O(CH$_2$)$_u$C(O)(CH$_2$)$_v$—, —(CH$_2$)$_u$N(R$_7$)S(O)$_2$(CH$_2$)$_v$—, —(CH$_2$)$_u$S(O)$_2$N(R$_7$)(CH$_2$)$_v$—, —(CH$_2$)$_u$S(O)$_2$O(CH$_2$)$_v$— and —(CH$_2$)$_u$OS(O)$_2$(CH$_2$)$_v$— wherein each group is inserted as drawn with the left end attached to E and the right end attached to F;

u is an integer of 0–6;

v is an integer of 0–6;

A and D are each independently selected from the group consisting of aryl, cycloalkyl and heterocycle;

B, C, E and F are each independently absent or each independently selected from the group consisting of aryl, cycloalkyl and heterocycle;

$R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$ and $R_{F5}$ and each independently absent or each independently selected from the group consisting of hydrogen, alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkylcarbonylalkyl, alkylcarbonylalkylthio, alkylcarbonyl(NR$_{11}$)sulfonylalky, alkylcarbonyloxy, alkylcarbonylthio, alkylsulfinyl, alkylsulfinylalkyl, alkylsulfonyl, alkylsulfonylalkyl, alkylsulfonyl($NR_{10}$)carboxylalkyl, alkylsulfonyl($NR_{10}$)carboxylalkoxy, alkylsulfonyl($NR_{10}$)alkyl($NR_{11}$)—, alkylthio, alkylthioalkyl, alkylthioalkoxy, alkynyl, alkynyloxy, alkynylthio, carboxy, carboxyalkoxy, carboxylalkoxyalkoxy, carboxyalkyl, cyano, cyanoalkoxy, cyanoalkyl, cyanoalkylthio, cycloalkylalkoxy, cycloalkyloxy, ethylenedioxy, formyl, formylalkoxy, formylalkyl, haloalkenyl, haloalkenyloxy, haloalkoxy, haloalkyl, haloalkynyl, haloalkynyloxy, halogen, hydroxy, hydroxyalkoxy, hydroxyalkyl, mercapto, mercaptoalkoxy, mercaptoalkyl, methylenedioxy, nitro, —$NR_8R_9$, ($NR_8R_9$)alkoxy, ($NR_8R_9$)alkyl, ($NR_8R_9$)carbonyl, ($NR_8R_9$)carbonylalkoxy, ($NR_8R_9$)carbonylalkyl, ($NR_{10}R_{11}$)sulfonyl, ($NR_{10}R_{11}$)sulfonylalkyl, —$NR_{10}S(O)_2R_{12}$, —$NR_{10}S(O)_2NR_{13}R_{14}$, and —$S(O)_2OH$;

$R_1$, $R_2$, and $R_3$ are each independently selected from the group consisting of hydrogen, alkoxycarbonyl, alkoxy, alkoxyalkyl, alkyl, alkylcarbonyl, carboxy, halogen, hydroxyalkyl, —$NR_{10}R_{11}$ and ($NR_{10}R_{11}$)alkyl;

$R_4$ is selected from the group consisting of hydrogen, alkenyl, alkoxy, alkoxyalkenyl, alkoxyalkoxy, alkoxyalkyl, alkoxyalkynyl, alkoxycarbonyl, alkoxycarbonylalkoxy, alkoxycarbonylalkenyl, alkoxycarbonylalkyl, alkoxycarbonylalkynyl, alkyl, alkylcarbonyl, alkylcarbonylalkenyl, alkylcarbonylalkoxy, alkylcarbonylalkyl, alkylcarbonylalkynyl, alkynyl, carboxy, carboxyalkenyl, carboxyalkyl, carboxyalkynyl, haloalkoxy, haloalkyl, haloalkenyl, haloalkynyl, halogen, hydroxyalkyl, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)carbonylalkenyl and ($NR_{10}R_{11}$)carbonylalkynyl;

$R_5$ is selected from the group consisting of hydrogen and alkyl; and $R_6$ is selected from the group consisting of hydrogen, alkoxycarbonyl, alkoxysulfonyl, alkyl, alkylcarbonyl, alkylsulfonyl, arylalkoxycarbonyl, arylalkylcarbonyl, arylalkylsulfonyl, arylcarbonyl, arylsulfonyl, cycloalkylcarbonyl, cycloalkylalkylcarbonyl, cycloalkylsulfonyl, cycloalkylalkylsulfonyl, heterocyclecarbonyl, heterocyclealkylcarbonyl, heterocyclesulfonyl, heterocyclealkylsulfonyl, ($NR_{13}R_{14}$)carbonyl and ($NR_{13}R_{14}$)sulfonyl;

$R_8$ and $R_9$ are each independently selected from the group consisting of hydrogen, alkenyl, alkoxyalkyl, alkoxycarbonyl, alkoxycarbonylalkyl, alkyl, alkylcarbonyl, alkylsulfonyl, alkynyl, carboxyalkylcarbonyl; cyanoalkyl, formyl, hydroxy, hydroxyalkyl, —$NR_{10}R_{11}$, ($NR_{10}R_{11}$)carbonyl and carboxyalkyl wherein the alkyl portion of carboxyalkyl is optionally substituted with one or two substituents selected from the group consisting of alkylthio, aryl, heterocycle, hydroxy, carboxy, —$NR_{10}R_{11}$ and ($NR_{10}R_{11}$)carboxy;

$R_{10}$ and $R_{11}$ are each independently selected from the group consisting of hydrogen and alkyl;

$R_{12}$ is selected from the group consisting of alkoxy, alkyl, aryl, arylalkyl, cycloalkyl, cycloalkylalkyl, heterocycle and heterocyclealkyl; and $R_{13}$ and $R_{14}$ are each independently selected from the group consisting of hydrogen, alkyl, aryl, arylalkyl, cycloalkyl, cycloalkylalkyl, heterocycle and heterocyclealkyl.

In another embodiment, compounds of the present invention have formula (I) wherein $L_A$ is a covalent bond; $L_D$ is a covalent bond; A is aryl; D is aryl; and $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$, $R_{F5}$, $R_1$, $R_2$, $R_3$, $R_4$, $R_5$, $R_6$, $L_B$, $L_C$, $L_E$, $L_F$, B, C, E, and F are as defined in formula (I).

In another embodiment, compounds of the present invention have formula (I) wherein $L_A$ is a covalent bond; $L_D$ is a covalent bond; A is heterocycle; D is aryl; and $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$, $R_{F5}$, $R_1$, $R_2$, $R_3$, $R_4$, $R_5$, $R_6$, $L_B$, $L_C$, $L_F$, $L_E$, $L_F$, B, C, E, and F are as defined in formula (I).

In another embodiment, compounds of the present invention have formula (I) wherein $L_A$ is a covalent bond; $L_D$ is a covalent bond; A is heterocycle; D is heterocycle; and $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$, $R_{F5}$, $R_1$, $R_2$, $R_3$, $R_4$, $R_5$, $R_6$, $L_B$, $L_C$, $L_E$, $L_F$, B, C, E, and F are as defined in formula (I).

In another embodiment, compounds of the present invention have formula (I) wherein $L_A$ is $C(X_{A1})(X_{A2})$; $L_D$ is a covalent bond; A is aryl; D is aryl; and $X_{A1}$, $X_{A2}$, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$, $R_{F5}$, $R_1$, $R_2$, $R_3$, $R_4$, $R_5$, $R_6$, $L_B$, $L_C$, $L_E$, $L_F$, B, C, E, and F are as defined in formula (I).

In another embodiment, compounds of the present invention have formula (I) wherein $L_A$ is $C(X_{A1})(X_{A2})$; $L_D$ is a covalent bond; A is heterocycle; D is aryl; and $X_{A1}$, $X_{A2}$, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$, $R_{F5}$, $R_1$, $R_2$, $R_3$, $R_4$, $R_5$, $R_6$, $L_B$, $L_C$, $L_E$, $L_F$, B, C, E, and F are as defined in formula (I).

In another embodiment, compounds of the present invention have formula (I) wherein $L_A$ is $C(X_{A1})(X_{A2})$; $L_D$ is a covalent bond; A is heterocycle; D is heterocycle; and $X_{A1}$, $X_{A2}$, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$, $R_{F5}$, $R_1$, $R_2$, $R_3$, $R_4$, $R_5$, $R_6$, $L_B$, $L_C$, $L_E$, $L_F$, B, C, E, and F are as defined in formula (I).

In another embodiment, compounds of the present invention have formula (I) wherein $L_A$ is $C(X_{A1})(X_{A2})$; $L_D$ is a covalent bond; A is aryl; D is heterocycle; and $X_{A1}$, $X_{A2}$, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$, $R_{F5}$, $R_1$, $R_2$, $R_3$, $R_4$, $R_5$, $R_6$, $L_B$, $L_C$, $L_E$, $L_F$, B, C, E, and F are as defined in formula (I).

In another embodiment, compounds of the present invention have formula (I) wherein $L_A$ is $C(X_{A1})(X_{A2})$; A is heterocycle; D is heterocycle; and $X_{A1}$, $X_{A2}$, $X_{D1}$, $X_{D2}$, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$, $R_{F5}$, $R_1$, $R_2$, $R_3$, $R_4$, $R_5$, $R_6$, $L_B$, $L_C$, $L_E$, $L_F$, B, C, E, and F are as defined in formula (I).

In another embodiment, compounds of the present invention have formula (I) wherein $L_A$ is $C(X_{A1})(X_{A2})$; $L_D$ is $C(X_{D1})(X_{D2})$; A is aryl; D is heterocycle; and $X_{A1}$, $X_{A2}$, $X_{D1}$, $X_{D2}$, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$, $R_{F5}$, $R_1$, $R_2$, $R_3$, $R_4$, $R_5$, $R_6$, $L_B$, $L_C$, $L_E$, $L_F$, B, C, E, and F are as defined in formula (I).

In another embodiment, compounds of the present invention have formula (I) wherein $L_A$ is $C(X_{A1})(X_{A2})$; $L_D$ is $C(X_{D1})(X_{D2})$; A is aryl; D is aryl; and $X_{A1}$, $X_{A2}$, $X_{D1}$, $X_{D2}$, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$, $R_{F5}$, $R_1$, $R_2$, $R_3$, $R_4$, $R_5$, $R_6$, $L_B$, $L_C$, $L_E$, $L_F$, B, C, E, and F are as defined in formula (I).

DETAILED DESCRIPTION OF THE INVENTION

Definition of Terms

As used throughout this specification and the appended claims, the following terms have the following meanings.

The term, "modulator," as used herein, refers to a chemical entity, whether a synthesized chemical entity or a natural endogenous chemical entity, that interacts with a steroid receptor, wherein said interation elicits a response by the receptor or blocks the response of the receptor when interacted with by a natural endogenous chemical entity, i.e., cortisol or corticosterone.

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenyloxy," as used herein, refers to an alkenyl group, as defined herein, appended to the parent molecular moiety through an oxygen atom. Representative examples of alkenyloxy include, but are not limited to, allyloxy, 2-butenyloxy, 3-butenyloxy and 3-pentenyloxy.

The term "alkenylthio," as used herein, refers to an alkenyl group, as defined herein, appended to the parent molecular moiety through a sulfur atom. Representative examples of alkenylthio include, but are not limited, allylsulfanyl, 2-butenylsulfanyl, 3-butenylsulfanyl and 3-pentenylsulfanyl.

The term "alkenylene," denotes a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, —CH$_2$—CH=CH—, —CH$_2$CH$_2$CH=CH— and —CH=C(CH$_3$)CH$_2$—.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkenyl," as used herein, refers to an alkoxy group, as defined herein, appended to the parent molecular moiety through an alkenyl group, as defined herein. Representative examples of alkoxyalkenyl include, but are not limited to, 3-methoxy-1-propenyl and 4-methoxy-1-butenyl.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkoxy," as used herein, refers to an alkoxyalkoxy group, as defined herein, appended to the parent molecular moiety through another alkoxy group, as defined herein. Representative examples of alkoxyalkoxy-alkoxy include, but are not limited to, (2-methoxyethoxy) methoxy and (2-methoxyethoxy)ethoxy.

The term "alkoxyalkoxyalkyl," as used herein, refers to an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxyalkynyl," as used herein, refers to an alkoxy group, as defined herein, appended to the parent molecular moiety through an alkynyl group, as defined herein. Representative examples of alkoxyalkynyl include, but are not limited to, 3-ethoxy-1-propynyl and 4-methoxy-1-butynyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkenyl," as used herein, refers to an alkoxycarbonyl group, as defined herein, appended to the parent molecular moiety through an alkenyl group, as defined herein. Representative examples of alkoxycarbonylalkenyl include, but are not limited to, 3-methoxy-3-oxo-1-propenyl and 3-ethoxy-3-oxo-1-propenyl.

The term "alkoxycarbonylalkoxy," as used herein, refers to an alkoxycarbonyl group, as defined herein, appended to the parent molecular moiety through an alkoxy group, as defined herein. Representative examples of alkoxycarbonylalkoxy include, but are not limited to, 3-methoxy-3-oxopropoxy, 3-ethoxy-3-oxopropoxy, 2-methoxy-2-oxoethoxy and 4-methoxy-4-oxobutoxy.

The term "alkoxycarbonylalkyl," as used herein, refers to an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxycarbonylalkynyl," as used herein, refers to an alkoxycarbonyl group, as defined herein, appended to the parent molecular moiety through an alkenyl group, as defined herein. Representative examples of alkoxycarbonylalkynyl include, but are not limited to, 3-methoxy-3-oxo-1-propynyl and 3-ethoxy-3-oxo-1-propynyl.

The term "alkoxysulfonyl," as used herein, refers to an alkoxy group, as defined herein, appended appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkenyl," as used herein, refers to an alkylcarbonyl group, as defined herein, appended to the parent molecular moiety through an alkenyl group, as defined herein. Representative examples of alkylcarbonylalkenyl include, but are not limited to, 3-oxo-1-butenyl and 3-oxo-1-pentenyl.

The term "alkylcarbonylalkoxy," as used herein, refers to an alkylcarbonyl group, as defined herein, appended to the parent molecular moiety through an alkoxy group, as defined herein. Representative examples of alkylcarbonylalkoxy include, but are not limited to, 3-oxopentyloxy, 3-oxobutoxy and 2-oxopropoxy.

The term "alkylcarbonylalkyl," as used herein, refers to an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonylalkynyl," as used herein, refers to an alkylcarbonyl group, as defined herein, appended to the parent molecular moiety through an alkynyl group, as defined herein. Representative examples of alkylcarbonylalkynyl include, but are not limited to, 3-oxo-1-pentynyl and 3-oxo-1-pentenyl.

The term "alkylcarbonylalkylthio," as used herein, refers to an alkylcarbonylalkyl group, as defined herein, appended to the parent molecular moiety through a sulfur atom, as defined herein. Representative examples of alkylcarbonylalkylthio include, but are not limited to, (2-oxopropyl)sulfanyl, (3-oxobutyl)sulfanyl and (3-oxopentyl)sulfanyl.

The term "alkylcarbonyloxy," as used herein, refers to an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylcarbonylthio," as used herein, refers to an alkylcarbonyl group, as defined herein, appended to the parent molecular moiety through a sulfur atom. Representative examples of alkylcarbonylthio include, but are not limited to, acetylsulfanyl, propionylsulfanyl and (2,2-dimethylpropanoyl)sulfanyl.

The term "alkylene," denotes a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkylsulfinyl," as used herein, refers to an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl," as used herein, refers to an alkylsulfinyl group, as defined herein, appended to the parent molecular moiety through an alkyl group, as defined herein. Representative examples of alkylsulfinylalkyl include, but are not limited to, methylsulfinylmethyl and ethylsulfinylmethyl.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl," as used herein, refers to an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "alkylthio," as used herein, refers to an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkylthioalkoxy," as used herein, refers to an alkylthio group, as defined herein, appended to the parent molecular moiety through an alkoxy group, as defined herein. Representative examples of alkylthioalkoxy include, but are not limited, 2-methylsulfanylethoxy and 2-ethylsulfanylethoxy.

The term "alkylthioalkyl," as used herein, refers to an alkylthio group, as defined herein, appended to the parent molecular moiety through an alkyl group, as defined herein. Representative examples of alkylthioalkyl include, but are not limited, methylsulfanylmethyl and 2-(ethylsulfanyl)ethyl.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynyloxy," as used herein, refers to an alkynyl group, as defined herein, appended to the parent molecular moiety through an oxygen atom. Representative examples of alkynyloxy include, but are not limited to, 3-pentynyloxy, 3-butynyloxy and 2-propynyloxy.

The term "alkynylthio," as used herein, refers to an alkynyl group, as defined herein, appended to the parent molecular moiety through a sulfur atom. Representative examples of alkynylthio include, but are not limited, 2-propynylsulfanyl, 3-butynylsulfanyl and 3-pentynylsulfanyl.

The term "alkynylene," denotes a divalent group derived from a straight or branched chain hydrocarbon of from 2 to 10 carbon atoms containing at least one triple bond. Representative examples of alkynylene include, but are not limited to, —C≡C—, —$CH_2$C≡C—, —CH($CH_3$)$CH_2$C≡C—, —C≡C$CH_2$—, and —C≡CCH($CH_3$)$CH_2$—.

The term "aryl," as used herein, refers to a monocyclic-ring system or a bicyclic-ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of this invention can be substituted with 1, 2, 3, 4 or 5 substituents independently selected from alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkylcarbonylalkyl, alkylcarbonylalkylthio, alkylcarbonyloxy, alkylcarbonylthio, alkylsulfinyl, alkylsulfinylalkyl, alkyl sulfonyl, alkylsulfonylalkyl, alkylthio, alkylthioalkyl, alkylthioalkoxy, alkynyl, alkynyloxy, alkynylthio, carboxy, carboxyalkoxy, carboxyalkyl, cyano, cyanoalkoxy, cyanoalkyl, cyanoalkylthio, ethylenedioxy, formyl, formylalkoxy, formylalkyl, haloalkenyl, haloalkenyloxy, haloalkoxy, haloalkyl, haloalkynyl, haloalkynyloxy, halogen, hydroxy, hydroxyalkoxy, hydroxyalkyl, mercapto, mercaptoalkoxy, mercaptoalkyl, methylenedioxy, nitro, —NR$_8$R$_9$, (NR$_8$R$_9$)alkoxy, (NR$_8$R$_9$)alkyl, (NR$_8$R$_9$)carbonyl, (NR$_8$R$_9$)carbonylalkoxy, (NR$_8$R$_9$)carbonylalkyl, (NR$_{10}$R$_{11}$)sulfonyl, (NR$_{10}$R$_{11}$)sulfonylalkyl, —NR$_{10}$S(O)$_2$R$_{12}$, —NR$_{10}$S(O)$_2$NR$_{14}$, and —S(O)$_2$OH.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl," as used herein, refers to an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethoxycarbonyl.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkylcarbonyl," as used herein, refers to an arylalkyl group, as defined herein, appended to the parent molecular moiety through a carbonyl group, as defined herein. Representative examples of arylalkylcarbonyl include, but are not limited to, phenylacetyl and 3-phenylpropanoyl.

The term "arylalkylsulfonyl," as used herein, refers to an arylalkyl group, as defined herein, appended to the parent molecular moiety through a sulfonyl group, as defined herein. Representative examples of arylalkylsulfonyl include, but are not limited to, benzylsulfonyl and 2-phenylethylsulfonyl.

The term "arylcarbonyl," as used herein, refers to an aryl group, as defined herein, appended to the parent molecular moiety through a carbonyl group, as defined herein. Representative examples of arylcarbonyl include, but are not limited to, benzoyl, 4-cyanobenzoyl, and naphthoyl.

The term "aryloxy," as used herein, refers to an aryl group, as defined herein, appended to the parent molecular moiety through an oxy moiety, as defined herein. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "arylsulfonyl," as used herein, refers to an aryl group, as defined herein, appended to the parent molecular moiety through a sulfonyl group, as defined herein. Representative examples of arylsulfonyl include, but are not limited to, phenylsulfonyl, 4-bromophenylsulfonyl and naphthylsulfonyl.

The term "carbonyl," as used herein, refers to a —C(O)— group.

The term "carboxy," as used herein, refers to a —CO$_2$H group.

The term "carboxyalkenyl," as used herein, refers to a carboxy group, as defined herein, appended to the parent molecular moiety through an alkenyl group, as defined herein. Representative examples of carboxyalkenyl include, but are not limited to, carboxymethoxy, carboxyethenyl and 3-carboxy-1-propenyl.

The term "carboxyalkoxy," as used herein, refers to a carboxy group, as defined herein, appended to the parent molecular moiety through an alkoxy group, as defined herein. Representative examples of carboxyalkoxy include, but are not limited to, carboxymethoxy, 2-carboxyethoxy and 3-carboxypropoxy.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "carboxyalkynyl," as used herein, refers to a carboxy group, as defined herein, appended to the parent molecular moiety through an alkynyl group, as defined herein. Representative examples of carboxyalkynyl include, but are not limited to, carboxymethoxy, carboxyethynyl and 3-carboxy-1-propynyl.

The term "cyano," as used herein, refers to a —CN group.

The term "cyanoalkoxy," as used herein, refers to a cyano group, as defined herein, appended to the parent molecular moiety through an alkoxy group, as defined herein. Representative examples of cyanoalkoxy include, but are not limited to, cyanomethoxy, 2-cyanoethoxy and 3-cyanopropoxy.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cyanoalkylthio," as used herein, refers to a cyanoalkyl group, as defined herein, appended to the parent molecular moiety through a sulfur atom, as defined herein. Representative examples of cyanoalkylthio include, but are not limited to, cyanomethylsulfanyl, 2-cyanoethylsulfanyl and 3-cyanopropylsulfanyl.

The term "cycloalkyl," as used herein, refers to a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycloalkyl groups of this invention can be substituted with 1, 2, 3, 4 or 5 substituents independently selected from alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkylcarbonylalkyl, alkylcarbonylalkylthio, alkylcarbonyloxy, alkylcarbonylthio, alkylsulfinyl, alkylsulfinylalkyl, alkyl sulfonyl, alkylsulfonylalkyl, alkylthio, alkylthioalkyl, alkylthioalkoxy, alkynyl, alkynyloxy, alkynylthio, carboxy, carboxyalkoxy, carboxyalkyl, cyano, cyanoalkoxy, cyanoalkyl, cyanoalkylthio, formyl, formylalkoxy, formylalkyl, haloalkenyl, haloalkenyloxy, haloalkoxy, haloalkyl, haloalkynyl, haloalkynyloxy, halogen, hydroxy, hydroxyalkoxy, hydroxyalkyl, mercapto, mercaptoalkoxy, mercaptoalkyl, nitro, —NR$_8$R$_9$, (NR$_8$R$_9$)alkoxy, (NR$_8$R$_9$)alkyl, (NR$_8$R$_9$)carbonyl, (NR$_8$R$_9$)carbonylalkoxy, (NR$_8$R$_9$)carbonylalkyl, (NR$_{10}$R$_{11}$)sulfonyl, (NR$_{10}$R$_{11}$)sulfonylalkyl, —NR$_{10}$S(O)$_2$R$_{12}$, —NR$_{10}$S(O)$_2$NR$_{13}$R$_{14}$, and —S(O)$_2$OH.

The term "cycloalkylalkoxy," as used herein, refers to a cycloalkyl group, as defined herein, appended to the parent molecular moiety through an alkoxy group, as defined herein. Representative examples of cycloalkylalkoxy include, but are not limited to, cyclopropylmethoxy, 2-cyclobutylethoxy, 2-cyclopropylethoxy, cyclopentylmethoxy, cyclohexylmethoxy, and 4-cycloheptylbutyl.

The term "cycloalkylalkyl," as used herein, refers to a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylalkylcarbonyl," as used herein, refers to cycloalkylalkyl group, as defined herein, appended to the parent molecular moiety through a carbonyl group, as defined herein. Representative examples of cycloalkylalkylcarbonyl include, but are not limited to, cyclopropylcarbonyl, cyclohexylacetyl and 3-cyclohexylpropanoyl.

The term "cycloalkylalkylsulfonyl," as used herein, refers to cycloalkylalkyl group, as defined herein, appended to the parent molecular moiety through a sulfonyl group, as defined herein. Representative examples of cycloalkylalkylsulfonyl include, but are not limited to, cyclohexylmethylsulfonyl and 2-cyclohexylethylsulfonyl.

The term "cycloalkylcarbonyl," as used herein, refers to cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "cycloalkyloxy," as used herein, refers to cycloalkyl group, as defined herein, appended to the parent molecular moiety through an oxy group, as defined herein. Representative examples of cycloalkyloxy include, but are not limited to, cyclopropyloxy and cyclobutyloxy.

The term "cycloalkylsulfonyl," as used herein, refers to cycloalkyl group, as defined herein, appended to the parent molecular moiety through a sulfonyl group, as defined herein. Representative examples of cycloalkylsulfonyl include, but are not limited to, cyclohexylsulfonyl and cyclobutylcarbonyl.

The term "ethylenedioxy," as used herein, refers to a —O(CH$_2$)$_2$O— group wherein the oxygen atoms of the ethylenedioxy group are attached to two adjacent carbon atoms of the parent molecular moiety forming a six membered ring.

The term "formyl," as used herein, refers to a —C(O)H group.

The term "formylalkoxy," as used herein, refers to a formyl group, as defined herein, appended to the parent molecular moiety through an oxygen atom, as defined herein. Representative examples of formylalkoxy include, but are not limited to, 2-formylethoxy and 3-formylpropoxy.

The term "formylalkyl," as used herein, refers to a formyl group, as defined herein, appended to the parent molecular moiety through an alkyl group, as defined herein. Representative examples of formylalkyl include, but are not limited to, formylmethyl and 2-formylethyl.

The term "halo" or "halogen," as used herein, refers to —Cl, —Br, —I or —F.

The term "haloalkenyl," as used herein, refers to at least one halogen, as defined herein, appended to the parent molecular moiety through an alkenyl group, as defined herein. Representative examples of haloalkenyl include, but are not limited to, 2-bromoethenyl, 3-bromo-2-propenyl and 1-bromo-2-propenyl.

The term "haloalkenyloxy," as used herein, refers to at least one halogen, as defined herein, appended to the parent molecular moiety through an alkenyloxy group, as defined herein. Representative examples of haloalkenyloxy include, but are not limited to, 3-bromo-2-propenyloxy and 4-bromo-3-butenyloxy.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkynyl," as used herein, refers to at least one halogen, as defined herein, appended to the parent molecular moiety through an alkynyl group, as defined herein. Representative examples of haloalkynyl include, but are not limited to, 2-bromoethynyl, 3-bromo-2-propynyl and 1-bromo-2-propynyl.

The term "haloalkynyloxy," as used herein, refers to at least one halogen, as defined herein, appended to the parent molecular moiety through an alkynyloxy group, as defined herein. Representative examples of haloalkynyloxy include, but are not limited to, (3-bromo-2-propynyl)oxy and (4-bromo-3-butynyl)oxy.

The term "heterocycle" or "heterocyclic," as used herein, refers to a monocyclic or bicyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered rings have from 0–3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another heterocyclic monocyclic ring system. Representative examples of bicyclic ring systems include but are not limited to, for example, benzimidazolyl, benzothiazolyl, benzothienyl, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, isobenzofuranyl, isobenzothienyl, isoindolyl, isoindolinyl, isoquinolinyl, phthalazinyl, pyranopyridyl, quinolinyl, quinolizinyl, quinoxalinyl, quinazolinyl, tetrahydroisoquinolinyl, tetrahydroquinolinyl, and thiopyranopyridyl.

The heterocycles of this invention can be substituted with 1, 2 or 3 substituents independently selected from alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkylcarbonylalkyl, alkylcarbonylalkylthio, alkylcarbonyloxy, alkylcarbonylthio, alkylsulfinyl, alkylsulfinylalkyl, alkyl sulfonyl, alkylsulfonylalkyl, alkylthio, alkylthioalkyl, alkylthioalkoxy, alkynyl, alkynyloxy, alkynylthio, carboxy, carboxyalkoxy, carboxyalkyl, cyano, cyanoalkoxy, cyanoalkyl, cyanoalkylthio, ethylenedioxy, formyl, formylalkoxy, formylalkyl, haloalkenyl, haloalkenyloxy, haloalkoxy, haloalkyl, haloalkynyl, haloalkynyloxy, halogen, hydroxy, hydroxyalkoxy, hydroxyalkyl, mercapto, mercaptoalkoxy, mercaptoalkyl, methylenedioxy, nitro, —NR$_8$R$_9$, (NR$_8$R$_9$)alkoxy, (NR$_8$R$_9$)alkyl, (NR$_8$R$_9$)carbonyl, (NR$_8$R$_9$)carbonylalkoxy, (NR$_8$R$_9$)carbonylalkyl, (NR$_{10}$R$_{11}$)sulfonyl, (NR$_{10}$R$_{11}$)sulfonylalkyl, —NR$_{10}$S(O)$_2$R$_{12}$, —NR$_{10}$S(O)$_2$NR$_{14}$, and —S(O)$_2$OH.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocyclealkylcarbonyl," as used herein, refers to a heterocyclealkyl, as defined herein, appended to the parent molecular moiety through a carbonyl group, as defined herein. Representative examples of heterocyclealkylcarbonyl include, but are not limited to, 3-(2-pyrimidinyl)propanoyl and 2-pyridinylacetyl.

The term "heterocyclealkylsulfonyl," as used herein, refers to a heterocyclealkyl, as defined herein, appended to the parent molecular moiety through a sulfonyl group, as defined herein. Representative examples of heterocyclealkylsulfonyl include, but are not limited to, 4-morpholinylsulfonyl and (2-pyrimidinylmethyl)sulfonyl.

The term "heterocyclecarbonyl," as used herein, refers to a heterocycle, as defined herein, appended to the parent molecular moiety through a carbonyl group, as defined herein. Representative examples of heterocyclecarbonyl include, but are not limited to, 1-piperidinylcarbonyl, 4-morpholinylcarbonyl, pyridin-3-ylcarbonyl and quinolin-3-ylcarbonyl.

The term "heterocyclesulfonyl," as used herein, refers to a heterocycle, as defined herein, appended to the parent molecular moiety through a sulfonyl group, as defined herein. Representative examples of heterocyclesulfonyl include, but are not limited to, 1-piperidinylcarbonyl, 1-piperidinylsulfonyl, 4-morpholinylsulfonyl, pyridin-3-ylsulfonyl and quinolin-3-ylsulfonyl.

The term "hydroxy," as used herein, refers to an —OH group.

The term "hydroxyalkoxy," as used herein, refers to a hydroxy group, as defined herein, appended to the parent molecular moiety through an alkoxy group, as defined herein, wherein the alkyl portion of the alkoxy group is optionally substituted with one or two hydroxy groups. Representative examples of hydroxyalkoxy include, but are not limited to, 2-hydroxyethoxy, 3-hydroxypropoxy and 2-ethyl-4-hydroxyheptyloxy.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, and 2-ethyl-4-hydroxyheptyl.

The term "mercapto," as used herein, refers to a —SH group.

The term "mercaptoalkoxy," as used herein, refers to a mercapto group, as defined herein, appended to the parent molecular moiety through an alkoxy group, as defined herein. Representative examples of mercaptoalkoxy include, but are not limited to, 2-mercaptoethoxy and 3-mercaptopropoxy.

The term "mercaptoalkyl," as used herein, refers to a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy," as used herein, refers to a —OCH$_2$O— group wherein the oxygen atoms of the methylenedioxy are attached to the parent molecular moiety through two adjacent carbon atoms.

The term "nitrogen protecting group" or "N-protecting group," refers to groups intended to protect an amino group against undersirable reactions during synthetic procedures. Commonly used nitrogen protecting groups are disclosed in T. W. Greene and P. G. M. Wuts, Protective Groups in Organic Synthesis, 3rd edition, John Wiley & Sons, New York (1999). Preferred nitrogen protecting groups are formyl, acetyl, benzoyl, pivaloyl, t-butylacetyl, phenylsulfonyl, benzyl, t-butoxycarbonyl (Boc), and benzyloxycarbonyl (Cbz).

The term "nitro," as used herein, refers to a —NO$_2$ group.

The term "oxo," as used herein, refers to a =O moiety.

The term "sulfinyl," as used herein, refers to a —S(O)— group.

The term "sulfonyl," as used herein, refers to a —SO$_2$— group.

In one embodiment, compounds of the present invention have formula (II)

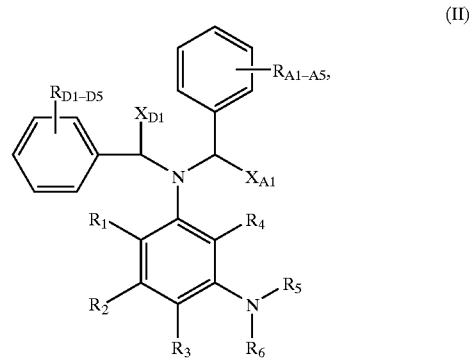

(II)

or a pharmaceutically acceptable salt or prodrug thereof, wherein $X_{A1}$, $X_{D1}$, $R_{A1}$, $R_{A2}$, $R_{A3}$, $R_{A4}$, $R_{A5}$, $R_{D1}$, $R_{D2}$, $R_{D3}$, $R_{D4}$, $R_{D5}$, $R_1$, $R_2$, $R_3$, $R_4$, $R_5$ and $R_6$ are as defined in formula (I).

In another embodiment, compounds of the present invention have formula (II) wherein $R_1$, $R_2$, $R_3$, $R_5$, $X_{A1}$ and $X_{D1}$ are each hydrogen; $R_4$ is alkyl; $R_6$ is alkylsulfonyl; and $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in formula (I).

In another embodiment, compounds of the present invention have formula (II) wherein $R_1$, $R_2$, $R_3$, $R_5$, $X_{A1}$ and $X_{D1}$ are each hydrogen; $R_4$ is alkyl; $R_6$ is (NR$_{12}$R$_{13}$)sulfonyl; and $R_{12}$, $R_{13}$, $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in formula (I).

In another embodiment, compounds of the present invention have formula (II) wherein $R_2$, $R_3$, $R_4$, $R_5$, $X_{A1}$ and $X_{D1}$ are each hydrogen; $R_1$ is alkoxy; $R_6$ is alkylsulfonyl; and $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in formula (I).

In another embodiment, compounds of the present invention have formula (II) wherein $R_1$, $R_2$, $R_3$, $R_5$ and $X_{D1}$ are each hydrogen; $X_{A1}$ is cyano; $R_4$ is alkyl; $R_6$ is alkylsulfonyl; and $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in formula (I).

In another embodiment, compounds of the present invention have formula (II) wherein $R_1$, $R_2$, $R_3$, $R_5$, $X_{A1}$ and $X_{D1}$ are each hydrogen; $R_4$ is selected from alkenyl, alkoxyalkyl, alkoxycarbonylalkenyl and hydroxyalkyl; $R_6$ is alkylsulfonyl; and $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in formula (I).

Representative compounds of formula (II) include, but are not limited to:

N{3-[bis(2-bromobenzyl)amino]-2-methylphenyl}methanesulfonamide;
N-[3-(dibenzylamino)-2-methylphenyl]-methanesulfonamide;
N-[3-(dibenzylamino)-2-methylphenyl]ethanesulfonamide;
N-[3-(dibenzylamino)-2-methylphenyl]-2-propanesulfonamide;
N-{3-[benzyl(4-methoxycarbonylbenzyl)amino]-2-methylphenyl}methanesulfonamide;
N-{3-[benzyl(2-bromobenzyl)amino]-2-methylphenyl}methanesulfonamide;
N-{3-[benzyl(4-nitrobenzyl)amino]-2-methylphenyl}methanesulfonamide;
N-{3-[benzyl(4-fluorobenzyl)amino]-2-methylphenyl}methanesulfonamid;
N-{3-[benzyl(2,4-difluorobenzyl)amino]-2-methylphenyl}methanesulfonamide;
N-{3-[benzyl(2-cyanobenzyl)amino]-2-methylphenyl}methanesulfonamide;
N-{3-[benzyl(4-methoxybenzyl)amino]-2-methylphenyl}methanesulfonamide;
N-{3-[benzyl(4-bromobenzyl)amino]-2-methylphenyl}methanesulfonamide;
N-{3-[benzyl(3-methoxybenzyl)amino]-2-methylphenyl}methanesulfonamide;
N-{3-[(1,3-benzodioxol-5-ylmethyl)(benzyl)amino]-2-methylphenyl}methanesulfonamide;
N-{3-[benzyl(2,3-dihydro-1,4-benzodioxin-6-ylmethyl)amino]-2-methylphenyl}methanesulfonamide;
N-{3-[benzyl(2-chlorobenzyl)amino]-2-methylphenyl}methanesulfonamide;
N-{3-[benzyl(2-fluorobenzyl)amino]-2-methylphenyl}methanesulfonamide;
N-{3-[[4-(allyloxy)benzyl](benzyl)amino]-2-methylphenyl}methanesulfonamide;
N-{3-[[4-(allyloxy)benzyl](2,4-difluorobenzyl)amino]-2-methylphenyl}methanesulfonamide;
N-{3-[(2-cyanobenzyl)(2-fluoro-4-methoxybenzyl)amino]-2-methylphenyl}methanesulfonamide;
N-{3-[(2,4-difluorobenzyl)(4-methoxybenzyl)amino]-2-methylphenyl}methanesulfonamide;
N-{3-[(2,4-difluorobenzyl)(2-fluorobenzyl)amino]-2-methylphenyl}methanesulfonamide;
N-{3-[bis(2,4-difluorobenzyl)amino]-2-methylphenyl}methanesulfonamide;
N-{3-[(2-cyanobenzyl)(2,4-difluorobenzyl)amino]-2-methylphenyl}methanesulfonamide;
N-{3-[benzyl(4-phenoxybenzyl)amino]-2-methylphenyl}methanesulfonamide;
N-{3-[benzyl(2-methylbenzyl)amino]-2-methylphenyl}methanesulfonamide;
N-{3-[benzyl(4-methylbenzyl)amino]-2-methylphenyl}methanesulfonamide;
N-{3-[benzyl(4-chlorobenzyl)amino]-2-methylphenyl}methanesulfonamide;
N-(3-{benzyl[4-(trifluoromethyl)benzyl]amino}-2-methylphenyl)methanesulfonamide;
N-(3-{benzyl[2-fluoro-4-(trifluoromethyl)benzyl]amino}-2-methylphenyl)methanesulfonamide;
N-{3-[benzyl(2,4-dichlorobenzyl)amino]-2-methylphenyl}methanesulfonamide;
N-{3-[benzyl(4-{[3-bromo-2-propenyl]oxy}benzyl)amino]-2-methylphenyl}methanesulfonamide;
N-(3-{benzyl[4-(methoxymethyl)benzyl]amino}-2-methylphenyl)methanesulfonamide;
N-(3-{benzyl[4-(hydroxymethyl)benzyl]amino}-2-methylphenyl)methanesulfonamide;
N-(3-{benzyl[4-(2-hydroxyethoxy)benzyl]amino}-2-methylphenyl)methanesulfonamide;
N-{3-[(2,4-difluorobenzyl)(4-propoxybenzyl)amino]-2-methylphenyl}methanesulfonamide;
N-[3-(dibenzylamino)-2-ethylphenyl]methanesulfonamide;
N'-[3-(dibenzylamino)-2-methylphenyl]-N,N-dimethylsulfamide;
N-{3-[bis(2-bromobenzyl)amino]-4-methoxyphenyl}methanesulfonamide;
N-(3-{(2-bromobenzyl)[cyano(phenyl)methyl]amino}-2-methylphenyl)methanesulfonamide;
N-[3-(dibenzylamino)-2-((E)-3-ethoxy-3-oxo-1-propenyl)phenyl]methanesulfonamide;
N-[3-(dibenzylamino)-2-(hydroxymethyl)phenyl]methanesulfonamide;
N-[3-(dibenzylamino)-2-vinylphenyl]methanesulfonamide;
N-[3-(dibenzylamino)-2-(methoxymethyl)phenyl]methanesulfonamide; and
N-[3-(dibenzylamino)-2-(ethoxymethyl)phenyl]methanesulfonamide.

The following additional compounds, representative of formula (II), may be prepared by one skilled in the art using known synthetic methodology or by using synthetic methodology described in the Schemes and Examples contained herein.

N-{3-[benzyl(4-chloro-2-fluorobenzyl)amino]-2-methylphenyl}methanesulfonamide;
N-{3-[benzyl(2-chloro-4-fluorobenzyl)amino]-2-methylphenyl}methanesulfonamide;
N-{3-[benzyl(2,4-dichlorobenzyl)amino]-2-methylphenyl}methanesulfonamide;
N-{3-[benzyl(4-bromo-2-fluorobenzyl)amino]-2-methylphenyl}methanesulfonamide;
N-{3-[(2,4-difluorobenzyl)(4-ethoxybenzyl)amino]-2-methylphenyl}methanesulfonamide;
N-(3-{(2,4-difluorobenzyl)[4-(3-pentynyloxy)benzyl]amino}-2-methylphenyl)methanesulfonamide;
N-{3-[benzyl(4-isopropoxybenzyl)amino]-2-methylphenyl}methanesulfonamide;
N-(3-{benzyl[4-(methylsulfanyl)benzyl]amino}-2-methylphenyl)methanesulfonamide;

N-[3-((2,4-difluorobenzyl){4-[(3-methyl-2-butenyl)oxy]benzyl}amino)-2-methylphenyl]methanesulfonamide;

N-{3-[[4-(3-butenyloxy)-2-fluorobenzyl](2,4-difluorobenzyl)amino]-2-methylphenyl}methanesulfonamide;

N-(3-{(2,4-difluorobenzyl)[4-(2-pentynyloxy)benzyl]amino}-2-methylphenyl)methanesulfonamide;

N-{3-[(2,4-difluorobenzyl)(4-propoxybenzyl)amino]-2-methylphenyl}methanesulfonamide; and N-{3-[benzyl(2,4,6-trifluorobenzyl)amino]-2-methylphenyl}methanesulfonamide.

In another embodiment, compounds of the present invention have formula (III)

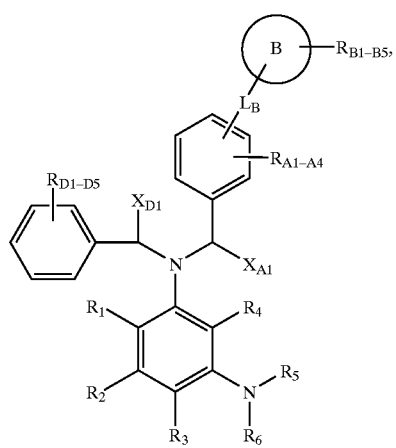

(III)

or a pharmaceutically acceptable salt or prodrug thereof wherein $X_{A1}$, $X_{D1}$, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$, $R_{D5}$, $R_1$, $R_2$, $R_3$, $R_4$, $R_5$, $R_6$, $L_B$ and B are as defined in formula (I).

In another embodiment, compounds of the present invention have formula (III) wherein B is aryl wherein said aryl is phenyl; $L_B$ is —$(CH_2)_mO(CH_2)_n$—; m and n are each 0; $R_1$, $R_2$, $R_3$, $R_5$, $X_{A1}$ and $X_{D1}$ are each hydrogen; $R_4$ is alkyl; $R_6$ is alkylsulfonyl and $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula (I).

In another embodiment, compounds of the present invention have formula (III) wherein B is aryl wherein said aryl is phenyl; $L_B$ is —$(CH_2)_mO(CH_2)_n$—; m is 0; n is 1–6; $R_1$, $R_2$, $R_3$, $R_5$, $X_{A1}$ and $X_{D1}$ are each hydrogen; $R_4$ is alkyl; $R_6$ is alkylsulfonyl; and $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula (I).

In another embodiment, compounds of the present invention have formula (III) wherein B is heterocycle; $L_B$ is —$(CH_2)_mO(CH_2)_n$—; m is 0; n is 1–6; $R_1$, $R_2$, $R_3$, $R_5$, $X_{A1}$ and $X_{D1}$ are each hydrogen; $R_4$ is alkyl; $R_6$ is alkylsulfonyl; and $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula (I).

In another embodiment, compounds of the present invention have formula (III) wherein B is aryl wherein said aryl is phenyl; $L_B$ is —$(CH_2)_mO(CH_2)_nCH_2CH=CH$—; m is 0; $R_1$, $R_2$, $R_3$, $R_5$, $X_{A1}$ and $X_{D1}$ are each hydrogen; $R_4$ is alkyl; $R_6$ is alkylsulfonyl; and n, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula (I).

In another embodiment, compounds of the present invention have formula (III) wherein B is heterocycle; $L_B$ is —$(CH_2)_mO(CH_2)_n$—; m is 0; n is 1–6; $R_1$, $R_2$, $R_3$, $R_5$, $X_{A1}$, $X_{D1}$ are each hydrogen; $R_4$ is alkyl; and $R_6$ is alkylsulfonyl, and $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula (I).

In another embodiment, compounds of the present invention have formula (III) wherein B is aryl wherein said aryl is phenyl; $L_B$ is —$(CH_2)_mC(O)(CH_2)_n$—; $R_1$, $R_2$, $R_3$, $R_5$, $X_{A1}$ and $X_{D1}$ are each hydrogen; $R_4$ is alkyl; $R_6$ is alkylsulfonyl and m, n, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula (I).

In another embodiment, compounds of the present invention have formula (III) wherein B is aryl wherein said aryl is phenyl; $L_B$ is —$(CH_2)_mS(CH_2)_n$—; $R_1$, $R_2$, $R_3$, $R_5$, $X_{A1}$ and $X_{D1}$ are each hydrogen; $R_4$ is alkyl; $R_6$ is alkylsulfonyl; and m, n, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula (I).

In another embodiment, compounds of the present invention have formula (III) wherein B is aryl wherein said aryl is phenyl; $L_B$ is alkylene; $R_1$, $R_2$, $R_3$, $R_5$, $X_{A1}$ and $X_{D1}$ are each hydrogen; $R_4$ is alkyl; $R_6$ is alkylsulfonyl; and $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula (I).

In another embodiment, compounds of the present invention have formula (III) wherein B is aryl wherein said aryl is phenyl; $L_B$ is —$(CH_2)_mC(OH)(CH_2)_n$—; $R_1$, $R_2$, $R_3$, $R_5$, $X_{A1}$ and $X_{D1}$ are each hydrogen; $R_4$ is alkyl; $R_6$ is alkylsulfonyl; and m, n, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula (I).

In another embodiment, compounds of the present invention have formula (III) wherein B is cycloalkyl; $L_B$ is —$(CH_2)_mO(CH_2)_n$—; $R_1$, $R_2$, $R_3$, $R_5$, $X_{A1}$ and $X_{D1}$ are each hydrogen; $R_4$ is alkyl; $R_6$ is alkylsulfonyl; and m, n, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula (I).

In another embodiment, compounds of the present invention have formula (III) wherein B is heterocycle; $L_B$ is —$(CH_2)_mC(O)(CH_2)_n$—; $R_1$, $R_2$, $R_3$, $R_5$, $X_{A1}$ $X_{D1}$ are each hydrogen; $R_4$ is alkyl; $R_6$ is alkylsulfonyl; and m, n, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula (I).

Representative compounds of formula (III) include, but are not limited to:

N-{3-[[4-(4-bromophenoxy)benzyl](2,4-difluorobenzyl)amino]-2-methylphenyl}methanesulfonamide;

N-{3-[(4-(4-(3-ethoxy-3-oxopropyl)phenoxy)benzyl)(2,4-difluorobenzyl)amino]-2-methylphenyl}methanesulfonamide;

N-{3-[(4-(4-(2-carboxyethyl)phenoxy)benzyl)(2,4-difluorobenzyl)amino]-2-methylphenyl}methanesulfonamide;

N-{3-[[4-(benzyloxy)benzyl](2,4-difluorobenzyl)amino]-2-methylphenyl}methanesulfonamide;

N-{3-[(2,4-difluorobenzyl)(4-[{3-phenyl-2-propenyl]oxy}benzyl)amino]-2-methylphenyl}methanesulfonamide;

N-{3-[(2,4-difluorobenzyl)(4-phenoxybenzyl)amino]-2-methylphenyl}methanesulfonamide;

methyl 4-{4-[((2,4-difluorobenzyl){2-methyl-3-[(methylsulfonyl)amino]phenyl}amino)methyl]phenoxy}benzoate;

N-{3-[(2,4-difluorobenzyl)(2-fluoro-4-phenoxybenzyl)amino]-2-methylphenyl}methanesulfonamide;

N-(3-{(2,4-difluorobenzyl)[4-(3-methoxyphenoxy)benzyl]amino}-2-methylphenyl)methanesulfonamide;

N-{3-[(2-fluorobenzyl)(4-phenoxybenzyl)amino]-2-methylphenyl}methanesulfonamide;

N-{3-[(4-methoxybenzyl)(4-phenoxybenzyl)amino]-2-methylphenyl}methanesulfonamide;

3-(4-{4-[((2,4-difluorobenzyl){2-methyl-3-[(methylsulfonyl)amino]phenyl}amino)methyl]phenoxy}phenyl)propanoic acid;
N-[3-(benzyl{4-[3-(2-methoxyethoxy)phenoxy]benzyl}amino)-2-methylphenyl]methanesulfonamide;
(3-{4-[(benzyl{2-methyl-3-[(methylsulfonyl)amino]phenyl}amino)methyl]phenoxy}phenoxy)acetic acid;
4-[4-{4-[(benzyl{2-methyl-3-[(methylsulfonyl)amino]phenyl}amino)methyl]phenoxy}-2-(2-methoxyethoxy)phenyl]butanoic acid;
ethyl 4-(4-{4-[(benzyl{2-methyl-3-[(methylsulfonyl)amino]phenyl}amino)methyl]phenoxy}phenyl)butanoate;
N-[3-(benzyl{4-[3-(3-hydroxypropyl)phenoxy]benzyl}amino)-2-methylphenyl]methanesulfonamide;
methyl 4-{4-[(benzyl{2-methyl-3-[(methylsulfonyl)amino]phenyl}amino)methyl]phenoxy}benzoate;
ethyl N-(4-{4-[((2,4-difluorobenzyl){2-methyl-3-[(methylsulfonyl)amino]phenyl}amino)methyl]phenoxy}benzoyl)-beta-alaninate;
methyl 3-{4-[((2,4-difluorobenzyl){2-methyl-3-[(methylsulfonyl)amino]phenyl}amino)methyl]phenoxy}benzoate;
N-{3-[benzyl(4-{3-[2-(2-methoxyethoxy)ethoxy]phenoxy}benzyl)amino]-2-methylphenyl}methanesulfonamide;
N-[3-(3-{4-[(benzyl{2-methyl-3-[(methylsulfonyl)amino]phenyl}amino)methyl]phenoxy}phenoxy)propyl]acetamide;
N-[3-(3-{4-[(benzyl{2-methyl-3-[(methylsulfonyl)amino]phenyl}amino)methyl]phenoxy}phenoxy)propyl]methanesulfonamide;
N-{3-[benzyl(4-{3-[3-(dimethylamino)propoxy]phenoxy}benzyl)amino]-2-methylphenyl}methanesulfonamide;
4-(4-{4-[((2,4-difluorobenzyl){2-methyl-3-[(methylsulfonyl)amino]phenyl}amino)methyl]phenoxy}phenyl)butanoic acid;
3-(4-{4-[((2-bromobenzyl){2-methyl-3-[(methylsulfonyl)amino]phenyl}amino)methyl]phenoxy}phenyl)propanoic acid;
(5-{4-[(benzyl{2-methyl-3-[(methylsulfonyl)amino]phenyl}amino)methyl]phenoxy}-2-bromophenoxy)acetic acid;
4-{[2-(3-{4-[(benzyl{2-methyl-3-[(methylsulfonyl)amino]phenyl}amino)methyl]phenoxy}phenoxy)ethyl]amino}-4-oxobutanoic acid;
5-{[2-(3-{4-[(benzyl{2-methyl-3-[(methylsulfonyl)amino]phenyl}amino)methyl]phenoxy}phenoxy)ethyl]amino}-5-oxopentanoic acid;
N-[2-(3-{4-[(benzyl{2-methyl-3-[(methylsulfonyl)amino]phenyl}amino)methyl]phenoxy}phenoxy)ethyl]acetamide;
N-[2-(3-{4-[(benzyl{2-methyl-3-[(methylsulfonyl)amino]phenyl}amino)methyl]phenoxy}phenoxy)ethyl]methanesulfonamide
methyl 2-(3-{4-[(benzyl{2-methyl-3-[(methylsulfonyl)amino]phenyl}amino)methyl]phenoxy}phenoxy)ethylcarbamate;
(3-{4-[((4-chloro-2-fluorobenzyl){2-methyl-3-[(methylsulfonyl)amino]phenyl}amino)methyl]phenoxy}phenoxy)acetic acid;
3-(4-{4-[((2-fluorobenzyl){2-methyl-3-[(methylsulfonyl)amino]phenyl}amino)methyl]phenoxy}phenyl)propanoic acid;
3-(4-{4-[((4-fluorobenzyl){2-methyl-3-[(methylsulfonyl)amino]phenyl}amino)methyl]phenoxy}phenyl)propanoic acid;
3-(4-{4-[((4-chloro-2-fluorobenzyl){2-methyl-3-[(methylsulfonyl)amino]phenyl}amino)methyl]phenoxy}phenyl)propanoic acid;
(3-{4-[((2,4-difluorobenzyl){2-ethyl-3-[(methylsulfonyl)amino]phenyl}amino)methyl]phenoxy}phenoxy)acetic acid;
(3-{4-[((2,4-difluorobenzyl){2-methyl-3-[(methylsulfonyl)amino]phenyl}amino)methyl]phenoxy}-5-methylphenoxy)acetic acid;
(3-{4-[((2,4-difluorobenzyl){2-methyl-3-[(methylsulfonyl)amino]phenyl}amino)methyl]phenoxy}-5-methoxyphenoxy)acetic acid;
(2-chloro-5-{4-[((2,4-difluorobenzyl){2-methyl-3-[(methylsulfonyl)amino]phenyl}amino)methyl]phenoxy}phenoxy)acetic acid;
(4-{4-[(benzyl{2-methyl-3-[(methylsulfonyl)amino]phenyl}amino)methyl]phenoxy}phenoxy)acetic acid;
4-{4-[(benzyl{2-methyl-3-[(methylsulfonyl)amino]phenyl}amino)methyl]phenoxy}benzoic acid;
N-[3-(benzyl{4-[4-(methoxymethoxy)phenoxy]benzyl}amino)-2-methylphenyl]methanesulfonamide;
N-[3-(benzyl{4-[4-(3-hydroxypropyl)phenoxy]benzyl}amino)-2-methylphenyl]methanesulfonamide;
4-(4-{4-[(benzyl{2-methyl-3-[(methylsulfonyl)amino]phenyl}amino)methyl]phenoxy}phenyl)butanoic acid;
N-[3-(benzyl{4-[4-(4-hydroxybutyl)phenoxy]benzyl}amino)-2-methylphenyl]methanesulfonamide;
N-{3-[(3-bromobenzyl)(4-phenoxybenzyl)amino]-2-methylphenyl}methanesulfonamide
N-{3-[(4-bromobenzyl)(4-phenoxybenzyl)amino]-2-methylphenyl}methanesulfonamide;
N-[3-(4-{4-[(benzyl{2-methyl-3-[(methylsulfonyl)amino]phenyl}amino)methyl]phenoxy}phenyl)propanoyl]glycine;
N-[3-(4-{4-[(benzyl{2-methyl-3-[(methylsulfonyl)amino]phenyl}amino)methyl]phenoxy}phenyl)propanoyl]-beta-alanine;
4-{[3-(4-{4-[(benzyl{2-methyl-3-[(methylsulfonyl)amino]phenyl}amino)methyl]phenoxy}phenyl)propanoyl]amino}butanoic acid;
N-[4-(4-{4-[(benzyl{2-methyl-3-[(methylsulfonyl)amino]phenyl}amino)methyl]phenoxy}phenyl)butanoyl]glycine;
N-[4-(4-{4-[(benzyl{2-methyl-3-[(methylsulfonyl)amino]phenyl}amino)methyl]phenoxy}phenyl)butanoyl]-beta-alanine;
4-{[4-(4-{4-[(benzyl{2-methyl-3-[(methylsulfonyl)amino]phenyl}amino)methyl]phenoxy}phenyl)butanoyl]amino}butanoic acid;
(3-{4-[((2,4-difluorobenzyl){2-methyl-3-[(methylsulfonyl)amino]phenyl}amino)methyl]phenoxy}phenoxy)acetic acid;
2-(3-{4-[(benzyl{2-methyl-3-[(methylsulfonyl)amino]phenyl}amino)methyl]phenoxy}phenoxy)propanoic acid;
2-(3-{4-[(benzyl{2-methyl-3-[(methylsulfonyl)amino]phenyl}amino)methyl]phenoxy}phenoxy)-4-hydroxybutanoic acid;
N-(3-{benzyl[4-(3-hydroxyphenoxy)benzyl]amino}-2-methylphenyl)methanesulfonamide;
4-(3-{4-[(benzyl{2-methyl-3-[(methylsulfonyl)amino]phenyl}amino)methyl]phenoxy}phenoxy)butanoic acid;
5-(3-{4-[(benzyl{2-methyl-3-[(methylsulfonyl)amino]phenyl}amino)methyl]phenoxy}phenoxy)pentanoic acid;
N-[3-(4-{4-[(benzyl{2-methyl-3-[(methylsulfonyl)amino]phenyl}amino)methyl]phenoxy}phenyl)propanoyl]-N-methylglycine;
N-[4-(4-{4-[(benzyl{2-methyl-3-[(methylsulfonyl)amino]phenyl}amino)methyl]phenoxy}phenyl)butanoyl]-N-methylglycine;

4-(3-{4-[((2,4-difluorobenzyl){2-methyl-3-[(methylsulfonyl)amino]phenyl}amino)methyl]phenoxy}phenoxy)butanoic acid;

5-(3-{4-[((2,4-difluorobenzyl){2-methyl-3-[(methylsulfonyl)amino]phenyl}amino)methyl]phenoxy}phenoxy)pentanoic acid;

N-[(3-{4-[(benzyl{2-methyl-3-[(methylsulfonyl)amino]phenyl}amino)methyl]phenoxy}phenoxy)acetyl]glycine;

N-[(3-{4-[(benzyl{2-methyl-3-[(methylsulfonyl)amino]phenyl}amino)methyl]phenoxy}phenoxy)acetyl]-beta-alanine;

N-[(3-{4-[(benzyl{2-methyl-3-[(methylsulfonyl)amino]phenyl}amino)methyl]phenoxy}phenoxy)acetyl]-N-methylglycine;

4-{[(3-{4-[(benzyl{2-methyl-3-[(methylsulfonyl)amino]phenyl}amino)methyl]phenoxy}phenoxy)acetyl]amino}butanoic acid;

ethyl 4-(3-{4-[(benzyl{2-methyl-3-[(methylsulfonyl)amino]phenyl}amino)methyl]phenoxy}phenoxy)butanoate;

ethyl 5-(3-{4-[(benzyl{2-methyl-3-[(methylsulfonyl)amino]phenyl}amino)methyl]phenoxy}phenoxy)pentanoate;

N-[4-(3-{4-[(benzyl{2-methyl-3-[(methylsulfonyl)amino]phenyl}amino)methyl]phenoxy}phenoxy)butanoyl]glycine;

N-[4-(3-{4-[(benzyl{2-methyl-3-[(methylsulfonyl)amino]phenyl}amino)methyl]phenoxy}phenoxy)butanoyl]-beta-alanine;

4-{[4-(3-{4-[(benzyl{2-methyl-3-[(methylsulfonyl)amino]phenyl}amino)methyl]phenoxy}phenoxy)butanoyl]amino}butanoic acid;

N-[5-(3-{4-[(benzyl{2-methyl-3-[(methylsulfonyl)amino]phenyl}amino)methyl]phenoxy}phenoxy)pentanoyl]glycine;

N-[5-(3-{4-[(benzyl{2-methyl-3-[(methylsulfonyl)amino]phenyl}amino)methyl]phenoxy}phenoxy)pentanoyl]-beta-alanine;

4-{[5-(3-{4-[(benzyl{2-methyl-3-[(methylsulfonyl)amino]phenyl}amino)methyl]phenoxy}phenoxy)pentanoyl]amino}butanoic acid;

N-[3-(benzyl{4-[3-(2-hydroxyethoxy)phenoxy]benzyl}amino)-2-methylphenyl]methanesulfonamide;

[2-(3-{4-[(benzyl{2-methyl-3-[(methylsulfonyl)amino]phenyl}amino)methyl]phenoxy}phenoxy)ethoxy]acetic acid;

2,4-dideoxy-6-O-(3-{4-[((2,4-difluorobenzyl){2-methyl-3-[(methylsulfonyl)amino]phenyl}amino)methyl]phenoxy}phenyl)-D-erythro-hexonic acid;

(3-{4-[((2-bromobenzyl){2-methyl-3-[(methylsulfonyl)amino]phenyl}amino)methyl]phenoxy}phenoxy)acetic acid;

N-{3-[[4-(3-acetylphenoxy)benzyl](2,4-difluorobenzyl)amino]-2-methylphenyl}methanesulfonamide;

N-(3-{(2,4-difluorobenzyl)[4-(3,4-dimethoxyphenoxy)benzyl]amino}-2-methylphenyl)methanesulfonamide;

N-(3-{(2,4-difluorobenzyl)[4-(pent-3-ynyloxy)benzyl]amino}-2-methylphenyl)methanesulfonamide;

N-(3-{(4-chloro-2-fluorobenzyl)[4-(methylthio)benzyl]amino}-2-methylphenyl)methanesulfonamide;

N-{3-[(4-chloro-2-fluorobenzyl)(2-fluorobenzyl)amino]-2-methylphenyl}methanesulfonamide;

N-(3-{benzyl[(2'-cyano-1,1'-biphenyl-4-yl)methyl]amino}-2-methylphenyl)methanesulfonamide;

3-(4-{4-[(benzyl{2-methyl-3-[(methylsulfonyl)amino]phenyl}amino)methyl]phenoxy}phenyl)-N-(5-hydroxypentyl)propanamide;

3-(4-{4-[(benzyl{2-methyl-3-[(methylsulfonyl)amino]phenyl}amino)methyl]phenoxy}phenyl)-N-(4-hydroxybutyl)propanamide;

3-(4-{4-[(benzyl{2-methyl-3-[(methylsulfonyl)amino]phenyl}amino)methyl]phenoxy}phenyl)-N-(3-hydroxypropyl)propanamide;

3-(4-{4-[(benzyl{2-methyl-3-[(methylsulfonyl)amino]phenyl}amino)methyl]phenoxy}phenyl)-N-(2-hydroxyethyl)propanamide;

3-(4-{4-[(benzyl{2-methyl-3-[(methylsulfonyl)amino]phenyl}amino)methyl]phenoxy}phenyl)-N-(6-hydroxyhexyl)propanamide;

N-(3-{benzyl[4-(3-isopropoxyphenoxy)benzyl]amino}-2-methylphenyl)methanesulfonamide;

N-[3-(benzyl{4-[3-(cyclobutyloxy)phenoxy]benzyl}amino)-2-methylphenyl]methanesulfonamide;

N-(3-{benzyl[4-(3-sec-butoxyphenoxy)benzyl]amino}-2-methylphenyl)methanesulfonamide;

N-[3-(benzyl{4-[3-(cyclopentyloxy)phenoxy]benzyl}amino)-2-methylphenyl]methanesulfonamide;

N-[3-(benzyl{4-[3-(1-methylbutoxy)phenoxy]benzyl}amino)-2-methylphenyl]methanesulfonamide;

N-[3-(benzyl{4-[3-(2-methoxy-1-methylethoxy)phenoxy]benzyl}amino)-2-methylphenyl]methanesulfonamide;

N-[3-(benzyl{4-[3-(cyclohexyloxy)phenoxy]benzyl}amino)-2-methylphenyl]methanesulfonamide;

N-{3-[benzyl(4-{3-[(3-methylcyclopentyl)oxy]phenoxy}benzyl)amino]-2-methylphenyl}methanesulfonamide;

N-[3-(benzyl{4-[3-(2-ethoxy-1-methylethoxy)phenoxy]benzyl}amino)-2-methylphenyl]methanesulfonamide;

N-{3-[benzyl(4-{3-[(4-methylcyclohexyl)oxy]phenoxy}benzyl)amino]-2-methylphenyl}methanesulfonamide;

N-[3-(benzyl{4-[3-(cycloheptyloxy)phenoxy]benzyl}amino)-2-methylphenyl]methanesulfonamide;

N-(3-{benzyl[4-(3-methoxyphenoxy)benzyl]amino}-2-methylphenyl)methanesulfonamide;

N-(3-{benzyl[4-(3-ethoxyphenoxy)benzyl]amino}-2-methylphenyl)methanesulfonamide;

N-(3-{benzyl[4-(3-propoxyphenoxy)benzyl]amino}-2-methylphenyl)methanesulfonamide;

N-[3-(benzyl{4-[3-(cyclopropylmethoxy)phenoxy]benzyl}amino)-2-methylphenyl]methanesulfonamide;

N-(3-{benzyl[4-(3-butoxyphenoxy)benzyl]amino}-2-methylphenyl)methanesulfonamide;

N-(3-{benzyl[4-(3-isobutoxyphenoxy)benzyl]amino}-2-methylphenyl)methanesulfonamide;

N-[3-(benzyl{4-[3-(pent-3-ynyloxy)phenoxy]benzyl}amino)-2-methylphenyl]methanesulfonamide;

N-{3-[benzyl(4-{3-[(2E)-pent-2-enyloxy]phenoxy}benzyl)amino]-2-methylphenyl}methanesulfonamide;

N-{3-[benzyl(4-{3-[(1-methylcyclopropyl)methoxy]phenoxy}benzyl)amino]-2-methylphenyl}methanesulfonamide;

N-[3-(benzyl{4-[3-(cyclobutylmethoxy)phenoxy]benzyl}amino)-2-methylphenyl]methanesulfonamide;

N-[3-(benzyl{4-[3-(2-cyclopropylethoxy)phenoxy]benzyl}amino)-2-methylphenyl]methanesulfonamide;

N-[3-(benzyl{4-[3-(pentyloxy)phenoxy]benzyl}amino)-2-methylphenyl]methanesulfonamide;

N-[3-(benzyl{4-[3-(2-methylbutoxy)phenoxy]benzyl}amino)-2-methylphenyl]methanesulfonamide;

N-[3-(benzyl{4-[3-(3-methylbutoxy)phenoxy]benzyl}amino)-2-methylphenyl]methanesulfonamide;

N-[3-(benzyl{4-[3-(2-ethoxyethoxy)phenoxy]benzyl}amino)-2-methylphenyl]methanesulfonamide;

N-{3-[benzyl(4-{3-[2-(methylthio)ethoxy]phenoxy}benzyl)amino]-2-methylphenyl}methanesulfonamide;

N-[3-(benzyl{4-[3-(cyclopentylmethoxy)phenoxy]benzyl}amino)-2-methylphenyl]methanesulfonamnide;

N-[3-(benzyl{4-[3-(hexyloxy)phenoxy]benzyl}amino)-2-methylphenyl]methanesulfonamide;
N-[3-(benzyl{4-[3-(3,3-dimethylbutoxy)phenoxy]benzyl}amino)-2-methylphenyl]methanesulfonamide;
N-[3-(benzyl{4-[3-(2-isopropoxyethoxy)phenoxy]benzyl}amino)-2-methylphenyl]methanesulfonamide;
N-[3-(benzy{4-[3-(cyclohexylmethoxy)phenoxy]benzyl}amino)-2-methylphenyl]methanesulfonamide;
N-[3-(benzyl{4-[3-(3-methoxy-3-methylbutoxy)phenoxy]benzyl}amino)-2-methylphenyl]methanesulfonamide;
(3-{4-[((2-methylbenzyl){2-methyl-3-[(methylsulfonyl)amino]phenyl}amino)methyl]phenoxy}phenoxy)acetic acid;
(3-{4-[((4-methylbenzyl){2-methyl-3-[(methylsulfonyl)amino]phenyl}amino)methyl]phenoxy}phenoxy)acetic acid;
(3-{4-[((2,4-dichlorobenzyl){2-methyl-3-[(methylsulfonyl)amino]phenyl}amino)methyl]phenoxy}phenoxy)acetic acid;
(3-{4-[((2-chloro-4-fluorobenzyl){2-methyl-3-[(methylsulfonyl)amino]phenyl}amino)methyl]phenoxy}phenoxy)acetic acid;
(3-{4-[((3,4-difluorobenzyl){2-methyl-3-[(methylsulfonyl)amino]phenyl}amino)methyl]phenoxy}phenoxy)acetic acid;
N-[3-(benzyl{4-[4-(4-hydrazino-4-oxobutyl)phenoxy]benzyl}amino)-2-methylphenyl]methanesulfonamide;
N~2~-[4-(4-{4-[(benzyl{2-methyl-3-[(methylsulfonyl)amino]phenyl}amino)methyl]phenoxy}phenyl)butanoyl]-L-asparagine;
N-[4-(4-{4-[(benzyl{2-methyl-3-[(methylsulfonyl)amino]phenyl}amino)methyl]phenoxy}phenyl)butanoyl]-D-valine;
N-[4-(4-{4-[(benzyl{2-methyl-3-[(methylsulfonyl)amino]phenyl}amino)methyl]phenoxy}phenyl)butanoyl]-L-tyrosine;
N-[4-(4-{4-[(benzyl{2-methyl-3-[(methylsulfonyl)amino]phenyl}amino)methyl]phenoxy}phenyl)butanoyl]-L-methionine;
N~2~-[4-(4-{4-[(benzyl{2-methyl-3-[(methylsulfonyl)amino]phenyl}amino)methyl]phenoxy}phenyl)butanoyl]-L-lysine;
N-[4-(4-{4-[(benzyl{2-methyl-3-[(methylsulfonyl)amino]phenyl}amino)methyl]phenoxy}phenyl)butanoyl]-L-serine;
N-[4-(4-{4-[(benzyl{2-methyl-3-[(methylsulfonyl)amino]phenyl}amino)methyl]phenoxy}phenyl)butanoyl]-L-phenylalanine;
N-[4-(4-{4-[(benzyl{2-methyl-3-[(methylsulfonyl)amino]phenyl}amino)methyl]phenoxy}phenyl)butanoyl]-D-tyrosine;
N~2~-[4-(4-{4-[(benzyl{2-methyl-3-[(methylsulfonyl)amino]phenyl}amino)methyl]phenoxy}phenyl)butanoyl]-L-glutamine;
N-[4-(4-{4-[(benzyl{2-methyl-3-[(methylsulfonyl)amino]phenyl}amino)methyl]phenoxy}phenyl)butanoyl]-L-isoleucine;
N-[4-(4-{4-[(benzyl{2-methyl-3-[(methylsulfonyl)amino]phenyl}amino)methyl]phenoxy}phenyl)butanoyl]-D-glutamic acid;
N-[4-(4-{4-[(benzyl{2-methyl-3-[(methylsulfonyl)amino]phenyl}amino)methyl]phenoxy}phenyl)butanoyl]-D-histidine;
N-[4-(4-{4-[(benzyl{2-methyl-3-[(methylsulfonyl)amino]phenyl}amino)methyl]phenoxy}phenyl)butanoyl]-L-valine;
N-[4-(4-{4-[(benzyl{2-methyl-3-[(methylsulfonyl)amino]phenyl}amino)methyl]phenoxy}phenyl)butanoyl]-L-aspartic acid;

ethyl 4-(4-{4-[(benzyl{2-methyl-3-[(methylsulfonyl)amino]phenyl}amino)methyl]phenoxy}phenoxy)butanoate;
4-(4-{4-[(benzyl{2-methyl-3-[(methylsulfonyl)amino]phenyl}amino)methyl]phenoxy}phenoxy)butanoic acid;
5-(4-{4-[(benzyl{2-methyl-3-[(methylsulfonyl)amino]phenyl}amino)methyl]phenoxy}phenoxy)pentanoic acid;
(5-{4-[((2,4-difluorobenzyl){2-methyl-3-[(methylsulfonyl)amino]phenyl}amino)methyl]phenoxy}-2-ethylphenoxy)acetic acid;
ethyl 4-{[4-(3-{4-[(benzyl{2-methyl-3-[(methylsulfonyl)amino]phenyl}amino)methyl]phenoxy}phenoxy)butanoyl]amino}butanoate;
(5-{4-[((2,4-difluorobenzyl){2-methyl-3-[(methylsulfonyl)amino]phenyl}amino)methyl]phenoxy}-2-hexylphenoxy)acetic acid;
ethyl N-[4-(3-{4-[(benzyl{2-methyl-3-[(methylsulfonyl)amino]phenyl}amino)methyl]phenoxy}phenoxy)butanoyl]-N-methylglycinate;
N-[4-(3-{4-[(benzyl{2-methyl-3-[(methylsulfonyl)amino]phenyl}amino)methyl]phenoxy}phenoxy)butanoyl]-N-methylglycine;
ethyl (2-chloro-5-{4-[((2,4-difluorobenzyl){2-methyl-3-[(methylsulfonyl)amino]phenyl}amino)methyl]phenoxy}phenoxy)acetate;
N-[4-(4-{4-[(benzyl{2-methyl-3-[(methylsulfonyl)amino]phenyl}amino)methyl]phenoxy}phenoxy)butanoyl]glycine;
N-[4-(4-{4-[(benzyl{2-methyl-3-[(methylsulfonyl)amino]phenyl}amino)methyl]phenoxy}phenoxy)butanoyl]-beta-alanine;
4-{[4-(4-{4-[(benzyl{2-methyl-3-[(methylsulfonyl)amino]phenyl}amino)methyl]phenoxy}phenoxy)butanoyl]amino}butanoic acid;
N-[4-(4-{4-[(benzyl{2-methyl-3-[(methylsulfonyl)amino]phenyl}amino)methyl]phenoxy}phenoxy)butanoyl]-N-methylglycine;
N-[4-(4-{4-[(benzyl{2-methyl-3-[(methylsulfonyl)amino]phenyl}amino)methyl]phenoxy}phenoxy)butanoyl]-L-glutamic acid;
N-[4-(4-{4-[(benzyl{2-methyl-3-[(methylsulfonyl)amino]phenyl}amino)methyl]phenoxy}phenoxy)butanoyl]-L-valine;
N-[4-(4-{4-[(benzyl{2-methyl-3-[(methylsulfonyl)amino]phenyl}amino)methyl]phenoxy}phenoxy)butanoyl]-L-serine;
N-[4-(4-{4-[(benzyl{2-methyl-3-[(methylsulfonyl)amino]phenyl}amino)methyl]phenoxy}phenoxy)butanoyl]-L-isoleucine;
N~2~-[4-(4-{4-[(benzyl{2-methyl-3-[(methylsulfonyl)amino]phenyl}amino)methyl]phenoxy}phenoxy)butanoyl]-L-glutamine;
N-[5-(4-{4-[(benzyl{2-methyl-3-[(methylsulfonyl)amino]phenyl}amino)methyl]phenoxy}phenoxy)pentanoyl]glycine;
N-[5-(4-{4-[(benzyl{2-methyl-3-[(methylsulfonyl)amino]phenyl}amino)methyl]phenoxy}phenoxy)pentanoyl]-beta-alanine;
4-{[5-(4-{4-[(benzyl{2-methyl-3-[(methylsulfonyl)amino]phenyl}amino)methyl]phenoxy}phenoxy)pentanoyl]amino}butanoic acid;
N-[5-(4-{4-[(benzyl{2-methyl-3-[(methylsulfonyl)amino]phenyl}amino)methyl]phenoxy}phenoxy)pentanoyl]-N-methylglycine;
N-[5-(4-{4-[(benzyl{2-methyl-3-[(methylsulfonyl)amino]phenyl}amino)methyl]phenoxy}phenoxy)pentanoyl]-L-glutamic acid;
N-[5-(4-{4-[(benzyl{2-methyl-3-[(methylsulfonyl)amino]phenyl}amino)methyl]phenoxy}phenoxy)pentanoyl]-L-valine;

N-[5-(4-{4-[(benzyl{2-methyl-3-[(methylsulfonyl)amino]phenyl}amino)methyl]phenoxy}phenoxy)pentanoyl]-L-serine;

N-[5-(4-{4-[(benzyl{2-methyl-3-[(methylsulfonyl)amino]phenyl}amino)methyl]phenoxy}phenoxy)pentanoyl]-L-isoleucine;

4-{[(4-{4-[(benzyl{2-methyl-3-[(methylsulfonyl)amino]phenyl}amino)methyl]phenoxy}phenoxy)acetyl]amino}butanoic acid;

N-[(4-{4-[(benzyl{2-methyl-3-[(methylsulfonyl)amino]phenyl}amino)methyl]phenoxy}phenoxy)acetyl]-N-methylglycine;

N-[(4-{4-[(benzyl{2-methyl-3-[(methylsulfonyl)amino]phenyl}amino)methyl]phenoxy}phenoxy)acetyl]-L-valine;

N-[(4-{4-[(benzyl{2-methyl-3-[(methylsulfonyl)amino]phenyl}amino)methyl]phenoxy}phenoxy)acetyl]-L-serine;

N~2~-[(4-{4-[(benzyl{2-methyl-3-[(methylsulfonyl)amino]phenyl}amino)methyl]phenoxy}phenoxy)acetyl]-L-asparagine;

N-[3-(benzyl{4-[4-(2-hydrazino-2-oxoethoxy)phenoxy]benzyl}amino)-2-methylphenyl]methanesulfonamide;

N-(3-{benzyl[4-(3-{[(2R)-2,3-dihydroxypropyl]oxy}phenoxy)benzyl]amino}-2-methylphenyl)methanesulfonamide;

N-[4-(3-{4-[(benzyl{2-methyl-3-[(methylsulfonyl)amino]phenyl}amino)methyl]phenoxy}phenoxy)butanoyl]-L-glutamic acid;

N-[4-(3-{4-[(benzyl{2-methyl-3-[(methylsulfonyl)amino]phenyl}amino)methyl]phenoxy}phenoxy)butanoyl]-L-leucine;

N-[4-(3-{4-[(benzyl{2-methyl-3-[(methylsulfonyl)amino]phenyl}amino)methyl]phenoxy}phenoxy)butanoyl]-L-aspartic acid;

N-[4-(3-{4-[(benzyl{2-methyl-3-[(methylsulfonyl)amino]phenyl}amino)methyl]phenoxy}phenoxy)butanoyl]-L-valine;

N-[4-(3-{4-[(benzyl{2-methyl-3-[(methylsulfonyl)amino]phenyl}amino)methyl]phenoxy}phenoxy)butanoyl]-L-serine;

N~2~-[4-(3-{4-[(benzyl{2-methyl-3-[(methylsulfonyl)amino]phenyl}amino)methyl]phenoxy}phenoxy)butanoyl]-L-glutamine;

(5-(4-(((2,4-difluorobenzyl)(2-methyl-3-((methylsulfonyl)amino)phenyl)amino)methyl)phenoxy)-2-fluorophenoxy)acetic acid;

(2-chloro-5-(4-(((2-fluorobenzyl)(2-methyl-3-((methylsulfonyl)amino)phenyl)amino)methyl)phenoxy)phenoxy)acetic acid;

(5-(4-(((2-bromobenzyl)(2-methyl-3-((methylsulfonyl)amino)phenyl)amino)methyl)phenoxy)-2-chlorophenoxy)acetic acid;

(5-(4-(((4-bromobenzyl)(2-methyl-3-((methylsulfonyl)amino)phenyl)amino)methyl)phenoxy)-2-chlorophenoxy)acetic acid;

(2-chloro-5-(4-(((2,4-dichlorobenzyl)(2-methyl-3-((methylsulfonyl)amino)phenyl)amino)methyl)phenoxy)phenoxy)acetic acid;

(2-chloro-5-(4-(((4-chloro-2-fluorobenzyl)(2-methyl-3-((methylsulfonyl)amino)phenyl)amino)methyl)phenoxy)phenoxy)acetic acid;

(2-chloro-5-(4-(((2-chloro-4-fluorobenzyl)(2-methyl-3-((methylsulfonyl)amino)phenyl)amino)methyl)phenoxy)phenoxy)acetic acid;

(5-(4-(((2-bromo-4-chlorobenzyl)(2-methyl-3-((methylsulfonyl)amino)phenyl)amino)methyl)phenoxy)-2-chlorophenoxy)acetic acid;

(2-chloro-5-(4-(((3,4-difluorobenzyl)(2-methyl-3-((methylsulfonyl)amino)phenyl)amino)methyl)phenoxy)phenoxy)acetic acid;

(5-(4-(((4-bromo-2-fluorobenzyl)(2-methyl-3-((methylsulfonyl)amino)phenyl)amino)methyl)phenoxy)-2-chlorophenoxy)acetic acid;

N-((2-chloro-5-(4-(((2,4-difluorobenzyl)(2-methyl-3-((methylsulfonyl)amino)phenyl)amino)methyl)phenoxy)phenoxy)acetyl)glycine;

N-((2-chloro-5-(4-(((2,4-difluorobenzyl)(2-methyl-3-((methylsulfonyl)amino)phenyl)amino)methyl)phenoxy)phenoxy)acetyl)-beta-alanine;

4-(((2-chloro-5-(4-(((2,4-difluorobenzyl)(2-methyl-3-((methylsulfonyl)amino)phenyl)amino)methyl)phenoxy)phenoxy)acetyl)amino)butanoic acid;

4-((4-(5-(4-((benzyl(2-methyl-3-((methylsulfonyl)amino)phenyl)amino)methyl)phenoxy)-2-chlorophenoxy)butanoyl)amino)butanoic acid;

4-((4-(2-chloro-5-(4-(((2,4-difluorobenzyl)(2-methyl-3-((methylsulfonyl)amino)phenyl)amino)methyl)phenoxy)phenoxy)butanoyl)amino)butanoic acid;

(2R)-2-(2-chloro-5-(4-(((2,4-difluorobenzyl)(2-methyl-3-((methylsulfonyl)amino)phenyl)amino)methyl)phenoxy)phenoxy)propanoic acid;

N-(3-((4-(4-chloro-3-hydroxyphenoxy)benzyl)(2,4-difluorobenzyl)amino)-2-methylphenyl)methanesulfonamide;

(2-bromo-5-(4-(((2,4-difluorobenzyl)(2-methyl-3-((methylsulfonyl)amino)phenyl)amino)methyl)phenoxy)phenoxy)acetic acid;

N-(4-(3-(4-(((2,4-difluorobenzyl)(2-methyl-3-((methylsulfonyl)amino)phenyl)amino)methyl)phenoxy)phenoxy)butanoyl)-beta-alanine;

4-((4-(3-(4-(((2,4-difluorobenzyl)(2-methyl-3-((methylsulfonyl)amino)phenyl)amino)methyl)phenoxy)phenoxy)butanoyl)amino)butanoic acid;

N-(4-(3-(4-(((2,4-difluorobenzyl)(2-methyl-3-((methylsulfonyl)amino)phenyl)amino)methyl)phenoxy)phenoxy)butanoyl)-N-methylglycine;

N-(3-{(2,4-difluorobenzyl)[4-(2-phenylethoxy)benzyl]amino}-2-methylphenyl)methanesulfonamide;

N-(3-{(2,4-difluorobenzyl)[4-(3-furylmethoxy)benzyl]amino}-2-methylphenyl)methanesulfonamide;

N-(3-{(2,4-difluorobenzyl)[4-(2-furylmethoxy)benzyl]amino}-2-methylphenyl)methanesulfonamide;

N-{3-[[4-(1,3-benzodioxol-5-ylmethoxy)benzyl](2,4-difluorobenzyl)amino]-2-methylphenyl}methanesulfonamide;

N-{3-[{4-[(6-chloro-1,3-benzodioxol-5-yl)methoxy]benzyl}(2,4-difluorobenzyl)amino]-2-methylphenyl}methanesulfonamide;

(3-{4-[(benzyl{2-methyl-3-[(methylsulfonyl)amino]phenyl}amino)methyl]benzoyl}phenoxy)acetic acid;

N-{3-[(4-benzoylbenzyl)(benzyl)amino]-2-methylphenyl}methanesulfonamide;

N-[3-(benzyl{4-[3-(2-cyclopropylethoxy)benzoyl]benzyl}amino)-2-methylphenyl]methanesulfonamide;

N-[3-(benzyl{4-[3-(cyclopentylmethoxy)benzoyl]benzyl}amino)-2-methylphenyl]methanesulfonamide;

N-(3-{benzyl[4-(4-{[(2R)-2,3-dihydroxypropyl]oxy}benzoyl)benzyl]amino}-2-methylphenyl)methanesulfonamide; and N-(3-{benzyl[4-(phenylthio)benzyl]amino}-2-methylphenyl)methanesulfonamide.

The following additional compounds, representative of formula (III), may be prepared by one skilled in the art using known synthetic methodology or by using synthetic methodology described in the Schemes and Examples contained herein.

N-[3-(benzyl{4-[3-(2-methoxyethoxy)phenoxy]benzyl}amino)-2-methylphenyl]methanesulfonamide;
N-[3-(benzyl{4-[4-(methoxycarbonyl)phenoxy]benzyl}amino)-2-methylphenyl]methanesulfonamide;
N-[3-(benzyl{4-[4-(3-hydroxypropyl)phenoxy]benzyl}amino)-2-methylphenyl]methanesulfonamide;
N-(3-{(2,4-difluorobenzyl)[4-(3,4-dimethoxyphenoxy)benzyl]amino}-2-methylphenyl)methanesulfonamide;
N-{3-[benzyl(4-{3-[2-(2-methoxyethoxy)ethoxy]phenoxy}benzyl)amino]-2-methylphenyl}methanesulfonamide;
N-{3-[(4-methoxybenzyl)(4-phenoxybenzyl)amino]-2-methylphenyl}methanesulfonamide;
N-(3-{benzyl[4-(4-(3-carboxypropyl)phenoxy)benzyl]amino}-2-methylphenyl)methanesulfonamide;
N-{3-[(2-fluorobenzyl)(4-phenoxybenzyl)amino]-2-methylphenyl}methanesulfonamide;
N-(3-{benzyl[4-(4-(4-ethoxy-4-oxobutyl)phenoxy)benzyl]amino}-2-methylphenyl)methanesulfonamide;
N-(3-{(2,4-difluorobenzyl)[4-(3-methoxyphenoxy)benzyl]amino}-2-methylphenyl)methanesulfonamide;
N-{3-[(4-benzoylbenzyl)(benzyl)amino]-2-methylphenyl}methanesulfonamide;
N-[3-{(2,4-difluorobenzyl){4-[4-(methoxycarbonyl)phenoxy]benzyl}amino}-2-methylphenyl]methanesulfonamide;
N-[3-(benzyl{4-[4-carboxyphenoxy]benzyl}amino)-2-methylphenyl]methanesulfonamide;
N-[3-(benzyl{4-[3-(3-hydroxypropyl)phenoxy]benzyl}amino)-2-methylphenyl]methanesulfonamide;
N-{3-[[4-(3-acetylphenoxy)benzyl](2,4-difluorobenzyl)amino]-2-methylphenyl}methanesulfonamide;
N-[3-(benzyl{4-[4-(methoxymethoxy)phenoxy]benzyl}amino)-2-methylphenyl]methanesulfonamide;
N-(3-{benzyl[4-(phenylsulfanyl)benzyl]amino}-2-methylphenyl)methanesulfonamide;
N-[3-(benzyl{4-[4-(4-hydroxybutyl)phenoxy]benzyl}amino)-2-methylphenyl]methanesulfonamide;
N-{3-[(2,4-difluorobenzyl)(4-phenoxybenzyl)amino]-2-methylphenyl}methanesulfonamide;
N-{3-[(2,4-difluorobenzyl)(2-fluoro-4-phenoxybenzyl)amino]-2-methylphenyl}methanesulfonamide;
N-[3-{(2,4-difluorobenzyl){4-[3-(methoxycarbonyl)phenoxy]benzyl}amino}-2-methylphenyl]methanesulfonamide;
ethyl 3-({4-[4-({(2,4-difluorobenzyl)-2-methyl-3-[(methylsulfonyl)amino]anilino}methyl)phenoxy]benzoyl}amino)propanoate;
N-(3-{(2,4-difluorobenzyl)[4-(4-methoxyphenoxy)benzyl]amino}-2-methylphenyl)methanesulfonamide;
N-{3-[[4-(4-acetylphenoxy)benzyl](2,4-difluorobenzyl)amino]-2-methylphenyl}methanesulfonamide;
N-(3-{(2,4-difluorobenzyl)[4-(3-ethoxyphenoxy)benzyl]amino}-2-methylphenyl)methanesulfonamide;
N-(3-{(2,4-difluorobenzyl)[4-(3,5-dimethylphenoxy)benzyl]amino}-2-methylphenyl)methanesulfonamide;
N-(3-{benzyl[4-(4-(2-carboxyethyl)phenoxy)benzyl]amino}-2-methylphenyl)methanesulfonamide;
4-[4-({(2,4-difluorobenzyl)-2-methyl-3-[(methylsulfonyl)amino]anilino}methyl)phenoxy]-N-(2-hydroxyethyl)benzamide;
4-[4-({(2,4-difluorobenzyl)-2-methyl-3-[(methylsulfonyl)amino]anilino}methyl)phenoxy]-N-(3-hydroxypropyl)benzamide;
N-{3-[(2,4-difluorobenzyl)(4-{[3-phenyl-2-propenyl]oxy}benzyl)amino]-2-methylphenyl}methanesulfonamide;
N-{3-[[4-(2-cyclopropylethoxy)benzyl](2,4-difluorobenzyl)amino]-2-methylphenyl}methanesulfonamide;
N-(3-{benzyl[4-(3-(2-carboxyethyl)phenoxy)benzyl]amino}-2-methylphenyl)methanesulfonamide;
N-[3-((2,4-difluorobenzyl){4-[4-(hydroxymethyl)phenoxy]benzyl}amino)-2-methylphenyl]methanesulfonamide;
N-{3-[{4-[4-(3-aminopropoxy)phenoxy]benzyl}(benzyl)amino]-2-methylphenyl}methanesulfonamide;
2-(5-(4-(((2,4-difluorobenzyl)(2-methyl-3-((methylsulfonyl)amino)phenyl)amino)methyl)phenoxy)-2-fluorophenoxy)-N-(methylsulfonyl)acetamide;
N-(3-((2,4-difluorobenzyl)(4-(4-fluoro-3-(2H-tetraazol-5-ylmethoxy)phenoxy)benzyl)amino)-2-methylphenyl)methanesulfonamide.

In another embodiment, compounds of the present invention have formula (IV)

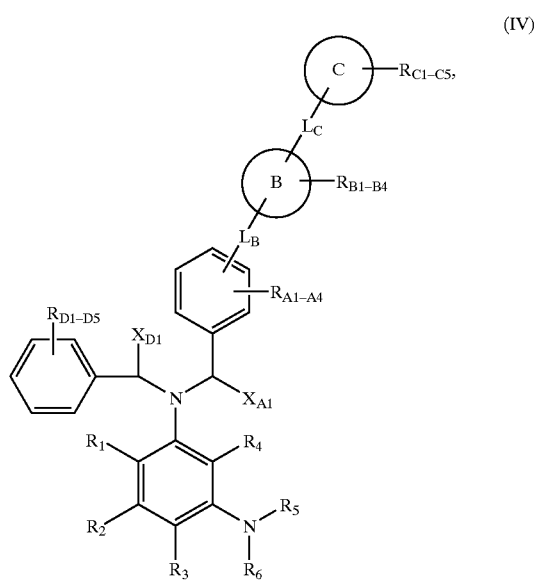

(IV)

or a pharmaceutically acceptable salt or prodrug thereof, wherein $X_{A1}$, $X_{D1}$, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_1$, $R_2$, $R_3$, $R_4$, $R_5$, $R_6$, $L_B$, $L_C$, B and C are as defined in formula (I).

In another embodiment, compounds of the present invention have formula (IV) wherein B is aryl wherein said aryl is phenyl; C is aryl wherein said aryl is phenyl; $L_B$ is —$(CH_2)_mO(CH_2)_n$—; $L_C$ is —$(CH_2)_pO(CH_2)_q$—; $R_1$, $R_2$, $R_3$, $R_5$, $X_{A1}$ and $X_{D1}$ are each hydrogen $R_4$ is alkyl; and $R_6$ is alkylsulfonyl; and m, n, p, q, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$ and $R_{D5}$ are as defined in formula (I).

In another embodiment, compounds of the present invention have formula (IV) wherein B is aryl wherein said aryl is phenyl; C is heterocycle; $L_B$ is —$(CH_2)_mO(CH_2)_n$—; $L_C$ is —$(CH_2)_pO(CH_2)_q$—; $R_1$, $R_2$, $R_3$, $R_5$, $X_{A1}$ and $X_{D1}$ are each hydrogen; $R_4$ is alkyl; $R_6$ is alkylsulfony; and m, n, p, q, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$ and $R_{D5}$ are as defined in formula (I).

In another embodiment, compounds of the present invention have formula (IV) wherein B is aryl wherein said aryl is phenyl; C is cycloalkyl; $L_B$ is —$(CH_2)_mO(CH_2)_n$—; $L_C$ is —$(CH_2)_pO(CH_2)_q$—; $R_1$, $R_2$, $R_3$, $R_5$, $X_{A1}$ and $X_{D1}$ are each hydrogen; $R_4$ is alkyl; $R_6$ is alkylsulfonyl, and m, n, p, q, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$ and $R_{D5}$ are as defined in formula (I).

In another embodiment, compounds of the present invention have formula (IV) wherein B is aryl wherein said aryl is phenyl; C is aryl wherein said aryl is phenyl; $L_B$ is —$(CH_2)_mO(CH_2)_n$—; $L_C$ is —$(CH_2)_pC(O)O(CH_2)_q$—; $R_1$, $R_2$, $R_3$, $R_5$, $X_{A1}$ and $X_{D1}$ are each hydrogen; $R_4$ is alkyl; $R_6$ is alkylsulfonyl; and m, n, p, q, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$ and $R_{D5}$ are as defined in formula (I).

In another embodiment, compounds of the present invention have formula (IV) wherein B is aryl wherein said aryl is phenyl; C is heterocycle; $L_B$ is —$(CH_2)_mO(CH_2)_n$—; $L_C$ is —$(CH_2)_pC(O)O(CH_2)_q$—; $R_1$, $R_2$, $R_3$, $R_5$, $X_{A1}$ and $X_{D1}$ are each hydrogen, $R_4$ alkyl; $R_6$ is alkylsulfonyl, and m, n, p, q, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$ and $R_{D5}$ are as defined in formula (I).

In another embodiment, compounds of the present invention have formula (IV) wherein B is aryl wherein said aryl is phenyl; C is heterocycle; $L_B$ is —$(CH_2)_mO(CH_2)_n$—; $L_C$ is —$O(CH_2)_pC(O)(CH_2)_q$—; $R_1$, $R_2$, $R_3$, $R_5$, $X_{A1}$ and $X_{D1}$ are each hydrogen; $R_4$ is alkyl; $R_6$ is alkylsulfonyl, and m, n, p, q, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$ and $R_{D5}$ are as defined in formula (I).

In another embodiment, compounds of the present invention have formula (IV) wherein B is aryl wherein said aryl is phenyl; C is aryl wherein said aryl is phenyl; $L_B$ is —$(CH_2)_mO(CH_2)_n$—; $L_C$ is —$(CH_2)_pC(O)N(R_7)(CH_2)_q$—; $R_1$, $R_2$, $R_3$, $R_5$, $X_{A1}$ and $X_{D1}$ are each hydrogen; $R_4$ is alkyl; $R_6$ is alkylsulfonyl; and m, n, p, q, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$ and $R_{D5}$ are as defined in formula (I).

In another embodiment, compounds of the present invention have formula (IV) wherein B is aryl wherein said aryl is phenyl; C is heterocycle; $L_B$ is —$(CH_2)_mO(CH_2)_n$—; $L_C$ is —$(CH_2)_pC(O)N(R_7)(CH_2)_q$—; $R_1$, $R_2$, $R_3$, $R_5$, $X_{A1}$ and $X_{D1}$ are each hydrogen; $R_4$ is alkyl; $R_6$ is alkylsulfonyl, and m, n, p, q, $R_{A1}$, $R_{A2}$, $R_{A3}$, $R_{A4}$, $R_{A5}$, $R_{B1}$, $R_{B2}$, $R_{B3}$, $R_{B4}$, $R_{B5}R_{C1}$, $R_{C2}$, $R_{C3}$, $R_{C4}$, $R_{C5}$, $R_{D1}$, $R_{D2}$, $R_{D3}$, $R_{D4}$ and $R_{D5}$ are as defined in formula (I).

In another embodiment, compounds of the present invention have formula (IV) wherein B is aryl wherein said aryl is phenyl; C is heterocycle; $L_B$ is —$(CH_2)_mO(CH_2)_n$—; $L_C$ is —$O(CH_2)_pC(O)N(R_7)(CH_2)_q$—; $R_1$, $R_2$, $R_3$, $R_5$, $X_{A1}$ and $X_{D1}$ are each hydrogen; $R_4$ is alkyl; $R_6$ is alkylsulfonyl, and m, n, p, q, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$ and $R_{D5}$ are as defined in formula (I).

In another embodiment, compounds of the present invention have formula (IV) wherein B is aryl wherein said aryl is phenyl; C is aryl wherein said aryl is phenyl; $L_B$ is —$(CH_2)_mC(O)(CH_2)$—; $L_C$ is —$(CH_2)_pO(CH_2)_q$—; $R_1$, $R_2$, $R_3$, $R_5$, $X_{A1}$ and $X_{D1}$ are each hydrogen; $R_4$ is alkyl; $R_6$ is alkylsulfonyl, and m, n, p, q, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$ and $R_{D5}$ are as defined in formula (I).

In another embodiment, compounds of the present invention have formula (IV) wherein B is aryl wherein said aryl is phenyl; C is heterocycle; $L_B$ is —$(CH_2)_mC(O)(CH_2)_n$—; $L_C$ is —$(CH_2)_pO(CH_2)_q$—; $R_1$, $R_2$, $R_3$, $R_5$, $X_{A1}$ and $X_{D1}$ are each hydrogen; $R_4$ is alkyl; $R_6$ is alkylsulfonyl, and m, n, p, q, $R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$ and $R_{D5}$ are as defined in formula (I).

The following compounds, representative of formula (IV), may be prepared by one skilled in the art using known synthetic methodology or by using synthetic methodology described in the Schemes and Examples contained herein.

N-[3-(benzyl{4-[3-(2-phenylethoxy)phenoxy]benzyl}amino)-2-methylphenyl]methanesulfonamide;

N-{3-[{4-[3-(1,3-benzodioxol-5-ylmethoxy)phenoxy]benzyl}(benzyl)amino]-2-methylphenyl}methanesulfonamide; and N-[3-(benzyl{4-[3-(benzyloxy)phenoxy]benzyl}amino)-2-methylphenyl]methanesulfonamide N-[3-(benzyl{4-[3-(3-morpholin-4-ylpropoxy)phenoxy]benzyl}amino)-2-methylphenyl]methanesulfonamide;

1-[2-(3-{4-[(benzyl{2-methyl-3-[(methylsulfonyl)amino]phenyl}amino)methyl]phenoxy}phenoxy)ethyl]piperidine-2-carboxylic acid;

N-{3-[benzyl(4-{3-[(1-methylpyrrolidin-3-yl)methoxy]phenoxy}benzyl)amino]-2-methylphenyl}methanesulfonamide;

N-{3-[(4-{3-[(1-acetylpyrrolidin-3-yl)methoxy]phenoxy}benzyl)(benzyl)amino]-2-methylphenyl}methanesulfonamide;

N-{3-[benzyl(4-{3-[(2-oxotetrahydrofuran-3-yl)oxy]phenoxy}benzyl)amino]-2-methylphenyl}methanesulfonamide;

N-[3-(benzyl{4-[3-(tetrahydrofuran-2-ylmethoxy)phenoxy]benzyl}amino)-2-methylphenyl]methanesulfonamide;

N-[3-(benzyl{4-[3-(tetrahydrofuran-3-ylmethoxy)phenoxy]benzyl}amino)-2-methylphenyl]methanesulfonamide;

N-[3-(benzyl{4-[3-(3-furylmethoxy)phenoxy]benzyl}amino)-2-methylphenyl]methanesulfonamide;

N-[3-(benzyl{4-[3-(2-furylmethoxy)phenoxy]benzyl}amino)-2-methylphenyl]methanesulfonamide;

N-[3-(benzyl{4-[3-(thien-3-ylmethoxy)phenoxy]benzyl}amino)-2-methylphenyl]methanesulfonamide;

N-[3-(benzyl{4-[3-(2-thien-3-ylethoxy)phenoxy]benzyl}amino)-2-methylphenyl]methanesulfonamide;

N-[3-(benzyl{4-[3-(thien-2-ylmethoxy)phenoxy]benzyl}amino)-2-methylphenyl]methanesulfonamide;

N-[3-(benzyl{4-[3-(2-thien-2-ylethoxy)phenoxy]benzyl}amino)-2-methylphenyl]methanesulfonamide;

N-{3-[benzyl(4-{3-[2-(4-methyl-1,3-thiazol-5-yl)ethoxy]phenoxy}benzyl)amino]-2-methylphenyl}methanesulfonamide;

N-{3-[benzyl(4-{3-[2-(2-oxopyrrolidin-1-yl)ethoxy]phenoxy}benzyl)amino]-2-methylphenyl}methanesulfonamide;

N-[3-(benzyl{4-[3-(2-morpholin-4-ylethoxy)phenoxy]benzyl}amino)-2-methylphenyl]methanesulfonamide;

N-(3-((2,4-difluorobenzyl)(4-(3-(((2S ,4R)-6-oxo-4-hydroxytetrahydro-2H-pyran-2-yl)methoxy)phenoxy)benzyl)amino)-2-methylphenyl)methanesulfonamide;

N-(3-(benzyl(4-(4-(((2S, 4R)-6-oxo-4hydroxytetrahydro-2H-pyran-2-yl)methoxy)phenoxy)benzyl)amino)-2-methylphenyl)methanesulfonamide;

N-(3-{benzyl[4-(3-{[(2S)-5-oxopyrrolidin-2-yl]methoxy}phenoxy)benzyl]amino}-2-methylphenyl)methanesulfonamide;

N-{3-[benzyl(4-{3-[(3-methyloxetan-3-yl)methoxy]phenoxy}benzyl)amino]-2-methylphenyl}methanesulfonamide;

N-[3-(benzyl{4-[3-(tetrahydro-2H-pyran-4-yloxy)phenoxy]benzyl}amino)-2-methylphenyl]methanesulfonamiide;

N-[3-(benzyl{4-[3-(tetrahydrofuran-3-yloxy)phenoxy]benzyl}amino)-2-methylphenyl]methanesulfonamide;

N-(3-{benzyl[4-(3-{[(2S)-1-methylpyrrolidin-2-yl]methoxy}phenoxy)benzyl]amino}-2-methylphenyl)methanesulfonamide;

N-[3-(benzyl{4-[3-(pyridin-3-ylmethoxy)phenoxy]benzyl}amino)-2-methylphenyl]methanesulfonamide;

N-{3-[benzyl(4-{3-[(2S)-pyrrolidin-2-ylmethoxy]phenoxy}benzyl)amino]-2-methylphenyl}methanesulfonamide;

N-{3-[benzyl(4-{3-[(1-methylpyrrolidin-3-yl)oxy]
phenoxy}benzyl)amino]-2-
methylphenyl}methanesulfonamide 2-[(3-{4-[(benzyl{2-
methyl-3-[(methylsulfonyl)amino]phenyl}amino)methyl]
phenoxy}phenoxy)methyl]cyclopropanecarboxylic acid;
4-(3-{4-[(benzyl{2-methyl-3-[(methylsulfonyl)amino]
phenyl}amino)methyl]phenoxy}phenoxy)
cyclohexanecarboxylic acid benzyl 3-(4-{4-[(benzyl{2-
methyl-3-[(methylsulfonyl)amino]phenyl}amino)methyl]
phenoxy}phenyl)propanoate 1-[4-(4-{4-[(benzyl{2-
methyl-3-[(methylsulfonyl)amino]phenyl}amino)methyl]
phenoxy}phenyl)butanoyl]-L-proline 1-[5-(4-{4-
[(benzyl{2-methyl-3-[(methylsulfonyl)amino]
phenyl}amino)methyl]phenoxy}phenoxy)pentanoyl]-L-
proline;
1-[4-(3-{4-[(benzyl{2-methyl-3-[(methylsulfonyl)amino]
phenyl}amino)methyl]phenoxy}phenoxy)butanoyl]
piperidine-3-carboxylic acid;
1-[4-(3-{4-[(benzyl{2-methyl-3-[(methylsulfonyl)amino]
phenyl}amino)methyl]phenoxy}phenoxy)butanoyl]
piperidine-4-carboxylic acid;
1-[4-(3-{4-[(benzyl{2-methyl-3-[(methylsulfonyl)amino]
phenyl}amino)methyl]phenoxy}phenoxy)butanoyl]
piperidine-2-carboxylic acid;
1-[4-(3-{4-[(benzyl{2-methyl-3-[(methylsulfonyl)amino]
phenyl}amino)methyl]phenoxy}phenoxy)butanoyl]
proline;
1-[(2-chloro-5-{4-[((2,4-difluorobenzyl){2-methyl-3-
[(methylsulfonyl)amino]phenyl}amino)methyl]
phenoxy}phenoxy)acetyl]piperidine-4-carboxamide;
4-(4-{4-[((2,4-difluorobenzyl){2-methyl-3-
[(methylsulfonyl)amino]phenyl}amino)methyl]
phenoxy}phenyl)-N-[3-(2-oxopyrrolidin-1-yl)propyl]
butanamide;
3-(4-{4-[(benzyl{2-methyl-3-[(methylsulfonyl)amino]
phenyl}amino)methyl]phenoxy}phenyl)-N-(2-
morpholin-4-ylethyl)propanamide;
3-(4-{4-[(benzyl{2-methyl-3-[(methylsulfonyl)amino]
phenyl}amino)methyl]phenoxy}phenyl)-N-[3-(2-
oxopyrrolidin-1-yl)propyl]propanamide;
4-{[4-(4-{4-[(benzyl{2-methyl-3-[(methylsulfonyl)amino]
phenyl}amino)methyl]phenoxy}phenyl)butanoyl]
amino}-1-methyl-1H-pyrrole-2-carboxylic acid;
4-(4-{4-[(benzyl{2-methyl-3-[(methylsulfonyl)amino]
phenyl}amino)methyl]phenoxy}phenyl)-N-(2-
oxotetrahydrofuran-3-yl)butanamide 2-(3-{4-[(benzyl{2-
methyl-3-[(methylsulfonyl)amino]phenyl}amino)methyl]
phenoxy}phenoxy)-N-[3-(2-oxopyrrolidin-1-yl)propyl]
acetamide;
4-{[4-(4-{4-[(benzyl{2-methyl-3-[(methylsulfonyl)amino]
phenyl}amino)methyl]phenoxy}phenoxy)butanoyl]
amino}-1-methyl-1H-pyrrole-2-carboxylic acid;
5-(4-{4-[(benzyl{2-methyl-3-[(methylsulfonyl)amino]
phenyl}amino)methyl]phenoxy}phenoxy)-N-(2-
oxotetrahydrofuran-3-yl)pentanamide;
2-(4-{4-[(benzyl{2-methyl-3-[(methylsulfonyl)amino]
phenyl}amino)methyl]phenoxy}phenoxy)-N-(2-
oxotetrahydrofuran-3-yl)acetamide;
4-(3-{4-[(benzyl{2-methyl-3-[(methylsulfonyl)amino]
phenyl}amino)methyl]phenoxy}phenoxy)-N-(2-
oxotetrahydrofuran-3-yl)butanamide;
2-(2-chloro-5-{4-[((2,4-difluorobenzyl){2-methyl-3-
[(methylsulfonyl)amino]phenyl}amino)methyl]
phenoxy}phenoxy)-N-[3-(2-oxopyrrolidin-1-yl)propyl]
acetamide;
2-(2-chloro-5-{4-[((2,4-difluorobenzyl){2-methyl-3-
[(methylsulfonyl)amino]phenyl}amino)methyl]
phenoxy}phenoxy)-N-(1,3-thiazol-5-ylmethyl)
acetamide;

2-(2-chloro-5-{4-[((2,4-difluorobenzyl){2-methyl-3-
[(methylsulfonyl)amino]phenyl}amino)methyl]
phenoxy}phenoxy)-N-(3-morpholin-4-ylpropyl)
acetamide;
N-[3-(benzyl{4-[3-(2-phenylethoxy)benzoyl]
benzyl}amino)-2-methylphenyl]methanesulfonamide;
and
N-[3-(benzyl{4-[3-(benzyloxy)benzoyl]benzyl}amino)-2-
methylphenyl]methanesulfonamide N-[3-(benzyl{4-[3-
(tetrahydrofuran-2-ylmethoxy)benzoyl]benzyl}amino)-2-
methylphenyl]methanesulfonamide;
N-[3-(benzyl{4-[3-(tetrahydrofuran-3-ylmethoxy)benzoyl]
benzyl}amino)-2-methylphenyl]methanesulfonamide;
N-{3-[benzyl(4-{3-[2-(2-oxopyrrolidin-1-yl)ethoxy]
benzoyl}benzyl)amino]-2-
methylphenyl}methanesulfonamide; and
N-{3-[benzyl(4-{3-[2-(4-methyl-1,3-thiazol-5-yl)ethoxy]
benzoyl}benzyl)amino]-2-
methylphenyl}methanesulfonamide.
N-{3-[benzyl(4-(4-(3-benzyloxy-3-oxopropyl)phenoxy)
benzyl)amino]-2-methylphenyl}methanesulfonamide;
and
N-benzyl-4-[4-({(2,4-difluorobenzyl)-2-methyl-3-
[(methylsulfonyl)amino]anilino}methyl)phenoxy]
benzamide.

In another embodiment, compounds of the present invention have formula (V)

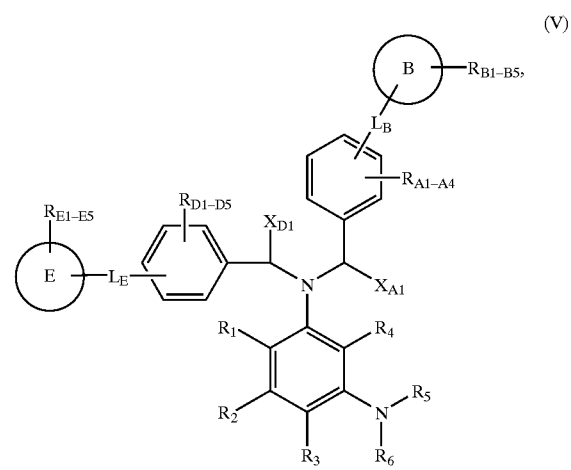

or a pharmaceutically acceptable salt or prodrug thereof,
wherein $X_{A1}$, $X_{D1}$, $R_{A1}$, $R_{A2}$, $R_{A3}$, $R_{A4}$, $R_{A5}$, $R_{B1}$, $R_{B2}$, $R_{B3}$,
$R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$,
$R_{D5}$, $R_1$, $R_2$, $R_3$, $R_4$, $R_5$, $R_6$, $L_B$, $L_C$, B and C are as defined
in formula (I).

In another embodiment, compounds of the present invention have formula (V) wherein B is aryl wherein said aryl is
phenyl; E is aryl wherein said aryl is phenyl; $L_B$ is —$(CH_2)_m$
$O(CH_2)_n$—; $L_E$ is —$(CH_2)_r C(O)(CH_2)_s$—; $R_1$, $R_2$, $R_3$, $R_5$,
$X_{A1}$ and $X_{D1}$ are each hydrogen; $R_4$ is alkyl; $R_6$ is alkylsulfonyl; and m, n, p, q, $R_{A1}$, $R_{A2}$, $R_{A3}$, $R_{A4}$, $R_{A5}$, $R_{B1}$, $R_{B2}$, $R_{B3}$,
$R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$ and
$R_{D5}$ are as defined in formula (I).

The following compounds, representative of formula (V),
may be prepared by one skilled in the art using known
synthetic methodology or by using synthetic methodology
described in the Schemes and Examples contained herein.
(3-{4-[((4-benzoylbenzyl){2-methyl-3-[(methylsulfonyl)
amino]phenyl}amino)methyl]phenoxy}phenoxy)acetic
acid; and
(5-(4-(((4-benzoylbenzyl)(2-methyl-3-((methylsulfonyl)
amino)phenyl)amino)methyl)phenoxy)-2-
chlorophenoxy)acetic acid.

Another embodiment of the present invention relates to pharmaceutical compositions comprising a therapeutically effective amount of a compound of formula (I–IV) in combination with a pharmaceutically acceptable carrier.

Another embodiment of the present invention relates to a method of selectively modulating the antagonism effects of the glucocorticoid receptor in a mammal comprising administering an effective amount of a compound of formula (I–IV).

Another embodiment of the present invention relates to a method of treating type II diabetes in a mammal comprising administering a therapeutically effective amount of a compound of formula (I–IV).

Another embodiment of the present invention relates to a method of treating type II diabetes in a mammal comprising administering a therapeutically effective amount of a glucocorticoid receptor antagonist.

Another embodiment of the present invention relates to a method of treating symptoms of type II diabetes including, but not limited to, hyperglycemia, hyperinsulinemia, inadequate, glucose clearance, obesity, hypertension and high glucocorticoid levels in a mammal comprising administering a therapeutically effective amount of a compound of formula (I–IV).

Methods for Radiolipand Binding Studies with Human Glucocorticoid and Progesterone Receptor Cytosol $^3$[H]-dexamethasone (TRK 645) hereafter referred to as $^3$[M]-dex was purchased from Pharmacia Amersham, Uppsala, Sweden. Dexamethasone hereafter referred to as dex was purchased from SIGMA. The Costar 96-well polypropylene plates (3794 or 3365) were purchased from Life Technologies AB, Täby, Sweden. The GF/B filter (1450-521), filter cassette (1450-104), MeltiLex scintillating wax (1450-441), sample bag (1450–42), Microbeta™ 1450-PLUS and Microsealer 1495-021 were all purchased from Wallac Oy, Turkku, Finland. Human glucocorticoid receptors were extracted from Sf9 cells infected with a recombinant baculovirus transfer vector containing the cloned hGR genes. Recombinant baculovirus was generated utilizing the BAC-TO-BAC expression system (Life Technologies) in accordance to instruction from the supplier. The hGR coding sequences were cloned into a baculovirus transfer vector by standard techniques. The recombinant baculoviruses expressing hGR were amplified and used to infect Sf9 cells. Infected cells were harvested 48 hrs post infection. The receptors were extracted from the cell pellet with a phosphate buffer (1 mM EDTA, 20 mM KPO$_4$ (pH8), 8.6% Glycerol, 12 mM MTG, 20 mM Na$_2$MoO$_4$). The concentration of hGR in the extract was measured as specific $^3$[H]-dex binding with the G25-assay as described in J. Steroid Biochem. Molec. Biol. 50, No. 5/6, 313–318, 1994 and estimated to approximately 25 nM. The extract was aliquoted and stored at −70° C.

The filter binding assay: Dilution series of the test compounds and dex as reference were made from 10 mM (1 mM dex) stock solutions in DMSO. 10 µl of the dilutions was added in duplicates to the wells. The cell extracts were diluted 10 fold in EPMo+MTG buffer (1 mM EDTA, HPO$_4$ 20 mM (pH8), 6 mM MTG). The diluted extract was added to the wells (110 µl). $^3$[H]-dex were diluted from the stock solution to 10–10.8 nM in EPMo+MTG buffer. 110 µl of the diluted $^3$[H]-dex were added to the wells. The final concentration of hGR in the experiment was estimated to 1 nM. All preparations were made in ambient temperature (20–25° C.) on ice and with +4° C. temperated buffers. The plates were incubated over night at +4° C. (15–20 hours).

The incubation was stopped by filtration through GF/B filter on the Tomtec Cellharvester. The filtration on the Tomtec Cellharvester was programmed as follows: 1) Preparation before filtration with EP buffer (1 mM EDTA 20 mM HPO$_4$ (pH8)) 2×[Wash/Asp 0.6 sec., Asp 0.5 sec.]; 2) Prewet of GF/B filter with EP+PEI buffer (EP buffer, 0.3% Polyethylenimine) [Asp 0.8 sec.]; 3) Filtration/harvesting of the 96-well incubation plate 3×[Wash/Asp 0.6 sec., Asp 0.5 sec.]. The GF/B filter was dried for at least 1 hour at 65° C. A MeltiLex scintillation wax was melted onto the filter with the Microsealer. The filter was placed in a samplebag, which was thereafter trimmed with scissors to fit the filter cassette. The cassette were placed in the Microbeta and measured for 1 min/position, returning ccpm (corrected counts per minute).

For compounds able to displace the $^3$[H]-dex from the receptor an IC$_{50}$-value (the concentration required to inhibit 50% of the binding of $^3$[H]-dex) was determined by a non-linear four parameter logistic model;

$$b=((b_{max}-b_{min})/(1+(I/IC_{50})^S))+b_{min}I$$

where b is the amount of bound ligand as measured by tritium counting, I is added concentration of binding inhibitor, IC$_{50}$ is the concentration for inhibitor at half maximal binding and S is a slope factor (Haggblad, J., Carlsson, B., Kivelä, P., Siitari H., (1995) Biotechniques 18, 146–151). For determinations of the concentration of $^3$[H]-dex in the solutions, regular scintillation counting in a Wallac Rackbeta 1214 was performed using the scintillation cocktail Supermix™ (Wallac).

The Microbeta-instrument generates the mean cpm (counts per minute) value/minute and corrects for individual variations between the detectors thus generating corrected cpm values. It was found that the counting efficiency between detectors differed with less than five percent.

A similar protocol was employed to measure affinity of the compounds of the present invention for progesterone receptor (PR).

Compounds of the present invention are active in the GR binding assay described above, and show selectivity for GR over PR, as indicated in Table 1.

TABLE 1

Glucocorticoid Receptor and Progesterone Receptor Binding

| Example Number | GR Binding (% Inhibition at 1.7 µM) | PR Binding (IC$_{50}$, nM) |
|---|---|---|
| 1 | 88.1 | 600 |
| 2 | 91.3 | 7,610 |
| 3 | 85.3 | ND |
| 4 | 78.2 | ND |
| 5 | 75.2 | ND |
| 6 | 74.1 | ND |
| 7 | 87.6 | ND |
| 8 | 75.9 | ND |
| 9 | 88.5 | 4,050 |
| 10 | 90.8 | 2,310 |
| 11 | 88.6 | >10,000 |
| 12 | 86.6 | 1,000 |
| 13 | 84.0 | 1,860 |
| 14 | 82.5 | 2,230 |
| 15 | 77.9 | ND |
| 16 | 75.6 | ND |
| 17 | 88.9 | 1,070 |
| 18 | 92.6 | 1,390 |
| 19 | 91.0 | ND |
| 20 | 84.2 | 430 |
| 21 | 71.5 | ND |

TABLE 1-continued

Glucocorticoid Receptor and Progesterone Receptor Binding

| Example Number | GR Binding (% Inhibition at 1.7 μM) | PR Binding (IC$_{50}$, nM) |
|---|---|---|
| 22 | 91.0 | 1,480 |
| 23 | 92.0 | 920 |
| 24 | 92.1 | 2,590 |
| 25 | 87.5 | 1,790 |
| 26 | 94.6 | 1,320 |
| 27 | 88.9 | 560 |
| 28 | 91.3 | 990 |
| 29 | 92.4 | >10,000 |
| 30 | 73.8 | ND |
| 31 | 76.9 | ND |
| 32 | 91.7 | 1,730 |
| 33 | 92.7 | >10,000 |
| 34 | 90.0 | >10,000 |
| 35 | 92.3 | >10,000 |
| 36 | 85.5 | 1,200 |
| 37 | 72.5 | ND |
| 38 | 79.6 | ND |
| 39 | 84.5 | ND |
| 40 | 87.0 | >10,000 |
| 41 | 81.2 | ND |
| 42 | 85.8 | 27,200 |
| 43 | 91.1 | 660 |
| 44 | 89.2 | ND |
| 45 | 92.0 | 1,720 |
| 46 | 81.0 | ND |
| 47 | 76.2 | ND |
| 48 | ND | ND |
| 49 | 84.7 | ND |
| 50 | 92.9 | 190 |
| 62 | 89.1 | 246 |
| 63 | 96.2 | 648 |
| 64 | 93.5 | 1178 |
| 65 | 94.0 | 633 |
| 66 | 92.3 | ND |
| 67 | 89.0 | 667 |
| 68 | 90.4 | ND |
| 69 | 86.9 | 122 |
| 70 | 93.6 | 251 |
| 71 | 95.2 | 537 |
| 72 | 92.0 | 462 |
| 73 | 95.0 | ND |
| 74 | 97.2 | ND |
| 75 | 98.3 | 2352 |
| 76 | 96.5 | 149 |
| 77 | 97.1 | 249 |
| 78 | 97.3 | >1000 |
| 79 | 97.2 | 1103 |
| 80 | 97.1 | >1000 |
| 81 | 96.2 | 622 |
| 82 | 96.9 | ND |
| 83 | 98.1 | 177 |
| 84 | 97.9 | 468 |
| 85 | 96.9 | 351 |
| 86 | 97.5 | 216 |
| 96 | 88.0 | >1000 |
| 97 | 90.1 | 772 |
| 98 | 87.4 | ND |
| 99 | 92.0 | ND |
| 100 | 92.7 | 788 |
| 101 | 92.9 | 1032 |
| 102 | ND | ND |
| 103 | 92.4 | 78.3 |
| 104 | 95.7 | 583 |
| 105 | 96.2 | 685 |
| 106 | 96.0 | 1292 |
| 107 | 95.9 | 743 |
| 108 | 96.1 | 362 |
| 109 | 96.6 | 642 |
| 110 | 96.5 | 214 |
| 111 | 95.3 | 773 |
| 112 | 96.9 | ND |
| 113 | 96.4 | ND |
| 114 | 96.7 | 1373 |
| 115 | 96.4 | 165 |
| 116 | 95.3 | ND |
| 117 | 98.1 | ND |
| 138 | 91.8 | ND |
| 139 | 92.5 | ND |
| 140 | 88.1 | ND |
| 141 | 85.4 | 8050 |
| 142 | 90.4 | ND |
| 143 | 89.3 | >10000 |
| 144 | 94.7 | 1300 |
| 145 | 94.0 | 357 |
| 146 | 28.1 | ND |
| 147 | 93.5 | 1326 |
| 148 | 95.6 | 1275 |
| 149 | 94.7 | 4287 |
| 150 | 94.3 | 2554 |
| 151 | 94.3 | 551 |
| 152 | 94.3 | 896 |
| 153 | 91.7 | 255 |
| 154 | 92.3 | 921 |
| 155 | 92.8 | 499 |
| 156 | 94.9 | ND |
| 157 | 91.8 | ND |
| 158 | 93.1 | ND |
| 231 | 96.0 | ND |
| 232 | 94.9 | ND |
| 233 | 96.8 | ND |
| 234 | 96.1 | ND |
| 235 | 96.7 | ND |
| 236 | 96.1 | ND |
| 237 | 96.7 | ND |
| 238 | 94.2 | ND |
| 239 | 93.4 | ND |
| 240 | 93.3 | ND |
| 241 | 90.6 | ND |
| 242 | 94.1 | ND |
| 243 | 92.0 | ND |
| 244 | 95.3 | ND |
| 245 | 96.3 | ND |
| 246 | 88.6 | ND |
| 247 | 90.9 | ND |
| 248 | 96.7 | ND |
| 249 | 95.4 | ND |
| 250 | 92.9 | ND |
| 251 | 94.2 | ND |
| 252 | 91.9 | ND |
| 253 | 93.2 | ND |
| 254 | 92.8 | ND |
| 255 | 93.6 | ND |
| 256 | 92.6 | ND |
| 257 | 90.6 | ND |
| 258 | 91.6 | ND |
| 259 | 91.2 | ND |
| 260 | 91.3 | ND |
| 261 | 91.5 | ND |
| 262 | 92.2 | ND |
| 263 | 91.7 | ND |
| 264 | 89.5 | ND |
| 265 | 90.0 | ND |
| 266 | 90.7 | ND |
| 267 | 92.2 | ND |
| 268 | 90.8 | ND |
| 269 | 90.7 | ND |
| 270 | 91.1 | ND |
| 271 | 91.0 | ND |
| 272 | 90.2 | ND |
| 273 | 91.2 | ND |
| 274 | 89.9 | ND |
| 275 | 90.5 | ND |
| 276 | 89.2 | ND |
| 277 | 90.6 | ND |
| 278 | 90.1 | ND |
| 279 | 91.7 | ND |
| 280 | 89.5 | ND |
| 281 | 90.0 | ND |

TABLE 1-continued

Glucocorticoid Receptor and Progesterone Receptor Binding

| Example Number | GR Binding (% Inhibition at 1.7 μM) | PR Binding (IC$_{50}$, nM) |
|---|---|---|
| 282 | 89.9 | ND |
| 283 | 89.7 | ND |
| 284 | 89.6 | ND |
| 285 | 89.7 | ND |
| 286 | 92.6 | ND |
| 287 | 89.2 | ND |
| 288 | 89.8 | ND |
| 289 | 87.8 | ND |
| 290 | 89.1 | ND |
| 291 | 87.7 | ND |
| 292 | 89.4 | ND |
| 305 | 96.6 | 8.9 |
| 306 | 97.0 | ND |
| 307 | 97.0 | ND |
| 308 | 95.7 | ND |
| 309 | 97.4 | ND |
| 310 | 97.5 | ND |
| 311 | 97.4 | ND |
| 312 | 97.3 | ND |
| 313 | 96.3 | ND |
| 314 | 96.6 | ND |
| 315 | 97.0 | ND |
| 316 | 96.3 | ND |
| 317 | 96.5 | ND |
| 318 | 95.1 | ND |
| 319 | 96.4 | ND |
| 320 | 96.8 | ND |
| 321 | 96.4 | ND |
| 322 | 98.5 | 360.5 |
| 323 | 98.2 | 66.6 |
| 324 | 97.4 | 122.9 |
| 325 | 97.7 | 122.2 |
| 326 | 97.0 | 183.3 |

The data in Table 1 indicates that the compounds of the present invention are selective for binding to glucocorticoid receptors over progesterone receptors and therefore may be useful for the treatment of type II diabetes and related metabolic disorders.

Compounds of the present invention may be used for the treatment of diseases associated with an excess or deficiency of glucocorticoids. Such diseases include but are not limited to the following: diabetes, obesity, Syndrome X, Cushing's Syndrome, Addison's diseases, inflammatory disease such as asthma, rhinitis and arthritis, allergy, autoimmune disease, immunodeficiency, anorexia, cachexia, bone loss or bone frailty, and wound healing.

For the treatment of diabetes or Syndrome X, compounds of the present invention may be used alone, or in combination with any existing anti-diabetic agent. Agents which may be used in combination with the compounds of the present invention include, but are not limited to insulin, an insulin analog such as mecasermin and the like, an insulin secretagogue such as nateglinide and the like, a biguanide such as metformin and the like, a sulfonylurea such as chlorpropanmde, glipizide, glyburide, and the like, an insulin sensitizing agent such as troglitazone, pioglitazone, rosiglitazone, and the like, an α-glucosidase inhibitor such as acarbose, voglibose, miglitol and the like, an aldose reductase inhibitor such as zopolrestat and the like, a metiglinide such as repaglinide and the like, or a glycogen phosphorylase inhibitor. Other such anti-diabetic agents are known to one skilled in the art. The ability of the compounds of the present invention to treat diabetes, alone or in combination with another agent, can be demonstrated according to the methods described by Friedman, J. E., Y. Sun, T. Ishizuka, C. J. Farrell, S. E. McCormack, L. M. Herron, P. Hakimi, P. Lechner, and J. S. Yun, in J. Biol. Chem. 272 (50): 31475–31481, 1997; or, according to the methods described herein.

For the treatment of obesity, compounds of the present invention may be used alone, or in combination with any existing anti-obesity agent. Agents which may be used in combination with the compounds of the present invention include, but are not limited to fatty acid uptake inhibitors such as orlistat and the like, monoamine reuptake inhibitors such as sibutramine and the like, anorectic agents such as dexfenfluramine, bromocryptine, and the like, sympathomimetics such as phentermine, phendimetrazine, mazindol, and the like, or thyromimetic agents. Other such anti-obesity agents are known to one skilled in the art. The ability of the compounds of the present invention to treat obesity, alone or in combination with another agent, can be demonstrated according to the methods described by Walker, H. C., and D. R. Romsos, in Am. J. Physiol. 262 (Endocrinol. Metab. 25): E110–E117, 1992; or according to the methods described by Langley, S. C., and D. A. York, in Am. J. Physiol. 259 (Regulaory Integrative Comp. Physiol. 28): R539–R544, 1990.

For the treatment of inflammatory diseases such as asthma, rhinitis and arthritis, compounds of the present invention may be used alone, or in combination with any existing anti-inflammatory agent. Agents which may be used in combination with the compounds of the present invention include, but are not limited to glucocorticoid receptor agonists such as prednisolone, cortisone, dexamethasone and the like, or non-steroidal anti-inflammatory agents such as ibuprofen, ketoprofen, diclofenac, and the like. Other such anti-inflammatory agents are known to one skilled in the art. The ability of the compounds of the present invention to treat inflammatory disease, alone or in combination with another agent, can be demonstrated according to the methods described by Taraye, J. P., M. Barbara, M. Aliaga, and J. Tisne-Versailles, in Arzneim.-Forsch./Drug Res. 40 (II)Nr. 10: 1125–1131, 1990. The ability of the compounds of the present invention to treat arthritis, alone or in combination with another agent, can be demonstrated according to the methods described by Smith, R. J., and L. M. Sly, in J. Pharmacol. Exp. Ther. 277 (3): 1801–1813, 1996. The ability of the compounds of the present invention to treat asthma, alone or in combination with another agent, can be demonstrated according to the methods described by Elwood, W., J. O. Lotvall, P. J. Barnes, and K. F. Chung, in Am. Rev. Respir. Dis. 145: 1289–1294, 1992; or, according to the methods described by De Bie, J. J., E. M. Hessel, I. Van Ark, B. Van Esch, G. Hofman, F. P. Nijkamp, and A. J. M. Van Oosterhout, in Brit. J. Pharmacol. 119: 1481–1490, 1996.

Abbreviations

Abbreviations which have been used in the descriptions of the schemes and the examples that follow are: BF$_3$.OEt$_2$ for boron trifluoride diethyl ether complex; DMF for N,N-dimethylformamide; DMSO for dimethylsulfoxide; EtOAc for ethyl acetate; EtOH for ethanol; MeOH for methanol; Ms for mesylate or —S(O)$_2$CH$_3$; Tf for triflate or —S(O)$_2$CF$_3$; THF for tetrahydrofuran; and Ts for tosylate or —S(O)$_2$-(para-CH$_3$Ph).

Preparation of Compounds of the Invention

The compounds and processes of the present invention will be better understood in connection with the following synthetic schemes and methods which illustrate a means by which the compounds of the invention can be prepared.

Scheme 1

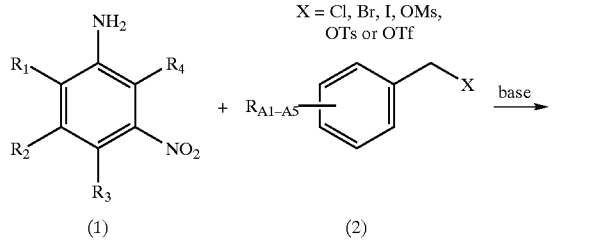

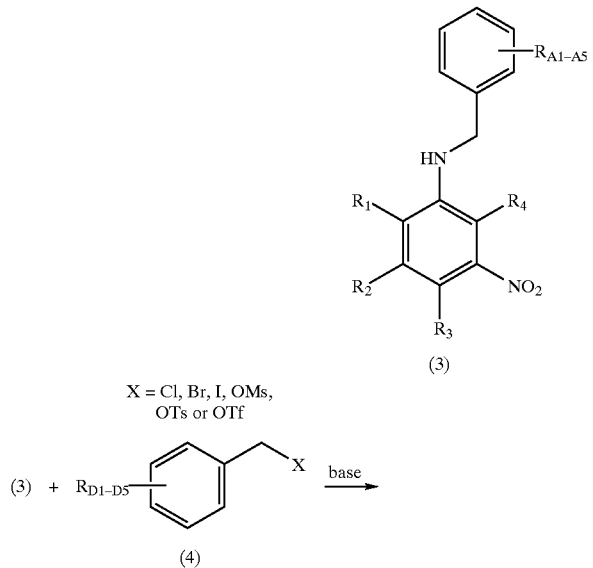

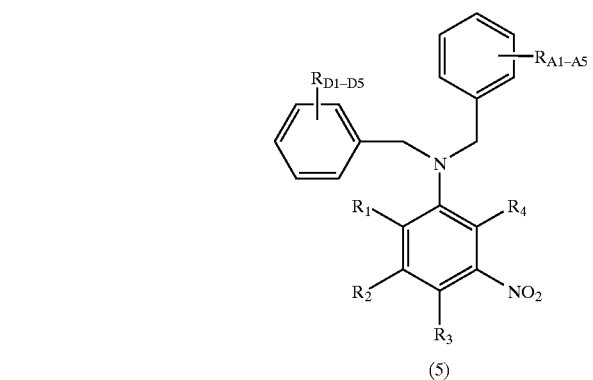

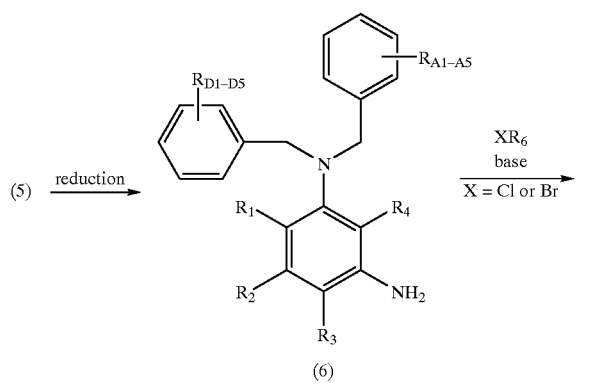

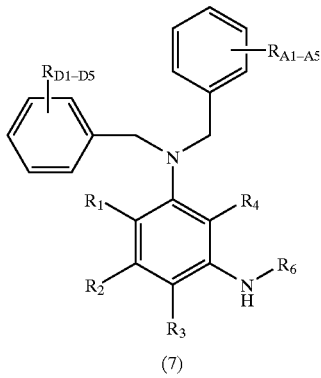

Diaminobenzenes of general formula (7), wherein $R_1$, $R_2$, $R_3$, $R_4$, $R_6$, $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in formula I, may be prepared as described in Scheme 1. Nitroanilines of general formula (1), purchased or prepared using methodology known to those in the art, may be treated with alkylating agents such as benzyl halides, mesylates, tosylates or triflates of general formula (2) and a base such as diisopropylamine to provide benzyl compounds of general formula (3). Benzyl compounds of general formula (3) may be treated with alkylating agents such as benzyl halides, mesylates, tosylates or triflates of general formula (4) and a base such as diisopropylamine to provide dibenzyl compounds of general formula (5). Dibenzyl compounds of general formula (5) may be reduced with a metal like iron or zinc or reduced by hydrogenation using a catalyst containing Pd, Rh or Pt to provide diamino compounds of general formula (6). Diamino compounds of general formula (6) may be alkylated, acylated, or sulfonylated with alkyl halides, acid chlorides or sulfonyl chlorides to provide diaminobenzenes of general formula (7).

Alternatively, nitroanilines of general formula (1) may be treated with 2.0 equivalents (or greater than 2.0 equivalents) of alkylating agents such as benzyl halides, mesylates, tosylates or triflates of general formula (2) or (4) in the presence of a base such as diisopropylamine to provide symmetrical dibenzyl compounds of general formula (5) directly.

Scheme 2

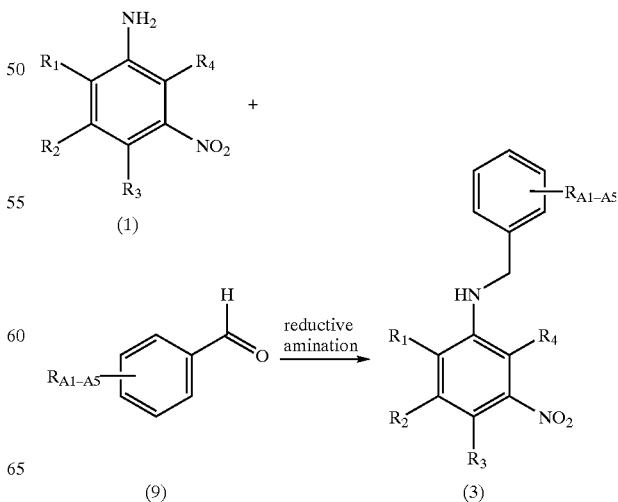

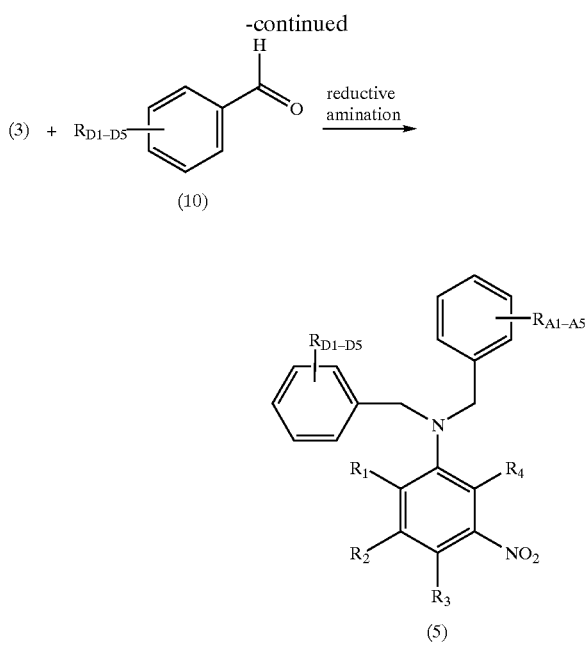

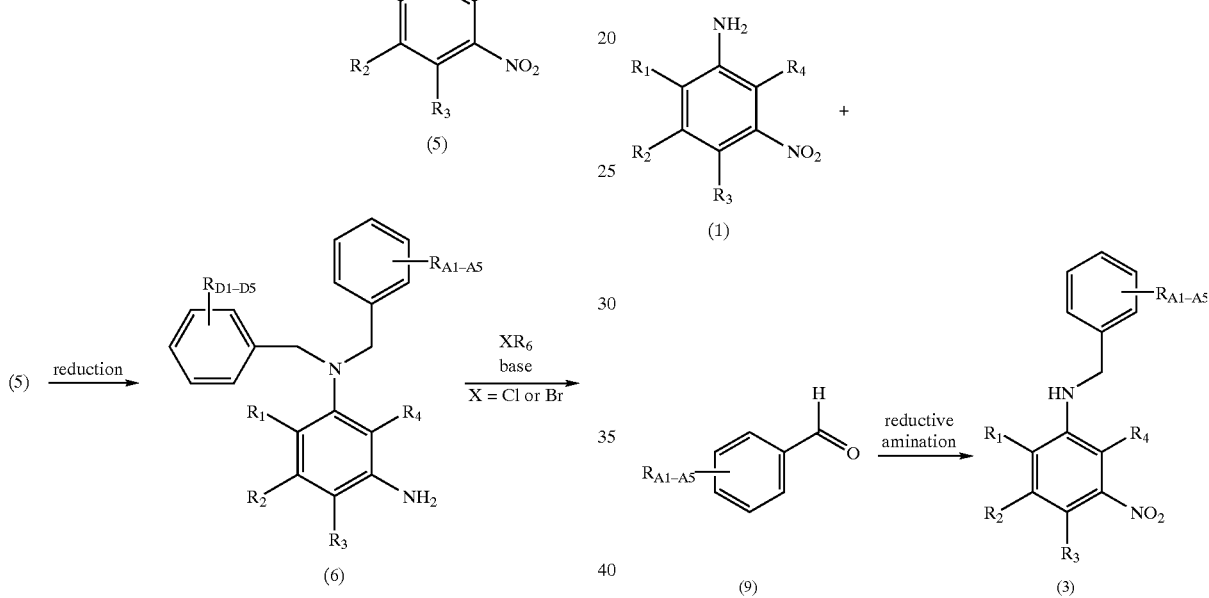

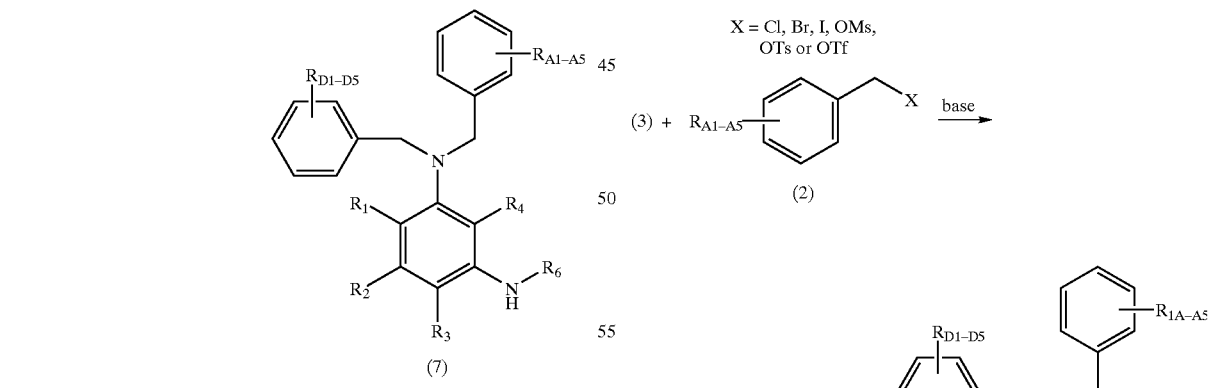

Diaminobenzenes of general formula (7), wherein $R_1$, $R_2$, $R_3$, $R_4$, $R_6$, $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in formula I, may be prepared as described in Scheme 2. Nitroanilines of general formula (1) may be treated with benzaldehydes of general formula (9) under reductive amination conditions well known to those in the art, for example in the presence of a hydride reducing agent like sodium borohydride, sodium cyanoborohydride, sodium triacetoxyborohydride or lithium aluminum hydride, to provide benzyl compounds of general formula (3). Benzaldehydes of general formula (9) may be purchased or prepared, for example from benzoic acids or benzyl alcohols, using methodology well known to those in the art. Benzyl compounds of general formula (3) may be treated with benzaldehydes of general formula (10) under reductive amination conditions well known to those in the art to provide dibenzyl compounds of general formula (5). Dibenzyl compounds of general formula (5) may be processed as described in Scheme 1 to provide diaminobenzenes of general formula (7).

Nitroanilines of general formula (1) may also be treated with 2.0 equivalents (or greater than 2.0 equivalents) of benzaldehydes of general formula (9) or (10) under reductive amination conditions to provide symmetrical dibenzyl compounds of general formula (5) directly.

Scheme 3

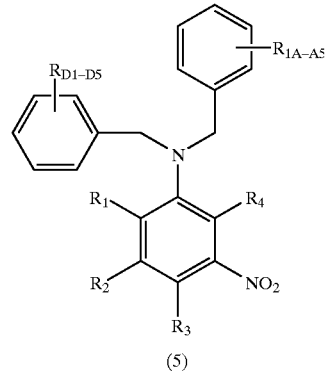

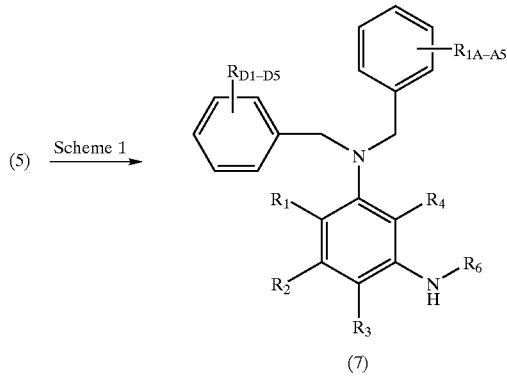

(5) Scheme 1 →

(7)

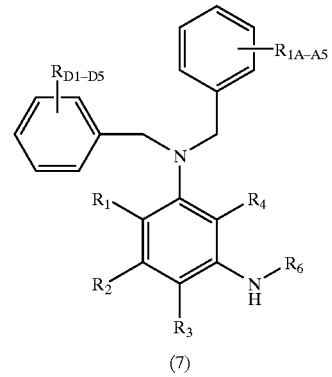

(13) Scheme 1, Scheme 2 or Scheme 3 →

(7)

Diaminobenzenes of general formula (7), wherein $R_1$, $R_2$, $R_3$, $R_4$, $R_6$, $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in formula I, may be prepared as described in Scheme 3. Nitroanilines of general formula (1) may be treated with benzaldehydes of general formula (9) under reductive amination conditions as described in Scheme 2 to provide benzyl compounds of general formula (3). Benzyl compounds of general formula (3) may then be treated with alkylating agents such as benzyl halides, mesylates, tosylates or triflates of general formula (2) and a base such as diisopropylamine to provide dibenzyl compounds of general formula (5). Dibenzyl compounds of general formula (5) may be processed as described in Scheme 1 to provide diaminobenzenes of general formula (7).

Nitroanilines of general formula (1) may also be monoalkylated first and the alkylation product subjected to reductive amination conditions second to provide dibenzyl compounds of general formula (5).

Diaminobenzenes of general formula (7), wherein $R_1$, $R_2$, $R_3$, $R_4$, $R_6$, $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in formula I, may also be prepared as described in Scheme 4. Nitroanilines of general formula (11) may be alkylated, acylated, or sulfonylated with alkyl halides, acid chlorides or sulfonyl chlorides to provide nitrobenzenes of general formula (12). Nitrobenzenes of general formula (12) may be reduced with a metal like iron or zinc or reduced by hydrogenation using a catalyst containing Pd, Rh or Pt to provide diamino compounds of general formula (13). Diamino compounds of general formula (13) may be processed as described in Schemes 1, 2 or 3 to provide diaminobenzenes of general formula (7).

Scheme 4

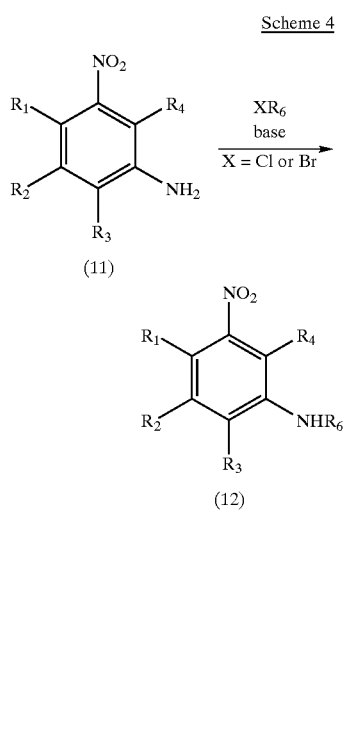

Scheme 5

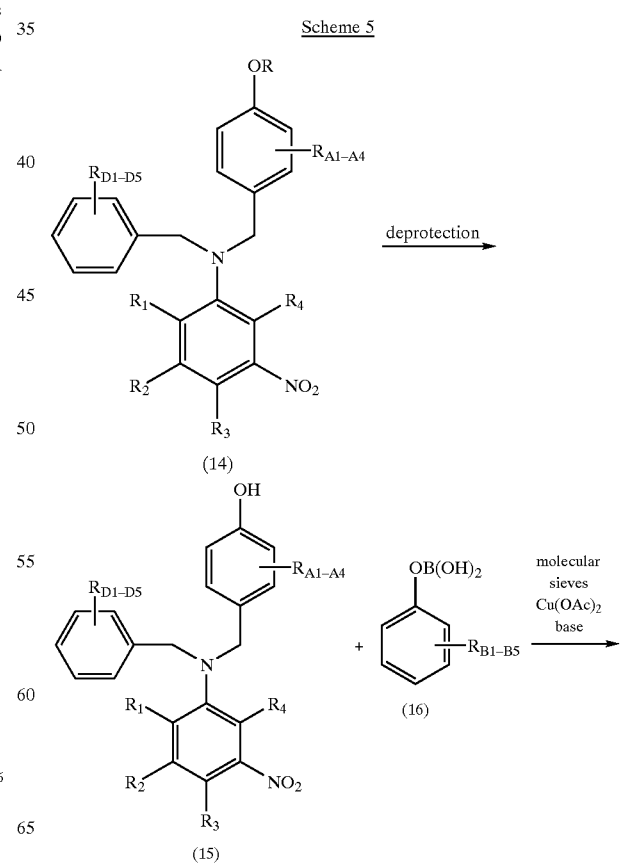

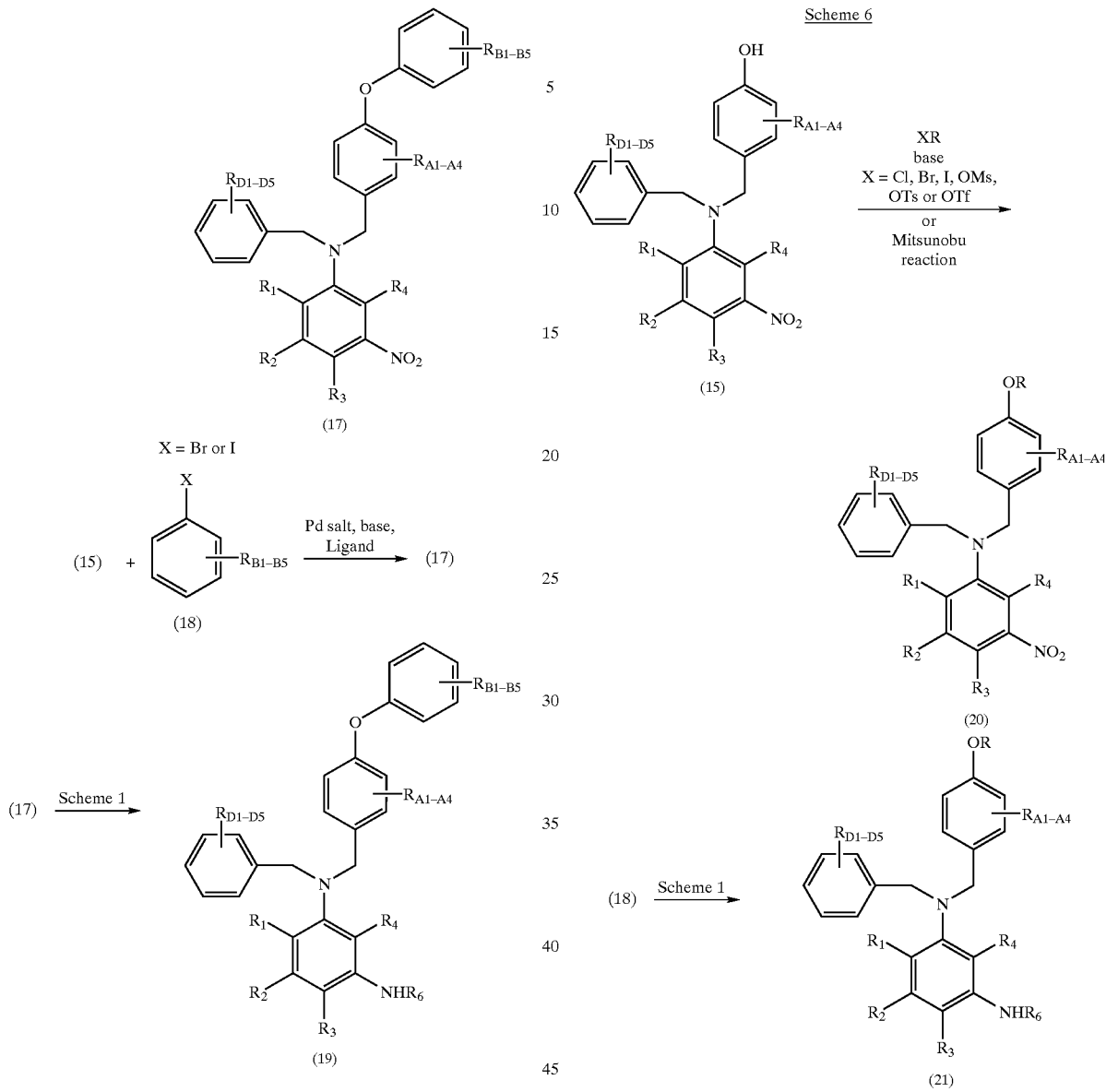

Diaminobenzenes of general formula (19), wherein $R_1$, $R_2$, $R_3$, $R_4$, $R_6$, $R_{A1}$, $R_{A2}$, $R_{A3}$, $R_{A4}$, $R_{D1}$, $R_{D2}$, $R_{D3}$, $R_{D4}$, $R_{D5}$, $R_{B1}$, $R_{B2}$, $R_{B3}$, $R_{B4}$ and $R_{B5}$ are as defined in Formula (I), may be prepared as described in Scheme 5. Nitroanilines of general formula (14), prepared as described in Schemes 1–3, may be deprotected to provide (15). A preferred protecting group is allyl which can be removed with tetrakis(triphenylphosphine)palladium(0) and phenylsilane. Other potential protecting groups are listed in T. W. Greene and P. G. M. Wuts, Protective Groups in Organic Synthesis, John Wiley & Sons, Inc., New York, 1999. Phenol (15) may be treated with an aryl group of general formula (16), copper (II) acetate and a base such as triethylamine to provide nitrobenzenes of general formula (17). Alternatively, phenol (15) may be treated with aryl halides (18), palladium salts, ligands, and bases to provide nitrobenzenes of general stucture (17). Nitrobenzenes of general formula (17) may be processed as described in Scheme 1 to provide diaminobenzenes of general formula (19).

Diaminobenzenes of general formula (21), wherein R is selected from alkenyl, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylthioalkyl, alkynyl, cyanoalkyl, haloalkenyl, haloalkyl, haloalkynyl, $(NR_8R_9)$carbonyl, $(NR_8R_9)$carbonylalkyl, $(NR_{10}R_{11})$sulfonyl and $(NR_{10}R_{11})$sulfonylalkyl and $R_1$, $R_2$, $R_3$, $R_4$, $R_6$, $R_{A1}$, $R_{A2}$, $R_{A3}$, $R_{A4}$, $R_{D1}$, $R_{D2}$, $R_{D3}$, $R_{D4}$, $R_{D5}$, $R_8$, $R_9$, $R_{10}$ and $R_{11}$ are as defined in formula (I), may be prepared as described in Scheme 6. Nitroanilines of general formula (15), prepared as described in Schemes 1–5, may be treated with a base such as sodium hydride and an alkylating agent to provide nitrobenzenes of general formula (18). Alternatively, Mitsunobu reaction of phenols (15) with an alcohol ROH, trialkyl phosphine (like triphenylphosphine), and dialkyl azodicarboxylate (like diethyl azodicarboxylate) can be used to prepare nitrobenzenes of general formula (20). Nitrobenzenes of general formula (20) may be processed as described in Scheme 1 to provide diaminobenzenes of general formula (21).

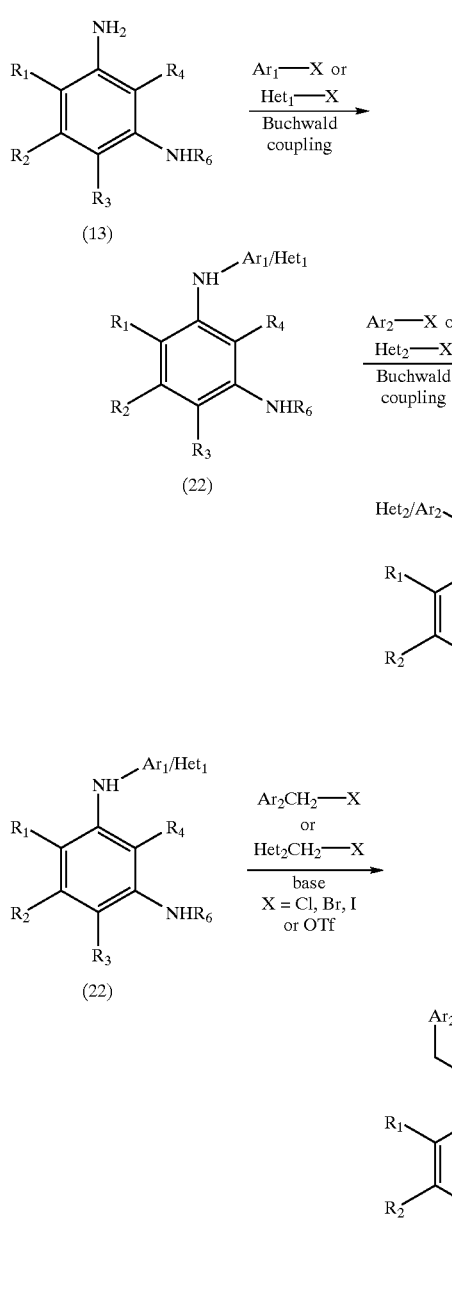

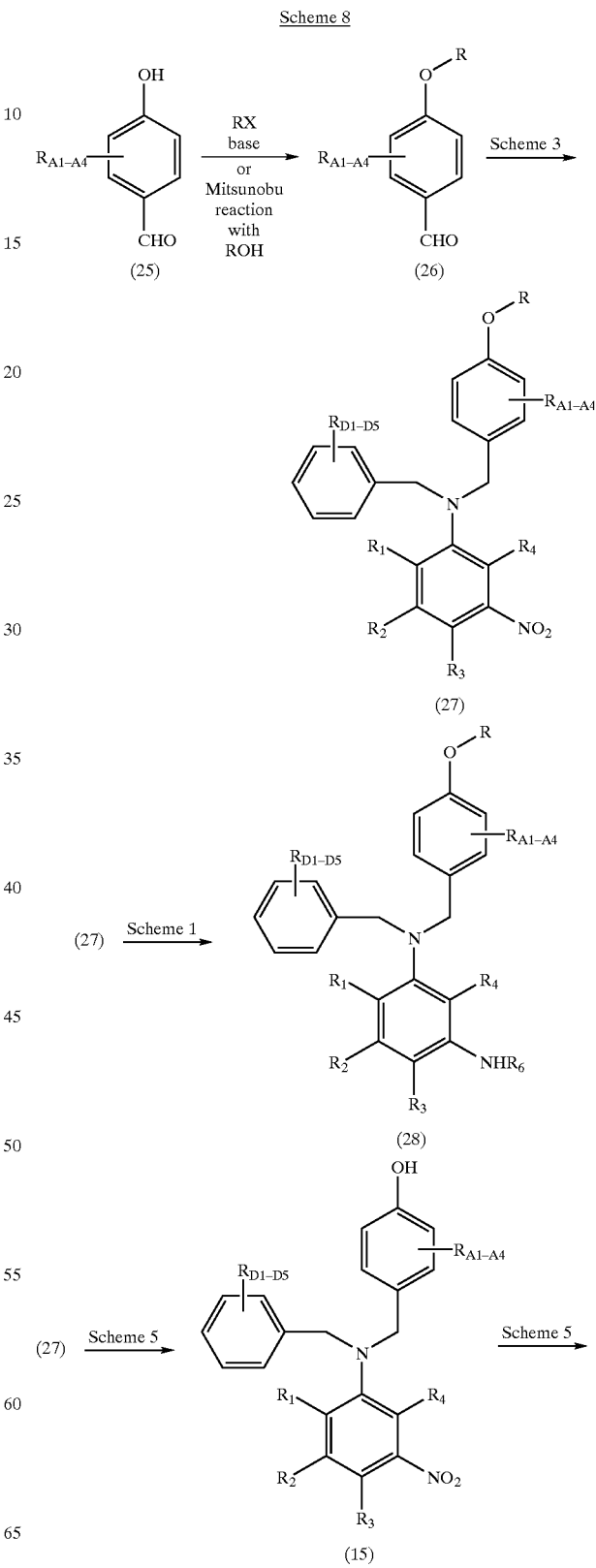

(23), or may be treated with a benzylic or heterocyclicmethyl halide in the presence of a base such as sodium carbonate or triethylamine to provide diamines of general formula (24).

Diaminobenzenes of general formula (23) and of general formula (24), wherein $R_1$, $R_2$, $R_3$, $R_4$, $R_6$ are as defined in Formula (I), $Ar_1$ and $Ar_2$ are each independently aryl, as defined herein, and $Het_1$ and $Het_2$ are each independently heterocycle, as defined herein, may be prepared as described in Scheme 7. Diaminobenzenes of general formula (13), prepared as described in Scheme 4 or purchased commercially, may be treated an aryl or heterocyclic halide or triflate under Buchwald coupling conditions (Wagaw and Buchwald, JOC (1996) 61, 7240–7241; Yang and Buchwald, J. Organometallic Chem., (1999) 576, 125–146; and Harris, Geis and Buchwald, JOC (1999) 64, 6016–6022) to provide secondary amines of general formula (22). Secondary amines of general formula (22) may be resubjected to Buchwald conditions to provide diamines of general formula

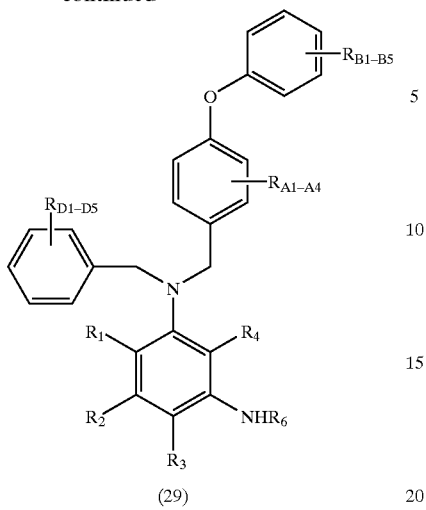

(29)

Diaminobenzenes of general formula (28) wherein R is selected from alkenyl, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylthioalkyl, alkynyl, cyanoalkyl, haloalkenyl, haloalkyl, haloalkynyl, $(NR_8R_9)$carbonyl, $(NR_8R_9)$carbonylalkyl, $(NR_{10}R_{11})$sulfonyl and $(NR_{10}R_{11})$sulfonylalkyl and $R_1$, $R_2$, $R_3$, $R_4$, $R_6$, $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in Formula (I), and diaminobenzenes of general formula (29), wherein $R_1$, $R_2$, $R_3$, $R_4$, $R_6$, $R_{A1}$, $R_{A2}$, $R_{A3}$, $R_{A4}$, $R_{A5}$, $R_{D1}$, $R_{D2}$, $R_{D3}$, $R_{D4}$, $R_{D5}$, $R_{B1}$, $R_{B2}$, $R_{B3}$, $R_{B4}$ and $R_{B5}$ are as defined in formula I, may be prepared as described in Scheme 8. Phenols of general formula (25), purchased or prepared using methodology known to those in the art, may be treated with alkylating agents such as benzyl halides, mesylates, tosylates or triflates and a base such as potassium carbonate to provide ethers of general formula (26). Alternatively, a Mitsunobu reaction can be used to prepare ethers (26) from phenols (25) and an alcohol (ROH). Aldehydes of general formula (26) may be processed as described in Scheme 3 to provide dibenzyl compounds of general formula (27). Dibenzyl compounds of general formula (27) may be processed as described in Scheme 1 to provide compounds of general formula (28). Compounds of general formula (27) may be deprotected as described in Scheme 5 to provide diaminobenzenes of general formula (15). Compounds of general formula (15) may be processed as described in Scheme 5 to provide diaminobenzenes of general formula (29).

Scheme 9

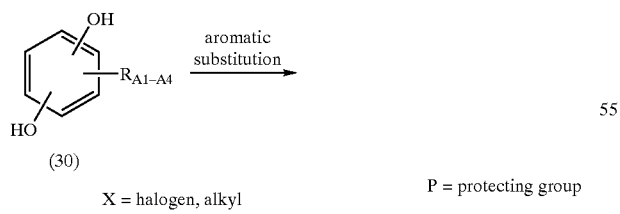

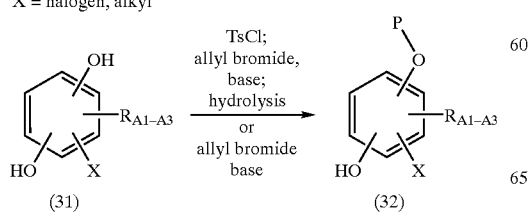

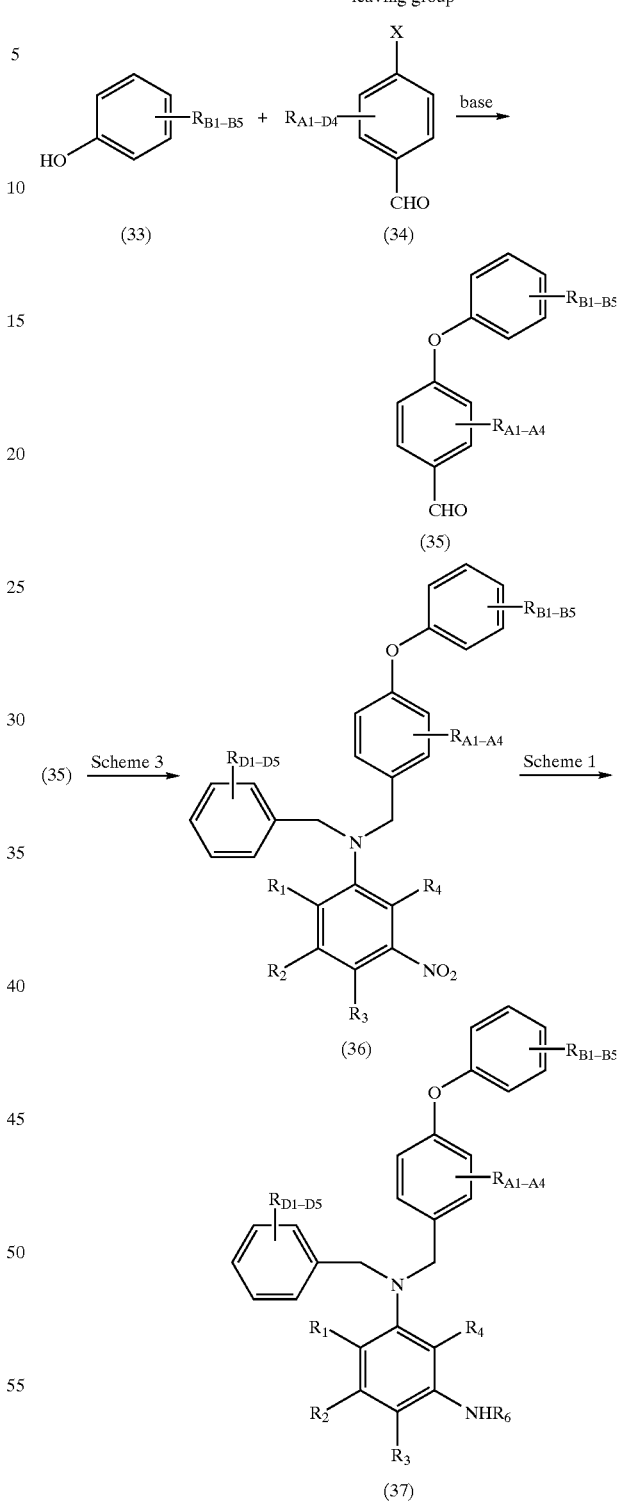

Diaminobenzenes of general formula (37), wherein $R_1$, $R_2$, $R_3$, $R_4$, $R_6$, $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in Formula (I), may be prepared described in Scheme 9. Phenols of general formula (30), purchased or prepared using methodology known to those in the art, may be treated with electrophilic agents such as 1-(chloromethyl)-4-fluoro-1,4-diazoniabicyclo[2.2.2]octane bis(tetrafluoroborate) to provide compounds of general formula (31). Compounds of general formula (31) may be may be protected on oxygen to provide dibenzyl compounds of general formula (32). An allyl protecting group is preferred and other potential protecting groups are listed in T. W. Greene and P. G. M. Wuts, Protective Groups in Organic Synthesis, John Wiley & Sons, Inc., New York, 1999. Compounds of general formula (31) may be alkylated directly using an alkylating agent like allyl bromide and a base like potassium carbonate to give phenols 32. Alternatively, one phenol can be reacted with TsCl and the other with an alkylating agent like allyl bromide and a base like potassium carbonate. The Ts group can then be removed by hydrolysis to give compounds of general formula (32). Phenols of general formula (33) may be purchased, prepared as in the preparation of compounds (32), or prepared using methodology known to those in the art. Phenols of general formula (33) can be reacted with aldehydes (34) to provide ethers of general formula (35). Ethers of general formula (35) may be processed as described in Scheme 3 to provide diaminobenzenes of general formula (36). Compounds of general formula (36) may be processed as described in Scheme 1 to provide diaminobenzenes of general formula (37).

Scheme 10

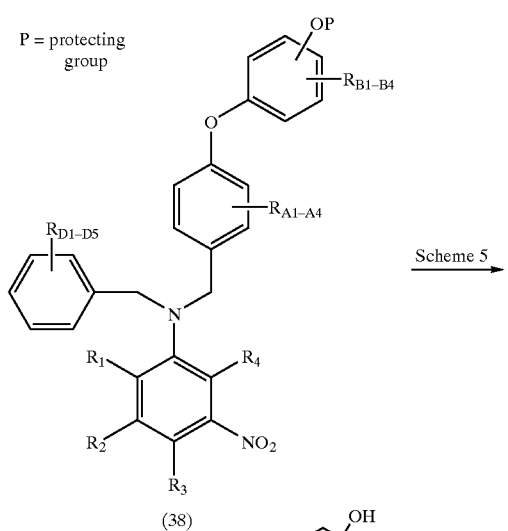

(38)

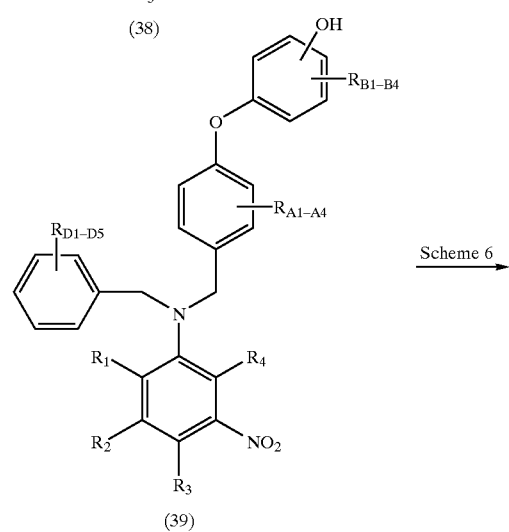

(39)

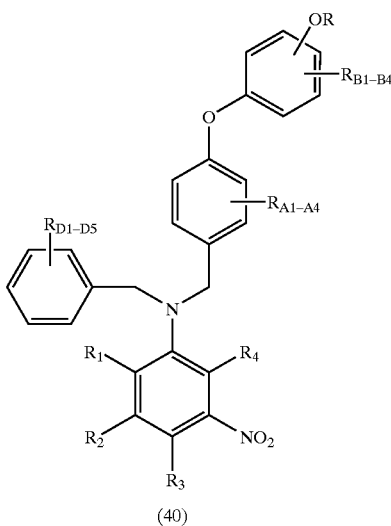

(40)

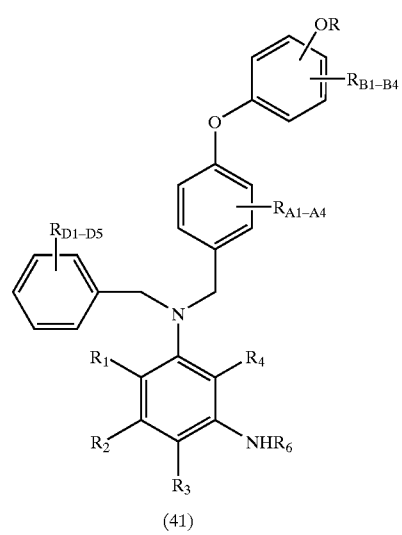

(41)

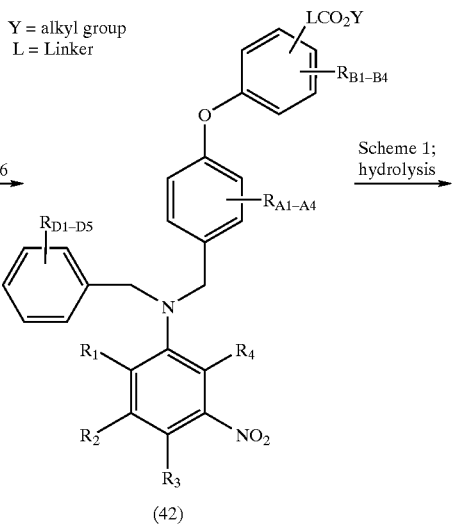

(42)

Scheme 11

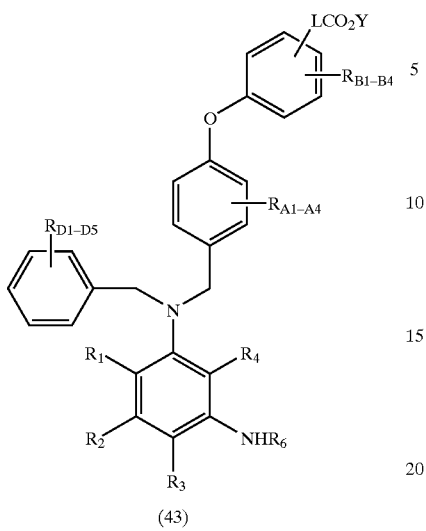

(43)

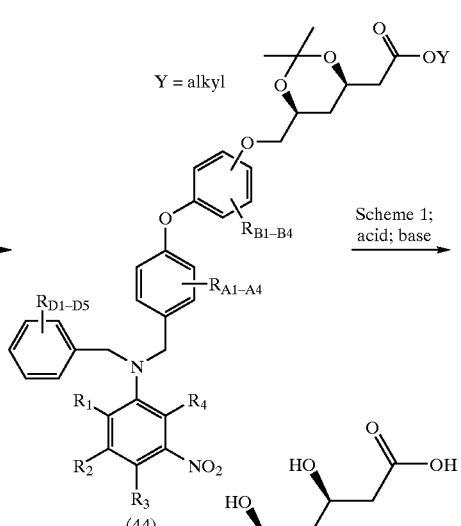

(44)

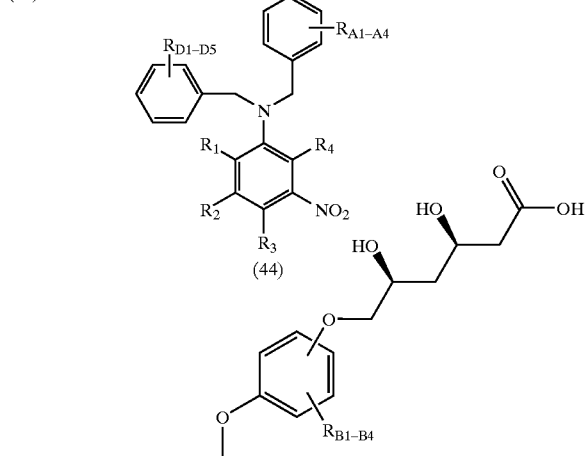

(45)

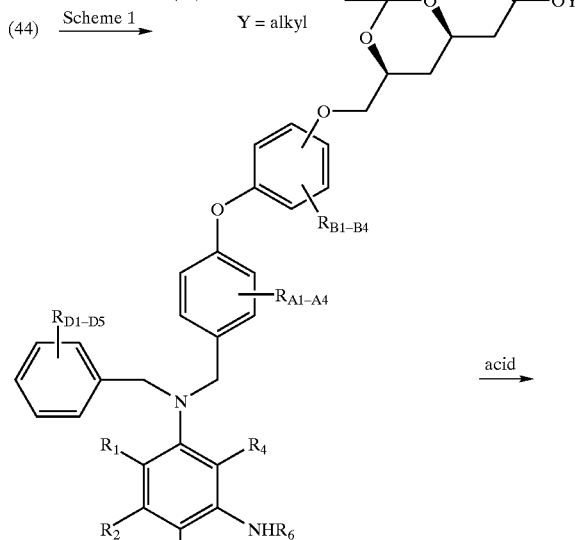

(46)

Diaminobenzenes of general formula (41) wherein R is selected from alkenyl, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylthioalkyl, alkynyl, cyanoalkyl, haloalkenyl, haloalkyl, haloalkynyl, $(NR_8R_9)$carbonyl, $(NR_8R_9)$carbonylalkyl, $(NR_{10}R_{11})$ sulfonyl and $(NR_{10}R_{11})$sulfonylalkyl and $R_1$, $R_2$, $R_3$, $R_4$, $R_6$, $R_{A1}$, $R_{A2}$, $R_{A3}$, $R_{A4}$, $R_{A5}$, $R_{B1}$, $R_{B2}$, $R_{B3}$, $R_{B4}$, $R_{D1}$, $R_{D2}$, $R_{D3}$, $R_{D4}$ and $R_{D5}$ are as defined in formula I, and diaminobenzenes of general formula (43), wherein $R_1$, $R_2$, $R_3$, $R_4$, $R_6$, $R_{A1}$, $R_{A2}$, $R_{A3}$, $R_{A4}$, $R_{A5}$, $R_{B1}$, $R_{B2}$, $R_{B3}$, $R_{B4}$, $R_{D1}$, $R_{D2}$, $R_{D3}$, $R_{D4}$ and $R_{D5}$ are as defined in formula I, L is a linker group, and Y is an alkyl group, may be prepared as described in Scheme 10. L is selected from those groups delineated for $R_{B1-B4}$ but has two attachment sites. P is a protecting group and allyl is preferred. Representative protecting groups are described in T. W. Greene and P. G. M. Wuts, Protective Groups in Organic Synthesis, John Wiley & Sons, Inc., New York, 1999. Nitroaromatics of general formula (38), prepared via methods described in Scheme 9 or using methodology known to those in the art, may be deprotected to provide phenols of general formula (39). A preferred protecting group is allyl which can be removed with tetrakis(triphenylphosphine)$_p$alladium(0) and phenylsilane. Phenols of general formula (39) may be alkylated as described in Scheme 6 to provide dibenzyl compounds of general formula (40). Dibenzyl compounds of general formula (40) may be reduced and N-substituted as described in Scheme 1 to provide diamino compounds of general formula (41). Alternatively, compounds of general formula (39) may be subjected to aryl substitution reactions as described in Scheme 6 to provide esters of general formula (42). Esters (42) may be processed as described in Scheme 1 followed by hydrolysis of the ester to provide diamino acids compounds of general formula (43).

-continued

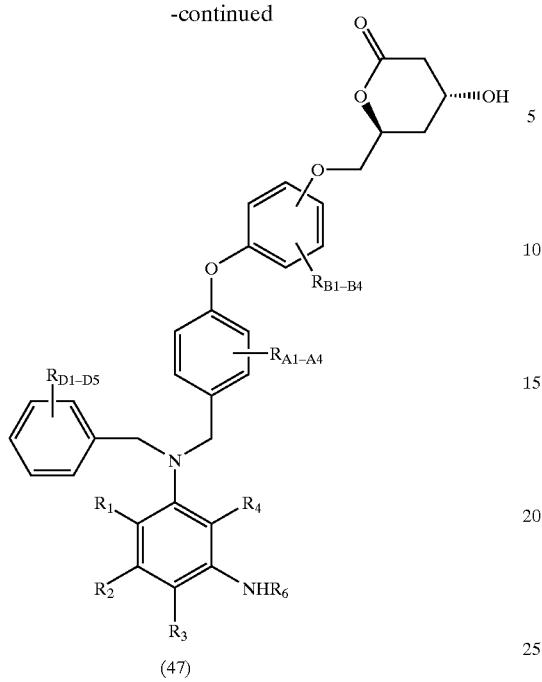

(47)

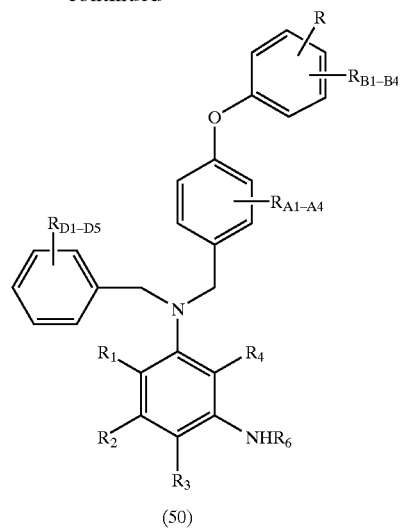

(50)

Diaminobenzenes of general formula (45) and (47), wherein $R_1$, $R_2$, $R_3$, $R_4$, $R_6$, $R_{A1}$, $R_{A2}$, $R_{A3}$, $R_{A4}$, $R_{A5}$, $R_{D1}$, $R_{D2}$, $R_{D3}$, $R_{D4}$, $R_{D5}$, $R_{B1}$, $R_{B2}$, $R_{B3}$ and $R_{B4}$ are as defined in formula I, may be prepared as described in Scheme 11. Nitrophenols of general formula (39) may be treated with alkylating agents such as benzyl halides, mesylates, tosylates or triflates and a base to provide compounds of general formula (44). Reduction of the nitro group followed by reaction of the resultant amine is accomplished as described in Scheme 1; treatment with an acid like aqueous hydrochloric acid or trifluoroacetic acid of the like to remove the acetonide protecting group followed by hydrolysis of the ester for example using hydroxide anion in an alcholic solvent provides dibenzyl dihydroxyacids of general formula (45). Alternatively dibenzyl compounds of general formula (44) may be reduced and reacted on nitrogen as described in Scheme 1 to provide diamino compounds of general formula (46). Removal of the acetonide under acidic conditions followed by acid-catalyzed lactonization provides diaminobenzenes hydroxylactones of general formula (47).

(50) → hydrolysis →

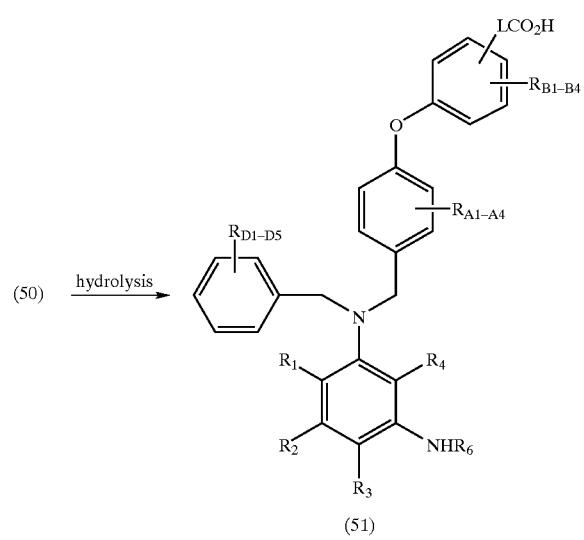

(51)

Scheme 12

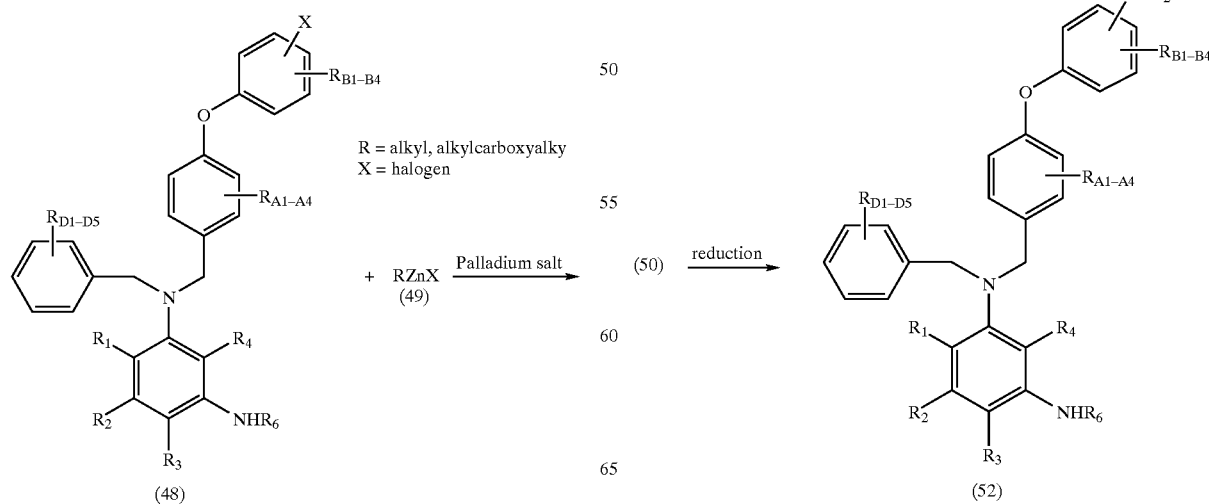

Diaminobenzenes of general formula (51) and (52), wherein $R_1$, $R_2$, $R_3$, $R_4$, $R_6$, $R_{A1}$, $R_{A2}$, $R_{A3}$, $R_{A4}$, $R_{B1}$, $R_{B2}$, $R_{B3}$, $R_{B4}$, $R_{D1}$, $R_{D2}$, $R_{D3}$, $R_{D4}$ and $R_{RD5}$ are as defined in formula I, and L is a linker group, may be prepared as described in Scheme 12. L is-selected from those groups delineated for $R_{B1-B4}$ but has two attachment sites. X is a halogen like chlorine, bromine, iodine. Halides of general formula (48), prepared according to Schemes 5 or 9, or using methodology known to those in the art, may be treated with zinc reagents such as 3-ethoxy-3-oxopropylzinc bromide of general formula (49) and a palladium catalyst such as tetrakis(triphenylphosphine)palladium (0) to provide compounds of general formula (50). Compounds of general formula (50) that contain an ester may optionally be hydrolyzed to provide dibenzyl diamino acids of general formula (51), or may optionally be reduced with diisobutylaluminum hydride or another reducing reagent to provide dibenzyl diamino alcohols of general formula (52).

Scheme 13

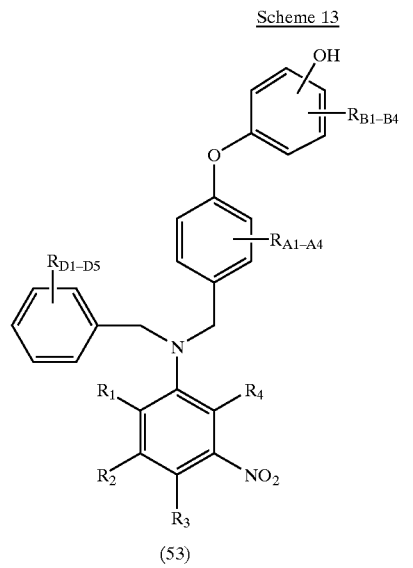

(53)

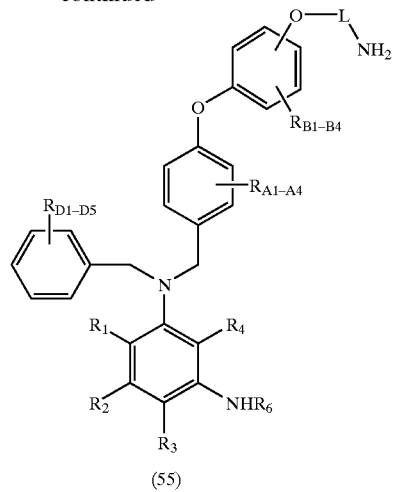

(55)

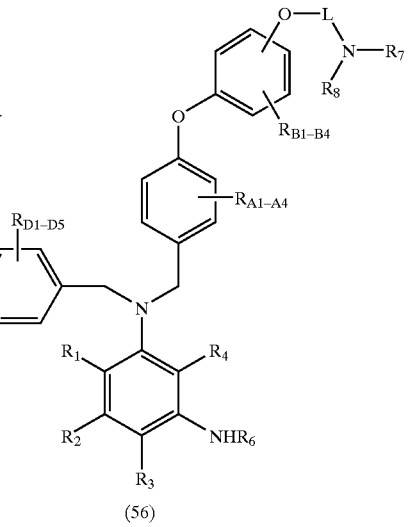

(56)

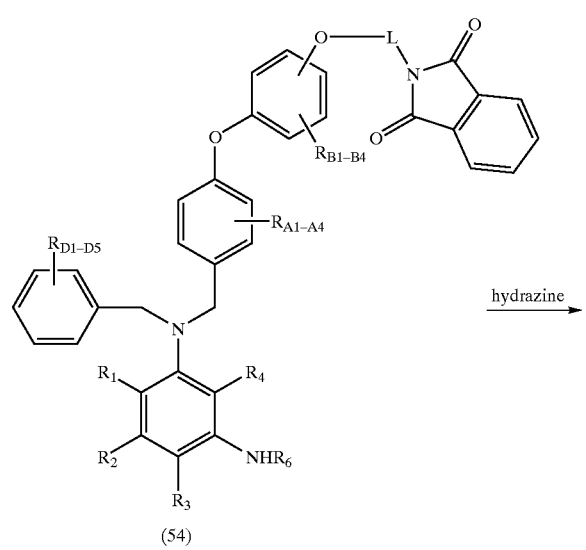

(54)

Diaminobenzenes of general formula (55) and (56), wherein $R_7$ and $R_8$ are selected from alkenyl, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylthioalkyl, alkynyl, cyanoalkyl, haloalkenyl, haloalkyl, haloalkynyl, $(NR_8R_9)$carbonyl, $(NR_8R_9)$carbonylalkyl, $(NR_{10}R_{11})$sulfonyl and $(NR_{10}R_{11})$sulfonylalkyl and $R_1$, $R_2$, $R_3$, $R_4$, $R_6$, $R_{A1}$, $R_{A2}$, $R_{A3}$, $R_{A4}$, $R_{B1}$, $R_{B2}$, $R_{B3}$, $R_{B4}$, $R_{D1}$, $R_{D2}$, $R_{D3}$, $R_{D4}$ and $R_{D5}$ are as defined in formula I, and L is a linker group, may be prepared as described in Scheme 13. L is-selected from those groups delineated for $R_{B1-B4}$ but has two attachment sites. Phenols of general formula (53), prepared using the methods described in Scheme 10 or using methodology known to those in the art, may be coupled with phthalimidoalkyl alcohols or phthalimidoalkyl halides as described in Schemes 6 and 1 to provide compounds of general formula (54). Phthalimide compounds of general formula (54) may be treated with hydrazine to provide primary amines of general formula (55). Amine compounds of general formula (55) may be alkylated, acylated, or sulfonylated with alkyl halides, acid chlorides or sulfonyl chlorides to provide diaminobenzenes of general formula (56).

Scheme 14

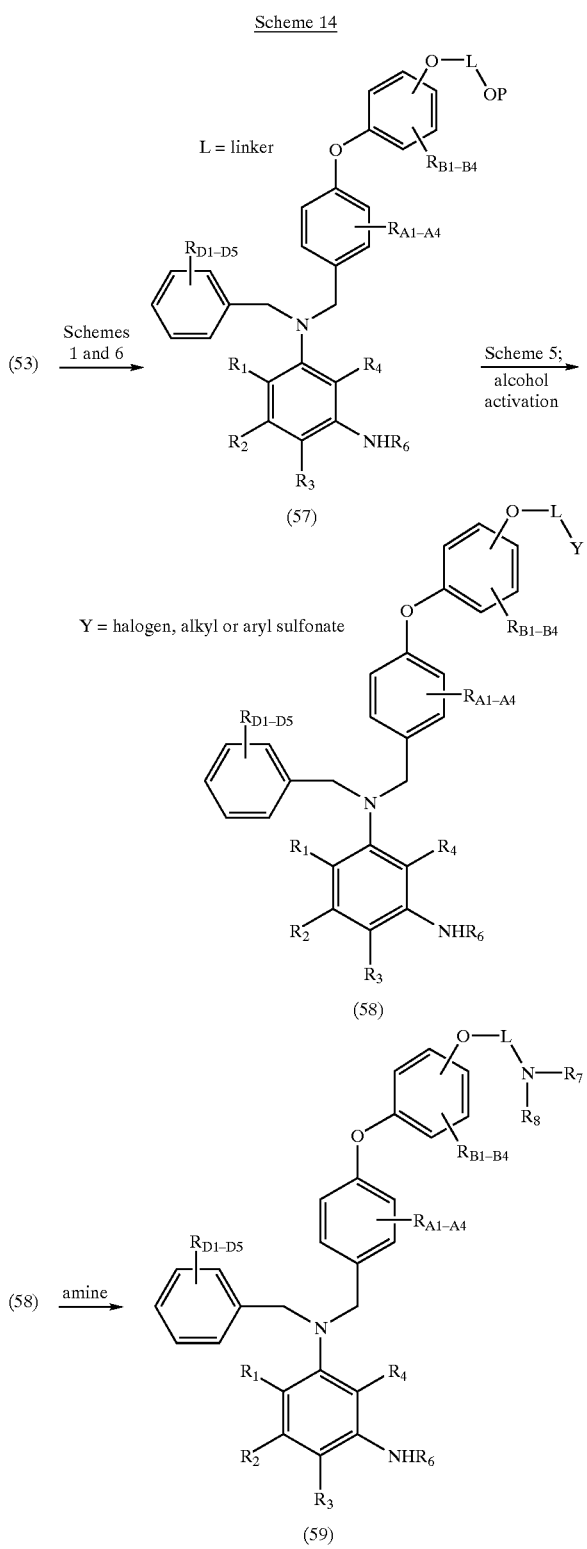

Diaminobenzenes of general formula (57) and (59), wherein $R_1$, $R_2$, $R_3$, $R_4$, $R_6$, $R_{A1}$, $R_{A2}$, $R_{A3}$, $R_{A4}$, $R_{A5}$, $R_{B1}$, $R_{B2}$, $R_{B3}$, $R_{B4}$, $R_{D1}$, $R_{D2}$, $R_{D3}$, $R_{D4}$ and $R_{D5}$ are as defined in formula I, L is a linker group, and P is an optional protecting group, and (59), wherein $R_7$ and $R_8$ are selected from alkenyl, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylthioalkyl, alkynyl, cyanoalkyl, haloalkenyl, haloalkyl, haloalkynyl, $(NR_8R_9)$carbonyl, $(NR_8R_9)$carbonylalkyl, $(NR_{10}R_{11})$sulfonyl and $(NR_{10}R_{11})$sulfonylalkyl and $R_1$, $R_2$, $R_3$, $R_4$, $R_6$, $R_{A1}$, $R_{A2}$, $R_{A3}$, $R_{A4}$, $R_{A5}$, $R_{D1}$, $R_{D2}$, $R_{D3}$, $R_{D4}$ and $R_{D5}$ are as defined in formula I, and L is a linker group, may be prepared as described in Scheme 14. L is selected from those groups delineated for $R_{B1-B4}$ but has two attachment sites. Representative protecting groups are described in T. W. Greene and P. G. M. Wuts, Protective Groups in Organic Synthesis, John Wiley & Sons, Inc., New York, 1999. Phenols of general formula (53) may be coupled with protected diols or protected hydroxyalkyl halides as described in Schemes 6 and 1 to provide compounds of general formula (57). Compounds of general formula (57) may be deprotected as described in Scheme 5 to the corresponding alcohol and the alcohols converted to the corresponding halide or alkylsulfonate, for example by treatment with triphenylphosphine and carbon tetrabromide or p-toluenesulfonyl chloride or the like, to provide compounds of general formula (58). Compounds of general formula (58) may be reacted with a primary or secondary amine to provide compounds of general formula (59).

Scheme 15

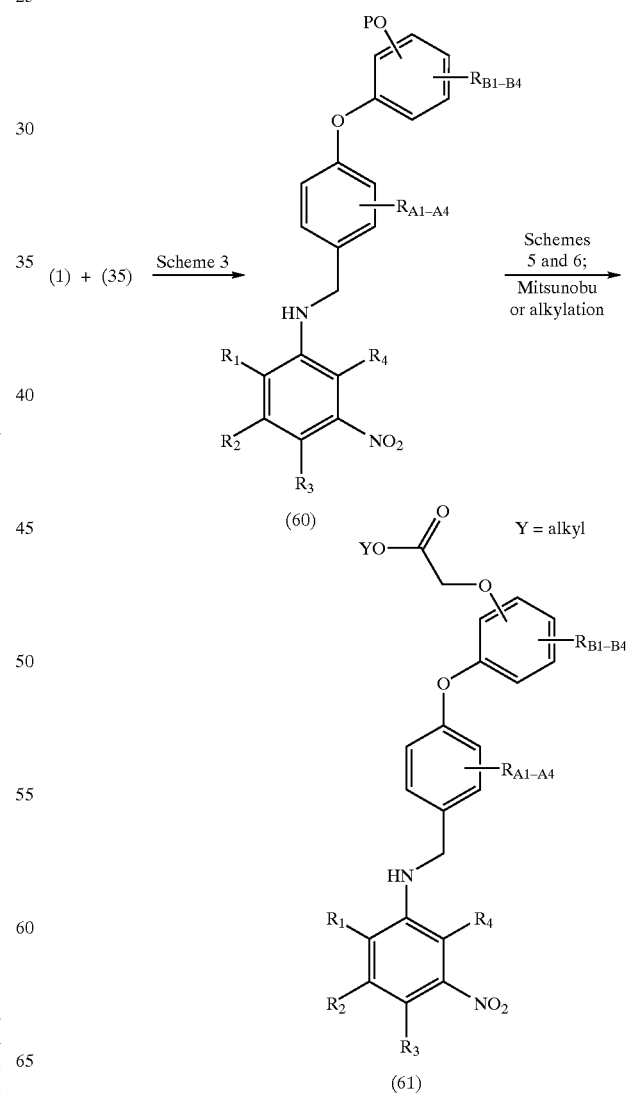

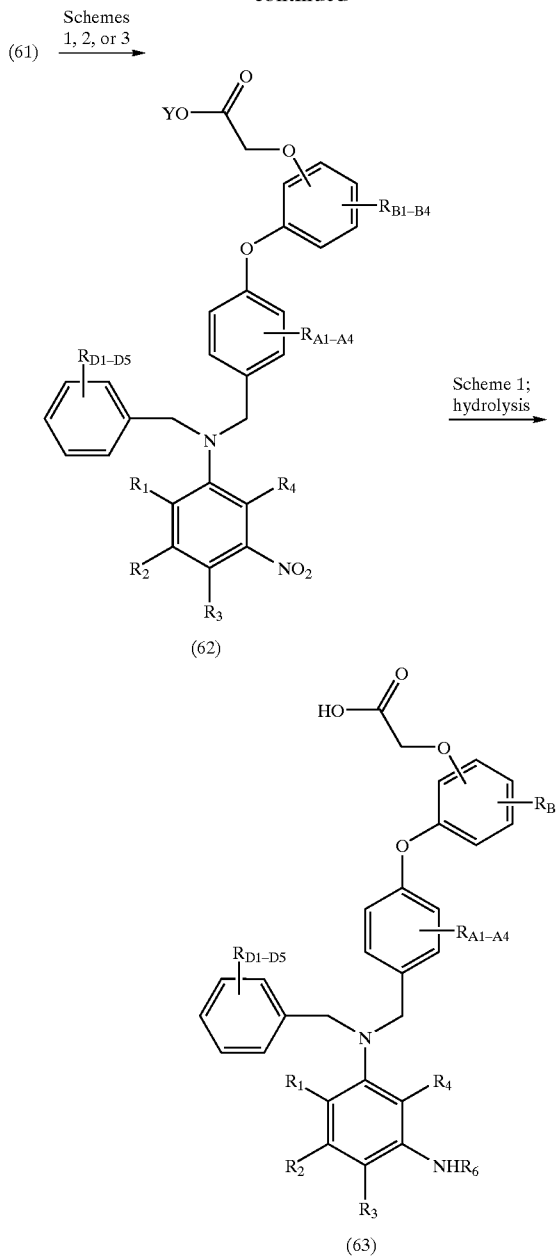

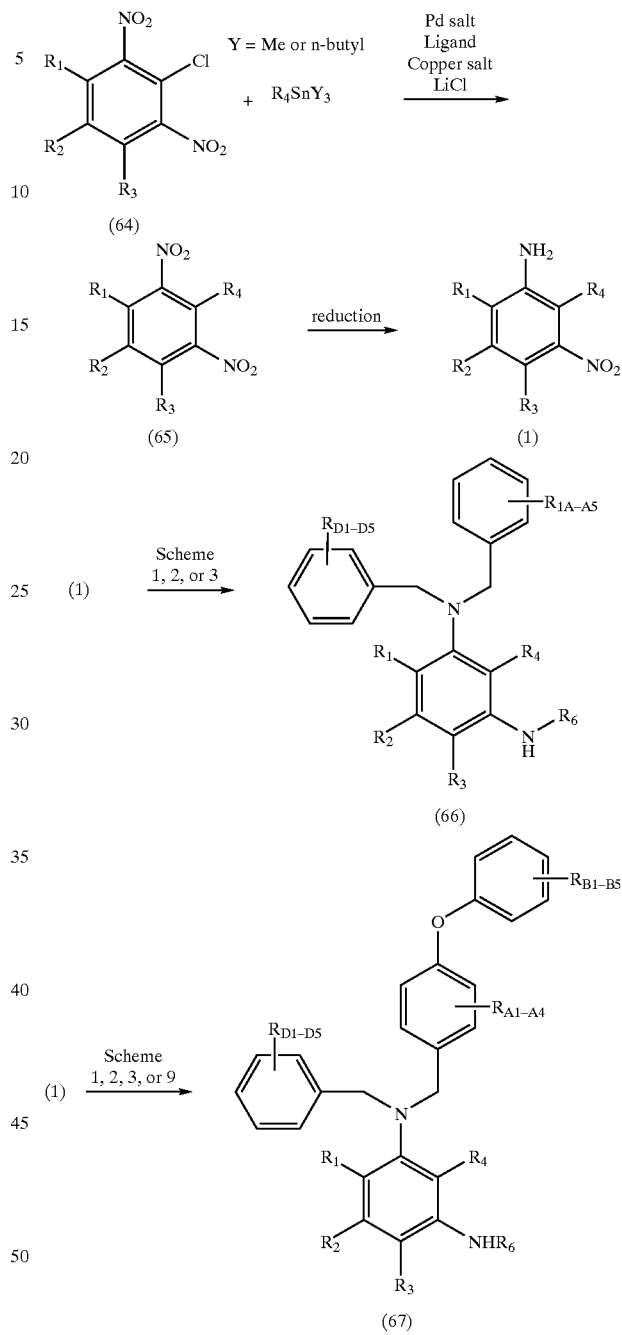

Diaminobenzenes of general formula (63), wherein $R_1$, $R_2$, $R_3$, $R_4$, $R_6$, $R_{A1}$, $R_{A2}$, $R_{A3}$, $R_{A4}$, $R_{B1}$, $R_{B2}$, $R_{B3}$, $R_{B4}$, $R_{D1}$, $R_{D2}$, $R_{D3}$, $R_{D4}$ and $R_{D5}$ are as defined in formula I, may be prepared as described in Scheme 15. Nitroanilines of general formula (1), purchased or prepared using methodology known to those in the art, may be treated with aldehydes (35) and processed as described in Scheme 3 to provide compounds of general formula (60). Compounds of general formula (61) may be deprotected as described in Scheme 5 and the resultant alcohol alkylated as described in Scheme 6 to provide compounds of general formula (61). Compounds of general formula (61) may be N-alkylated as described in Schemes 1, 2, or 3 to provide compounds of general formula (62). Nitroaromatic compounds of general formula (62) may be reduced and alkylated, acylated, or sulfonylated with alkyl halides, acid chlorides or sulfonyl chlorides as described in Scheme 1. Hydrolysis of the ester moiety provides diaminobenzenes of general formula (63).

Diaminobenzenes of general formula (66) and (67), wherein $R_1$, $R_2$, $R_3$, $R_4$, $R_6$, $R_{A1}$, $R_{A2}$, $R_{A3}$, $R_{A4}$, $R_{B1}$, $R_{B2}$, $R_{B3}$, $R_{B4}$, $R_{D1}$, $R_{D2}$, $R_{D3}$, $R_{D4}$ and $R_{D5}$ are as defined in formula I, may be prepared as described in Scheme 16. Dinitrohalides of general formula (64), purchased or prepared using methodology known to those in the art, may be treated with tin reagents such as trimethyl or tri-n-butyl stannanes, a palladium catalyst (palladium salt plus ligand), copper salt, and LiCl in a Stille reaction to provide nitroaromatic compounds of general formula (65). The dinitrohalides of general formula (65) may be reduced using methodology known to those in the art to provide nitroanilines of general formula (1). Compounds of general formula (1) may be processed as described in Schemes 1, 2, or 3 to provide diamino compounds of general formula (66). Compounds of general formula (1) may also be processed as described in Schemes 1, 2, 3, or 9 to provide diamino compounds of general formula (67).
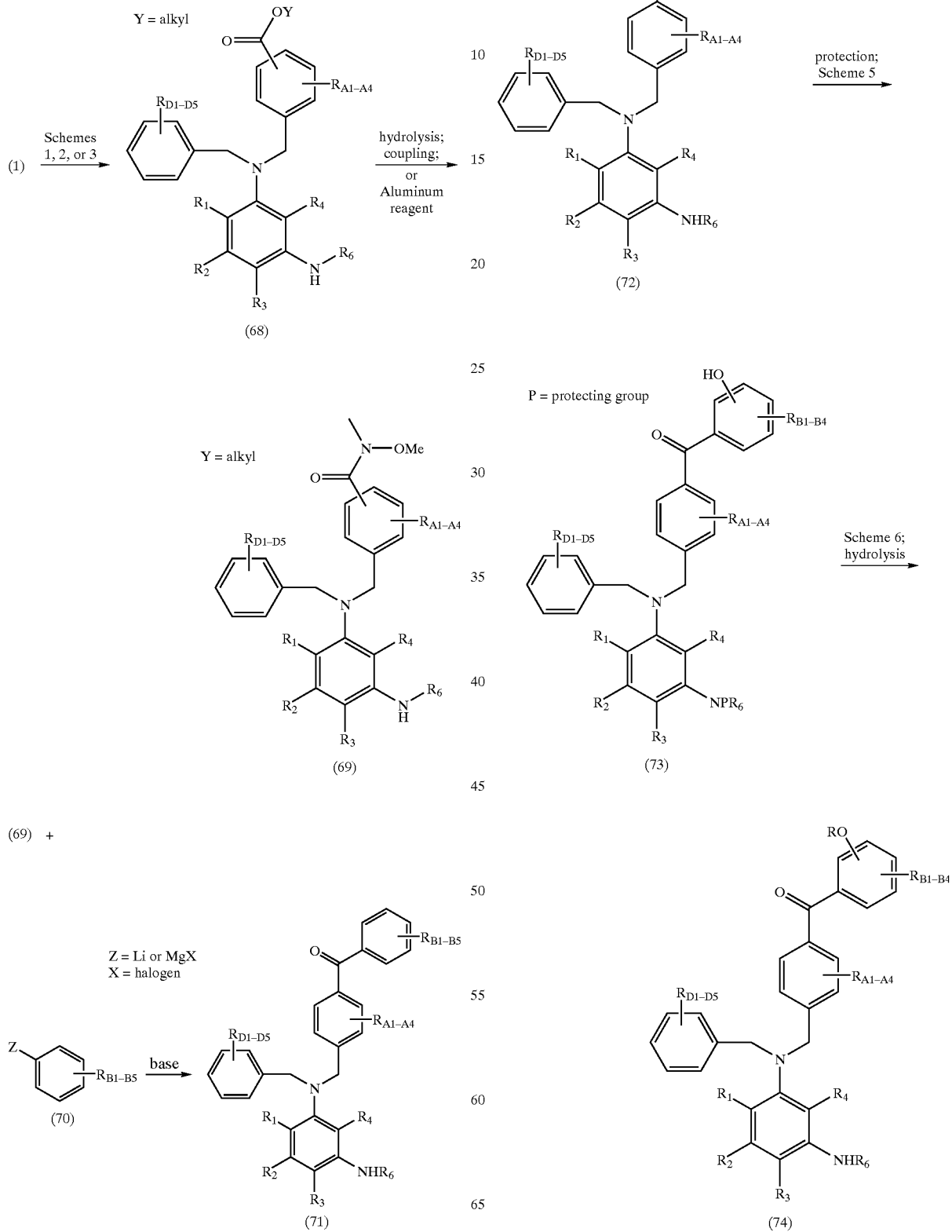
Scheme 17

Diaminobenzenes of general formula (71, 72, 73, and 74), wherein R is selected from alkenyl, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylthioalkyl, alkynyl, cyanoalkyl, haloalkenyl, haloalkyl, haloalkynyl, $(NR_8R_9)$carbonyl, $(NR_8R_9)$carbonylalkyl, $(NR_{10}R_{11})$sulfonyl and $(NR_{10}R_{11})$sulfonylalkyl and $R_1$, $R_2$, $R_3$, $R_4$, $R_6$, $R_{A1}$, $R_{A2}$, $R_{A3}$, $R_{A4}$, $R_{B1}$, $R_{B2}$, $R_{B3}$, $R_{B4}$, $R_{B5}$, $R_{D1}$, $R_{D2}$, $R_{D3}$, $R_{D4}$ and $R_{D5}$ are as defined in formula I, and P is an optional protecting group, may be prepared as described in Scheme 17. Nitroanilines of general formula (1), purchased or prepared using methodology known to those in the art, may be processed as described in Schemes 1, 2, or 3 to provide ester compounds of general formula (68). Ester compounds of general formula (68) may be hydrolyzed and subjected to amide forming coupling conditions in the presence of N,O-dimethylhydroxylamine hydrochloride to provide compounds of general formula (69). Alternatively ester compounds of general formula (68) may be treated with the reagent derived from N,O-dimethylhydroxylamine hydrochloride and trimethylaluminum to provide compounds of general formula (69). Compounds of general formula (69) may be treated with aryl lithium or aryl Grignard compounds, prepared using methodology known to those in the art, to provide diamino ketones of general formula (71). For the specific case where $R_{B5}$ is an alcohol, diamino compounds of general formula (72) may be protected on the anilino nitrogen (mesylate protecting group is preferred) for example using methanesulfonyl chloride or the like, and deprotected on oxygen as described in Scheme 5, to provide diaminobenzenes of general formula (73). Phenol compounds of general formula (73) may be reacted with alcohols or alkyl halides as described in Scheme 6 to give pheyl ethers; after hydrolysis, or other deprotection, to provide diphenylketones of general structure (74). Cleavage of the preferred mesylate protecting group occurs under basic hydrolytic conditions.

Scheme 18

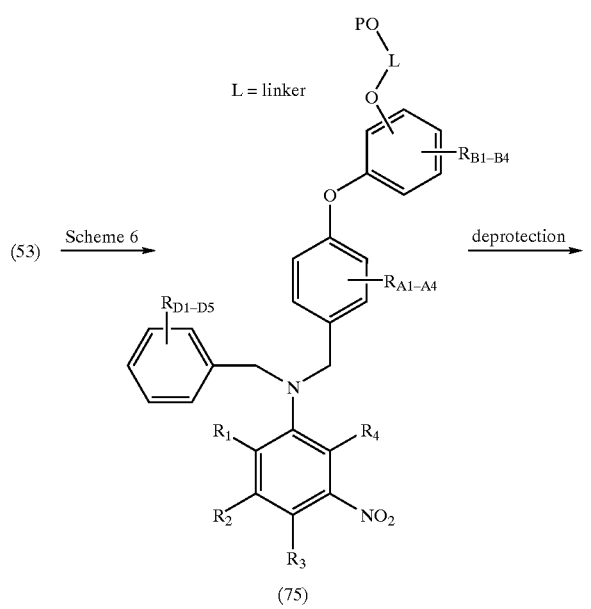

(75)

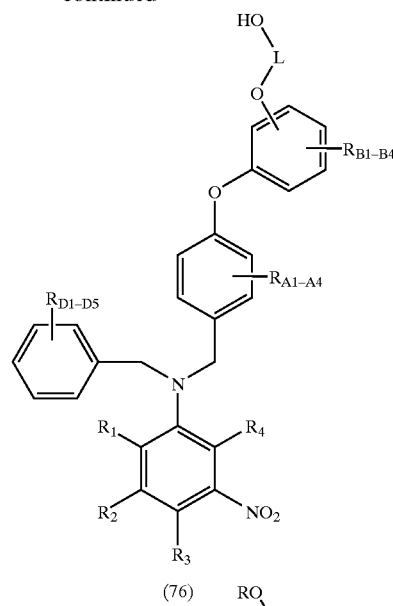

(76)

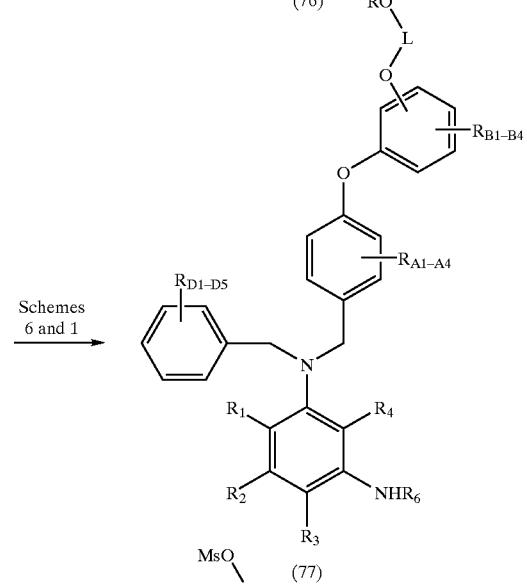

(77)

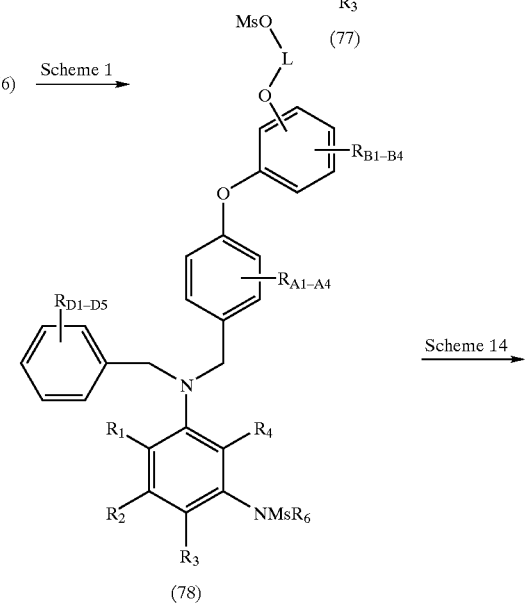

(78)

Scheme 19

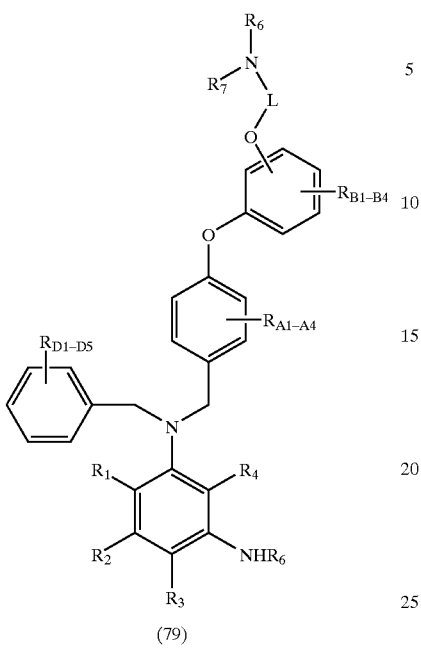

(79)

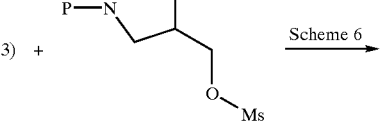

(80)

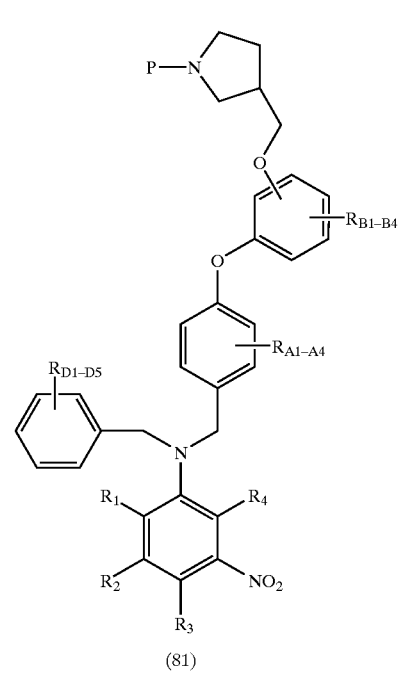

(81)

Diaminobenzenes of general formula (77) wherein R is selected from alkenyl, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylthioalkyl, alkynyl, cyanoalkyl, haloalkenyl, haloalkyl, haloalkynyl, $(NR_8R_9)$carbonyl, $(NR_8R_9)$carbonylalkyl, $(NR_{10}R_{11})$sulfonyl and $(NR_{10}R_{11})$sulfonylalkyl-$R_1$, $R_2$, $R_3$, $R_4$, $R_6$, $R_{A1}$, $R_{A2}$, $R_{A3}$, $R_{A4}$, $R_{B1}$, $R_{B2}$, $R_{B3}$, $R_{B4}$, $R_{D1}$, $R_{D2}$, $R_{D3}$, $R_{D4}$ and $R_{D5}$ are as defined in formula I, and L is a linker group, and (79), wherein $R_7$ and $R_8$ are selected from alkenyl, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylthioalkyl, alkynyl, cyanoalkyl, haloalkenyl, haloalkyl, haloalkynyl, $(NR_8R_9)$carbonyl, $(NR_8R_9)$carbonylalkyl, $(NR_{10}R_{11})$sulfonyl and $(NR_{10}R_{11})$sulfonylalkyl and $R_1$, $R_2$, $R_3$, $R_4$, $R_6$, $R_{A1}$, $R_{A2}$, $R_{A3}$, $R_{A4}$, $R_{B1}$, $R_{B2}$, $R_{B3}$, $R_{B4}$, $R_{D1}$, $R_{D2}$, $R_{D3}$, $R_{D4}$ and $R_{D5}$ are as defined in formula I, and L is a linker group, may be prepared as described in Scheme 18. L is selected from those groups delineated for $R_{B1-B4}$ but has two attachment sites. Compounds of general formula (53) may be reacted with protected diols or protected hydroxyalkyl halides according to Scheme 6 to provide nitroaromatic compounds of general formula (75). Nitroaromatic compounds of general formula (75) may be deprotected to provide alcohol compounds of general formula (76). Alcohol compounds of general formula (76) may be reacted with alcohols or alkyl halides according to Schemes 6 and 1 to provide diamino compounds of general formula (77). Alternatively, alcohol compounds of general formula (76) may be mesylated with mesyl chloride to provide mesylates of general formula (78). Mesylates of general formula (78) may be reacted with primary or secondary amines according to Scheme 14 to provide diamino compounds of general formula (79).

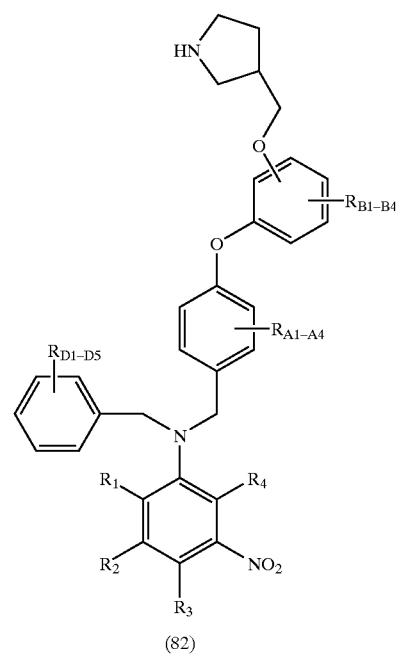

(82)

-continued

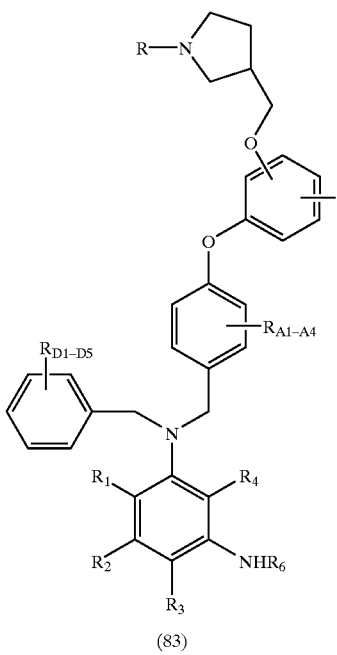

Scheme 20

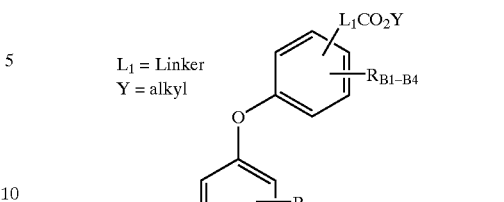

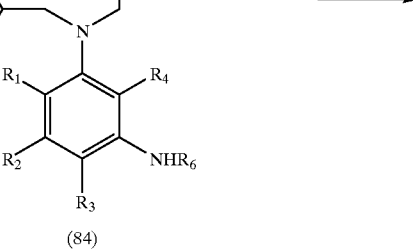

(84)

hydrolysis

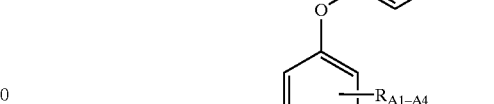

(85)

+

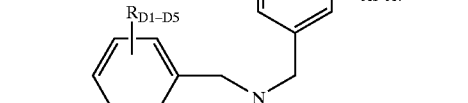

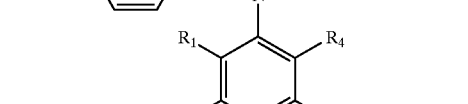

(86) coupling reagents

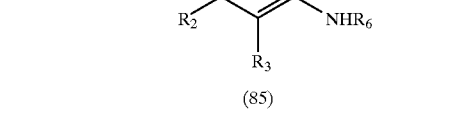

(87)

Diaminobenzenes of general formula (82) and (83), wherein R is selected from alkenyl, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylthioalkyl, alkynyl, cyanoalkyl, haloalkenyl, haloalkyl, haloalkynyl, $(NR_8R_9)$carbonyl, $(NR_8R_9)$carbonylalkyl, $(NR_{10}R_{11})$sulfonyl and $(NR_{10}R_{11})$sulfonylalkyl and $R_1$, $R_2$, $R_3$, $R_4$, $R_6$, $R_{A1}$, $R_{A2}$, $R_{A3}$, $R_{A4}$, $R_{B1}$, $R_{B2}$, $R_{B3}$, $R_{B4}$, $R_{D1}$, $R_{D2}$, $R_{D3}$, $R_{D4}$ and $R_{D5}$ are as defined in formula I, and P is a protecting group, may be prepared as described in Scheme 19. Phenols of general formula (53) may be treated with N-protected pyrollidinol mesylates of general formula (80) and a base to provide compounds of general formula (81). Compounds of general formula (81) may be deprotected to provide amine compounds of general formula (82). The pyrrolidine moiety in the amine compounds of general formula (82) may be alkylated, acylated, or sulfonylated with alkyl halides, acid chlorides or sulfonyl chlorides as described in Schemes 1, 2, or 3; reduction of the nitro group and reaction of the resultant amine with alkyl halides, acid chlorides or sulfonyl chlorides as described in Scheme 1 provides compounds of general formula (83).

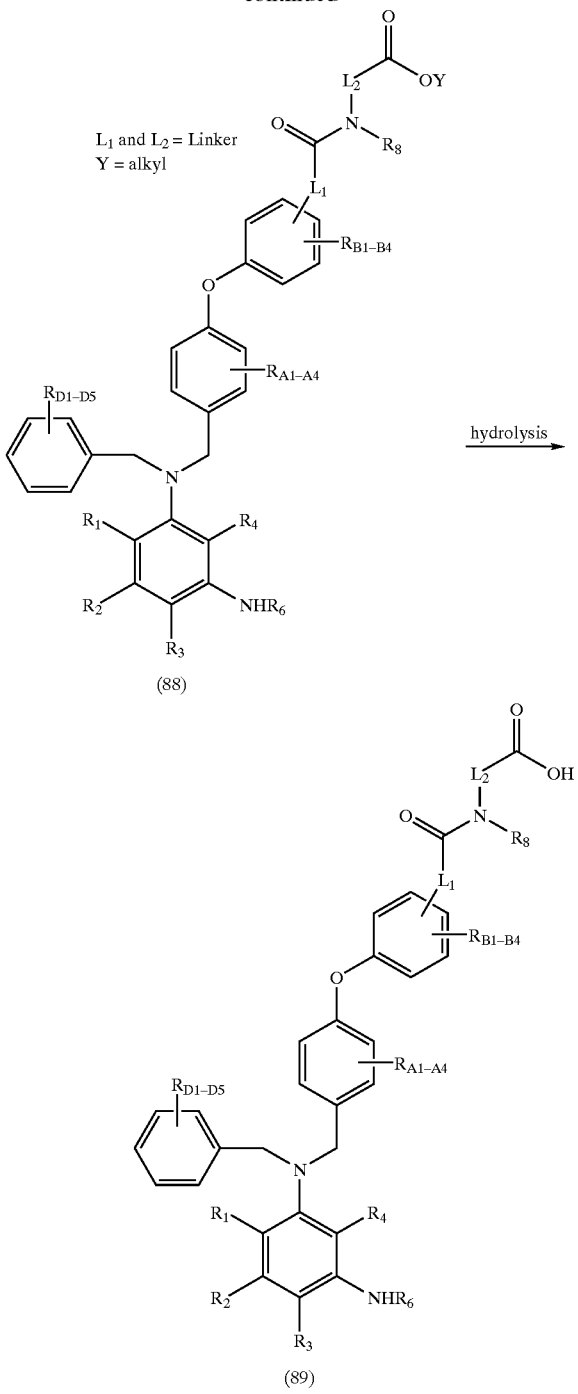

Diaminobenzenes of general formula (85, 87, 88, and 89), wherein $R_7$ and $R_8$ are selected from alkenyl, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylthioalkyl, alkynyl, cyanoalkyl, haloalkenyl, haloalkyl, haloalkynyl, $(NR_8R_9)$carbonyl, $(NR_8R_9)$carbonylalkyl, $(NR_{10}R_{11})$sulfonyl and $(NR_{10}R_{11})$sulfonylalkyl and $R_1$, $R_2$, $R_3$, $R_4$, $R_6$, $R_{A1}$, $R_{A2}$, $R_{A3}$, $R_{A4}$, $R_{B1}$, $R_{B2}$, $R_{B3}$, $R_{B4}$, $R_{D1}$, $R_{D2}$, $R_{D3}$, $R_{D4}$ and $R_{D5}$ are as defined in formula I, and $L_1$ and $L_2$ are independently linkers, may be prepared as described in Scheme 20. $L_1$ and $L_2$ are selected from those groups delineated for $R_{B1-B4}$ but have two attachment sites. Esters of general formula (84), prepared by methods described in Scheme 9 or by using methodology known to those in the art, may be hydrolyzed to provide acids of general formula (85). Acid compounds of general formula (85) may be coupled with amines of general formula (86) using appropriate coupling reagents, for example an acid anhydride or sulfonyl halide or carbodiimine reagent or the like, to provide compounds of general formula (87). For the specific case where the compounds of formula (86) are amino esters, the resultant ester compounds of general formula (88) may be hydrolyzed to provide acid compounds of general formula (89).

The compounds and processes of the present invention will be better understood by reference to the following examples, which are intended as an illustration of and not a limitation upon the scope of the invention.

EXAMPLE 1

N-{3-[bis(2-bromobenzyl)amino]-2-methylphenyl}methanesulfonamide

EXAMPLE 1A

N-(2-methyl-3-nitrophenyl)methanesulfonamide

2-Methyl-3-nitroaniline (10.0 g, 65.7 mmoles, purchased from Aldrich) in pyridine (70 mL) was treated with methanesulfonyl chloride (5.09 mL, 65.7 mmoles) at 0° C. The reaction mixture was allowed warmed to room temperature and stirred for 2 hours. The reaction mixture was concentrated under reduced pressure and the crude products were diluted with diethyl ether (700 mL). The mixture was washed with 1N HCl (250 mL), water (250 mL) and brine (250 mL). The organic layer was dried ($Na_2SO_4$), filtered, and concentrated under reduced pressure to provide the title compound which was used in the next step without further purification.

EXAMPLE 1B

N-(3-amino-2-methylphenyl)methanesulfonamide

The crude product from Example 1A and 10% palladium on carbon (1.4 g) were stirred vigorously in ethyl acetate (70 mL) for 24 hours under one atmosphere of hydrogen. The reaction was placed under a nitrogen atmosphere, filtered through a 1 inch pad of 1:1 Celite:silica gel eluting with ethyl acetate and the filtrate was concentrated under reduced pressure. The residue was purified by flash chromatography (silica gel, ethyl acetate) to provide the title compound as a brown solid (11.06 g, 84%).

EXAMPLE 1C

N-{3-[bis(2-bromobenzyl)amino]-2-methylphenyl}methanesulfonamide

The product from Example 1B (1.525 g, 7.625 mmoles) and 2-bromobenzaldehyde (1.5 mL, 12.96 mmoles) in dichloroethane (26.7 mL) were treated with glacial acetic acid (1.75 mL, 30.5 mmoles). The yellow reaction was stirred for 4 hours at room temperature and was treated with sodium triacetoxyborohydride (3.23 g, 15.25 mmoles). After stirring overnight at room temperature, the mixture was poured into saturated aqueous $NaHCO_3$ (200 mL), extracted with diethyl ether (200 mL) and the phases separated. The organic phase was washed with brine (100 mL), dried ($Na_2SO_4$), filtered and concentrated under reduced pressure. The residue was purified by flash chromatography (silica gel, 5:2→1:1 hexanes:ethyl acetate) to provide two products. The title compound, a brown solid, was isolated as the minor product (0.29 g, 7% yield). The major product isolated was the monobenzylated analogue, N-{3-[(2-bromobenzyl)amino]-2-methylphenyl}methanesulfonamide. A portion of the minor product was repurified by preparative HPLC (CH$_3$CN:0.1% TFA in H$_2$O) on a YMC ODS Guardpak column. $^1$H NMR (300 MHz, CDCl$_3$) δ7.50 (dd, J=8.0, 0.7 Hz, 2H), 7.35 (d, J=8.1 Hz, 2H), 7.18 (m, 2H), 7.07 (m, 2H), 6.03 (s, 1H), 4.30 (s, 4H), 2.90 (s, 3H), 2.16 (s, 3H); MS (APCI+) m/z 539 (M+H)$^+$.

EXAMPLE 2

N-[3-(dibenzylamino)-2-methylphenyl]methanesulfonamide

EXAMPLE 2A

N,N-dibenzyl-N-(2-methyl-3-nitrophenyl)amine

2-Methyl-3-nitroaniline (3.4 g, 22.3 mmoles, purchased from Aldrich) and diisopropylethylamine (19.5 mL, 112 mmoles) in DMF (34 mL) were treated with benzyl bromide (8.0 mL, 67 mmoles) and heated for 18 hours at 90° C. After cooling to room temperature, the mixture was diluted with diethyl ether (800 mL). The mixture was washed with saturated ammonium chloride (400 mL), water (2×400 mL), brine (400 mL), dried (Na$_2$SO$_4$), filtered and the filtrate was concentrated under reduced pressure. The residue was purified by flash chromatography (silica gel, 10:1 hexanes:ethyl acetate) to provide the title compound as a yellow oil (6.38 g, 86%).

EXAMPLE 2B

N$^1$,N$^1$-dibenzyl-2-methyl-1,3-benzenediamine

The product from Example 2A (3.4 g, 16.2 mmoles) in acetic acid (20 mL) was treated with zinc powder (2.68 g, 41 mmoles, purchased from Aldrich) and stirred for 48 hours. An additional portion of zinc (1.0 g, 15.3 mmoles) was added and stirring continued for 4 hours. The reaction was filtered through a pad of Celite with CH$_2$Cl$_2$ and concentrated. Purification by flash chromatography (silica gel, 4:1 hexanes:ethyl acetate) provided the title compound as a yellow solid (1.98 g, 64%).

EXAMPLE 2C

N-[3-(dibenzylamino)-2-methylphenyl]methanesulfonamide

The product from Example 2B was processed as described in Example 1A. The residue was purified by flash chromatography (silica gel, 1:1 hexanes:ethyl acetate) to provide the title compound as a brown solid. $^1$H NMR (300 MHz, CDCl$_3$) δ7.24 (m, 11H), 7.12 (t, J=8.0 Hz, 1H), 6.90 (d, J=7.8 Hz, 1H), 6.18 (s, 1H), 4.05 (s, 4H), 2.93 (s, 3H), 2.34 (s, 3H); MS (APCI+) m/z 381 (M+H)$^+$; HRMS (CI) m/z (calcd for C$_{22}$H$_{24}$N$_2$O$_5$S$_1$) 380.1558, observed. 380.155.

EXAMPLE 3

N-[3-(dibenzylamino)-2-methylphenyl]ethanesulfonamide

The product from Example 2B (0.03 g, 0.1 mmoles) in pyridine (2 mL) at 0° C. was treated with ethanesulfonyl chloride (0.01 g, 0.12 mmoles). The reaction mixture was quenched after 1 hour with water (2 mL), extracted with diethyl ether (5 mL), washed with water (2×2 mL), rinsed with brine (2 mL), dried (Na$_2$SO$_4$), filtered, and the filtrate concentrated under reduced pressure. The residue was purified by preparative HPLC (CH$_3$CN:0.1% TFA in H2O) on a YMC ODS Guardpak column to provide the title compound. $^1$H NMR (500 MHz, DMSO-d$_6$) δ1.22 (t, 3H, J=7.3 Hz), 2.40 (s, 3H), 3.02 (dd, 2H, J=14.6, 7.5 Hz), 4.05 (s, 4H), 6.94 (m, 2H), 7.01 (m, 1H), 7.20 (m, 2H), 7.27 (m, 7H), 8.92 (s, 1H); MS (APCI+) m/z 395 (M+H)$^+$.

EXAMPLE 4

N-[3-(dibenzylamino)-2-methylphenyl]-2-propanesulfonamide

The product from Example 2B and isopropylsulfonylchloride were processed as described in Example 3 to provide the title compound. $^1$H NMR (500 MHz, DMSO-d$_6$) δ1.23 (d, 6H, J=6.5 Hz), 2.39 (s, 3H), 3.18 (m, 1H), 4.04 (s, 4H), 6.91 (dd, 1H, J=7.5, 1.6 Hz), 6.97 (m, 2H), 7.19 (m, 2H), 7.26 (m, 8H), 8.86 (s, 1H); MS (APCI+) m/z 409 (M+H)$^+$.

EXAMPLE 5

N'-[3-(dibenzylamino)-2-methylphenyl]-N,N-dimethylsulfamide

The product from Example 2B and N,N-dimethylsulfamoylchloride were processed as described in Example 3 to provide the title compound. $^1$H NMR (500 MHz, DMSO-d$_6$) δ2.25 (s, 3H), 2.33 (m, 6H), 3.88 (s, 4H), 6.72 (dd, 1H, J=7.7, 1.5 Hz), 6.82 (m, 2H), 7.03 (m, 2H), 7.10 (m, 8H), 8.73 (s, 1H); MS (APCI+) m/z 410 (M+H)$^+$.

EXAMPLE 6

N-{3-[benzyl(4-methoxycarbonylbenzyl)amino]-2-methylphenyl}methanesulfonamide

EXAMPLE 6A

N-benzyl-2-methyl-3-nitroaniline

2-Methyl-3-nitroaniline (3.40 g, 22.3 mmoles) and benzaldehyde (3.9 mL, 38 mmoles) in dichloroethane (78 mL) were treated with glacial acetic acid (5.1 mL, 89 mmoles). The yellow reaction mixture was stirred for 4 hours at room temperature, treated with sodium triacetoxyborohydride (9.5 g, 44.6 mmoles) and allowed to stir overnight at room temperature. The mixture was poured into saturated aqueous NaHCO$_3$ (400 mL), extracted with diethyl ether (400 mL) and the phases separated. The organic phase was washed with brine (200 mL), dried (Na$_2$SO$_4$), filtered, and the filtrate was concentrated under reduced pressure. The residue was purified by flash chromatography (silica gel, 10:1→4:1 hexanes:ethyl acetate) to provide the title compound as a yellow solid (4.72 g, 87%).

EXAMPLE 6B

N-benzyl-N-(4-methoxycarbonylbenzyl)-2-methyl-3-nitroaniline

The product from Example 6A (0.92 g, 3.8 mmoles) and diisopropylethylamine (1.7 mL, 9.5 mmoles) in DMF (9.5 mL) were treated with methyl 4-(bromomethyl)benzoate (0.74 g, 7.6 mmoles) and heated for 18 hours at 90° C. After cooling to room temperature, the mixture was diluted with diethyl ether (200 mL). The mixture was washed with saturated ammonium chloride (200 mL), water (2×200 mL), brine (150 mL), dried (Na$_2$SO$_4$), filtered and the filtrate was concentrated under reduced pressure. The residue was purified by flash chromatography (silica gel, 10:1→4:1 hexanes:ethyl acetate) to provide the title compound as a yellow solid (1.26 g, 85%).

EXAMPLE 6C

N$^1$-benzyl-N$^1$-(4-methoxycarbonylbenzyl)-2-methyl-1,3-benzenediamine

The product from Example 6B (1.43 g, 3.67 mmoles) and NH$_4$Cl (0.14 g, 2.57 mmoles) in ethanol (18.4 mL) and water (6.4 mL) were treated with iron powder (1.43 g, 25.7 mmoles) and heated at 80° C. for one hour. The reaction mixture was allowed to cool to room temperature, diluted with CH$_2$Cl$_2$ (100 mL), filtered through Celite with ethyl acetate, and the filtrate was concentrated under reduced pressure to provide the title compound which was used without further purification.

EXAMPLE 6D

N-{3-[benzyl(4-methoxycarbonylbenzyl)amino]-2-methylphenyl}methanesulfonamide

The crude product from Example 6C in pyridine (8.8 mL) was treated with methanesulfonyl chloride (0.28 mL, 3.60 mmoles) at 0° C. The reaction mixture turned from clear and colorless to yellow. After 30 minutes, the mixture was quenched with water (5.0 mL) and was concentrated under reduced pressure. The residue was dissolved in diethyl ether (200 mL), washed with water (2×100 mL), brine (100 mL), dried (Na$_2$SO$_4$), filtered, and the filtrate was concentrated under reduced pressure. The residue was purified by flash chromatography (silica gel, 4:1→1:1 hexanes:ethyl acetate) to provide the title compound as a yellow solid (1.33 g, 83%). A small portion of the residue (0.1 g) was repurified by preparative HPLC (CH$_3$CN:0.1% TFA in H$_2$O) on a YMC ODS Guardpak column. $^1$H NMR (300 MHz, CDCl$_3$) δ7.92 (d, J=6.8 Hz, 2H), 7.21 (m, 8H), 7.11 (t, J=8.0 Hz, 1H), 6.89 (d, J=8.0 Hz, 1H), 6.11 (s, 1H), 4.12 (s, 2H), 4.05 (s, 2H), 3.90 (s, 3H), 2.95 (s, 3H), 2.34 (s, 3H); MS (APCI+) m/z 439 (M+H)$^+$.

EXAMPLE 7

N-{3-[benzyl(2-bromobenzyl)amino]-2-methylphenyl}methanesulfonamide

The product from Example 6A and 1-bromo-2-(bromomethyl)benzene were processed as described in Examples 6B–D to provide the title compound. $^1$H NMR (300 MHz, CDCl$_3$) δ7.50 (dd, J=8.0, 1.1 Hz, 1H), 7.34 (dd, J=7.4, 1.7 Hz, 1H), 7.03–7.29 (m, 9H), 7.01 (dd, J=8.0, 1.2 Hz, 1H), 6.04 (s, 1H), 4.20 (s, 2H), 4.13 (s, 2H), 2.90 (s, 3H), 2.23 (s, 3H); MS (ESI+) m/z 461 (M+H)$^+$.

EXAMPLE 8

N-{3-[benzyl(4-nitrobenzyl)amino]-2-methylphenyl}methanesulfonamide

EXAMPLE 8A

N-[3-(benzylamino)-2-methylphenyl]methanesulfonamide

The product from Example 1B and benzaldehyde were processed as described in Example 1C to provide the title compound.

EXAMPLE 8B

N-{3-[benzyl(4-nitrobenzyl)amino]-2-methylphenyl}methanesulfonamide

Glacial acetic acid (0.37 mL, 6.4 mmoles) was added to a solution of Example 8A (0.46 g, 1.6 mmoles) and 4-nitrobenzaldehyde (0.48 g, 3.2 mmoles) in dichloroethane (3.2 mL) and CH$_3$CN (4.0 mL). The reaction was stirred for 4 hours at room temperature and was treated with sodium triacetoxyborohydride (0.68 g, 3.2 mmoles). The reaction mixture was stirred overnight at room temperature. The mixture was poured into saturated aqueous NaHCO$_3$ (150 mL) and extracted with diethyl ether (150 mL). The organic phase was washed with brine (150 mL), dried (Na$_2$SO$_4$), filtered, and the filtrate concentrated under reduced pressure. The residue was purified by flash chromatography (5:2→1:1 hexanes:ethyl acetate) to provide the title compound as a brown solid (0.034 g, 5% yield). $^1$H NMR (300 MHz, CDCl$_3$) δ8.12 (d, J=8.9 Hz, 2H), 7.37 (d, J=8.9 Hz, 2H), 7.27 (m, 6H), 7.12 (t, J=7.8 Hz, 1H), 6.87 (d, J=8.1 Hz, 1H), 6.14 (s, 1H), 4.18 (s, 2H), 4.06 (s, 2H), 2.99 (s, 3H), 2.38 (s, 3H); MS (APCI+) m/z 426 (M+H)$^+$.

EXAMPLE 9

N-{3-[benzyl(4-fluorobenzyl)amino]-2-methylphenyl}methanesulfonamide

The product from Example 8A and 4-fluorobenzaldehyde were processed as described in Example 1C to provide the title compound. $^1$H NMR (300 MHz, CDCl$_3$) δ7.07–7.32 (m, 9H), 7.00–6.85 (m, 3H), 6.10 (s, 1H), 4.03 (s, 2H), 4.02 (s, 2H), 2.95 (s, 3H), 2.33 (s, 3H); MS (ESI+) m/z 399 (M+H)$^+$; Analysis calculated for C$_{22}$H$_{23}$FN$_2$O$_2$S 0.75 TFA: C, 58.26; H, 4.95; N, 5.79. Found: C, 58.26; H, 5.17; N, 5.63.

EXAMPLE 10

N-{3-[benzyl(2,4-difluorobenzyl)amino]-2-methylphenyl}methanesulfonamide

The product from Example 8A and 2,4-difluorobenzaldehyde were processed as described in Example 1C to provide the title compound. $^1$H NMR (300 MHz, CDCl$_3$) δ7.40–7.18 (m, 6H), 7.11 (m, 2H), 6.92 (m, 1H), 6.72 (m, 2H), 6.07 (s, 1H), 4.07 (s, 4H), 2.93 (s, 3H), 2.30 (s, 3H); MS(ESI+) m/z 417 (M+H)$^+$.

EXAMPLE 11

N-{3-[benzyl(2-cyanobenzyl)amino]-2-methylphenyl}methanesulfonamide

The product from Example 6A and 1-(bromomethyl)-2-cyanobenzene were processed as described in Examples 6B–D to provide the title compound. $^1$H NMR (300 MHz, CDCl$_3$) δ7.58 (d, J=7.2 Hz, 1H), 7.46 (m, 2H), 7.24 (m, 8H), 7.13 (t, J=8.0 Hz, 1H), 6.97 (dd, J=7.8, 1.0 Hz, 1H), 6.13 (s, 1H), 4.32 (s, 2H), 4.12 (s, 2H), 2.93 (s, 3H), 2.29 (s, 3H); MS (APCI+) m/z 406 (M+H)$^+$.

EXAMPLE 12

N-{3-[benzyl(4-methoxybenzyl)amino]-2-methylphenyl}methanesulfonamide

The product from Example 6A and 1-(chloromethyl)-4-methoxybenzene were processed as described in Examples 6B–D to provide the title compound. ¹H NMR (300 MHz, CDCl$_3$) δ7.22 (m, 6H), 7.11 (t, J=8.1 Hz, 1H), 7.08 (d, J=8.9 Hz, 2H), 6.92 (dd, J=8.2, 1.2 Hz, 1H), 6.78 (d, J=8.9 Hz, 2H), 6.10 (s, 1H), 4.10 (s, 2H), 4.05 (s, 2H), 3.77 (s, 3H), 2.92 (s, 3H), 2.29 (s, 3H); MS (APCI+) m/z 411 (M+H)⁺.

EXAMPLE 13

N-{3-[benzyl(4-bromobenzyl)amino]-2-methylphenyl}methanesulfonamide

The product from Example 6A and 1-(bromomethyl)-4-bromobenzene were processed as described in Examples 6B–D to provide the title compound. ¹H NMR (300 MHz, CDCl$_3$) δ7.37 (d, J=8.1 Hz, 2H), 7.21 (m, 6H), 7.12 (t, J=8.0 Hz, 1H), 7.05 (d, J=8.1 Hz, 2H), 6.89 (dd, J=8.1, 1.0 Hz, 1H), 6.11 (s, 1H), 4.06 (s, 2H), 4.03 (s, 2H), 2.95 (s, 3H), 2.31 (s, 3H); MS (APCI+) m/z 460 (M+H)⁺.

EXAMPLE 14

N-{3-[benzyl(3-methoxybenzyl)amino]-2-methylphenyl}methanesulfonamide

The product from Example 6A and 1-(chloromethyl)-3-methoxybenzene were processed as described in Examples 6B–D to provide the title compound. ¹H NMR (300 MHz, CDCl$_3$) δ7.21 (m, 7H), 7.12 (t, J=8.0 Hz, 1H), 6.92 (dd, J=8.0, 1.1 Hz, 1H), 6.78 (m, 3H), 6.14 (s, 1H), 4.11 (s, 2H), 4.08 (s, 2H), 3.74 (s, 3H), 2.94 (s, 3H), 2.33 (s, 3H); MS (APCI+) m/z 411 (M+H)⁺.

EXAMPLE 15

N-{3-[(1,3-benzodioxol-5-ylmethyl)(benzyl)amino]-2-methylphenyl}methanesulfonamide

EXAMPLE 15A

N-(1,3-benzodioxol-5-ylmethyl)-N-(2-methyl-3-nitrophenyl)amine

2-Methyl-3-nitroaniline and 1,3-benzodioxole-5-carbaldehyde were processed as described in Example 1C to provide the title compound.

EXAMPLE 15B

N-{3-[(1,3-benzodioxol-5-ylmethyl)(benzyl)amino]-2-methylphenyl}methanesulfonamide The product from Example 15A and benzyl bromide were processed as described in Examples 6B–D to provide the title compound. ¹H NMR (300 MHz, CDCl$_3$) δ7.16–7.37 (m, 7H), 7.05 (d, J=8.1 Hz, 1H), 6.70 (s, 1H), 6.67 (s, 2H), 6.10 (s, 1H), 5.91 (s, 2H), 4.35 (s, 2H), 4.29 (s, 2H), 2.86 (s, 3H), 2.17 (s, 3H); MS (ESI+) m/z 425 (M+H)⁺; Analysis calculated for C$_{23}$H$_{24}$N$_2$O$_4$S 0.90 TFA: C, 56.51; H, 4.76; N, 5.31. Found: C, 56.59; H, 4.68; N, 5.24.

EXAMPLE 16

N-{3-[benzyl(2,3-dihydro-1,4-benzodioxin-6-ylmethyl)amino]-2-methylphenyl}methanesulfonamide

EXAMPLE 16A

N-(2,3-dihydro-1,4-benzodioxin-6-ylmethyl)-N-(2-methyl-3-nitrophenyl)amine

2-Methyl-3-nitroaniline and 2,3-dihydro-1,4-benzodioxine-6-carbaldehyde were processed as described in Example 1C to provide the title compound.

EXAMPLE 16B

N-{3-[benzyl(2,3-dihydro-1,4-benzodioxin-6-ylmethyl)amino]-2-methylphenyl}methanesulfonamide The product from Example 16A and benzyl bromide were processed as described in Examples 6B–D to provide the title compound. ¹H NMR (300 MHz, CDCl$_3$) δ7.30–7.25 (m, 6H), 7.10 (t, J=8.0 Hz, 1H), 6.89 (dd, J=7.8, 1.0 Hz, 1H), 6.75 (m, 2H), 6.66 (dd, J=8.1, 2.0 Hz, 1H), 6.11 (s, 1H), 4.23 (s, 4H), 4.04 (s, 2H), 3.93 (s, 2H), 2.95 (s, 3H), 2.35 (s, 3H); MS (ESI+) m/z 439 (M+H)⁺; Analysis calculated for C$_{24}$H$_{26}$N$_2$O$_4$S 0.25 CHCl$_3$: C; 62.19, H, 5.65; N, 5.98. Found: C, 62.18; H, 5.66; N, 5.88.

EXAMPLE 17

N-{3-[benzyl(2-chlorobenzyl)amino]-2-methylphenyl}methanesulfonamide

The product from Example 6A and 1-(bromomethyl)-2-chlorobenzene were processed as described in Examples 6B–D to provide the title compound. ¹H NMR (300 MHz, CDCl$_3$) δ7.08–7.37 (m, 11H), 7.01 (dd, J=7.9, 1.2 Hz, 1H), 6.09 (s, 1H), 4.24 (s, 2H), 4.14 (s, 2H), 2.90 (s, 3H), 2.24 (s, 3H); MS (ESI+) m/z 415 (M+H)⁺; Analysis calculated for C$_{22}$H$_{23}$ClN$_2$O$_2$S 0.25 TFA: C, 60.94; H, 5.28; N, 6.32. Found: C, 60.99; H, 5.53; N, 6.17.

EXAMPLE 18

N-{3-[benzyl(2-fluorobenzyl)amino]-2-methylphenyl}methanesulfonamide

The product from Example 8A and 2-fluorobenzaldehyde were processed as described in Example 1C to provide the title compound. ¹H NMR (300 MHz, CDCl$_3$) δ7.22 (m, 8H), 7.10 (t, J=8.0 Hz, 1H), 6.98 (m, 3H), 6.11 (s, 1H), 4.13 (s, 2H), 4.10 (s, 2H), 2.91 (s, 3H), 2.31 (s, 3H); MS (ESI+) m/z 399 (M+H)⁺; Analysis calculated for C$_{22}$H$_{23}$FN$_2$O$_2$S 0.20 TFA: C, 63.96; H, 5.55; N, 6.65. Found: C, 64.11; H, 5.69; N, 6.61.

EXAMPLE 19

N-{3-[[4-(allyloxy)benzyl](benzyl)amino]-2-methylphenyl}methanesulfonamide

EXAMPLE 19A

N-[4-(allyloxy)benzyl]-N-(2-methyl-3-nitrophenyl)amine

2-Methyl-3-nitroaniline and 4-allyloxybenzaldehyde were processed as described in Example 1C to provide the title compound.

EXAMPLE 19B

N-{3-[[4-(allyloxy)benzyl](benzyl)amino]-2-methylphenyl}methanesulfonamide

The product from Example 19A and benzyl bromide were processed as described in Examples 6B–D to provide the title compound. ¹H NMR (300 MHz, CDCl$_3$) δ7.21 (m, 6H), 7.11 (t, J=8.0 Hz, 1H), 7.08 (d, J=8.5 Hz, 2H), 6.89 (dd, J=8.1, 1.0 Hz, 1H), 6.81 (d, J=8.8, Hz, 2H), 6.09 (s, 1H), 6.04 (m, 1H), 5.40 (ddd, J=17.3, 3.4, 1.7 Hz, 1H), 5.28 (ddd, J=10.5, 2.7, 1.4 Hz, 1H), 4.50 (dt, J=5.4, 1.4 Hz, 2H), 4.04 (s, 2H), 3.49 (s, 2H), 2.94 (s, 3H), 2.32 (s, 3H); MS (APCI+) m/z 437 (M+H)⁺.

EXAMPLE 20

N-{3-[[4-(allyloxy)benzyl](2,4-difluorobenzyl)amino]-2-methylphenyl}methanesulfonamide

EXAMPLE 20A

N-[4-(allyloxy)benzyl]-N-(2,4-difluorobenzyl)-N-(2-methyl-3-nitrophenyl)amine

The product from Example 19A and 2,4-difluorobenzyl bromide were processed as described in Example 6B to provide the title compound.

EXAMPLE 20B

N-{3-[[4-(allyloxy)benzyl](2,4-difluorobenzyl)amino]-2-methylphenyl}methanesulfonamide The product from Example 20A was processed as described in Examples 6C and 6D to provide the title compound. $^1$H NMR (300 MHz, CDCl$_3$) δ7.20 (d, J=7.1 Hz, 1H), 7.11 (m, 4H), 6.89 (d, J=7.5 Hz, 1H), 6.82 (d, J=8.8 Hz, 2H), 6.71 (m, 2H), 6.15 (s, 1H), 6.02 (s, 1H), 5.40 (ddd, J=17.3, 3.1, 1.3 Hz, 1H), 5.28 (ddd, J=10.5, 2.7, 1.4 Hz), 4.51 (dt, J=5.4, 1.5 Hz), 4.05 (s, 2H), 3.99 (s, 2H), 2.93 (s, 3H), 2.30 (s, 3H); MS (APCI+) m/z 473 (M+H)$^+$.

EXAMPLE 21

N-{3-[(2-cyanobenzyl)(2-fluoro-4-methoxybenzyl)amino]-2-methylphenyl}methanesulfonamide

EXAMPLE 21A

N-(2-fluoro-4-methoxybenzyl)-N-(2-methyl-3-nitrophenyl)amine

2-Methyl-3-nitroaniline and 2-fluoro-4-methoxybenzaldehyde were processed as described in Example 1C to provide the title compound.

EXAMPLE 21B

N-{3-[(2-cyanobenzyl)(2-fluoro-4-methoxybenzyl)amino]-2-methylphenyl}methanesulfonamide The product from Example 21A and 2-(bromomethyl)benzonitrile were processed as described in Examples 6B–D to provide the title compound. $^1$H NMR (300 MHz, CDCl$_3$) δ7.58 (d, J=7.8 Hz, 1H), 7.49 (m, 2H), 7.31 (m, 1H), 7.23 (dd, J=8.1, 1.0 Hz, 1H), 7.12 (t, J=8.0 Hz, 1H), 6.96 (m, 2H), 6.54 (m, 2H), 6.09 (s, 1H), 4.33 (s, 2H), 4.08 (s, 2H), 3.76 (s, 3H), 2.92 (s, 3H), 2.27 (s, 3H); MS (APCI+) m/z 454 (M+H)$^+$.

EXAMPLE 22

N-{3-[(2,4-difluorobenzyl)(4-methoxybenzyl)amino]-2-methylphenyl}methanesulfonamide

EXAMPLE 22A

N-(2,4-difluorobenzyl)-N-(2-methyl-3-nitrophenyl)amine

2-Methyl-3-nitroaniline and 2,4-difluorobenzaldehyde were processed as described in Example 1C to provide the title compound.

EXAMPLE 22B

N-{3-[(2,4-difluorobenzyl)(4-methoxybenzyl)amino]-2-methylphenyl}methanesulfonamide The product from Example 22A and 4-methoxybenzyl chloride were processed as described in Examples 6B–D to provide the title compound. $^1$H NMR (300 MHz, CDCl$_3$) δ7.21 (dd, J=8.0, 1.0 Hz, 1H), 7.12 (m, 4H), 6.91 (d, J=8.1 Hz, 1H), 6.79 (d, J=8.8 Hz, 2H), 6.71 (m, 2H), 6.10 (s, 1H), 4.10 (s, 2H), 4.04 (s, 2H), 3.78 (s, 3H), 2.93 (s, 3H), 2.28 (s, 3H); MS (APCI+) m/z 447 (M+H)$^+$.

EXAMPLE 23

N-{3-[(2,4-difluorobenzyl)(2-fluorobenzyl)amino]-2-methylphenyl}methanesulfonamide The product from Example 22A and 2-fluorobenzyl bromide were processed as described in Examples 6B–D to provide the title compound. $^1$H NMR (300 MHz, CDCl$_3$) δ7.21 (m, 4H), 7.11 (t, J=8.1 Hz, 1H), 6.94 (m, 6.94 (m, 3H), 6.72 (m, 2H), 6.13 (s, 1H), 4.15 (s, 2H), 4.13 (s, 2H), 2.91 (s, 3H), 2.25 (s, 3H); MS (APCI+) m/z 435 (M+H)$^+$.

EXAMPLE 24

N-{3-[bis(2,4-difluorobenzyl)amino]-2-methylphenyl}methanesulfonamide

The product from Example 22A and 2,4-difluorobenzyl bromide were processed as described in Examples 6B–D to provide the title compound. $^1$H NMR (300 MHz, CDCl$_3$) δ7.21 (m, 1H), 7.14 (m, 3H), 6.99 (dd, J=8.1, 1.0 Hz, 1H), 6.72 (m, 4H), 6.14 (s, 1H), 4.09 (s, 4H), 2.93 (s, 3H), 2.25 (s, 3H); MS (APCI+) m/z 453 (M+H)$^+$.

EXAMPLE 25

N-{3-[(2-cyanobenzyl)(2,4-difluorobenzyl)amino]-2-methylphenyl}methanesulfonamide The product from Example 22A and 2-(bromomethyl)benzonitrile were processed as described in Examples 6B–D to provide the title compound. $^1$H NMR (CDCl$_3$, 300 MHz) δ7.59 (m, 1H), 7.48 (m, 2H), 7.32 (m, 1H), 7.24 (m, 1H), 7.11 (m, 2H), 6.95 (m, 1H), 6.10 (s, 1H), 4.32 (s, 2H), 4.13 (s, 2H), 2.93 (s, 3H), 2.26 (s, 3H); MS (APCI+) m/z 442 (M+H)$^+$.

EXAMPLE 26

N-{3-[benzyl(4-phenoxybenzyl)amino]-2-methylphenyl}methanesulfonamide

EXAMPLE 26A

N-(2-methyl-3-nitrophenyl)-N-(4-phenoxybenzyl)amine 2-Methyl-3-nitroaniline and 4-phenoxybenzaldehyde were processed as described in Example 1C to provide the title compound.

EXAMPLE 26B

N-{3-[benzyl(4-phenoxybenzyl)amino]-2-methylphenyl}methanesulfonamide

The product from Example 26A and benzyl bromide were processed as described in Examples 6B–D to provide the title compound. $^1$H NMR (300 MHz, CDCl$_3$) δ7.33 (m, 2H), 7.21 (m, 6H), 7.14 (m, 4H), 6.97 (m, 3H), 6.88 (d, J=8.5 Hz, 2H), 6.10 (s, 1H), 4.18 (s, 2H), 4.15 (s, 2H), 2.91 (s, 3H), 2.27 (s, 3H); MS (ESI+) m/z 473 (M+H)$^+$.

EXAMPLE 27

N-{3-[benzyl(2-methylbenzyl)amino]-2-methylphenyl}methanesulfonamide

The product from Example 6A and 1-(bromomethyl)-2-methylbenzene were processed as described in Examples 6B–D to provide the title compound. $^1$H NMR (500 MHz, DMSO-$d_6$) δ2.16 (s, 3H), 2.28 (s, 3H), 2.88 (s, 3H), 4.06 (d, 4H, J=17.8 Hz), 7.03 (m, 6H), 7.24 (m, 6H), 8.91 (s, 1H); MS (APCI+) m/z 395 (M+H)$^+$.

EXAMPLE 28

N-{3-[benzyl(4-methylbenzyl)amino]-2-methylphenyl}methanesulfonamide

The product from Example 6A and 1-(bromomethyl)-4-methylbenzene were processed as described in Examples 6B–D to provide the title compound. $^1$H NMR (500 MHz, DMSO-$d_6$) δ2.24 (s, 3H), 2.39 (s, 3H), 2.91 (s, 3H), 4.01 (d, 4H, J=18.7 Hz), 6.90–7.30 (m, 12H), 8.94 (s, 1H); MS (APCI+) (M+H)$^+$ at m/z 395.

EXAMPLE 29

N-{3-[benzyl(4-chlorobenzyl)amino]-2-methylphenyl}methanesulfonamide

The product from Example 6A and 4-chlorobenzyl bromide were processed as described in Examples 6B–D to provide the title compound. $^1$H NMR (500 MHz, DMSO-$d_6$) δ2.39 (s, 3H), 2.92 (s, 3H), 4.05 (br.s, 4H), 6.98 (s, 3H), 7.27 (m, 9H), 8.95 (s, 1H); MS (APCI+) m/z 415 (M+H)$^+$.

EXAMPLE 30

N-(3-{benzyl[4-(trifluoromethyl)benzyl]amino}-2-methylphenyl)methanesulfonamide

The product from Example 6A and 4-trifluoromethylbenzyl bromide were processed as described in Examples 6B–D to provide the title compound. $^1$H NMR (500 MHz, DMSO-$d_6$) δ2.40 (s, 3H), 2.92 (s, 3H), 4.07 (s, 2H), 4.16 (s, 2H), 7.00 (m, 3H), 7.25 (m, 5H), 7.49 (d, 2H, J=8.1 Hz), 7.63 (d, 2H, J=8.1 Hz), 8.95 (s, 1H); MS (APCI+) m/z 448 (M+H)$^+$.

EXAMPLE 31

N-(3-{benzyl[2-fluoro-4-(trifluoromethyl)benzyl]amino}-2-methylphenyl)methanesulfonamide The product from Example 6A and 2-fluoro-4-trifluoromethylbenzyl bromide were processed as described in Examples 6B–D to provide the title compound. $^1$H NMR (500 MHz, DMSO-$d_6$) δ2.34 (s, 3H), 2.88 (s, 3H), 4.11 (s, 2H), 4.21 (s, 2H), 6.98 (m, 2H), 7.05 (t, 1H, J=8.0 Hz)), 7.22 (m, 1H), 7.28 (d, 4H, J=4.4 Hz), 7.50 (s, 2H), 7.56 (d, 1H, J=9.4 Hz), 8.96 (s, 1H); MS (APCI+) m/z 467 (M+H)$^+$.

EXAMPLE 32

N-{3-[benzyl(2,4-dichlorobenzyl)amino]-2-methylphenyl}methanesulfonamide

EXAMPLE 32A 2,4-dichloro-1-(iodomethyl)benzene 2,4-Dichloro-1-(chloromethyl)benzene (0.8 mmoles) in acetone (2 mL) was treated with NaI (0.48 g) and stirred at room temperature overnight. The solvent was removed under reduced pressure and the residue extracted with DMF to provide the title compound.

EXAMPLE 32B

N-{3-[benzyl(2,4-dichlorobenzyl)amino]-2-methylphenyl}methanesulfonamide

The product from Example 6A and the product from Example 32A were processed as described in Examples 6B–D to provide the title compound. $^1$H NMR (500 MHz, DMSO-$d_6$) δ2.32 (s, 3H), 2.89 (s, 3H), 4.12 (s, 2H), 4.16 (s, 2H), 6.98 (t, 2H, J=8.0 Hz), 7.05 (t, 1H, J=7.8 Hz), 7.24 (m, 5H), 7.33 (dd, 1H, J=8.2, 2.0 Hz), 7.40 (d, 1H, J=8.1 Hz), 7.52 (d, 1H, J=1.9 Hz), 8.83–9.05 (br.s, 1H); MS (APCI+) m/z 450 (M+H)$^+$.

EXAMPLE 33

N-{3-[(2,4-difluorobenzyl)(4-{[3-phenyl-2-propenyl]oxy}benzyl)amino]-2-methylphenyl}methanesulfonamide

EXAMPLE 33A

N-(2,4-difluorobenzyl)-N-(4-hydroxybenzyl)-2-methyl-3-nitroaniline

The product from Example 20A (1.19 g, 2.81 mmoles) and Pd(PPh$_3$)$_4$ (0.16 g, 0.14 mmoles) in CH$_2$Cl$_2$ (11.2 mL) was treated with phenylsilane (0.7 mL, 5.63 mmoles) and allowed to stir for 2 hours at room temperature. The residue was purified by flash chromatography (silica gel, 4:1 hexanes:ethyl acetate) to provide the title compound as a yellow oil (1.03 g, 96%).

EXAMPLE 33B

N-(2,4-difluorobenzyl)-2-methyl-3-nitro-N-(4-{[3-phenyl-2-propenyl]oxy}benzyl)aniline The product from Example 33A (0.1 g, 26 mmoles) in DMF (0.65 mL) was treated with sodium hydride (0.011 g, 0.26 mmoles). After 10 minutes, the reaction mixture was treated with cinnamyl bromide (0.10 g, 0.52 mmoles) and shaken overnight. The mixture was diluted with diethyl ether (50 mL), washed with saturated ammonium chloride (50 mL) and water (2×50 mL), brine (50 mL), dried (Na$_2$SO$_4$), filtered and the filtrate concentrated under reduced pressure to provide the title compound which was used in the next step without further purification.

EXAMPLE 33C

N-{3-[(2,4-difluorobenzyl)(4-{[3-phenyl-2-propenyl]oxy}benzyl)amino]-2-methylphenyl}methanesulfona The crude product from Example 33B was processed as described in Examples 6C and 6D to provide the title compound as a brown solid (0.020 g, 14%). $^1$H NMR (300 MHz, CDCl$_3$) δ7.50 (m, 2H), 7.33 (m, 2H), 7.21 (m, 2H), 7.13 (m, 3H), 6.94 (d, J=7.8 Hz, 1H), 6.85 (d, J=8.8 Hz, 2H), 6.21 (m, 2H), 6.39 (dt, J=15.9, 5.8 H), 6.09 (s, 1H), 4.67 (dd, J=5.9, 1.5 Hz, 2H), 4.15 (s, 2H), 4.08 (s, 2H), 2.91 (s, 3H), 2.26 (s, 3H); MS (APCI+) m/z 549 (M+H)$^+$.

EXAMPLE 34

N-{3-[[4-(benzyloxy)benzyl](2,4-difluorobenzyl)amino]-2-methylphenyl}methanesulfonamide

EXAMPLE 34A

N-[4-(benzyloxy)benzyl]-N-(2,4-difluorobenzyl)-2-methyl-3-nitroaniline

The product from Example 33A and benzyl bromide were processed as described in Example 33B to provide the title compound.

EXAMPLE 34B

N-{3-[[4-(benzyloxy)benzyl](2,4-difluorobenzyl)amino]-2-methylphenyl}methanesulfonamide The product from Example 34A was processed as described in Examples 6C and 6D to provide the title compound. $^1$H NMR (300 MHz, CDCl$_3$) δ7.38 (m, 3H), 7.23 (m, 1H), 7.13 (m, 3H), 6.97 (J=7.1 Hz, 1H), 6.86 (d, J=8.8 Hz, 2H), 6.73 (m, 2H), 6.08 (s, 1H), 5.02 (s, 2H), 4.22 (s, 2H), 4.14 (s, 2H), 2.89 (s, 3H), 2.21 (s, 3H); MS(ESI+) m/z 523 (M+H)$^+$.

EXAMPLE 35

N-{3-[benzyl(4-{[3-bromo-2-propenyl]oxy}benzyl)amino]-2-methylphenyl}methanesulfonamide

EXAMPLE 35A

N-(4-{[3-bromo-2-propenyl]oxy}benzyl)-N-(2,4-difluorobenzyl)-2-methyl-3-nitroaniline The product from Example 33A and 1,3-dibromo-1-propene were processed as described in Example 33B to provide the title compound.

EXAMPLE 35B

N-{3-[benzyl(4-{[3-bromo-2-propenyl]oxy}benzyl)amino]-2-methylphenyl}methanesulfonamide The product from Example 35A was processed as described in Examples 6C and 6D to provide the title compound. $^1$H NMR (300 MHz, CDCl$_3$) δ7.24 (m, 5H), 7.19 (d, J=7.8 Hz, 2H), 7.08 (d, J=8.8 Hz, 2H), 6.87 (m, 1H), 6.78 (d, J=8.8 Hz, 1H), 6.44 (m, 2H), 6.14 (s, 1H), 4.45 (d, J=4.4 Hz, 2H), 4.03 (s, 2H), 3.98 (s, 2H), 2.95 (s, 3H), 2.34 (s, 3H); MS (APCI+) m/z 515 (M)+.

EXAMPLE 36

N-{3-[bis(2-bromobenzyl)amino]-4-methoxyphenyl}methanesulfonamide

EXAMPLE 36A

N,N-bis(2-bromobenzyl)-N-(2-methoxy-5-nitrophenyl)amine

2-Methoxy-5-nitroaniline and 1-bromo-2-(bromomethyl)benzene were processed as described in Example 2A to provide the title compound.

EXAMPLE 36B

N-{3-[bis(2-bromobenzyl)amino]-4-methoxyphenyl}methanesulfonamide

The product from Example 36A was processed as described in Examples 6C and 6D to provide the title compound. $^1$H NMR (300 MHz, CDCl$_3$) δ7.55–7.45 (m, 4H), 7.22 (td, J=7.5, 1.1 Hz, 2H), 7.07 (td, J=7.7, 1.7 Hz, 2H), 6.90 (dd, J=8.6, 2.5 Hz, 1H), 6.82 (d, J=8.8 Hz, 1H), 6.60 (d, J=2.0 Hz, 1H), 6.03 (bs, 1H), 4.48 (s, 4H), 3.80 (s, 3H), 2.58 (s, 3H); MS (ESI+) m/z 555 (M+H)$^+$; Analysis calculated for C$_{22}$H$_{22}$Br$_2$N$_2$O$_3$S 0.40 TFA: C, 45.65; H, 3.76; N, 4.67. Found: C, 45.66; H, 3.84; N, 4.67.

EXAMPLE 37

N-(3-{(2-bromobenzyl)[cyano(phenyl)methyl]amino}-2-methylphenyl)methanesulfonamide The major product from Example 1C (0.21 g), potassium cyanide (0.10 g, 1.06 mmoles), and benzaldehyde (0.14 mL, 1.41 mmoles) in methanol (1.86 mL) and acetonitrile (1.0 mL) were treated with acetic acid (0.86 mL). The reaction was shaken vigorously overnight and was then concentrated under reduced pressure. The residue was purified by flash chromatography (silica gel, 4:1→1:1 hexanes:ethyl acetate) to provide the title compound as a brown solid (0.22 g, 83%). A portion of the product (0.1 g) was repurified by preparative HPLC (CH$_3$CN:0.1% TFA in H2O) on a YMC ODS Guardpak column. $^1$H NMR (300 MHz, CDCl$_3$) δ7.66 (dd, J=7.1, 2.0 Hz, 1H), 7.50 (d, J=7.1 Hz, 1H), 7.32 (m, 7H), 7.08 (m, 3H), 5.91 (s, 1H), 5.25 (s, 1H), 4.56 (d, J=13.6 Hz, 1H), 4.21 (d, J=13.6 Hz, 1H), 2.78 (s, 3H), 1.84 (s, 3H); MS (APCI+) m/z 486 (M+H)$^+$.

EXAMPLE 38

N-(3-{benzyl[4-(methoxymethyl)benzyl]amino}-2-methylphenyl)methanesulfonamide

EXAMPLE 38A

N-benzyl-N-(4-hydroxymethylbenzyl)-2-methyl-3-nitroaniline

The product from Example 6B (0.55 g, 1.4 mmoles) in THF (3.5 mL) was treated with diisobutylaluminum hydride (DIBAL) (2.94 mL, 2.94 mmoles, 1.0M in hexanes) dropwise at −78° C. After 30 minutes, an additional portion of DIBAL (1.5 mL) was added dropwise. After an additional 30 minutes, the acetone/dry ice bath was removed and the reaction mixture was carefully quenched with saturated NH$_4$Cl. The mixture was diluted with diethyl ether (200 mL) and saturated sodium potassium tartrate (250 mL) and stirred vigorously for 2.5 hours. The two phases were separated and the organic phase was washed with brine, dried (Na$_2$SO$_4$), filtered, and the filtrate concentrated under reduced pressure. The residue was purified by flash chromatography (silica gel, 4:1→1:1 hexanes:ethyl acetate) to provide the title compound as a yellow oil (0.46 g, 91%).

EXAMPLE 38B

N-benzyl-N-[4-(methoxymethyl)benzyl]-2-methyl-3-nitroaniline

The product from Example 38A (0.1 g, 0.276 mmoles) in DMF (0.7 mL) was treated with sodium hydride (0.012 g, 0.3 mmoles, 60% dispersion). After 10 minutes, the reaction mixture was treated with iodomethane (0.02 mL, 0.36 mmoles) and then stirred overnight at room temperature. The mixture was diluted with diethyl ether (100 mL), washed with saturated ammonium chloride (50 mL) and water (50 mL) twice, washed with brine (50 mL), dried (Na$_2$SO$_4$), filtered and concentrated under reduced pressure to provide the title compound which was used in the next step without further purification.

EXAMPLE 38C

N-(3-{benzyl[4-(methoxymethyl)benzyl]amino}-2-methylphenyl)methanesulfonamide

The crude product from Example 38B was processed as described in Examples 6C and 6D to provide the title compound as a brown oil (0.056 g, 48%). $^1$H NMR (300 MHz, CDCl$_3$) δ7.20 (m, 10H), 7.10 (t, J=8.0 Hz, 1H), 6.89 (d, J=7.5 Hz, 1H), 6.10 (s, 1H), 4.41 (s, 2H), 4.05 (s, 4H), 3.39 (s, 3H), 2.95 (s, 3H), 2.34 (s, 3H); MS (APCI+) m/z 425 (M+H)$^+$.

EXAMPLE 39

N-(3-{benzyl[4-(hydroxymethyl)benzyl]amino}-2-methylphenyl)methanesulfonamide

The product from Example 6D and diisobutylaluminum hydride were processed as described in Example 38A to provide the title compound. $^1$H NMR (300 MHz, CDCl$_3$) δ7.21 (m, 10H), 7.97 (t, J=8.0 Hz, 1H), 6.88 (dd, J=8.5, 1.0 Hz, 1H), 6.12 (s, 1H), 4.67 (d, J=8 Hz, 2H), 4.05 (s, 2H), 4.03 (s, 2H), 2.96 (s, 3H), 2.37 (s, 2H; MS (APCI+) m/z 411 (M+H)$^+$.

EXAMPLE 40

N-[3-(dibenzylamino)-2-((E)-3-ethoxy-3-oxo-1-propenyl)phenyl]methanesulfonamide

EXAMPLE 40A

N,N-dibenzyl-N-[2-(1,3-dioxolan-2-yl)-3-nitrophenyl]amine

Benzyl bromide (2.14 mL, 17.98 mmoles) was added to a solution of 2-(1,3-dioxolan-2-yl)-3-nitroaniline (prepared according to Wall, M. E.; Wani, M. C.; Nicholas, A. W.; Manikumar, G.; Tele, C.; Moore, L.; Truesdale, A.; Leitner, P.; Besterman, J. M.; J. Med. Chem. 1993, 36, 2689) (1.888 g, 8.99 mmoles) and diisopropylethylamine (3.1 mL, 17.98 mmoles) in DMF (18.0 mL) and the reaction was heated at 85° C. overnight. After cooling to room temperature, the mixture was diluted with diethyl ether (250 mL), washed with saturated ammonium chloride (200 mL), water (2×200 mL), brine (150 mL), dried (Na$_2$SO$_4$), filtered, and the filtrate concentrated under reduced pressure. The residue was purified by flash chromatography (silica gel, 4:1 hexanes:ethyl acetate) to provide the title compound (1.51 g, 43%) as a black oil.

EXAMPLE 40B

N,N-dibenzyl-N-[2-(formyl)-3-nitrophenyl]amine

The product from Example 40A (1.51 g) was processed as described in Example 6C to provide the title compound (0.76 g, 72%).

EXAMPLE 40C ethyl (2E)-3-[2-amino-6-(dibenzylamino)phenyl]-2-propenoate

Sodium hydride (0.046 g, 1.14 mmoles, 60% dispersion) was added to a solution of triethylphosphonoacetate (0.23 mL, 1.14 mmoles) in TBF (1.4 mL) at 0° C. After 15 minutes, the product from Example 40B (0.3 g, 0.95 mmoles) in THF (1.4 mL) was added dropwise and the reaction mixture was stirred overnight. The mixture was diluted with diethyl ether (150 mL), washed with water (100 mL), brine (100 mL), dried (Na$_2$SO$_4$), filtered, and the filtrate concentrated under reduced pressure. The residue was purified by flash chromatography (silica gel, 4:1 hexanes:ethyl acetate) to provide the title compound (0.29 g, 78%).

EXAMPLE 40D

N-[3-(dibenzylamino)-2-((E)-3-ethoxy-3-oxo-1-propenyl)phenyl]methanesulfonamide

The product from Example 40C was processed as described in Example 6D to provide the title compound as a brown solid. A portion of the product (0.1 g) was purified by preparative HPLC (CH$_3$CN:0.1% TFA in H$_2$O) on a YMC ODS Guardpak column. $^1$H-NMR (300 MHz, CDCl$_3$) δ8.06 (d, J=17.0 Hz), 7.22 (m, 12H), 6.85 (dd, J=7.8, 1.0 Hz, 1H), 6.78 (s, 1H), 6.27 (d, J=17.0, 1H), 4.29 (s, 4H), 2.99 (s, 3H); MS (APCI+) m/z 465 (M+H)$^+$.

EXAMPLE 41

N-(3-{benzyl[4-(2-hydroxyethoxy)benzyl]amino}-2-methylphenyl)methanesulfonamide

EXAMPLE 41A

N-(3-{benzyl[4-(2,3-dihydroxypropoxy)benzyl]amino}-2-methylphenyl)methanesulfonamide The product from Example 19B (2.93 g, 6.72 mmoles) and 4-methyl-morpholine N-oxide (0.8660 g, 7.4 mmoles) in acetone (30 mL) and water (4.3 mL) were treated with osmium tetroxide (1.7 mL, 0.0168 mmoles, 2.5 wt % solution in 2-methyl-2-propanol) and allowed to stirr at room temperature overnight. The mixture was then treated with 1,4-Diazabicyclo[2.2.2]octane (0.05 g) and 4-methyl-morpholine N-oxide (0.8660 g, 7.4 mmoles) and allowed to stir for an additional 24 hours. Saturated NaHSO$_3$ (250 mL) and ethyl acetate (250 mL) were added and the reaction mixture was stirred vigorously for 2.5 hours. The mixture was partitioned and the organic phase washed with brine, dried (Na$_2$SO$_4$), filtered and the filtrate concentrated under reduced pressure. The residue was purified by flash chromatography (silica gel, ethyl acetate) to provide the title compound as a yellow oil (3.0 g, 95%).

EXAMPLE 41B

N-(3-{benzyl[4-(2-hydroxyethoxy)benzyl]amino}-2-methylphenyl)methanesulfonamide

The product from Example 41A (0.6 g, 1.27 mmoles) in benzene (11.6 mL) and ethanol (11.6 mL) was treated with lead tetraacetate (0.6215 g, 1.4 mmoles) at 0° C. The reaction mixture turned from clear and colorless to light yellow and was stirred for 15 minutes. The mixture was diluted with diethyl ether (100 mL), filtered through a 1 inch pad of 1:1 Celite:silica gel and the filtrate was concentrated under reduced pressure. The residue (0.07 g, 0.16 mmoles) was dissolved in ethanol (1.0 mL) and treated with sodium borohydride (0.006 g, 0.16 mmoles). After 30 minutes, the reaction mixture was filtered through silica gel using 2:1 ethyl acetate:hexanes and concentrated under reduced pressure. The residue was purified by preparative HPLC (CH$_3$CN:0.1% TFA in H$_2$O) on a YMC ODS Guardpak column to provide the title compound as a brown oil (0.055 g). $^1$H NMR (300 MHz, CDCl$_3$) δ7.21 (m, 10H), 6.75 (dd, J=8.8, 1.7 Hz, 2H), 6.04 (s, 1H), 4.66 (dd, J=5.4, 3.7 Hz, 1H), 4.57 (d, J=10.3 Hz, 2H), 4.52 (d, J=10.3 Hz, 2H), 4.21 (s, 1H), 4.02 (m, 1H), 3.95 (m, 1H), 3.72 (s, 1H), 2.76 (s, 3H), 1.98 (s, 3H); MS (APCI+) m/z 441 (M+H)$^+$.

EXAMPLE 42

N-[3-(dibenzylamino)-2-(hydroxymethyl)phenyl]methanesulfonamide

EXAMPLE 42A

N-[3-(dibenzylamino)-2-formylphenyl]methanesulfonamide

The product from Example 40B was processed as described in Example 6D to provide the title compound.

EXAMPLE 42B

N-[3-(dibenzylamino)-2-(hydroxymethyl)phenyl]methanesulfonamide

The product from Example 42A (0.017 g, 0.043 mmoles) in ethanol (2 mL) was treated with sodium borohydride (0.002 g, 0.053 mmoles). After stirring two hours at room temperature, the reaction mixture was quenched with saturated ammonium chloride and extracted with chloroform. The extracts were combined, dried with sodium sulfate, filtered and the filtrate concentrated under reduced pressure. The residue was purified by flash chromatography (silica gel, 30% ethyl acetate/hexanes) to provide the title compound (0.015 g, 88%). $^1$H NMR (300 MHz, CDCl$_3$) δ7.63 (s, 1H), 7.12–7.38 (m, 13H), 4.67 (s, 2H), 4.06 (s, 4H), 2.85 (s, 3H); MS (ESI+) m/z 397 (M+H)$^+$.

EXAMPLE 43

N-{3-[(2,4-difluorobenzyl)(4-propoxybenzyl)amino]-2-methylphenyl}methanesulfonamide

EXAMPLE 43A

N-(2,4-difluorobenzyl)-2-methyl-3-nitro-N-(4-propoxybenzyl)aniline

The product from Example 33A and 1-iodopropane were processed as described in Example 33B to provide the title compound.

EXAMPLE 43B

N-{3-[(2,4-difluorobenzyl)(4-propoxybenzyl)amino]-2-methylphenyl}methanesulfonamide The product from Example 43A was processed as described in Examples 6C and 6D to provide the title compound. $^1$H NMR (300 MHz, CDCl$_3$) δ7.30–7.10 (m, 4H), 6.96 (m, 1H), 6.63–6.83 (m, 5H), 6.07 (s, 1H), 3.96–4.32 (m, 4H), 3.87 (t, J=6.6 Hz, 2H), 2.88 (s, 3H), 2.26 (s, 3H), 1.78 (m, 2H), 1.02 (t, J=7.5 Hz, 3H); MS (ESI+) m/z 475 (M+H)$^+$.

EXAMPLE 44

N-[3-(dibenzylamino)-2-vinylphenyl]methanesulfonamide

EXAMPLE 44A 1,3-dinitro-2-vinylbenzene

1-Chloro-2,6-dinitrobenzene (1.00 g, 4.94 mmoles, purchased from Lancaster) tris(dibenzylideneacetone)dipalladium (0.113 g, 0.123 mmoles), tri-2-furylphosphine (0.229 g, 0.987 mmoles), copper(I) iodide (0.094 g, 0.494 mmoles), and lithium chloride (0.628 g, 14.8 mmoles) in N,N-dimethylformamide (15 mL) were treated with tributylethenylstannane (2.90 mL, 9.87 mmoles). The reaction mixture was degassed with nitrogen, stirred overnight at room temperature and then heated at 80° C. for 4 hours. The reaction mixture was then diluted with ethyl acetate and washed with water and brine. The organic phase was dried with sodium sulfate, filtered and the filtrate concentrated under reduced pressure. The residue was purified by flash chromatography (silica gel, 10% ethyl acetate/hexanes) to provide the title compound (0.669 g, 70%). MS (DCI) m/z 194 (M+H)$^+$.

EXAMPLE 44B 3-nitro-2-vinylaniline

The product from Example 44A (0.669 g, 3.45 mmoles) in 3:1 ethanol:water (40 mL) was treated with sodium sulfide nonahydrate (1.66 g, 6.90 mmoles) and heated at reflux for 30 minutes. The mixture was allowed to cool to room temperature and then concentrated under reduced pressure. The residue was mixed with water and extracted with chloroform (2×). The chloroform extracts were combined, washed with brine, dried with sodium sulfate and the filtrate concentrated under reduced pressure. The residue was purified by flash chromatography (silica gel, 25% ethyl acetate/hexanes) to provide the title compound (0.137 g, 24%). MS (DCI) m/z 165 (M+H)$^+$.

EXAMPLE 44C

N,N-dibenzyl-N-(3-nitro-2-vinylphenyl)amine

The product from Example 44B and benzyl bromide were processed as described in Example 2A to provide the title compound.

EXAMPLE 44D

N-[3-(dibenzylamino)-2-vinylphenyl]methanesulfonamide

The product from Example 44C was processed as described in Examples 6C and 6D to provide the title compound. $^1$H NMR (300 MHz, CDCl$_3$) δ7.10–7.32 (m, 13H), 6.96 (dd, J=18.6, 11.6 Hz, 1H), 6.75 (dd, J=8.2, 1.0 Hz, 1H), 5.77 (dd, J=11.5, 1.4 Hz, 1H), 5.51 (dd, J=18.5, 1.2 Hz, 1H), 2.95 (s, 4H), 1.53 (s, 3H); MS (ESI+) m/z 393 (M+H)$^+$.

EXAMPLE 45

N-[3-(dibenzylamino)-2-ethylphenyl]methanesulfonamide

The product from Example 44D (0.040 g, 0.102 mmoles) and p-toluenesulfonhydrazide (0.150 g, 1.02 mmoles) in ethylene glycol dimethyl ether (5 mL) at reflux were treated dropwise over a four hour period with a solution of sodium acetate trihydrate (0.232 g, 1.70 mmoles) in water. After the addition, the reaction mixture was allowed to cool to room temperature, poured into water and extracted with methylene chloride (3×). The extracts were combined, dried with sodium sulfate, filtered and concentrated under reduced pressure. The residue was purified by preparative HPLC (CH$_3$CN:0.1% TFA in H$_2$O) on a YMC ODS Guardpak column. $^1$H NMR (300 MHz, CDCl$_3$) δ7.32 (dd, J=8.0, 1.2 Hz, 1H), 7.35–7.15 (m, 11H), 7.09 (dd, J=8.0, 1.2 Hz, 1H), 6.14 (s, 1H), 4.09 (s, 4H), 2.85 (s, 3H), 2.74 (q, J=7.6 Hz, 2H), 1.00 (t, J=7.6 Hz, 3H); MS (ESI+) m/z 395 (M+H)$^+$.

EXAMPLE 46

N-[3-(dibenzylamino)-2-(methoxymethyl)phenyl]methanesulfonamide

EXAMPLE 46A

N,N-dibenzyl-2-formyl-3-nitroaniline

The product from Example 40A (1.88 g, 4.83 mmoles) in tetrahydrofuran (30 mL) was treated with an aqueous solution of 2N sulfuric acid (1.24 mL) and allowed to stirr overnight at 65° C. The mixture was cooled to room temperature, quenched with saturated sodium bicarbonate, and concentrated under reduced pressure. The residue was mixed with diethylether and washed with water, brine, dried with sodium sulfate, filtered, and the filtrate was concentrated under reduced pressure to provide the title compound. MS (ESI+) at m/z 347 (M+H)+.

EXAMPLE 46B

N,N-dibenzyl-2-hydroxymethyl-3-nitroaniline

The product from Example 46A (1.5 g, 4.33 mmoles) in ethanol (10 mL) and tetrahydrofuran (4 mL) was treated with sodium borohydride (0.164 g, 4.33 mmoles). After stirring for 30 minutes at room temperature, the mixture was quenched with saturated ammonium chloride and diluted with diethyl ether. The diethyl ether was washed with saturated ammonium chloride, brine, dried with sodium sulfate, filtered and the filtrate concentrated under reduced pressure. The residue was purified by flash chromatography (silica gel, 10:1 to 4:1 hexanes:ethyl acetate) to provide the title compound (1.39 g, 92%). MS (ESI+) m/z 348 (M+H)+.

EXAMPLE 46C

N,N-dibenzyl-2-(methoxymethyl)-3-nitroaniline

The product from Example 46B (0.12 g, 0.33 mmoles) in anhydrous N,N-dimethylformamide (1 mL) was treated with 60% sodium hydride (0.016 g, 0.40 mmoles). After stirring for 10 minutes at room temperature, the mixture was treated with iodomethane (0.031 mL, 0.50 mmoles) and allowed to stir overnight at room temperature. The reaction mixture was quenched with saturated ammonium chloride and extracted with ethyl acetate (3×). The ethyl acetate phases were combined, dried with sodium sulfate, filtered and the filtrate concentrated under reduced pressure to provide the title compound. MS (ESI+) m/z 363 (M+H)+.

EXAMPLE 46D

N-[3-(dibenzylamino)-2-(methoxymethyl)phenyl] methanesulfonamide

The product from Example 46C was processed as described in Examples 6C and 6D to provide the title compound. $^1$H NMR (300 MHz, CDCl$_3$) δ7.99 (s, 1H), 7.32 (d, J=8.1 Hz, 1H), 7.30–7.10 (m, 11H), 6.96 (d, J=7.7 Hz, 1H), 4.64 (s, 2H), 4.09 (s, 4H), 3.25 (s, 3H), 2.90 (s, 3H); MS (ESI+) m/z 411 (M+H)+.

EXAMPLE 47

N-[3-(dibenzylamino)-2-(ethoxymethyl)phenyl] methanesulfonamide

EXAMPLE 47A

N,N-dibenzyl-2-(ethoxymethyl)-3-nitroaniline

The product from Example 46B and iodoethane were processed as described in Example 46C to provide the title compound.

EXAMPLE 47B

N-[3-(dibenzylamino)-2-(ethoxymethyl)phenyl] methanesulfonamide

The product from Example 47A was processed as described in Examples 6C and 6D to provide the title compound. $^1$H NMR (300 MHz, CDCl$_3$) δ8.17 (s, 1H), 7.34 (d, J=7.8 Hz, 1H), 7.10–7.31 (m, 1H), 6.98 (d, J=8.4 Hz, 1H), 4.66 (s, 2H), 4.14 (bs, 4H), 3.39 (q, J=7.0 Hz, 2H), 2.87 (s, 3H), 1.17 (t, J=6.9 Hz, 3H); MS (ESI+) m/z 425 (M+H)+.

EXAMPLE 48

N-{3-[[4-(4-bromophenoxy)benzyl](2,4-difluorobenzyl)amino]-2-methylphenyl}methanesulfonamide

EXAMPLE 48A

N-[4-(4-bromophenoxy)benzyl]-N-(2,4-difluorobenzyl)-2-methyl-3-nitroaniline

The product from Example 33A (1.0 g, 2.6 mmoles), 4 Å molecular sieves, Cu(OAc)$_2$ (0.71 g, 3.91 mmoles) and 4-bromophenylboronic acid (1.57 g, 7.81 mmoles) in CH$_2$Cl$_2$ (20 mL) was treated with triethylamine (1.81 mL, 13.0 mmoles) and the resulting solution was stirred vigorously overnight. An additional equivalent of Cu(OAc)$_2$, 4-bromophenylboronic acid, and triethylamine were added and the reaction mixture was stirred vigorously for 5 hours. The mixture was filtered through a 1 inch pad of Celite using CH$_2$Cl$_2$ and the filtrate was concentrated under reduced pressure. The residue was purified by flash chromatography (silica gel, 10:1 hexanes:ethyl acetate) to provide the title compound as a yellow oil (0.87 g, 62%).

EXAMPLE 48B

N-{3-[[4-(4-bromophenoxy)benzyl](2,4-difluorobenzyl)amino]-2-methylphenyl}methanesulfonamide The product from Example 48A was processed as described in Examples 6C and 6D to provide the title compound. $^1$H NMR (300 MHz, CDCl$_3$) δ7.42 (m, 2H), 7.20 (m, 6H), 7.05–7.19 (m, 2H), 6.90 (d, J=8.8 Hz, 2H), 6.84 (m, 2H), 6.68–6.76 (m, 2H), 6.11 (s, 1H), 4.07 (s, 21), 4.05 (s, 2H), 2.96 (s, 3H), 2.32 (s, 3H); MS(ESI+) (M)+ at m/z 587.

EXAMPLE 49

N-{3-[(4-(4-(3-ethoxy-3-oxopropyl)phenoxy) benzyl -difluorobenzyl)amino]-2-methylphenyl}methanesulfonamide The product from Example 48B (0.14 g, 0.23 mmoles) and Pd(PPh$_3$)$_4$ (0.027 g, 0.023 mmoles) was treated with 2-ethoxycarbonylethylzincbromide (0.5M in THF, 1.87 mL, 0.93 mmoles, purchased from Aldrich). The resulting solution was degassed and heated at 75° C. overnight. The mixture was filtered through a 1 inch pad of Celite using diethyl ether and the filtrate was concentrated under reduced pressure. The residue was purified by flash chromatography (silica gel, 4:1→1:1 hexanes:ethyl acetate) to provide the title compound (0.11 g, 77%). $^1$H NMR (300 MHz, CDCl$_3$) δ7.06–7.22 (m, 8H), 6.86–6.93 (m, 4H), 6.69–6.77 (m, 2H), 6.09 (s, 1H), 4.12 (q, J=7.1 Hz, 2H), 4.07 (s, 2H), 4.03 (s, 2H), 2.95 (s, 3H), 2.93 (t, J=8.1 Hz, 2H), 2.61 (t, J=8.1 Hz, 2H), 2.31 (s, 3H), 1.24 (t, J=7.1 Hz, 3H); MS (APCI+) (M+H)+ at m/z 609.

EXAMPLE 50

N-{3-[(4-(4-(2-carboxyethyl)phenoxy)benzyl)(2,4-difluorobenzyl)amino]-2-methylphenyl}methanesulfonamide The product from Example 49 was treated with aqueous sodium hydroxide in methanol and allowed to stir overnight.

The mixture was concentrated under reduced pressure, diluted with water and extracted with diethyl ether. The aqueous phase was acidified with 2N aqueous hydrochloric acid and extracted with ethyl acetate. The ethyl acetate phase was dried over sodium sulfate, filtered and the filtrate concentrated under reduced pressure to provide the title compound. $^1$H NMR (CDCl$_3$, 300 MHz) δ7.09–7.23 (m, 8H), 6.87–6.94 (m, 4H), 6.68–6.77 (m, 2H), 6.14 (s, 1H), 4.10 (s, 2H), 4.05 (s, 2H), 2.95 (t, J=7.6 Hz, 2H), 2.94 (s, 3H), 2.68 (t, J=7.6 Hz, 2H), 2.28 (s, 3H); MS (APCI+) (M+H)$^+$ at m/z 581.

EXAMPLE 51

N-{3-[(2,4-difluorobenzyl)(4-phenoxybenzyl) amino]-2-methylphenyl}methanesulfonamide The product from Example 26A and 2,4-difluorobenzyl bromide were processed as described in Examples 6B–D to provide the title compound. $^1$H NMR (300 MHz, CDCl$_3$) δ7.33 (m, 2 H), 7.15 (m, 6 H), 6.94 (m, 5 H), 6.72 (m, 2 H), 6.10 (s, 1 H), 4.10 (s, 2 H), 4.06 (s, 2 H), 2.95 (s, 3 H), 2.30 (s, 3 H); MS (APCI) m/z 509 (M+H$^+$).

EXAMPLE 52 methyl 4-{4-[((2,4-difluorobenzyl){2-methyl-3-[(methylsulfonyl)amino]phenyl}amino)methyl] phenoxy}benzoate

EXAMPLE 52A methyl 4-(4-{[(2,4-difluorobenzyl)(2-methyl-3-nitrophenyl)amino)methyl]phenoxy}benzoate The product from Example 33A (0.1520 g, 0.396 mmoles), methyl-4-bromobenzoate (0.1702 g, 0.792 mmoles), K$_3$PO$_4$ (0.1680 g, 0.792 mmoles), Pd(OAc)$_2$ (0.0070 g, 0.032 mmoles), and 2-(di-tert-butylphosphino) biphenyl (0.0140 g, 0.048 mmoles) was treated with toluene (1.16 mL) under a nitrogen atmosphere. The resulting red solution was degassed, stirred for 10 min, and heated to 100° C. overnight. The black solution was diluted with diethyl ether, extracted with sat. NH$_4$Cl and sat. NaCl, dried (Na$_2$SO$_4$), and concentrated under reduced pressure. The residue was purified by flash chromatography (10:1 hexane-:ethyl acetate) on silica gel to provide the title compound (0.1886 g, 92%) as a yellow oil.

EXAMPLE 52B methyl 4-{4-[((2,4-difluorobenzyl){2-methyl-3-[(methylsulfonyl)amino]phenyl}amino)methyl] phenoxy}benzoate The product from Example 52A was processed as described in Examples 6C and D to provide the title compound. $^1$H NMR (300 MHz, CDCL$_3$) δ8.01 (m, 2 H), 7.22 (m, 3 H), 7.11 (m, 2 H), 6.95 (m, 5 H), 6.73 (m, 2 H), 6.08 (s, 1 H), 4.11 (s, 2 H), 4.09 (s, 2 H), 3.90 (s, 3 H), 2.96 (s, 3 H), 2.32 (s, 3 H); MS (APCI) m/z 567 (M+H$^+$).

EXAMPLE 53

N-{3-[(2,4-difluorobenzyl)(2-fluoro-4-phenoxybenzyl)amino]-2-methylphenyl}methanesulfonamide

EXAMPLE 53A 4-(allyloxy)-2-fluorobenzonitrile

2-Fluoro-4-hydroxybenzonitrile (5.00 g, 36.5 mmoles) and allyl bromide (3.47 mL, 40.1 mmoles) in anhydrous DMF (40 mL) were treated with K$_2$CO$_3$ (10.0 g, 72.9 mmoles) and stirred overnight at 80° C. Reaction mixture cooled and diluted with ethyl acetate, washed with H$_2$O (2×) and brine, dried (Na$_2$SO$_4$), filtered, and concentrated under reduced pressure to provide the title compound with no further purification.

EXAMPLE 53B 4-(allyloxy)-2-fluorobenzaldehyde

The product from Example 53A (6.42 g, 36.5 mmoles) in anhydrous THF (50 mL) was treated with diisobutylaluminum hydride (DIBAL) (37.0 mL, 37.0 mmoles, 1.0M in hexanes) dropwise at −78° C. After 30 minutes, an additional portion of DIBAL (37.0 mL) was added dropwise. After an additional 30 minutes, the acetone/dry ice bath was removed, and the reaction mixture was warmed to 0° C. After an additional 30 minutes, the reaction was carefully quenched with saturated NH$_4$Cl. The mixture was diluted with diethyl ether (200 mL) and saturated sodium potassium tartrate (250 mL) and stirred vigorously for 2.0 hours. The two phases were separated, and the organic phase was washed with brine, dried (Na$_2$SO$_4$), filtered, and the filtrate concentrated under reduced pressure to provide the title compound with no further purification. MS (DCI) m/z 181 (M+H)$^+$.

EXAMPLE 53C

N-[4-(allyloxy)-2-fluorobenzyl]-N-(2-methyl-3-nitrophenyl)amine

The product from Example 53B and 2-methyl-3-nitroaniline were processed as described in Example 6A to provide the title compound. MS (ESI−) m/z 315 (M−H)$^−$.

EXAMPLE 53D

N-[4-(allyloxy)-2-fluorobenzyl]-N-(2,4-difluorobenzyl)-N-(2-methyl-3-nitrophenyl)amine The product from Example 53C and 2,4-diflurobenzyl bromide were processed as described in Example 6B to provide the title compound. MS (ESI+) m/z 443 (M+H)$^+$.

EXAMPLE 53E

4-{[(2,4-difluorobenzyl)(2-methyl-3-nitrophenyl) amino]methyl}-3-fluorophenol

The product from Example 53D was processed as described in Example 33A to provide the title compound. MS (ESI+) m/z 403 (M+H)$^+$.

EXAMPLE 53F

N-(2,4-difluorobenzyl)-N-(2-fluoro-4-phenoxybenzyl)-N-(2-methyl-3-nitrophenyl)amine The product from Example 53E and phenylboronic acid were processed as described in Example 48A to provide the title compound.

EXAMPLE 53G

N-{3-[(2,4-difluorobenzyl)(2-fluoro-4-phenoxybenzyl)amino]-2-methylphenyl}methanesulfonamide The product from Example 53F was processed as described in Examples 6C and D to provide the title compound. ¹H NMR (300 MHz, CDCl₃) δ7.36 (m, 2 H), 7.16 (m, 5 H), 6.97 (m, 3 H), 6.56–6.80 (m, 4 H), 6.10 (s, 1 H), 4.11 (s, 2 H), 4.08 (s, 2 H), 2.94 (s, 3 H), 2.27 (s, 3 H); MS (APCI) m/z 527 (M+H⁺).

EXAMPLE 54

N-{3-[benzyl(4-bromo-2-fluorobenzyl)amino]-2-methylphenyl}methanesulfonamide

The product from Example 6A and 2-fluoro-4-bromo-1-(bromomethyl)benzene were processed as described in Examples 6B–D to provide the title compound. ¹H NMR (500 MHz, DMSO-d6) δ ppm 8.94 (s, 1 H), 7.43 (dd, 1 H), 7.30 (dd, 1 H), 7.27 (m, 4 H), 7.20 (m, 2 H), 7.04 (t, 1 H), 6.98 (d, 1 H), 6.94 (d, 1 H), 4.08 (d, 4 H), 2.89 (s, 3 H), 2.34 (s, 3 H); MS (APCI+) m/z 477 (M+H)⁺.

EXAMPLE 55

N-{3-[benzyl(2-chloro-4-fluorobenzyl)amino]-2-methylphenyl}methanesulfonamide

The product from Example 6A and 2-chloro-4-fluoro-1-(bromomethyl)benzene were processed as described in Examples 6B–D to provide the title compound. ¹H NMR (500 MHz, DMSO-d6) δ ppm 8.93 (s, 1 H), 7.41 (dd, 1 H), 7.34 (dd, 1 H), 7.26 (m, 4 H), 7.21 (m, 1 H), 7.12 (t, 1 H), 7.05 (t, 1 H), 6.98 (d, 2 H), 4.13 (d, 4 H), 2.89 (s, 3 H), 2.31 (s, 3 H); MS (APCI+) m/z 433 (M+H)⁺.

EXAMPLE 56

N-(3-{(2,4-difluorobenzyl)[4-(3-methoxyphenoxy)benzyl]amino}-2-methylphenyl)methanesulfonamide

EXAMPLE 56A

N-(2,4-difluorobenzyl)-N-[4-(3-methoxyphenoxy)benzyl]-N-(2-methyl-3-nitrophenyl)amine The product from Example 33A and 3-methoxyphenylboronic acid were processed as described in Example 48A to provide the title compound.

EXAMPLE 56B

N-(3-{(2,4-difluorobenzyl)[4-(3-methoxyphenoxy)benzyl]amino}-2-methylphenyl)methanesulfonamide The product from Example 56A was processed as described in Examples 6C and D to provide the title compound. ¹H NMR (300 MHz, CDCl₃) δ7.00–7.25 (m, 6 H), 6.92 (m, 3 H), 6.74 (m, 2 H), 6.64 (m, 1 H), 6.54 (m, 2 H), 6.13 (s, 1 H), 4.08 (s, 2 H), 4.04 (s, 2 H), 3.77 (s, 3 H), 2.95 (s, 3 H), 2.30 (s, 3 H); MS (APCI) m/z 539 (M+H⁺).

EXAMPLE 57

N-{3-[benzyl(4-{[(2Z)-3-bromoprop-2-enyl]oxy}benzyl)amino]-2-methylphenyl}methanesulfonamide

EXAMPLE 57A

4-{[(2Z)-3-bromoprop-2-enyl]oxy}benzaldehyde

4-Hydroxybenzaldehyde and 1,3-dibromo-1-propene were processed as described in Example 33B to provide the title compound.

EXAMPLE 57B

N-(4-{[(2Z)-3-bromoprop-2-enyl]oxy}benzyl)-N-(2-methyl-3-nitrophenyl)amine

The product from Example 57A and 2-methyl-3-nitroaniline were processed as described in Example 6A to provide the title compound.

EXAMPLE 57C

N-{3-[benzyl(4-{[(2Z)-3-bromoprop-2-enyl]oxy}benzyl)amino]-2-methylphenyl}methanesulfonamide The product from Example 57B and benzyl bromide were processed as described in Examples 6B–D to provide the title compound. ¹H NMR (300 MHz, CDCl₃) δ7.25 (m, 6 H), 7.15 (m, 3 H), 6.90 (d, 1 H), 6.80 (d, 2 H), 6.30–6.50 (m, 2 H), 6.11 (s, 1 H), 4.68 (d, 2 H), 4.04 (s, 2 H), 4.00 (s, 2 H), 2.93 (s, 3 H), 2.33 (s, 3 H); MS (ESI+) m/z 515, 517 (M+H)⁺.

EXAMPLE 58

N-{3-[(2-fluorobenzyl)(4-phenoxybenzyl)amino]-2-methylphenyl}methanesulfonamide

The product from Example 26A and 2-fluorobenzyl bromide were processed as described in Examples 6B–D to provide the title compound. ¹H NMR (300 MHz, CDCl₃) δ7.32 (m, 2 H), 7.20 (m, 5 H), 7.10 (m, 3 H), 6.95 (m, 6 H), 6.12 (s, 1 H), 4.12 (s, 2 H), 4.06 (s, 2 H), 2.93 (s, 3 H), 2.31 (s, 3 H); MS (APCI) m/z 539 (M+H⁺).

EXAMPLE 59

N-{3-[(4-methoxybenzyl)(4-phenoxybenzyl)amino]-2-methylphenyl}methanesulfonamide The product from Example 26A and 4-methoxybenzyl chloride were processed as described in Examples 6B–D to provide the title compound. ¹H NMR (300 MHz, CDCL₃) δ7.32 (m, 2 H), 7.15 (m, 7 H), 6.96 (m, 3 H), 6.87 (m, 2 H), 6.77 (m, 2 H), 6.10 (s, 1 H), 4.15 (s, 2 H), 4.12 (s, 2 H), 3.77 (s, 3 H), 2.91 (s, 3 H), 2.25 (s, 3H); MS (ESI) m/z 503 (M+H⁺).

EXAMPLE 60

6-O-(4-{4-[(benzyl{2-methyl-3-[(methylsulfonyl)amino]phenyl}amino)methyl]phenoxy}phenyl)-2,4-dideoxy-D-erythro-hexonic acid

EXAMPLE 60A 4-(allyloxy)phenol

Allyl iodide (8.2 mL, 89 mmoles) was added to a solution of hydroquinone (7.84 g, 71.2 mmoles) and K₂CO₃ (19.7 g, 142.4 mmoles) in acetone (102 mmoles). The resulting mixture was heated to 40° C. overnight and concentrated under reduced pressure. The crude products were filtered through a pad of silica with 1:1 hexanes:ethyl acetate. The residue was purified by flash chromatography on a pre-packed Biotage column (hexane to 1:1 hexane:ethyl acetate) on silica gel to provide the title compound (4.40 g, 41%).

EXAMPLE 60B

4-[4-(allyloxy)phenoxy]benzaldehyde

4-Fluorobenzaldehyde (3.8 mL, 35.1 mmoles) was added to a solution of the product from Example 60A (4.39 g, 29.3 mmoles) and K₂CO₃ (8.90 g, 64.4 mmoles) in DMF (29.3 mL). The resulting mixture was heated to 100° C. for 2.5 days and then cooled to room temperature. The crude products were diluted with diethyl ether, extracted with sat. NH₄Cl, extracted with H₂O (2×), washed with brine, dried (Na₂SO₄), and concentrated under reduced pressure. The residue was purified by flash chromatography on a pre-packed Biotage column (hexane→9:1 hexane:ethyl acetate) on silica gel to provide the title compound (3.50 g, 81%) as a clear colorless oil.

EXAMPLE 60C

N-{4-[4-(allyloxy)phenoxy]benzyl}-N-(2-methyl-3-nitrophenyl)amine

The product from Example 60B was processed as described in Example 6A to provide the title compound.

EXAMPLE 60D

N-{4-[4-(allyloxy)phenoxy]benzyl}-N-benzyl-N-(2-methyl-3-nitrophenyl)amine

The product from Example 60C and benzyl bromide was processed as described in Example 6B to provide the title compound.

EXAMPLE 60E 4-(4-{[benzyl(2-methyl-3-nitrophenyl)amino]methyl}phenoxy)phenol The product from Example 60D was processed as described in Example 33A to provide the title compound.

EXAMPLE 60F tert-butyl 6-O-[4-(4-{[benzyl(2-methyl-3-nitrophenyl)amino]methyl}phenoxy)phenyl]-2,4-dideoxy-3,5-O-(1-methylethylidene)-D-erythro-hexonate A solution of the product from Example 60E (0.2411 g, 0.55 mmoles), (3R, 5S)-6-[methylsulfonyl)oxy]-3,5-O-isopropylidene-3,5-dihydroxyhexanoic acid tert-butyl ester (prepared according to Jendralla, H.; Granzer, B.; Kerekjarto, B. v.; Krause, R.; Schacht, U.; Baader, E.; Bartmann, W.; Beck, G.; Bergmann, A.; Kesseler, D.; Wess, G.; Chen, L.-J.; Granata, S.; Herchen, J.; Kleine, H.; Schüssler, H.; Wagner, K. J. Med. Chem. 1991, 34, 2962) (0.1852 g, 0.55 mmoles), $K_2CO_3$ (0.1515 g, 1.1 mmoles), and 18-Crown-6 (0.0072 g, 0.027 mmoles) in DMSO (1.62 mL) under a nitrogen atmosphere was heated to 80° C. for 18 h. The crude products were diluted with diethyl ether, extracted with sat. $NH_4Cl$, extracted with $H_2O$ (2x), washed with brine, dried ($Na_2SO_4$), and concentrated under reduced pressure. The residue was purified by flash chromatography (4:1 hexane:ethyl acetate→3:1 hexane:ethyl acetate) on silica gel to provide the title compound (0.2460 g, 62%) as a yellow oil.

EXAMPLE 60G tert-butyl 6-O-(4-{4-[(benzyl{2-methyl-3-[(methylsulfonyl)amino]phenyl}amino)methyl]phenoxy}phenyl)-2,4-dideoxy-3,5-O-(1-methylethylidene)-D-erythro-hexonate The product from Example 60F was processed as described in Examples 6C and D to provide the title compound.

EXAMPLE 60H

6-O-(4-{4-[(benzyl{2-methyl-3-[(methylsulfonyl)amino]phenyl}amino)methyl]phenoxy}phenyl)-2,4-dideoxy-D-erythro-hexonic acid A solution of the product from Example 60G (0.3000 g, 0.41 mmoles) in EtOH (2.0 mL) and THF (1.0 mL) was treated with 3N HCl (0.15 mL). The resulting mixture was stirred at rt overnight, neutralized with pH 7 buffer and extracted with ethyl acetate (2x). The combined organic layers were rinsed with $H_2O$ and brine, dried ($Na_2SO_4$), and concentrated under reduced pressure. Half of the crude products were dissolved in EtOH (2.3 mL) and treated with 3 M NaOH (0.14 mL). After 2.5 h, the reaction was concentrated under reduced pressure, diluted with $CH_3CN$ and $H_2O$, and purified by preparative HPLC ($CH_3CN$:0.1% TRIFLUOROACETIC ACID in $H_2O$) on a YMC ODS Guardpak column. The procedure yielded the title compound (0.0937g, 72%) as a white solid. $^1H$ NMR (300 MHz, DMSO-$d_6$) δ7.22 (m, 11 H), 6.98 (m, 4 H), 6.82 (d, 2 H), 4.04 (s, 2 H), 3.99 (s, 2 H), 3.94 (m, 2 H), 3.82 (m, 2 H), 2.91 (s, 3 H), 2.39 (s, 3 H),2.23 (m, 1 H), 2.08 (m, 1 H), 1.89 (s, 3 H), 1.56 (m, 2 H); MS (ESI) m/z 635 (M+H$^+$).

EXAMPLE 61

N-[3-(benzyl{4-[3-(2-methoxyethoxy)phenoxy]benzyl}amino)-2-methylphenyl]methanesulfonamide

EXAMPLE 61A 3-(allyloxy)phenyl acetate

Resorcinol monoacetate (10.0 g, 65.7 mmoles) in anhydrous DMF (100 mL) was treated with $K_2CO_3$ (18.2 g, 131 mmoles) and allyl bromide (6.83 mL, 78.9 mmoles). The mixture was heated at 80° C. overnight, cooled to room temperature, and diluted with ethyl acetate. The mixture was washed with $H_2O$, brine, dried ($Na_2SO_4$), filtered, and the filtrate concentrated under reduced pressure. The residue was purified by flash chromatography (silica gel, 8% to 10% ethyl acetate:hexanes) to provide the title compound as a colorless oil (7.19 g, 57%). MS (DCI) m/z 193 (M+H)$^+$.

EXAMPLE 61B 3-(allyloxy)phenol

The product from Example 61A (7.19 g, 37.4 mmoles) in THF (30 mL) was treated with 4N NaOH (19 mL, 75 mmoles) and MeOH (5 mL). After one hour, the reaction mixture was concentrated under reduced pressure. The residue was dissolved in ethyl acetate, washed with aqueous $NH_4Cl$, brine, dried ($Na_2SO_4$), filtered, and the filtrate concentrated under reduced pressure to provide the title compound without further purification.

EXAMPLE 61C

4-[3-(allyloxy)phenoxy]benzaldehyde

The crude product from Example 61B in anhydrous DMF (40 mL) was treated with $K_2CO_3$ (15.5 g, 112 mmoles) and 4-fluorobenzaldehyde (4.82 mL, 44.9 mmoles). The reaction mixture was stirred overnight at 100° C. After cooling to room temperature, the reaction mixture was diluted with ethyl acetate. The mixture was washed with $H_2O$ (2x), brine, dried ($Na_2SO_4$), filtered, and the filtrate concentrated under reduced pressure. The residue was purified by flash chromatography (silica gel, 8% ethyl acetate:hexanes) to provide the title compound (5.75 g, 60%).

EXAMPLE 61D

N-{4-[3-(allyloxy)phenoxy]benzyl}-N-(2-methyl-3-nitrophenyl)amine

The product from Example 61C and 2-methyl-3-nitroaniline were processed as described in Example 6A to provide the title compound (7.20 g, 82%).

EXAMPLE 61E

N-{4-[3-(allyloxy)phenoxy]benzyl}-N-benzyl-N-(2-methyl-3-nitrophenyl)amine

The product from Example 61D and benzyl bromide were processed as described in Example 6B to provide the title compound

EXAMPLE 61F 3-(4-{[benzyl(2-methyl-3-nitrophenyl)amino]methyl}phenoxy)phenol

The product from Example 61E was processed as described in Example 33A to provide the title compound. MS (ESI−) m/z 439 (M−H)⁻.

EXAMPLE 61G

N-benzyl-N-{4-[3-(2-methoxyethoxy)phenoxy]benzyl}-N-(2-methyl-3-nitrophenyl)amine The product from Example 61F (0.100 g, 0.227 mmoles), polystyrene supported triphenylphosphine (0.151 g, 0.454 mmoles, 3 mmoles P/g resin), and di-t-butylazodicarboxylate (0.079 g, 0.341 mmoles) in THF (2 mL) were treated with 2-methoxyethanol (0.022 g, 0.284 mmoles). The reaction mixture was shaken overnight at room temperature. The mixture was diluted with ethyl acetate, washed with $H_2O$, brine, dried ($Na_2SO_4$), filtered, and the filtrate concentrated under reduced pressure to provide the title compound without further purification.

EXAMPLE 61H

N-[3-(benzyl{4-[3-(2-methoxyethoxy)phenoxy]benzyl}amino)-2-methylphenyl]methanesulfonamide The crude product from Example 61G was processed as described in Examples 6C and D to provide the title compound. $^1$H NMR (300 MHz, $CDCl_3$) δ7.25 (m, 6 H), 7.15 (m, 4 H), 6.95 (dd, 1 H), 6.89 (d, 2 H), 6.66 (ddd, 1 H), 6.57 (ddd, 1 H), 6.52 (t, 1 H), 6.15 (s, 1 H), 4.14 (s, 2 H), 4.11 (s, 2 H), 4.05 (m, 2 H), 3.75 (m, 2 H), 3.44 (s, 3 H), 2.92 (s, 3 H), 2.29 (s, 3 H); MS (ESI+) m/z 547 (M+H)⁺.

EXAMPLE 62

(3-{4-[(benzyl{2-methyl-3-[(methylsulfonyl)amino]phenyl}amino)methyl]phenoxy}phenoxy)acetic acid

EXAMPLE 62A ethyl[3-(4-{[benzyl(2-methyl-3-nitrophenyl)amino]methyl}phenoxy)phenoxy]acetate The product from Example 61F (1.29 g, 2.93 mmoles), triphenylphophine (1.54 g, 5.86 mmoles), and di-t-butylazodicarboxylate (1.01 g, 4.40 mmoles) in anhydrous THF (6 mL) were treated with ethyl glycolate (0.35 mL, 3.66 mmoles). The reaction was stirred overnight at room temperature. The mixture was diluted with ethyl acetate, washed with $H_2O$, brine, dried ($Na_2SO_4$), filtered, and the filtrate concentrated under reduced pressure. The residue was purified by chromatography on a pre-packed Biotage silica gel column (hexanes to 10% ethyl acetate:hexanes) to provide the title compound.

EXAMPLE 62B ethyl(3-(4-((benzyl(2-methyl-3-((methylsulfonyl)amino)phenyl)amino)methyl)phenoxy)phenoxy)acetate The product from Example 62A was processed as described in Examples 6C and D to provide the title compound. MS (ESI+) m/z 575 (M+H)⁺.

EXAMPLE 62C (3-{4-[(benzyl{2-methyl-3-[(methylsulfonyl)amino]phenyl}amino)methyl]phenoxy}phenoxy)acetic acid The product from Example 62B was processed as described in Example 50 to provide the title compound. $^1$H NMR (300 MHz, $CDCl_3$) δ7.25 (m, 7 H), 7.15 (t, 1 H), 7.05 (m, 3 H), 6.86 (d, 2 H), 6.69 (dd, 1 H), 6.65 (m, 2 H), 6.51 (t, 1 H), 4.63 (s, 2 H), 4.09 (s, 2 H), 3.99 (s, 2 H), 2.92 (s, 3 H), 2.20 (s, 3 H); MS (ESI+) m/z 547 (M+H)⁺.

EXAMPLE 63

4-[4-{4-[(benzyl{2-methyl-3-[(methylsulfonyl)amino]phenyl}amino)methyl]phenoxy{-2-(2-methoxyethoxy)phenyl]butanoic acid

EXAMPLE 63A 3-(allyloxy)-4-bromophenyl 4-methylbenzenesulfonate p-Toluenesulfonylchloride (2.14 g, 11.2 mmoles) was added to a solution of 4-bromoresorcinol (2.12 g, 11.2 mmoles) and $K_2CO_3$ (10.0 g, 72.4 mmoles) in acetone (150 mL). The reaction was heated to 60° C. overnight, treated with allyl bromide (2.6 mL, 30.3 mmoles), and heated to 60° C. for 24 h (according to Bos, M. E.; Wulff, W. D.; Miller, R. A.; Chamberlin, S.; Brandvoid, T. A. *J. Am. Chem. Soc.* 1991, 113, 9293). The reaction was cooled to room temperature, quenched with aqueous $NH_4Cl$, and concentrated under reduced pressure. The crude products were diluted with diethyl ether, extracted with $H_2O$, washed with brine, dried ($Na_2SO_4$), and concentrated under reduced pressure. The residue was purified by flash chromatography on a prepacked Biotage colum (hexane to 4:1 hexane:ethyl acetate) on silica gel to provide the title compound (3.50 g, 81%) as a clear colorless oil.

EXAMPLE 63B 3-(allyloxy)-4-bromophenol

Potassium Hydroxide (11.2 g, 200 mmoles) was added to a solution of the product from Example 63A (3.5 g, 9.14 mmoles) in EtOH (180 mL) and $H_2O$ (180 mL). The reaction was heated to 90° C. for 2 hours, cooled to room temperature, and concentrated under reduced pressure. The residue was purified by flash chromatography on a pre-packed Biotage colum (hexane to 4:1 hexane:ethyl acetate) on silica gel to provide the title compound (1.76 g, 84%).

EXAMPLE 63C

4-[3-(allyloxy)-4-bromophenoxy]benzaldehyde

4-Flurorbenzaldehyde (1.15 mL, 10.76 mmoles) was added to a solution of the product from Example 63B (1.76 g, 7.69 mmoles) and $K_2CO_3$ (3.19 g, 23.1 mmoles) in DMF (7.7 mL). The reaction mixture was heated to 100° C. for 14 h and was cooled to room temperature The crude products were diluted with diethyl ether, extracted with sat. $NH_4Cl$, extracted with $H_2O$ (2×), rinsed with brine, dried ($Na_2SO_4$), and concentrated under reduced pressure. The residue was purified by flash chromatography on a prepacked Biotage colum (hexane to 4:1 hexane:ethyl acetate) on silica gel to provide the title compound (2.13 g, 83%) as a white solid.

EXAMPLE 63D

N-{4-[3-(allyloxy)-4-bromophenoxy]benzyl}-N-(2-methyl-3-nitrophenyl)amine

The product from example 63C was processed as described in Example 6A to provide the title compound.

EXAMPLE 63E

N-{4-[3-(allyloxy)-4-bromophenoxy]benzyl}-N-benzyl-N-(2-methyl-3-nitrophenyl)amine The product from example 63D and benzylbromide were processed as described in Example 6B to provide the title compound.

EXAMPLE 63F 5-(4-{[benzyl(2-methyl-3-nitrophenyl)amino]methyl}phenoxy)-2-bromophenol The product from example 63E was processed as described in Example 33A to provide the title compound.

EXAMPLE 63G

N-benzyl-N-{4-[4-bromo-3-(2-methoxyethoxy)phenoxy]benzyl}-N-(2-methyl-3-nitrophenyl)amine The product from example 63F was processed as described in Example 62A substituting 2-methoxyethanol for ethyl glycolate to provide the title compound.

EXAMPLE 63H

N-[3-(benzyl{4-[4-bromo-3-(2-methoxyethoxy)phenoxy]benzyl}amino)-2-methylphenyl]methanesulfonamide The product from Example 63G was processed as described in Examples 6C and 6D to provide the title compound.

EXAMPLE 63I

4-[4-{4-[(benzyl{2-methyl-3-[(methylsulfonyl)amino]phenyl}amino)methyl]phenoxy}-2-(2-methoxyethoxy)phenyl]butanoic acid The product from Example 63H was processed as described in Examples 49 and 50 to provide the title compound. $^1$H NMR (300 MHz, CDCL$_3$) δ7.08–7.34 (m, 10 H), 7.04 (d, 1 H), 6.97 (d, 1 H), 6.86 (d, 2 H), 6.47 (m, 2 H), 6.26 (s, 1 H), 4.18 (s, 2 H), 4.15 (s, 2 H), 4.01 (t, 2 H), 3.74 (t, 2 H), 3.44 (s, 3 H), 2.90 (s, 3 H), 2.66 (t, 2 H), 2.37 (t, 2 H), 2.28 (s, 3 H), 1.93 (m, 2H); MS (APCI) m/z 633 (M+H$^+$).

EXAMPLE 64 ethyl 4-(4-{4-[(benzyl{2-methyl-3-[(methylsulfonyl)amino]phenyl}amino)methyl]phenoxy}phenyl)butanoate

EXAMPLE 64A 4-(4-bromophenoxy)benzaldehyde 4-bromophenol was processed as described in Example 63C to provide the title compound.

EXAMPLE 64B

N-[4-(4-bromophenoxy)benzyl]-N-(2-methyl-3-nitrophenyl)amine

The product from Example 64A was processed as described in Example 6A to provide the title compound.

EXAMPLE 64C

N-benzyl-N-[4-(4-bromophenoxy)benzyl]-N-(2-methyl-3-nitrophenyl)amine

The product from Example 64B and benzyl bromide were processed as described in Example 6B to provide the title compound.

EXAMPLE 64D

N-(3-{benzyl[4-(4-bromophenoxy)benzyl]amino}-2-methylphenyl)methanesulfonamide

The product from Example 64C was processed as described in Examples 6C and 6D to provide the title compound.

EXAMPLE 64E ethyl 4-(4-{4-[(benzyl{2-methyl-3-[(methylsulfonyl)amino]phenyl}amino)methyl]phenoxy}phenyl)butanoate The product from Example 64C was processed as described in Example 49 with 4-ethoxycarbonylbutylzincbromide to provide the title compound. $^1$H NMR (300 MHz, CDCL$_3$) δ7.25 (m, 8 H), 7.13 (m, 4 H), 6.90 (m, 4 H), 6.11 (s, 1 H), 4.13 (dd, 2H), 4.09 (s, 2 H), 4.05 (s, 2 H), 2.94 (s, 3 H), 2.63 (t, 2 H), 2.32 (t, 2 H), 2.32 (s, 3 H), 1.86–2.08 (m, 2 H), 1.26 (t, 3 H); MS (ESI) m/z 587 (M+H$^+$).

EXAMPLE 65

N-[3-(benzyl{4-[3-(3-hydroxypropyl)phenoxy]benzyl}amino)-2-methylphenyl]methanesulfonamide

EXAMPLE 65A

N-[4-(allyloxy)benzyl]-N-benzyl-N-(2-methyl-3-nitrophenyl)amine

The product from Example 19A and benzyl bromide were processed as described in Example 6B to provide the title compound. MS (ESI+) m/z 389 (M+H)$^+$.

EXAMPLE 65B

4-{[benzyl(2-methyl-3-nitrophenyl)amino]methyl}phenol

The product from Example 65A was processed as described in Example 33A to provide the title compound.

EXAMPLE 65C

N-benzyl-N-[4-(3-bromophenoxy)benzyl]-N-(2-methyl-3-nitrophenyl)amine

The product from Example 65B and 3-bromophenylboronic acid were processed as described in Example 48A to provide the title compound. MS (ESI+) m/z 504 (M+H)$^+$.

EXAMPLE 65D

N-(3-{benzyl[4-(3-bromophenoxy)benzyl]amino}-2-methylphenyl)methanesulfonamide

The product from Example 65C was processed as described in Example 6C and D to provide the title compound.

EXAMPLE 65E ethyl 3-(3-{4-[(benzyl{2-methyl-3-[(methylsulfonyl)amino]phenyl}amino)methyl]phenoxy}phenyl)propanoate The product from Example 65D and 3-ethoxy-3-oxopropylzinc bromide (purchased from Aldrich) were processed as described in Example 49 to provide the title compound. MS (ESI+) m/z 573 (M+H)+.

EXAMPLE 65F

N-[3-(benzyl{4-[3-(3-hydroxypropyl)phenoxy] benzyl}amino)-2-methylphenyl]methanesulfonamide The product from Example 65E was processed as described in Example 38A to provide the title compound. $^1$H NMR (300 MHz, CDCl$_3$) δ7.25 (m, 7 H), 7.15 (m, 3 H), 6.94 (t, 2 H), 6.88 (d, 2 H), 6.82 (d, 1 H), 6.79 (d, 1 H), 6.24 (s, 1 H), 4.06 (s, 2 H), 4.03 (s, 2 H), 3.66 (t, 2 H), 2.93 (s, 3 H), 2.65 (m, 2 H), 2.31 (s, 3 H), 1.85 (m, 2 H), 1.35 (br.s, 1 H); MS (ESI+) m/z 531 (M+H)+.

EXAMPLE 66 methyl 4-{4-[(benzyl{2-methyl-3-[(methylsulfonyl) amino]phenyl}amino)methyl]phenoxy}benzoate

EXAMPLE 66A methyl 4-(4-{[benzyl(2-methyl-3-nitrophenyl) amino]methyl}phenoxy)benzoate The product from Example 65B (0.4618 g, 1.33 mmoles), methyl-4-bromobenzoate (0.5707 g, 2.65 mmoles), K$_3$PO$_4$ (0.5634 g, 2.65 mmoles), Pd(OAc)$_2$ (0.0238 g, 0.106 mmoles), and 2-(di-tert-butylphosphino)biphenyl (0.0475 g, 0.159 mmoles) was treated with toluene (3.9 mL) under a nitrogen atmosphere. The resulting red solution was degassed, stirred for 10 min, and heated to 100° C. overnight. The black solution was diluted with diethyl ether, extracted with sat. NH$_4$Cl and sat. NaCl, dried (Na$_2$SO$_4$), and concentrated under reduced pressure. The residue was purified by flash chromatography (10:1 to 4:1 hexane:ethyl acetate) on silica gel to provide the title compound (0.5904 g, 92%) as a yellow oil.

EXAMPLE 66B methyl 4-{4-[(benzyl{2-methyl-3-[(methylsulfonyl) amino]phenyl}amino)methyl]phenoxy}benzoate The product from Example 66B was processed as described in Examples 6C and 6D to provide the title compound. $^1$H NMR (300 MHz, CDCL$_3$) δ7.83–8.11 (m, 2 H), 7.03–7.42 (m, 9 H), 6.92 (m, 5 H), 6.15 (s, 1 H), 4.11 (s, 2 H), 4.10 (s, 2 H), 3.89 (s, 3 H), 2.95 (s, 3 H), 2.34 (s, 3 H); MS (ESI) m/z 531 (M+H+).

EXAMPLE 67 methyl 3-{4-[((2,4-difluorobenzyl){2-methyl-3-[(methylsulfonyl)amino]phenyl}amino)methyl] phenoxy}benzoate

EXAMPLE 67A methyl 4-(4-{[(2,4-difluorobenzyl)(2-methyl-3-nitrophenyl)amino]methyl}phenoxy)benzoate The product from Example 33A and methyl-3-bromobenzoate were processed as described in Example 52A to provide the title compound. MS (ESI+) m/z 519 (M+H)+.

EXAMPLE 67B methyl 3-{4-[((2,4-difluorobenzyl){2-methyl-3-[(methylsulfonyl)amino]phenyl}amino)methyl] phenoxy}benzoate The product from Example 67A was processed as described in Example 6C and D to provide the title compound. $^1$H NMR (300 MHz, CDCl$_3$) δ7.74 (dt, 1 H), 7.45 (m, 1 H), 7.40 (t, 1 H), 7.25 (m, 2 H), 7.15 (m, 4 H), 7.05 (m, 1 H), 6.90 (d, 2 H), 6.75 (m, 2 H), 6.47 (s, 1 H), 4.18 (s, 2 H), 4.12 (s, 2 H), 3.91 (s, 3 H), 2.89 (s, 3 H), 2.21 (s, 3 H); MS (ESI+) m/z 567 (M+H)+.

EXAMPLE 68 ethyl N-(4-{4-[((2,4-difluorobenzyl){2-methyl-3-[(methylsulfonyl)amino]phenyl}amino)methyl] phenoxy}benzoyl)-beta-alaninate

EXAMPLE 68A methyl 4-(4-(((2,4-difluorobenzyl)(2-methyl-3-nitrophenyl)amino)methyl)phenoxy)benzoate The product from Example 33A and methyl-4-bromobenzoate were processed as described in Example 52A to provide the title compound. MS (ESI+) m/z 519 (M+H)+.

EXAMPLE 68B methyl 4-(4-(((2,4-difluorobenzyl)(2-methyl-3-((methylsulfonyl)amino)phenyl)amino)methyl) phenoxy)benzoate The product from Example 68A was processed as described in Example 6C and D to provide the title compound. MS (ESI+) m/z 567 (M+H)+.

EXAMPLE 68C

4-{4-[((2,4-difluorobenzyl){2-methyl-3-[(methylsulfonyl)amino]phenyl}amino)methyl] phenoxy}benzoic acid The product from Example 68B was processed as described in Example 50 to provide the title compound.

EXAMPLE 68D ethyl N-(4-{4-[((2,4-difluorobenzyl){2-methyl-3-[(methylsulfonyl)amino]phenyl}amino)methyl] phenoxy}benzoyl)-beta-alaninate The product from Example 68C (0.050 g, 0.096 mmoles), 1-hydroxybenzotriazole hydrate (0.015 g, 0.109 mmoles), and 1-[3-(dimethylamino)propyl]-3-ethylcarbodiimide hydrochloride (0.021 g, 0.109 mmoles) in DMF (1.5 mL) were treated with β-alanine ethyl ester hydrochloride (0.121 g, 0.136 mmoles) and triethylamine (0.025 mL, 0.181 mmoles). The reaction mixture was shaken at room temperature overnight. The mixture was diluted with ethyl acetate, washed with H$_2$O, saturated aqueous NaHCO$_3$ (2x), 1N H$_3$PO$_4$ (2x), and brine, dried (Na$_2$SO$_4$), filtered, and the filtrate concentrated under reduced pressure. The residue was purified by preparative HPLC (CH$_3$CN:0.1% trifluoroacetic acid in H$_2$O) on a YMC ODS Guardpak column to provide the title compound. $^1$H NMR (300 MHz, CDCl$_3$) δ7.73 (d, 2 H), 7.25 (m, 2 H), 7.15 (m, 2 H), 6.95 (m, 6 H), 6.75 (m, 2 H), 6.15 (s, 1 H), 4.18 (q, 2 H), 4.13 (s, 2 H), 4.11 (s, 2 H), 3.73 (dd, 2 H), 2.96 (s, 3 H), 2.65 (t, 2 H), 2.30 (s, 3 H), 1.28 (t, 3 H); MS (ESI+) m/z 652 (M+H)+.

EXAMPLE 69

N-{3-[benzyl(4-{3-[2-(2-methoxyethoxy)ethoxy] phenoxy}benzyl)amino]-2-methylphenyl}methanesulfonamide

EXAMPLE 69A

N-benzyl-N-(4-{3-[2-(2-methoxyethoxy)ethoxy] phenoxy}benzyl)-N-(2-methyl-3-nitrophenyl)amine The product from Example 61F and di(ethylene glycol) methyl ether were processed as described in Example 61G to provide the title compound.

EXAMPLE 69B

N-{3-[benzyl(4-{3-[2-(2-methoxyethoxy)ethoxy]phenoxy}benzyl)amino]-2-methylphenyl}methanesulfonamide The product from Example was processed as described in Examples 6C and D to provide the title compound. $^1$H NMR (300 MHz, CDCl$_3$) δ7.25 (m, 6 H), 7.15 (m, 4 H), 6.93 (dd, 1 H), 6.89 (d, 2 H), 6.64 (ddd, 1 H), 6.57 (ddd, 1 H), 6.51 (t, 1 H), 6.19 (s, 1 H), 4.10 (m, 4 H), 4.05 (m, 2 H), 3.85 (m, 2 H), 3.70 (m, 2 H), 3.55 (m, 2 H), 3.37 (s, 3 H), 2.93 (s, 3 H), 2.32 (s, 3 H); MS (ESI+) m/z 591 (M+H)$^+$.

EXAMPLE 70

N-[3-(3-{4-[(benzyl{2-methyl-3-[(methylsulfonyl)amino]phenyl}amino)methyl]phenoxy}phenoxy)propyl]acetamide

EXAMPLE 70A

2-{3-[3-(4-{[benzyl(2-methyl-3-nitrophenyl)amino]methyl}phenoxy)phenoxy]propyl}-1H-isoindole-1,3(2H)-dione The product from Example 61F and N-(3-hydroxypropyl)phthalimide were processed as described in Example 61G to provide the title compound.

EXAMPLE 70B

N-{3-[benzyl(4-{3-[3-(1,3-dioxo-1,3-dihydro-2H-isoindol-2-yl)propoxy]phenoxy}benzyl)amino]-2-methylphenyl}methanesulfonamide The product from Example 70A was processed as described in Examples 6C and D to provide the title compound. MS (ESI+) m/z 676 (M+H)$^+$.

EXAMPLE 70C

N-{3-[{4-[3-(3-aminopropoxy)phenoxy]benzyl}(benzyl)amino]-2-methylphenyl}methanesulfonamide The product from Example 70B (0.323 g, 0.479 mmoles) in EtOH (5 mL) was treated with hydrazine hydrate (0.15 mL, 4.79 mmoles). The reaction was heated overnight at 60 C. Reaction mixture concentrated under reduced pressure, and residue dissolved in ethyl acetate. The mixture was washed with H$_2$O (2×), brine, dried (Na$_2$SO$_4$), filtered, and the filtrate concentrated under reduced pressure. The residue was purified by flash chromatography (silica gel, 10% to 20% MeOH:CHCl$_3$) to provide the title compound (0.160 g, 61%). MS (ESI+) m/z 546 (M+H)$^+$.

EXAMPLE 70D

N-[3-(3-{4-[(benzyl{2-methyl-3-[(methylsulfonyl)amino]phenyl}amino)methyl]phenoxy}phenoxy)propyl]acetamide The product from Example 70C (0.028 g, 0.0514 mmoles) in CH2Cl2 (1 mL) was treated with acetic anhydride (0.0060 mL, 0.0617 mmoles) and stirred overnight at room temperature. The reaction was concentrated under reduced pressure, and the residue was purified by preparative HPLC (CH$_3$CN:0.1% trifluoroacetic acid in H$_2$O) on a YMC ODS Guardpak column. $^1$H NMR (300 MHz, CDCl$_3$) δ7.10–7.30 (m, 10 H), 6.96 (d, 1 H), 6.89 (d, 2 H), 6.60 (m, 2 H), 6.44 (t, 1 H), 6.29 (s, 1 H), 5.85 (br.s, 1 H), 4.09 (s, 2 H), 4.06 (s, 2 H), 3.98 (t, 2 H), 3.44 (dd, 2 H), 2.91 (s, 3 H), 2.31 (s, 3 H), 1.98 (s, 3 H), 1.90–2.10 (m, 2 H); MS (ESI+) mn/z 588 (M+H)$^+$.

EXAMPLE 71

N-[3-(3-{4-[(benzyl{2-methyl-3-[(methylsulfonyl)amino]phenyl}amino)methyl]phenoxy}phenoxy)propyl]methanesulfonamid The product from Example 70C was processed as described in Examples 6D to provide the title compound. $^1$H NMR (300 MHz, CDCl$_3$) δ7.25 (m, 8 H), 7.15 (m, 3 H), 6.85 (d, 2 H), 6.65 (m, 2 H), 6.42 (s, 1 H), 6.39 (t, 1 H), 4.65 (br.s, 1 H), 4.48 (s, 2 H), 4.45 (s, 2 H), 4.01 (t, 2 H), 3.35 (m, 2 H), 2.95 (s, 3 H), 2.78 (s, 3 H), 2.09 (s, 3 H), 2.05 (m, 2 H); MS (ESI–) m/z 622 (M–H)$^-$.

EXAMPLE 72

N-{3-[benzyl(4-{3-[3-(dimethylamino)propoxy]phenoxy}benzyl)amino]-2-methylphenyl}methanesulfonamide

EXAMPLE 72A

N-benzyl-N-{4-[3-(3-{[tert-butyl(dimethyl)silyl]oxy}propoxy)phenoxy]benzyl}-N-(2-methyl-3-nitrophenyl)amine The product from Example 61F and 1-t-butyldimethylsilyloxypropan-3-ol were processed as in Example 61G to provide the title compound.

EXAMPLE 72B

N-[3-(benzyl{4-[3-(3-{[tert-butyl(dimethyl)silyl]oxy}propoxy)phenoxy]benzyl}amino)-2-methylphenyl]methanesulfonamide The product from Example 72A was processed as in Example 6C and D to provide the title compound. MS (ESI+) m/z 661 (M+H)$^+$.

EXAMPLE 72C

N-[3-(benzyl{4-[3-(3-hydroxypropoxy)phenoxy]benzyl}amino)-2-methylphenyl]methanesulfonamide The product from Example 72B(0.368 g, 0.558 mmoles) in anhydrous TBF (2 mL) was treated with 1.0 M tetrabutylammonium fluoride (0.67 mL, 0.669 mmoles) and mixed overnight at room temperature. Reaction diluted with ethyl acetate, washed with saturated NH4Cl, H$_2$O, and brine, dried (Na$_2$SO$_4$), filtered, and the filtrate concentrated under reduced pressure to provide the title compound without further purification.

EXAMPLE 72D

N-[3-(benzyl{4-[3-(3-bromopropoxy)phenoxy]benzyl}amino)-2-methylphenyl]methanesulfonamide The crude product from Example 72C and triphenylphosphine (0.730 g, 2.78 mmoles) in anhydrous DMF (5 mL) at 0° C. were treated with N-bromosuccinimide (0.396 g, 2.24 mmoles). Reaction mixed at 0° C. for 30 minutes. Reaction diluted with ethyl acetate, washed with H$_2$O (2×), brine, dried (Na$_2$SO$_4$), filtered, and the filtrate concentrated under reduced pressure. The residue was purified by flash chromatography (silica gel, 30% ethyl acetate:hexanes) to provide the title compound (0.214 g, 63%). MS (ESI+) m/z 609 (M+H)+.

EXAMPLE 72E

N-{3-[benzyl(4-{3-[3-(dimethylamino)propoxy]phenoxy}benzyl)amino]-2-methylphenyl}methanesulfonamide The product from Example 72D in anhydrous THF (1 mL) was treated with 2.0 M dimethylamine (1.0 mL, 1.97 mmoles) in THF and heated to 70° C. overnight. Reaction mixture concentrated under reduced pressure and the residue was purified by preparative HPLC (CH$_3$CN:0.1% trifluoroacetic acid in H$_2$O) on a YMC ODS Guardpak column to provide the title compound. $^1$H NMR (300 MHz, CDCl$_3$) δ7.10–7.30 (m, 11 H), 6.86 (d, 2 H), 6.72 (s, 1 H), 6.50–6.70 (m, 2 H), 6.32 (t, 1 H), 4.39 (s, 2 H), 4.35 (s, 2 H), 3.98 (t, 2 H), 3.30 (m, 2 H), 2.91 (s, 3 H), 2.90 (s, 3 H), 2.83 (s, 3 H), 2.25 (m, 2 H), 2.13 (s, 3 H); MS (ESI+) m/z 574 (M+H)+.

EXAMPLE 73

N-[3-(benzyl{4-[3-(3-morpholin-4-ylpropoxy)phenoxy]benzyl}amino)-2-methylphenyl]methanesulfonamide The product from Example 72D and morpholine were processed as described in Example 72E to provide the title compound. $^1$H NMR (300 MHz, CDCl$_3$) δ7.10–7.30 (m, 11 H), 6.86 (d, 2 H), 6.63 (d, 1 H), 6.55 (m, 2 H), 6.33 (t, 1 H), 4.31 (s, 2 H), 4.28 (s, 2 H), 4.00 (m, 6 H), 3.65 (m, 2 H), 3.25 (m, 2 H), 2.95 (m, 2 H), 2.85 (s, 3 H), 2.25 (m, 2 H), 2.17 (s, 3 H); MS (ESI+) m/z 616 (M+H)+.

EXAMPLE 74

4-(4-{4-[((2,4-difluorobenzyl){2-methyl-3-[(methylsulfonyl)amino]phenyl}amino)methyl]phenoxy}phenyl)butanoic acid

EXAMPLE 74A ethyl 4-(4-{4-[((2,4-difluorobenzyl){2-methyl-3-[(methylsulfonyl)amino]phenyl}amino)methyl]phenoxy}phenyl)butanoate The product from Example 48B and 4-ethoxy-4-oxobutylzinc bromide (purchased from Aldrich) were processed as described in Example 49 to provide the title compound. MS (ESI+) m/z 623 (M+H)+.

EXAMPLE 74B 4-(4-{4-[((2,4-difluorobenzyl){2-methyl-3-[(methylsulfonyl)amino]phenyl}amino)methyl]phenoxy}phenyl)butanoic acid The product from Example 74A was processed as described in Example 50 to provide the title compound. $^1$H NMR (300 MHz, CDCl$_3$) δ7.10–7.40 (m, 8 H), 6.85 (m, 6 H), 6.16 (d, 1 H), 4.26 (s, 2 H), 4.20 (s, 2 H), 2.76 (s, 3 H), 2.65 (m, 2 H), 2.56 (s, 3 H), 2.35 (m, 2 H), 1.95 (m, 2 H); MS (ESI+) m/z 595 (M+H)+.

EXAMPLE 75

4-(4-{4-[((2,4-difluorobenzyl){2-methyl-3-[(methylsulfonyl)amino]phenyl}amino)methyl]phenoxy}phenyl)-N-[3-(2-oxopyrrolidin-1-yl)propyl]butanamide The product from Example 74B and 1-(3-aminoprpyl)-2-pyrrolidinone were processed as described in Example 68D to provide the title compound. $^1$H NMR (300 MHz, CDCl$_3$) δ7.00–7.30 (m, 8 H), 6.60–6.90 (m, 6 H), 6.25 (s, 1 H), 4.16 (s, 2 H), 4.11 (s, 2 H), 3.30–3.50 (m, 4 H), 3.20 (m, 2 H), 2.84 (s, 3 H), 2.65 (m, 2 H), 2.45 (m, 2 H), 2.24 (s, 3 H), 1.90–2.10 (m, 6 H), 1.65 (m, 2 H); MS (ESI+) m/z 719 (M+H)+.

EXAMPLE 76

3-(4-{4-[((2-bromobenzyl){2-methyl-3-[(methylsulfonyl)amino]phenyl}amino)methyl]phenoxy}phenyl)propanoic acid

EXAMPLE 76A

3-[4-(4-formylphenoxy)phenyl]propanoic acid

4-Fluorobenzaldehyde and 3-(4-hydroxyphenyl)propionic were processed as described in Example 61C to provide the title compound.

EXAMPLE 76B

3-[4-(4-{[(2-methyl-3-nitrophenyl)amino]methyl}phenoxy)phenyl]propanoic acid

The product from Example 76A and 2-methyl-3-nitroaniline were processed as described in Example 6A to provide the title compound.

EXAMPLE 76C methyl 3-[4-(4-{[(2-methyl-3-nitrophenyl)amino]methyl}phenoxy)phenyl]propanoate The product from Example 76B (9.78 g, 24.1 mmoles) in MeOH (24 mL) was treated with concentrated H$_2$SO$_4$ (1 mL) and heated at reflux overnight. Reaction cooled and quenched with saturated NaHCO$_3$. Reaction mixture diluted with ethyl acetate, washed with H$_2$O, brine, dried (Na$_2$SO$_4$), filtered, and the filtrate concentrated under reduced pressure. The residue was purified by flash chromatography (silica gel, 20% ethyl acetate:hexanes) to provide the title compound. MS (ESI−) m/z 419 (M−H)−.

EXAMPLE 76D methyl 3-[4-(4-{[(2-bromobenzyl)(2-methyl-3-nitrophenyl)amino]methyl}phenoxy)phenyl]propanoate The product from Example 76C and 2-bromobenzyl bromide were processed as described in Example 6B to provide the title compound.

EXAMPLE 76E methyl 3-(4-(4-(((2-bromobenzyl)(2-methyl-3-((methylsulfonyl)amino)phenyl)amino)methyl)phenoxy)phenyl)propanoate The product from Example 76D was processed as described in Example 6C and D to provide the title compound.

EXAMPLE 76F 3-(4-{4-[((2-bromobenzyl){2-methyl-3-[(methylsulfonyl)amino]phenyl}amino)methyl]phenoxy}phenyl)propanoic acid The product from Example 76E was processed as described in Example 50 to provide the title compound. $^1$H NMR (300 MHz, CDCl$_3$) δ7.49 (dd, 2 H), 7.10–7.30 (m, 6 H), 7.05 (m, 3 H), 6.85 (m, 4 H), 6.18 (s, 1 H), 4.33 (s, 2 H), 4.18 (s, 2 H), 2.95 (m, 2 H), 2.88 (s, 3 H), 2.65 (m, 2 H), 2.22 (s, 3 H); ); MS (ESI+) m/z 625 (M+H)$^+$.

EXAMPLE 77

(5-{4-[(benzyl{2-methyl-3-[(methylsulfonyl)amino] phenyl}amino)methyl]phenoxy}-2-bromophenoxy) acetic acid

EXAMPLE 77A

[5-(4-{[benzyl(2-methyl-3-nitrophenyl)amino] methyl}phenoxy)-2-bromophenoxy]acetic acid The product from Example 63F and ethyl glycolate were processed as described in Example 62A to provide the title compound.

EXAMPLE 77B ethyl (5-(4-((benzyl(2-methyl-3-((methylsulfonyl) amino)phenyl)amino)methyl)phenoxy)-2-bromophenoxy)acetate The product from Example 77A was processed as described in Example 6C and D to provide the title compound.

EXAMPLE 77C (5-{4-[(benzyl{2-methyl-3-[(methylsulfonyl)amino] phenyl}amino)methyl]phenoxy}-2-bromophenoxy) acetic acid The product from Example 77D was processed as described in Example 50 to provide the title compound. $^1$H NMR (300 MHz, CDCl$_3$) δ7.49 (d, 1 H), 7.40 (d, 2 H), 7.25 (m, 7 H), 7.05 (m, 2 H), 6.80 (d, 2 H), 6.68 (dd, 1 H), 6.59 (d, 1 H), 4.64 (s, 2 H), 4.20–4.40 (br.s, 2 H), 4.00–4.20 (br.s, 2 H), 2.86 (s, 3 H), 2.03 (s, 3 H); MS (ESI+) m/z 625 (M+H)$^+$.

EXAMPLE 78

4-{[2-(3-{4-[(benzyl{2-methyl-3-[(methylsulfonyl) amino]phenyl}amino)methyl]phenoxy}phenoxy) ethyl]amino}-4-oxobutanoic acid

EXAMPLE 78A

2-{2-[3-(4-{[benzyl(2-methyl-3-nitrophenyl)amino] methyl}phenoxy)phenoxy]ethyl}-1H-isoindole-1,3 (2H)-dione The product from Example 61F and N-(2-hydroxyethyl)-phthalimide were processed as described in Example 62A to provide the title compound.

EXAMPLE 78B

N-{3-[benzyl(4-{3-[2-(1,3-dioxo-1,3-dihydro-2H-isoindol-2-yl)ethoxy]phenoxy}benzyl)amino]-2-methylphenyl}methanesulfonamide The product from Example 78A was processed as described in Example 6C and D to provide the title compound. MS (ESI+) m/z 662 (M+H)$^+$.

EXAMPLE 78C

N-{3-[{4-[3-(2-aminoethoxy)phenoxy]benzyl} (benzyl)amino]-2-methylphenyl}methanesulfonamide The product from Example 78B was processed as described in Example 70C to provide the title compound. MS (ESI+) m/z 532 (M+H)$^+$.

EXAMPLE 78D benzyl 4-((2-(3-(4-((benzyl(2-methyl-3-((methylsulfonyl)amino)phenyl)amino)methyl) phenoxy)phenoxy)ethyl)amino)-4-oxobutanoate The product from Example 78C and benzyl succinic acid were processed as described in Example 68D to provide the title compound.

EXAMPLE 78E

4-{[2-(3-{4-[(benzyl{2-methyl-3-[(methylsulfonyl) amino]phenyl}amino)methyl]phenoxy}phenoxy) ethyl]amino}-4-oxobutanoic acid The product from Example 78D was processed as described in Example 50 to provide the title compound. $^1$H NMR (300 MHz, CDCl$_3$) δ7.10–7.30 (m, 10 H), 7.03 (d, 1 H), 6.87 (d, 2 H), 6.75 (m, 2 H), 6.65 (br.s, 1 H), 6.29 (s, 1 H), 6.21 (t, 1 H), 4.10–4.30 (m, 4 H), 3.91 (t, 2 H), 3.65 (m, 2 H), 2.86 (s, 3 H), 2.65 (m, 2 H), 2.55 (m, 2 H), 2.25 (s, 3 H); MS (ESI+) m/z 632 (M+H)$^+$.

EXAMPLE 79

5-{[2-(3-{4-[(benzyl{2-methyl-3-[(methylsulfonyl) amino]phenyl}amino)methyl]phenoxy}phenoxy) ethyl]amino}-5-oxopentanoic acid

EXAMPLE 79A benzyl 5-((2-(3-(4-((benzyl(2-methyl-3-((methylsulfonyl)amino)phenyl)amino)methyl) phenoxy)phenoxy)ethyl)amino)-5-oxopentanoate The product from Example 78C and benzyl glutaric acid were processed as described in Example 68D to provide the title compound.

EXAMPLE 79B

5-{[2-(3-{4-[(benzyl{2-methyl-3-[(methylsulfonyl) amino]phenyl}amino)methyl]phenoxy}phenoxy) ethyl]amino}-5-oxopentanoic acid The product from Example 79A was processed as described in Example 50 to provide the title compound. $^1$H NMR (300 MHz, CDCl$_3$) δ7.10–7.30 (m, 10 H), 7.04 (d, 1 H), 6.87 (d, 2 H), 6.75 (br.s, 1 H), 6.65 (m, 2 H), 6.37 (s, 1 H), 6.05 (m, 1 H), 4.10–4.30 (m, 4 H), 3.95 (t, 2 H), 3.63 (dd, 2 H), 2.87 (s, 3 H), 2.41 (t, 2 H), 2.30 (m, 2 H), 2.28 (s, 3 H), 1.95 (m, 2 H); MS (ESI+) m/z 646 (M+H)$^+$.

EXAMPLE 80

N-[2-(3-{4-[(benzyl{2-methyl-3-[(methylsulfonyl) amino]phenyl}amino)methyl]phenoxy}phenoxy) ethyl]acetamide The product from Example 78C was processed as described in Example 70D to provide the title compound. $^1$H NMR (300 MHz, CDCl$_3$) δ7.10–7.30 (m, 11 H), 7.05 (m, 1 H), 6.88 (d, 2 H), 6.55 (m, 2 H), 6.40 (s, 1 H), 5.95 (br.s, 1 H), 4.00–4.30 (m, 4H), 3.94 (t, 2 H), 3.65 (m, 2 H), 2.88 (s, 3 H), 2.29 (s, 3 H), 2.00 (s, 3 H); MS (ESI+) m/z 574 (M+H)$^+$.

EXAMPLE 81

N-[2-(3-{4-[(benzyl{2-methyl-3-[(methylsulfonyl) amino]phenyl}amino)methyl]phenoxy}phenoxy) ethyl]methanesulfonamide The product from Example 78C was processed as described in Example 6D to provide the title compound. $^1$H NMR (300 MHz, CDCl$_3$) δ7.10–7.40 (m, 10 H), 7.05 (m, 1 H), 6.87 (d, 2 H), 6.60 (m, 2 H), 6.39 (t1 H), 6.30 (s, 1 H), 4.85 (br.s, 1 H), 4.10–4.40 (m, 4 H), 4.05 (m, 2 H), 3.52 (dd, 2 H), 3.01 (s, 3 H), 2.86 (s, 3 H), 2.23 (s, 3 H); MS (ESI+) m/z 610 (M+H)$^+$.

EXAMPLE 82 methyl 2-(3-{4-[(benzyl{2-methyl-3-[(methylsulfonyl)amino]phenyl}amino)methyl]phenoxy}phenoxy)ethylcarbamate The product from Example 78C (0.050 g, 0.0942 mmoles) in anhydrous THF (1 mL) was treated with methyl chloroformate (0.009 mL, 0.113 mmoles) and mixed overnight at room temperature. Reaction mixture concentrated under reduced pressure, and the residue was purified by preparative HPLC (CH$_3$CN:0.1% trifluoroacetic acid in H$_2$O) on a YMC ODS Guardpak column to provide the title compound. $^1$H NMR (300 MHz, CDCl$_3$) δ7.10–7.30 (mn, 10 H), 6.95 (m, 1 H), 6.89 (d, 2 H), 6.55 (m, 2 H), 6.43 (s, 1 H), 6.26 (d, 1 H), 5.15 (br.s, 1 H), 4.00–4.20 (m, 4 H), 3.96 (t, 2 H), 3.68 (s, 3 H), 3.55 (m, 2 H), 2.90 (s, 3 H), 2.30 (s, 3 H); MS (ESI+) m/z 590 (M+H)$^+$.

EXAMPLE 83

(3-{4-[((4-chloro-2-fluorobenzyl){2-methyl-3-[(methylsulfonyl)amino]phenyl}amino)methyl]phenoxy}phenoxy)acetic acid

EXAMPLE 83A 3-(4-{[(2-methyl-3-nitrophenyl)amino]methyl}phenoxy)phenol

The product from Example 61D was processed as described in Example 33A to provide the title compound.

EXAMPLE 83B ethyl [3-(4-{[(2-methyl-3-nitrophenyl)amino]methyl}phenoxy)phenoxy]acetate The product from Example 83A was processed as described in Example 62A to provide the title compound.

EXAMPLE 83C ethyl [3-(4-{[(4-chloro-2-fluorobenzyl)(2-methyl-3-nitrophenyl)amino]methyl}phenoxy)phenoxy]acetate The product from Example 83B and 4-chloro-2-fluorobenzyl bromide were processed as described in Example 6B to provide the title compound.

EXAMPLE 83D ethyl (3-(4-(((4-chloro-2-fluorobenzyl)(2-methyl-3-((methylsulfonyl)amino)phenyl)amino)methyl)phenoxy)phenoxy)acetate The product from Example 83C was processed as described in Example 6C and D to provide the title compound.

EXAMPLE 83E (3-{4-[((4-chloro-2-fluorobenzyl){2-methyl-3-[(methylsulfonyl)amino]phenyl}amino)methyl]phenoxy}phenoxy)acetic acid The product from Example 83D was processed as described in Example 50 to provide the title compound. $^1$H NMR (300 MHz, CDCl$_3$) δ7.10 (d, 2 H), 7.10–7.30 (m, 5 H), 7.05 (m, 2 H), 6.86 (d, 2 H), 6.60–6.80 (m, 3 H), 6.48 (t, 1 H), 4.62 (s, 2 H), 4.25 (m, 2 H), 4.05 (m, 2 H), 2.89 (s, 3 H), 2.12 (s, 3 H); MS (ESI+) m/z 599 (M+H)$^+$.

EXAMPLE 84

3-(4-{4-[((2-fluorobenzyl){2-methyl-3-[(methylsulfonyl)amino]phenyl}amino)methyl]phenoxy}phenyl)propanoic acid

EXAMPLE 84A methyl 3-[4-(4-{[(2-fluorobenzyl)(2-methyl-3-nitrophenyl)amino]methyl}phenoxy)phenyl]propanoate The product from Example 76C and 2-fluorobenzyl bromide were processed as described in Example 6B to provide the title compound.

EXAMPLE 84B methyl 3-(4-(4-(((2-fluorobenzyl)(2-methyl-3-((methylsulfonyl)amino)phenyl)amino)methyl)phenoxy)phenyl)propanoate The product from Example 84A was processed as described in Example 6C and D to provide the title compound.

EXAMPLE 84C 3-(4-{4-[((2-fluorobenzyl){2-methyl-3-[(methylsulfonyl)amino]phenyl}amino)methyl]phenoxy}phenyl)propanoic acid The product from Example 84B was processed as described in Example 50 to provide the title compound. $^1$H NMR (300 MHz, CDCl$_3$) δ7.10–7.30 (m, 8 H), 7.00 (m, 3 H), 6.85 (m, 4 H), 6.20 (s, 1 H), 4.22 (s, 2 H), 4.14 (s, 2 H), 2.94 (t, 2 H), 2.90 (s, 3 H), 2.68 (t, 2 H), 2.27 (s, 3 H); MS (ESI+) m/z 563 (M+H)$^+$.

EXAMPLE 85

3-(4-{4-[((4-fluorobenzyl){2-methyl-3-[(methylsulfonyl)amino]phenyl}amino)methyl]phenoxy}phenyl)propanoic acid

EXAMPLE 85A methyl 3-[4-(4-{[(4-fluorobenzyl)(2-methyl-3-nitrophenyl)amino]methyl}phenoxy)phenyl]propanoate The product from Example 76C and 4-fluorobenzyl bromide were processed as described in Example 6B to provide the title compound.

EXAMPLE 85B methyl 3-(4-(4-(((4-fluorobenzyl)(2-methyl-3-((methylsulfonyl)amino)phenyl)amino)methyl)phenoxy)phenyl)propanoate The product from Example 85A was processed as described in Example 6C and D to provide the title compound.

EXAMPLE 85C 3-(4-{4-[((4-fluorobenzyl){2-methyl-3-[(methylsulfonyl)amino]phenyl}amino)methyl]phenoxy}phenyl)propanoic acid The product from Example 85B was processed as described in Example 50 to provide the title compound. $^1$H NMR (300 MHz, CDCl₃) δ7.10–7.30 (m, 8 H), 6.80–7.00 (m, 7 H), 6.26 (s, 1 H), 4.10–4.30 (m, 4 H), 2.94 (t, 2 H), 2.90 (s, 3 H), 2.68 (t, 2 H), 2.24 (s, 3 H); MS (ESI+) m/z 563 (M+H)⁺.

EXAMPLE 86

3-(4-{4-[((4-chloro-2-fluorobenzyl){2-methyl-3-[(methylsulfonyl)amino]phenyl}amino)methyl]phenoxy}phenyl)propanoic acid

EXAMPLE 86A methyl 3-[4-(4-{[(4-chloro-2-fluorobenzyl)(2-methyl-3-nitrophenyl)amino]methyl}phenoxy)phenyl]propanoate The product from Example 76C and 4-chloro-2-fluorobenzyl bromide were processed as described in Example 6B to provide the title compound.

EXAMPLE 86B methyl 3-(4-(4-(((4-chloro-2-fluorobenzyl)(2-methyl-3-((methylsulfonyl)amino)phenyl)amino)methyl)phenoxy)phenyl)propanoate The product from Example 86A was processed as described in Example 6C and D to provide the title compound.

EXAMPLE 86C 3-(4-{4-[((4-chloro-2-fluorobenzyl){2-methyl-3-[(methylsulfonyl)amino]phenyl}amino)methyl]phenoxy}phenyl)propanoic acid The product from Example 86B was processed as described in Example 50 to provide the title compound. ¹H NMR (300 MHz, CDCl₃) δ7.10–7.30 (m, 7 H), 6.95 (m, 3 H), 6.85 (m, 4 H), 6.22 (s, 1 H), 4.21 (s, 2 H), 4.14 (s, 2 H), 2.95 (t, 2 H), 2.91 (s, 3 H), 2.68 (t, 2 H), 2.27 (s, 3 H); MS (ESI+) m/z 597 (M+H)⁺.

EXAMPLE 87

(3-{4-[((2,4-difluorobenzyl){2-ethyl-3-[(methylsulfonyl)amino]phenyl}amino)methyl]phenoxy}phenoxy)acetic acid

EXAMPLE 87A

N-{4-[3-(allyloxy)phenoxy]benzyl}-N-(3-nitro-2-vinylphenyl)amine

The product from Example 44B and the product from Example 61C were processed as in Example 6A to provide the title compound.

EXAMPLE 87B

N-{4-[3-(allyloxy)phenoxy]benzyl}-N-(2,4-difluorobenzyl)-N-(3-nitro-2-vinylphenyl)amine The product from Example 87A and 2,4-difluorobenzyl bromide were processed as described in Example 6B to provide the title compound. MS (ESI+) m/z 529 (M+H)⁺.

EXAMPLE 87C 3-(4-{[(2,4-difluorobenzyl)(3-nitro-2-vinylphenyl)amino]methyl}phenoxy)phenol The product from Example 87B was processed as described in Example 33A to provide the title compound.

EXAMPLE 87D

[3-(4-{[(2,4-difluorobenzyl)(3-nitro-2-vinylphenyl)amino]methyl}phenoxy)phenoxy]acetic acid The product from Example 87C was processed as described in Example 62A to provide the title compound. MS (ESI+) m/z 575 (M+H)⁺.

EXAMPLE 87E

[3-(4-{[(3-amino-2-ethylphenyl)(2,4-difluorobenzyl)amino]methyl}phenoxy)phenoxy]acetic acid The product from Example 87D (0.045 g, 0.0784 mmoles) in 1:1 ethyl acetate/TBF (4 mL) was added to a degassed flask charged with 10% palladium on carbon catalyst (0.050 g). Reaction mixture was degassed again and stirred vigorously at room temperature under an atmosphere of hydrogen for one hour. The reaction mixture was filtered through a pad of celite, and filtrate concentrated under reduced pressure to provide the title compound with no further purification (0.035 g, 82%). MS (ESI+) m/z 547 (M+H)⁺.

EXAMPLE 87F ethyl (3-(4-(((2,4-difluorobenzyl)(2-ethyl-3-((methylsulfonyl)amino)phenyl)amino)methyl)phenoxy)phenoxy)acetate The product from Example 87E was processed as described in Example 6D to provide the title compound.

EXAMPLE 87G (3-{4-[((2,4-difluorobenzyl){2-ethyl-3-[(methylsulfonyl)amino]phenyl}amino)methyl]phenoxy}phenoxy)acetic acid The product from Example 87F was processed as described in Example 50 to provide the title compound. ¹H NMR (300 MHz, CDCl₃) δ7.20 (m, 2 H), 7.20–7.40 (m, 4 H), 7.10 (d, 2 H), 6.87 (d, 2 H), 6.75 (m, 2 H), 6.65 (m, 2 H), 6.59 (s, 1 H), 4.63 (s, 2 H), 4.24 (s, 2 H), 4.13 (s, 2 H), 2.91 (s, 3 H), 2.62 (q, 2 H), 0.91 (t, 3 H); MS (ESI+) m/z 597 (M+H)⁺.

EXAMPLE 88

(3-{4-[(benzyl{2-methyl-3-[(methylsulfonyl)amino]phenyl}amino)methyl]benzoyl}phenoxy)acetic acid

EXAMPLE 88A

4-[(benzyl{2-methyl-3-[(methylsulfonyl)amino]phenyl}amino)methyl]benzoic acid

The product from Example 6D was processed as described in Example 50 to provide the title compound.

EXAMPLE 88B

4-[(benzyl{2-methyl-3-[(methylsulfonyl)amino]phenyl}amino)methyl]-N-methoxy-N-methylbenzamide The product from Example 88A and N,O-dimethylhydroxylamine hydrochloride were processed as described in Example 68D to provide the title compound. MS (ESI+) m/z 468 (M+H)⁺.

EXAMPLE 88C

1-(allyloxy)-3-bromobenzene

3-Bromophenol (10.0 g, 57.8 mmoles) in anhydrous DMF (60 mL) was treated with $K_2CO_3$ (24.0 g, 173 mmoles) and allyl iodide (5.81 mL, 63.6 mmoles). Reaction stirred overnight at 80° C. Reaction allowed to cool to room temperature and diluted with ethyl acetate. The mixture was washed with $H_2O$ (2×), brine, dried ($Na_2SO_4$), filtered, and the filtrate concentrated under reduced pressure to provide the title compound with no further purification.

EXAMPLE 88D

N-{3-[{4-[3-(allyloxy)benzoyl]benzyl}(benzyl)amino]-2-methylphenyl}methanesulfonamide The product from Example 88C (0.983 g, 3.80 mmoles) in anhydrous THF (10 mL) at −78° C. was treated dropwise with 1.7 M t-butyllithium (4.46 mL, 7.59 mmoles). Reaction stirred 30 minutes at −78° C. and was then treated with the product from Example 88B (1.00 g, 1.90 mmoles. Reaction stirred 15 minutes at −78° C. and then allowed to warm to 0° C. Reaction quenched with saturated $NH_4Cl$ and warmed to room temperature. The mixture was diluted with ethyl acetate, washed with $H_2O$, brine, dried ($Na_2SO_4$), filtered, and the filtrate concentrated under reduced pressure. The residue was purified by chromatography on a pre-packed Biotage silica gel column (30% ethyl acetate:hexanes) to provide the title compound (0.369 g, 36%). MS (ESI−) m/z 539 (M−H)−.

EXAMPLE 88E

N-{3-[{4-[3-(allyloxy)benzoyl]benzyl}(benzyl)amino]-2-methylphenyl}di-methanesulfonamide The product from Example 88D was processed as described in Example 6D to provide the title compound.

EXAMPLE 88F

N-(3-{benzyl[4-(3-hydroxybenzoyl)benzyl]amino}-2-methylphenyl)di-methanesulfonamide The product from Example 88E was processed as described in Example 33A to provide the title compound.

EXAMPLE 88G ethyl (3-(4-((benzyl(3-(bis(methylsulfonyl)amino)-2-methylphenyl)amino)methyl)benzoyl)phenoxy)acetate The product from Example 88F and ethyl glycolate were processed as described in Example 62A to provide the title compound. MS (ESI+) m/z 665 (M+H)+.

EXAMPLE 88H

(3-{4-[(benzyl{2-methyl-3-[(methylsulfonyl)amino]phenyl}amino)methyl]benzoyl}phenoxy)acetic acid The product from Example 88G was processed as described in Example 50 to provide the title compound. $^1$H NMR (300 MHz, CDCl$_3$) δ7.65 (d, 2 H), 7.45 (m, 2 H), 7.10–7.30 (m, 11 H), 7.04 (d, 1 H), 6.50 (s, 1 H), 4.69 (s, 2 H), 4.21 (s, 2 H), 4.18 (s, 2 H), 2.93 (s, 3 H), 2.01 (s, 3 H); MS (ESI+) m/z 559 (M+H)+.

EXAMPLE 89

(3-{4-[((2,4-difluorobenzyl){2-methyl-3-[(methylsulfonyl)amino]phenyl}amino)methyl]phenoxy}-5-methylphenoxy)acetic acid

EXAMPLE 89A

3-(allyloxy)-5-methylphenol

Orcinol and allyl iodide were processed as described in Example 88C to provide the title compound. MS (DCI) m/z 165 (M+H)+.

EXAMPLE 89B

4-[3-(allyloxy)-5-methylphenoxy]benzaldehyde

The product from Example 89A and 4-fluorobenzaldehyde were processed as in Example 61C to provide the title compound. MS (DCI) m/z 269 (M+H)+.

EXAMPLE 89C

N-{4-[3-(allyloxy)-5-methylphenoxy]benzyl}-N-(2-methyl-3-nitrophenyl)amine

The product from Example 89B and 2-methyl-3-nitroaniline were processed as in Example 6A to provide the title compound. MS (ESI−) m/z 403 (M−H)−.

EXAMPLE 89D

N-{4-[3-(allyloxy)-5-methylphenoxy]benzyl}-N-(2,4-difluorobenzyl)-N-(2-methyl-3-nitrophenyl)amine The product from Example 89C and 2,4-difluorobenzyl bromide were processed as described in Example 6B to provide the title compound.

EXAMPLE 89E

3-(4-{[(2,4-difluorobenzyl)(2-methyl-3-nitrophenyl)amino]methyl}phenoxy)-5-methylphenol The product from Example 89D was processed as described in Example 33A to provide the title compound.

EXAMPLE 89F ethyl [3-(4-{[(2,4-difluorobenzyl)(2-methyl-3-nitrophenyl)amino]methyl}phenoxy)-5-methylphenoxy]acetate The product from Example 89E and ethyl glycolate were processed as described in Example 62A to provide the title compound.

EXAMPLE 89G ethyl (3-(4-(((2,4-difluorobenzyl)(2-methyl-3-((methylsulfonyl)amino)phenyl)amino)methyl)phenoxy)-5-methylphenoxy)acetate The product from Example 89F was processed as described in Example 6C and D to provide the title compound.

EXAMPLE 89H

(3-{4-[((2,4-difluorobenzyl){2-methyl-3-[(methylsulfonyl)amino]phenyl}amino)methyl]phenoxy}-5-methylphenoxy)acetic acid The product from Example 89G was processed as described in Example 50 to provide the title compound. $^1$H NMR (400 MHz, CDCl$_3$) δ7.15 (m, 3 H), 7.10 (d, 2 H), 7.01 (dd, 1 H), 6.86 (d, 2 H), 6.75 (m, 2 H), 6.61 (s, 1 H), 6.48 (d, 2 H), 6.28 (t, 1 H), 4.59 (s, 2 H), 4.14 (s, 2 H), 4.06 (s, 2 H), 2.91 (s, 3 H), 2.28 (s, 3 H), 2.18 (s, 3 H); MS (ESI+) m/z 597 (M+H)+.

EXAMPLE 90

(3-{4-[((2,4-difluorobenzyl){2-methyl-3-[(methylsulfonyl)amino]phenyl}amino)methyl]phenoxy}-5-methoxyphenoxy)acetic acid

EXAMPLE 90A

3-(allyloxy)-5-methoxyphenol

5-Methoxyresorcinol and allyl iodide were processed as described in Example 88C to provide the title compound. MS (DCI) m/z 181 (M+H)+.

EXAMPLE 90B

4-[3-(allyloxy)-5-methoxyphenoxy]benzaldehyde

The product from Example 90A and 4-fluorobenzaldehyde were processed as in Example 61C to provide the title compound. MS (DCI) m/z 285 (M+H)+.

EXAMPLE 90C

N-{4-[3-(allyloxy)-5-methoxyphenoxy]benzyl}-N-(2-methyl-3-nitrophenyl)amine

The product from Example 90B and 2-methyl-3-nitroaniline were processed as in Example 6A to provide the title compound. MS (ESI−) m/z 419 (M−H)−.

EXAMPLE 90D

N-{4-[3-(allyloxy)-5-methoxyphenoxy]benzyl}-N-(2,4-difluorobenzyl)-N-(2-methyl-3-nitrophenyl)amine The product from Example 90C and 2,4-difluorobenzyl bromide were processed as described in Example 6B to provide the title compound. MS (APCI+) m/z 547 (M+H)+.

EXAMPLE 90E 3-(4-{[(2,4-difluorobenzyl)(2-methyl-3-nitrophenyl)amino]methyl}phenoxy)-5-methoxyphenol The product from Example 90D was processed as described in Example 33A to provide the title compound.

EXAMPLE 90F ethyl [3-(4-{[(2,4-difluorobenzyl)(2-methyl-3-nitrophenyl)amino]methyl}phenoxy)-5-methoxyphenoxy]acetate The product from Example 90E and ethyl glycolate were processed as described in Example 62A to provide the title compound. MS (ESI+) m/z 593 (M+H)+.

EXAMPLE 90G ethyl (3-(4-(((2,4-difluorobenzyl)(2-methyl-3-((methylsulfonyl)amino)phenyl)amino)methyl)phenoxy)-5-methoxyphenoxy)acetate The product from Example 90F was processed as described in Example 6C and D to provide the title compound.

EXAMPLE 90H (3-{4-[((2,4-difluorobenzyl){2-methyl-3-[(methylsulfonyl)amino]phenyl}amino)methyl]phenoxy}-5-methoxyphenoxy)acetic acid The product from Example 90G was processed as described in Example 50 to provide the title compound. $^1$H NMR (400 MHz, CDCl$_3$) δ7.25 (m, 2 H), 7.16 (t, 1 H), 7.10 (d, 2 H), 7.05 (d, 1 H), 6.87 (d, 2 H), 6.75 (m, 2 H), 6.64 (s, 1 H), 6.20 (m, 2 H), 6.03 (t, 1 H), 4.58 (s, 2 H), 4.21 (s, 2 H), 4.12 (s, 2 H), 3.74 (s, 3 H), 2.89 (s, 3 H), 2.15 (s, 3 H); MS (ESI+) m/z 613 (M+H)+.

EXAMPLE 91

(2-chloro-5-{4-[((2,4-difluorobenzyl){2-methyl-3-[(methylsulfonyl)amino]phenyl}amino)methyl]phenoxy}phenoxy)acetic acid

EXAMPLE 91A 3-(allyloxy)-4-chlorophenyl 4-methylbenzenesulfonate

4-Chlororesorcinol was processed as described in Example 63A.

EXAMPLE 91B 3-(allyloxy)-4-chlorophenol

The product from Example 91A was processed as described in Example 63B.

EXAMPLE 91C

4-[3-(allyloxy)-4-chlorohenoxy]benzaldehyde

The product from Example 91B and 4-fluorobenzaldehyde were processed as in Example 61C to provide the title compound. MS (DCI) m/z 289 (M+H)+.

EXAMPLE 91D

N-{4-[3-(allyloxy)-4-chlorophenoxy]benzyl}-N-(2-methyl-3-nitrophenyl)amine

The product from Example 91C and 2-methyl-3-nitroaniline were processed as in Example 6A to provide the title compound. MS (ESI−) m/z 423 (M−H)−.

EXAMPLE 91E

N-{4-[3-(allyloxy)-4-chlorophenoxy]benzyl}-N-(2,4-difluorobenzyl)-N-(2-methyl-3-nitrophenyl)amine The product from Example 91D and 2,4-difluorobenzyl bromide were processed as described in Example 6B to provide the title compound. MS (ESI+) m/z 573 (M+H)+.

EXAMPLE 91F 2-chloro-5-(4-{[(2,4-difluorobenzyl)(2-methyl-3-nitrophenyl)amino]methyl}phenoxy)phenol The product from Example 91E was processed as described in Example 33A to provide the title compound.

EXAMPLE 91G ethyl [2-chloro-5-(4-{[(2,4-difluorobenzyl)(2-methyl-3-nitrophenyl)amino]methyl}phenoxy)phenoxy]acetate The product from Example 91F and ethyl glycolate were processed as described in Example 62A to provide the title compound. MS (ESI+) m/z 597 (M+H)+.

EXAMPLE 91H ethyl (2-chloro-5-(4-(((2,4-difluorobenzyl)(2-methyl-3-((methylsulfonyl)amino)phenyl)amino)methyl)phenoxy)phenoxy)acetate The product from Example 91G was processed as described in Example 6C and D to provide the title compound.

EXAMPLE 91I (2-chloro-5-{4-[((2,4-difluorobenzyl){2-methyl-3-[(methylsulfonyl)amino]phenyl}amino)methyl]phenoxy}phenoxy)acetic acid The product from Example 91H was processed as described in Example 50 to provide the title compound. $^1$H NR (300 MHz, CDCl$_3$) δ7.32 (d, 2 H), 7.25 (m, 3 H), 7.20 (m, 2 H), 6.96 (d, 2 H), 6.81 (d, 2 H), 6.77 (s, 1 H), 6.75 (m, 1 H), 6.62 (d, 1 H), 4.65 (s, 2 H), 4.17 (s, 2 H), 3.98 (s, 2 H), 2.91 (s, 3 H), 1.97 (s, 3 H); MS (ESI+) m/z 617 (M+H)+.

EXAMPLE 92

1-[2-(3-{4-[(benzyl{2-methyl-3-[(methylsulfonyl)amino]phenyl}amino)methyl]phenoxy}phenoxy)ethyl]piperidine-2-carboxylic acid

EXAMPLE 92A

N-benzyl-N-(2-methyl-3-nitrophenyl)-N-(4-{3-[2-(tetrahydro-2H-pyran-2-yloxy)ethoxy]phenoxy}benzyl)amine The product from Example 61F and 2-(tetrahydro-2H-pyran-2-yloxy)ethanol (purchased from Fluka) were processed as described in Example 62A to provide the title compound.

EXAMPLE 92B

2-[3-(4-{[benzyl(2-methyl-3-nitrophenyl)amino]methyl}phenoxy)phenoxy]ethanol

The product from Example 92A (0.480 g, 0.845 mmoles) in EtOH (2.0 mL) was treated with pyridinium p-toluenesulfonate (0.0106 g, 0.0422 mmoles) and heated at 55° C. for four hours. The reaction was diluted with ethyl acetate, washed with H$_2$O, brine, dried (Na$_2$SO$_4$), filtered, and the filtrate concentrated under reduced pressure. The residue was purified by chromatography on a pre-packed Biotage silica gel column (hexanes to 50% ethyl acetate:hexanes) to provide the title compound.

EXAMPLE 92C 2-(3-{4-[(benzyl{2-methyl-3-[(methylsulfonyl)amino]phenyl}amino)methyl]phenoxy}phenoxy)ethyl methanesulfonate The product from Example 92B was processed as described in Example 6C and D to provide the title compound. MS (ESI+) m/z 611 (M+H)$^+$.

EXAMPLE 92D ethyl 1-[2-(3-{4-[(benzyl{2-methyl-3-[(methylsulfonyl)amino]phenyl}amino)methyl]phenoxy}phenoxy)ethyl]piperidine-2-carboxylate The product from Example 92C (0.057 g, 0.0934 mmoles) in anhydrous DMF (1.0 mL) was treated with ethyl pipecolinate (0.072 mL, 0.467 mmoles) and heated at 80° C. overnight. The reaction was diluted with ethyl acetate, washed with H$_2$O (2x), brine, dried (Na$_2$SO$_4$), filtered, and the filtrate concentrated under reduced pressure.

EXAMPLE 92E

1-[2-(3-{4-[(benzyl{2-methyl-3-[(methylsulfonyl)amino]phenyl}amino)methyl]phenoxy}phenoxy)ethyl]piperidine-2-carboxylic acid The product from Example 92D was processed as described in Example 50 to provide the title compound. $^1$H NMR (500 MHz, DMSO) δ8.97 (s, 1 H), 7.25 (m, 7 H), 7.20 (m, 1 H), 7.05 (m, 1 H), 6.98 (d, 2 H), 6.93 (d, 2 H), 6.75 (dd, 1 H), 6.62 (t, 1 H), 6.56 (dd, 1 H), 4.35 (m, 2 H), 4.07 (s, 2 H), 4.04 (s, 2 H), 3.65 (m, 2 H), 3.55 (m, 2 H), 3.25 (m, 1 H), 2.92 (s, 3 H), 2.40 (s, 3 H), 2.15 (m, 1 H), 1.50–1.80 (m, 5 H); MS (ESI+) m/z 644 (M+H)$^+$.

EXAMPLE 93

N-{3-[benzyl(4-{3-[(1-methylpyrrolidin-3-yl)methoxy]phenoxy}benzyl)amino]-2-methylphenyl}methanesulfonamide

EXAMPLE 93A tert-butyl 3-}[(methylsulfonyl)oxy]methyl}pyrrolidine-1-carboxylate N-t-butylcarbonyl-3-hydroxymethylpyrrolidine (0.220 g, 1.09 mmoles) and triethylamine (0.168 mL, 1.20 mmoles) in anhydrous CH$_2$Cl$_2$ at −10° C. were treated dropwise with methanesulfonyl chloride (0.093 mL, 1.20 mmoles). Reaction stirred one hour at 0° C. and overnight at room temperature. Reaction diluted with Na$_2$CO$_3$ and extracted with CH$_2$Cl$_2$ (2x). Combined extracts were washed with H$_2$O, brine, dried (Na$_2$SO$_4$), filtered, and the filtrate concentrated under reduced pressure to provide the title compound with no further purification. MS (DCI) m/z 280 (M+H)$^+$.

EXAMPLE 93B tert-butyl 3-{[3-(4-{[benzyl(2-methyl-3-nitrophenyl)amino]methyl}phenoxy)phenoxy]methyl}pyrrolidine-1-carboxylate The product from Example 93A and Example 61F were processed as described in Example 60F MS (ESI+) m/z 624 (M+H)$^+$.

EXAMPLE 93C tert-butyl 3-[(3-{4-[(benzyl{2-methyl-3-[(methylsulfonyl)amino]phenyl}amino)methyl]phenoxy}phenoxy)methyl]pyrrolidine-1-carboxylate The product from Example 93B was processed as described in Example 6C and D to provide the title compound.

EXAMPLE 93D

N-[3-(benzyl{4-[3-(pyrrolidin-3-ylmethoxy)phenoxy]benzyl}amino)-2-methylphenyl]methanesulfonamide The product from Example 93C (0.108 g, 0.161 mmoles) was treated with 4 N HCl (2.0 mL/8.00 mmoles) in dioxane and stirred at room temperature for one hour. Reaction quenched with saturated NaHCO$_3$ and extracted with CH$_2$Cl$_2$. Extracts dried (Na$_2$SO$_4$), filtered, and the filtrate concentrated under reduced pressure to provide the title compound with no further purification.

EXAMPLE 93E

N-{3-[benzyl(4-{3-[(1-methylpyrrolidin-3-yl)methoxy]phenoxy}benzyl)amino]-2-methylphenyl}methanesulfonamide The product from Example 93D (0.030 g, 0.0525 mmoles) in 1:1 CH$_3$CN/MeOH (2 mL) was treated with 37% aqueous formaldehyde (0.020 mL, 0.263 mmoles) and sodium cyanoborohydride (0.008 g, 0.131 mmoles). Reaction mixed overnight at room temperature. Reaction quenched with two drops acetic acid and concentrated under reduced pressure. The residue was purified by preparative HPLC (CH$_3$CN:0.1% TRIFLUOROACETIC ACID in H$_2$O) on a YMC ODS Guardpak column to provide the title compound. $^1$H NMR (500 MHz, DMSO) δ8.96 (s, 1 H), 7.25 (m, 7 H), 7.20 (m, 1 H), 7.05 (m, 1 H), 6.97 (d, 2 H), 6.92 (d, 2 H), 6.70 (m, 1 H), 6.56 (dd, 1 H), 6.53 (dd, 1 H), 4.06 (s, 2 H), 4.03 (s, 2 H), 3.95 (m, 1 H), 3.50–3.80 (m, 1 H), 3.30–3.50 (m, 1 H), 3.00–3.20 (m, 2 H), 2.92 (s, 3 H), 2.80 (m, 5 H), 2.40 (s, 3 H), 2.00–2.30 (m, 1 H), 1.80 (m, 1 H); MS (ESI+) m/z 586 (M+H)$^+$.

EXAMPLE 94

N-{3-[(4-{3-[(1-acetylpyrrolidin-3-yl)methoxy]phenoxy}benzyl)(benzyl)amino]-2-methylphenyl}methanesulfonamide The product from Example 93D was processed as described in Example 70D to provide the title compound. 1H NMR (400 MHz, CDCl3) δ (rotamer) 7.11 (d, 1 H), 7.10–7.30 (m, 8 H), 6.95 (m, 1 H), 6.90 (d, 2 H), 6.65 (m, 1 H), 6.60 (m, 2 H), 6.52 (6.45) (t, 1 H), 6.35 (6.22) (s, 1 H), 4.08 (s, 2 H), 4.05 (s, 2 H), 3.80–4.00 (m, 2 H), 3.50–3.80 (m, 2 H), 3.30–3.50 (m, 2 H), 2.94 (2.92) (s, 3 H), 2.70 (m, 1 H), 2.33 (2.32) (s, 3 H), 2.15 (m, 1 H), 2.08 (s, 3 H), 1.80 (m, 1 H); MS (ESI+) m/z 614 (M+H)+.

EXAMPLE 95

(4-{4-[(benzyl{2-methyl-3-[(methylsulfonyl)amino]phenyl}amino)methyl]phenoxy}phenoxy)acetic acid

EXAMPLE 95A ethyl [4-(4-{[benzyl(2-methyl-3-nitrophenyl)amino]methyl}phenoxy)phenoxy]acetate The product from Example 60E and ethyl glycolate were processed as described in Example 62A to provide the title compound. MS (ESI+) m/z 527 (M+H)$^+$.

EXAMPLE 95B ethyl (4-(4-((benzyl(2-methyl-3-((methylsulfonyl)amino)phenyl)amino)methyl)phenoxy)phenoxy)acetate The product from Example 95A was processed as described in Example 6C and D to provide the title compound. MS (ESI+) m/z 575 (M+H)$^+$.

EXAMPLE 95C (4-{4-[(benzyl{2-methyl-3-[(methylsulfonyl)amino]phenyl}amino)methyl]phenoxy}phenoxy)acetic acid The product from Example 95B was processed as described in Example 50 to provide the title compound. $^1$H NMR (400 MHz, CDCl$_3$) δ7.25 (m, 6 H), 7.15 (m, 3 H), 6.95 (m, 5 H), 6.83 (d, 2 H), 6.29 (s, 1 H), 4.66 (s, 2 H), 4.05 (s, 2 H), 4.01 (s, 2 H), 2.94 (s, 3 H), 2.33 (s, 3 H); MS (ESI+) m/z 547 (M+H)$^+$.

EXAMPLE 96

4-{4-[(benzyl{2-methyl-3-[(methylsulfonyl)amino]phenyl}amino)methyl]phenoxy}benzoic acid The product from Example 52 was processed as described in Example 50 to provide the title compound. $^1$H NMR (300 MHz, CDCL$_3$) δ7.91–8.22 (m, 2 H), 7.06–7.37 (m, 9 H), 6.94 (m, 5 H), 6.21 (s, 1 H), 4.08 (s, 2 H), 4.07 (s, 2 H), 3.85 (br s, 1H), 2.97 (s, 3 H), 2.37 (s, 3 H); MS (ESI) m/z 517 (M+H$^+$).

EXAMPLE 97

N-[3-(benzyl{4-[4-(methoxymethoxy)phenoxy]benzyl}amino)-2-methylphenyl]methanesulfonamide

EXAMPLE 97A

N-benzyl-N-{4-[4-(methoxymethoxy)phenoxy]benzyl}-N-(2-methyl-3-nitrophenyl)amine The product from Example 65B and methoxymethyl-4-bromophenyl ether was processed as described in Example 66A to provide the title compound.

EXAMPLE 97B

N-[3-(benzyl{4-[4-(methoxymethoxy)phenoxy]benzyl}amino)-2-methylphenyl]methanesulfonamide The product from Example 97A was processed as described in Examples 6C and 6D to provide the title compound. 1H NMR (300 MHz, CDCL3) δ7.07–7.34 (m, 10 H), 6.92 (m, 3 H), 6.77 (ddd, 1 H), 6.66 (t, 1 H), 6.61 (ddd, 1 H), 6.15 (s, 1 H), 5.14 (s, 2 H), 4.06 (s, 2 H), 4.01 (s, 2 H), 3.47 (s, 3 H), 2.94 (s, 3 H), 2.32 (s, 3 H); MS (ESI) m/z 533 (M+H+).

EXAMPLE 98 benzyl 3-(4-{4-[(benzyl{2-methyl-3-[(methylsulfonyl)amino]phenyl}amino)methyl]phenoxy}phenyl)propanoate

EXAMPLE 98A

3-[4-(4-{[(2-methyl-3-nitrophenyl)amino]methyl}phenoxy)phenyl]propanoic acid

A solution of 4-hydroxyphenylpropionic acid (4.02 g, 24.2 mmoles), 4-fluorobenzaldehye (3.63 mL, 33.9 mmoles), and K$_2$CO$_3$ (6.69 g, 48.4 mmoles) in DMF (24.2 mL) was heated to 100° C. for 48 h. The crude products were diluted with H$_2$O, washed with diethyl ether, acidified with 3N HCl, and extracted with ethyl acetate. The organic layer was washed with H$_2$O (2×), rinsed with brine, dried (Na$_2$SO$_4$), and concentrated under reduced pressure to yield crude aldehyde. The title compound was prepared as described in Example 6A using the crude aldehyde.

EXAMPLE 98B benzyl 3-[4-(4-{[benzyl(2-methyl-3-nitrophenyl)amino]methyl}phenoxy)phenyl]propanoate The product from example 98A and benzyl bromide were processed as described in Example 6B to provide the title compound.

EXAMPLE 98C benzyl 3-(4-{4-[(benzyl{2-methyl-3-[(methylsulfonyl)amino]phenyl}amino)methyl]phenoxy}phenyl)propanoate The product from Example 98B was processed as described in Examples 6C and 6D to provide the title compound. $^1$H NMR (300 MHz, CDCL3) δ7.02–7.45 (m, 16 H), 6.88 (m, 5 H), 6.11 (s, 1 H), 5.11 (s, 2 H), 4.04 (s, 2 H), 4.01 (s, 2 H), 2.95 (s, 3 H), 2.95 (t, 2 H), 2.67 (t2 H), 2.34 (s, 3 H); MS (ESI) m/z 634 (M+).

EXAMPLE 99

N-[3-(benzyl{4-[4-(3-hydroxypropyl)phenoxy[benzyl}amino)-2-methylphenyl]methanesulfonamide The product from Example 98C was processed as described in Example 38A to provide the title compound. $^1$H NMR (300 MHz, CDCL$_3$) δ7.19 (m, 12 H), 6.90 (m, 4 H), 6.09 (s, 1 H), 3.93–4.24 (br.s, 4 H), 3.69 (t, 2 H), 2.95 (s, 3 H), 2.69 (m, 2 H), 2.32 (s, 3 H), 1.88 (m, 2 H), 1.25 (m, 1 H); MS (ESI) m/z 531 (M+H$^+$).

EXAMPLE 100

4-(4-{4-[(benzyl{2-methyl-3-[(methylsulfonyl)amino]phenyl}amino)methyl]phenoxy}phenyl)butanoic acid The product from Example 64E was processed as described in Example 50 to provide the title compound. $^1$H NMR (300 MHz, CDCL$_3$) δ7.08–7.31 (m, 11 H), 6.89 (m, 5 H), 6.19 (s, 1 H), 4.07 (s, 2 H), 4.03 (s, 2 H), 3.48 (dd, 1 H), 2.94 (s, 3 H), 2.66 (t, 2 H), 2.38 (t, 2 H), 2.33 (s, 3 H), 1.96 (m, 2 H); MS (ESI) m/z 559 (M+H$^+$).

EXAMPLE 101

N-[3-(benzyl{4-[4-(4-hydroxybutyl)phenoxy] benzyl}amino)-2-methylphenyl]methanesulfonamide The product from Example 64E was processed as described in Example 38A to provide the title compound. $^1$H NMR (300 MHz, CDCL$_3$) δ7.26 (m, 7 H), 7.11 (m, 5 H), 6.86 (m, 4 H), 6.11 (s, 1 H), 4.25–4.49 (m, 6 H), 3.41–3.80 (m, 3 H), 2.84 (s, 3 H), 2.63 (m, 2 H), 2.14 (s, 3 H), 1.53–1.90 (m, 2 H); MS (ESI) m/z 545 (M+H$^+$).

EXAMPLE 102

N-{3-[(3-bromobenzyl)(4-phenoxybenzyl)amino]-2-methylphenyl}methanesulfonamide

The product from Example 26A and 3-bromobenzyl bromide were processed as described in Examples 6B–D to provide the title compound. $^1$H NMR (300 MHz, CDCL$_3$) δ7.34 (m, 4 H), 7.22 (m, 1 H), 7.12 (m, 5 H), 6.99 (m, 2 H), 6.90 (m, 4 H), 6.12 (s, 1 H), 4.04 (s, 2 H), 4.02 (s, 2 H), 2.96 (s, 3 H), 2.34 (s, 3 H); MS (APCI) m/z 553 (M+H$^+$).

EXAMPLE 103

N-{3-[(4-bromobenzyl)(4-phenoxybenzyl)amino]-2-methylphenyl}methanesulfonamide

The product from Example 26A and 4-bromobenzyl bromide were processed as described in Examples 6B–D to provide the title compound. $^1$H NMR (300 MHz, CDCL$_3$) δ6.80–7.46 (m, 16 H), 6.12 (s, 1 H), 4.01 (s, 4 H), 2.96 (s, 3 H), 2.33 (s, 3 H); MS (ESI) m/z 553 (M+H$^+$).

EXAMPLE 104

N-[3-(4-{4-[(benzyl{2-methyl-3-[(methylsulfonyl) amino]phenyl}amino)methyl]phenoxy}phenyl) propanoyl]glycine

EXAMPLE 104A 3-(4-{4-[(benzyl{2-methyl-3-[(methylsulfonyl) amino]phenyl}amino)methyl]phenoxy}phenyl) propanoic acid The product from Example 64D was processed as described in Examples 49 and 50 to provide the title compound.

EXAMPLE 104B

N-[3-(4-{4-[(benzyl{2-methyl-3-[(methylsulfonyl) amino]phenyl}amino)methyl]phenoxy}phenyl) propanoyl]glycine A solution of the product from Example 104A (0.065 g, 0.119 mmoles), glycine methyl ester hydrochloride (0.0300 g, 0.24 mmoles), and diisopropylethylamine (0.042 mL, 0.24 mmoles) in DMF (0.3 mL) was treated with EDAC (0.032 g, 0.167 mmoles) and HOBT (0.0225 g, 0.167 mmoles). The resulting mixture was shaken for 12 h. The crude products were diluted with diethyl ether, extracted with sat. NH$_4$Cl, extracted with H$_2$O (2×), rinsed with brine, dried (Na$_2$SO$_4$), and concentrated under reduced pressure. The residue was purified by flash chromatography on silica gel. The product was dissolved in EtOH (0.5 mL) and THF (0.5 mL) and treated with 2N NaOH (1.0 mL) for 4 h. The resulting mixture was poured into 3N HCl and extracted with ethyl acetate (2×). The combined organics were rinsed with brine, dried (Na$_2$SO$_4$), and concentrated under reduced pressure. Purification by preparative HPLC (CH$_3$CN:0.1% trifluoroacetic acid in H$_2$O) on a YMC ODS Guardpak column yielded the title compound (0.0625 g, 87%) as a white solid. $^1$H NMR (300 MHz, DMSO-d$_6$) δ8.97 (s, 1 H), 8.18 (t, 1 H), 7.23 (m, 9 H), 7.00 (m, 3 H), 6.86 (m, 4 H), 4.05 (s, 2 H), 4.01 (s, 2 H), 3.73 (d, 2 H), 2.91 (s, 3 H), 2.79 (t, 2 H), 2.40 (m, 3 H), 2.39 (s, 3 H); MS (APCI) m/z 602 (M+H$^+$).

EXAMPLE 105

N-[3-(4-{4-[(benzyl{2-methyl-3-[(methylsulfonyl) amino]phenyl}amino)methyl]phenoxy}phenyl) propanoyl]-beta-alanine The product from Example 104A and β-alanine ethyl ester hydrochloride were processed as described in Example 104B to provide the title compound. $^1$H NMR (300 MHz, DMSO-d$_6$) δ8.97 (s, 1 H), 7.90 (t, 1 H), 7.14–7.34 (m, 8 H), 7.01 (m, 4 H), 6.87 (d, 4 H), 4.06 (s, 2 H), 4.02 (s, 2 H), 7.71 (br s, 1H), 3.22 (dd, 2 H), 2.91 (s, 3 H), 2.77 (t, 2 H), 2.34 (m, 7 H); MS (APCI) m/z 616 (M+H$^+$).

EXAMPLE 106

4-{[3-(4-{4-[(benzyl{2-methyl-3-[(methylsulfonyl) amino]phenyl}amino)methyl]phenoxy}phenyl) propanoyl]amino}butanoic acid The product from Example 104A and ethyl 4-aminobutyrate hydrochloride were processed as described in Example 104B to provide the title compound. $^1$H NMR (300 MHz, DMSO-d6) δ8.96 (s, 1 H), 7.80 (m, 1 H), 7.14–7.35 (m, 8 H), 6.92–7.13 (m, 4 H), 6.87 (m, 4 H), 3.96–4.29 (m, 4 H), 2.96–3.16 (m, 3 H), 2.91 (s, 3 H), 2.76 (m, 2 H), 2.09–2.47 (m, 7 H), 1.49–1.69 (m, 2 H); MS (APCI) m/z 630 (M+H$^+$).

EXAMPLE 107

N-[4-(4-{4-[(benzyl{2-methyl-3-[(methylsulfonyl) amino]phenyl}amino)methyl]phenoxy}phenyl) butanoyl]glycine The product from Example 100 was processed as described in Example 104B to provide the title compound. $^1$H NMR (300 MHz, DMSO-d$_6$) δ8.97 (s, 1 H), 8.13 (t, 1 H), 7.13–7.34 (m, 8 H), 7.01 (m, 4 H), 6.89 (m, 4 H), 4.05 (s, 2 H), 4.01 (s, 2 H), 3.72 (d, 2 H), 2.91 (s, 3 H), 2.55 (t, 2 H), 2.39 (s, 3 H), 2.14 (t, 2 H), 2.07 (s, 1 H), 1.80 (m, 2 H), MS (ESI) m/z 616 (M+H$^+$).

EXAMPLE 108

N-[4-(4-{4-[(benzyl{2-methyl-3-[(methylsulfonyl) amino]phenyl}amino)methyl]phenoxy}phenyl) butanoyl]-beta-alanine The product from Example 100 and β-alanine ethyl ester hydrochloride were processed as described in Example 104B to provide the title compound. $^1$H NMR (300 MHz, DMSO-d$_6$) δ8.96 (s, 1 H), 7.88 (br.s, 1 H), 7.12–7.35 (m, 8 H), 7.02 (m, 4 H), 6.89 (m, 4 H), 4.04 (m, 4 H), 3.22 (m, 2 H), 2.91 (s, 3 H), 2.39 (s, 3 H), 2.37 (m, 5 H), 2.05 (m, 2 H), 1.76 (m, 2 H); MS (APCI) m/z 630 (M+H$^+$).

EXAMPLE 109

4-{[4-(4-{4-[(benzyl{2-methyl-3-[(methylsulfonyl)amino]phenyl}amino)methyl]phenoxyl}phenyl)butanoyl]amino}butanoic acid The product from Example 100 and ethyl 4-aminobutyrate hydrochloride were processed as described in Example 104B to provide the title compound. $^1$H NMR (300 MHz, DMSO-$d_6$) δ 8.97 (s, 1 H), 7.80 (br.s, 1 H), 7.13–7.33 (m, 8 H), 7.01 (m, 4 H), 6.88 (m, 4 H), 3.94–4.16 (m, 4 H), 3.06 (m, 4 H), 2.91 (s, 3 H), 2.39 (s, 2 H), 2.20 (m, 2 H), 2.07 (m, 2 H), 1.79 (m, 2 H), 1.61 (m, 2 H); MS (APCI) m/z 644 (M+H$^+$).

EXAMPLE 110

(3-{4-[((2,4-difluorobenzyl){2-methyl-3-[(methylsulfonyl)amino]phenyl}amino)methyl]phenoxy}phenoxy)acetic acid

EXAMPLE 110A ethyl [3-(4-{[(2,4-difluorobenzyl)(2-methyl-3-nitrophenyl)amino]methyl}phenoxy)phenoxy]acetate The product from Example 83B and 2,4 difluorobenzyl bromide were processed as described in Example 6B to provide the title compound.

EXAMPLE 110B (3-{4-[((2,4-difluorobenzyl){2-methyl-3-[(methylsulfonyl)amino]phenyl}amino)methyl]phenoxy}phenoxy)acetic acid The product from Example 110A was processed as described in Examples 6C, 6D, and 50 to provide the title compound. 1H NMR (300 MHz, CDCL3) δ 7.02–7.38 (m, 7 H), 6.59–7.00 (m, 7 H), 6.47 (m, 1 H), 4.62 (s, 3 H), 4.21–4.42 (br.s, 2 H), 4.15 (br.s, 2 H), 2.88 (s, 3 H), 2.68–3.05 (br.s, 1 H), 2.10 (s, 2 H); MS (APCI) m/z 583 (M+H+).

EXAMPLE 111

2-(3-{4-[(benzyl{2-methyl-3-[(methylsulfonyl)amino]phenyl}amino)methyl]phenoxy}phenoxy)propanoic acid

EXAMPLE 111A butyl 2-[3-(4-{[benzyl(2-methyl-3-nitrophenyl)amino]methyl}phenoxy)phenoxy]propanoate The product from Example 61F and butyl lactate was processed as described in Example 62A to provide the title compound.

EXAMPLE 111B 2-(3-{4-[(benzyl{2-methyl-3-[(methylsulfonyl)amino]phenyl}amino)methyl]phenoxy}phenoxy)propanoic acid The product from Example 111A was processed as described in Examples 6C, 6D, and 50 to provide the title compound. $^1$H NMR (300 MHz, DMSO-$d_6$) δ 8.97 (s, 1 H), 7.24 (m, 8 H), 6.88–7.08 (m, 5 H), 6.61 (m, 1 H), 6.50 (ddd, 1 H), 6.44 (t, 1 H), 4.79 (q, 1 H), 4.06 (s, 2 H), 4.03 (s, 2 H), 3.92 (br.s, 1 H), 2.91 (s, 3 H), 2.40 (s, 3 H), 1.46 (d, 3 H); MS (ESI) m/z 561 (M+H$^+$).

EXAMPLE 112

N-{3-[benzyl(4-{3-[(2-oxotetrahydrofuran-3-yl)oxy]phenoxy}benzyl)amino]-2-methylphenyl}methanesulfonamide

EXAMPLE 112A

3-[3-(4-{[benzyl(2-methyl-3-nitrophenyl)amino]methyl}phenoxy)phenoxy]dihydrofuran-2(3H)-one The product from Example 61F and α-hydroxy-γ-butyrolactone were processed as described in Example 62A to provide the title compound.

EXAMPLE 112B

N-{3-[benzyl(4-{3-[(2-oxotetrahydrofuran-3-yl)oxy]phenoxy}benzyl)amino]-2-methylphenyl}methanesulfonamide The product from Example 112A was processed as described in Examples 6C and 6D to provide the title compound. $^1$H NMR (300 MHz, DMSO-$d_6$) δ 8.97 (s, 1 H), 7.13–7.34 (m, 8 H), 6.89–7.12 (m, 5 H), 6.80 (dd, 1 H), 6.66 (t, 1 H), 6.56 (ddd, 1 H), 5.32 (dd, 1 H), 4.41 (td, 1 H), 4.25 (m, 1 H), 4.06 (s, 2 H), 4.03 (s, 2 H), 2.91 (s, 3 H), 2.73 (m, 1 H), 2.40 (s, 3 H), 2.23 (m, 1 H); MS (ESI) m/z 573 (M+H$^+$).

EXAMPLE 113

2-(3-{4-[(benzyl{2-methyl-3-[(methylsulfonyl)amino]phenyl}amino)methyl]phenoxy}phenoxy)-4-hydroxybutanoic acid The product from Example 112B was processed as described in Example 50 to provide the title compound. $^1$H NMR (300 MHz, DMSO-$d_6$) δ 8.97 (s, 1 H), 7.24 (m, 6 H), 6.88–7.13 (m, 5 H), 6.81 (m, 1 H), 6.41–6.70 (m, 6 H), 5.32 (m, 1 H), 4.73 (m, 1 H), 4.41 (m, 1 H), 4.06 (s, 2 H), 4.03 (s, 2 H), 3.54 (m, 1 H), 2.91 (s, 3 H), 2.40 (s, 3 H), 1.82–2.04 (m, 1 H); MS (ESI) m/z 591 (M+H$^+$).

EXAMPLE 114

2-(3-{4-[(benzyl{2-methyl-3-[(methylsulfonyl)amino]phenyl}amino)methyl]phenoxy}phenoxy)-N-[3-(2-oxopyrrolidin-1-yl)propyl]acetamide The product from Example 62C and 1-(3-aminopropyl)-2-pyrolidinone was processed as described in Example 68D to provide the title compound. $^1$H NMR (300 MHz, DMSO-d6) δ 8.97 (s, 1 H), 8.07 (m, 1 H), 7.23 (m, 8 H), 6.85–7.06 (m, 4 H), 6.45–6.79 (m, 4 H), 4.43 (s, 2 H), 4.08 (s, 2 H), 4.06 (s, 2 H), 2.99–3.39 (m, 6 H), 2.91 (s, 3 H), 2.40 (s, 3 H), 2.17 (m, 2 H), 1.87 (m, 2 H), 1.56 (m, 2 H); MS (APCI) m/z 671 (M+H+).

EXAMPLE 115

N-(3-{benzyl[4-(3-hydroxyphenoxy)benzyl]amino}-2-methylphenyl)methanesulfonamide

EXAMPLE 115A ethyl 3-[3-(4-{benzyl(2-methyl-3-nitrophenyl)amino]methyl}phenoxy)phenoxy]propanoate The product from Example 61F and ethyl 3-bromopropionate was processed as described in Example 33B to provide the title compound.

EXAMPLE 115B

N-(3-{benzyl[4-(3-hydroxyphenoxy)benzyl]amino}-2-methylphenyl)methanesulfonamide The product from Example 115A was processed as described in Examples 6C, 6D and 50 to provide the title compound. $^1$H NMR (300 MHz, DMSO-$d_6$) δ9.54 (br.s, 1 H), 8.97 (s, 1 H), 6.87–7.33 (m, 13 H), 6.51 (ddd, 1 H), 6.37 (m, 1 H), 6.32 (t, 1 H), 4.06 (s, 2 H), 4.02 (s, 2 H), 2.92 (s, 3 H), 2.40 (s, 3 H); MS (ESI) m/z 489 (M+H$^+$).

EXAMPLE 116

4-(3-{4-[(benzyl{2-methyl-3-[(methylsulfonyl)amino]phenyl}amino)methyl]phenoxy}phenoxy)butanoic acid

EXAMPLE 116A ethyl 4-[3-(4-{[benzyl(2-methyl-3-nitrophenyl)amino]methyl}phenoxy)phenoxy]butanoate A solution of the product from Example 61F (0.1000 g, 0.227 mmoles) in DMF (0.57 mL) was treated with NaH (0.0109 g, 0.27 mmoles, 60% dispersion). After 15 min, ethyl 4-bromobutyrate (0.039 mL, 0.27 mmoles) was added and the reaction was stirred overnight. The crude products were diluted with diethyl ether, washed with sat. NH$_4$Cl, extracted with H$_2$O (2×), washed with brine, dried (Na$_2$SO$_4$), and concentrated under reduced pressure. The residue was purified by flash chromatography on silica gel (hexane to 7:1 hexane:ethyl acetate) to provide the title compound as a yellow oil.

EXAMPLE 116B 4-(3-{4-[(benzyl{2-methyl-3-[(methylsulfonyl)amino]phenyl}amino)methyl]phenoxy}phenoxy)butanoic acid The product from Example 116A was processed as described in Examples 6C, 6D, and 50 to provide the title compound. $^1$H NMR (300 MHz, DMSO-$d_6$) δ8.97 (s, 1 H), 7.23 (m, 8 H), 6.88–7.08 (m, 5 H), 6.68 (dd, 1 H), 6.49 (m, 2 H), 4.06 (s, 2 H), 4.02 (s, 2 H), 3.93 (t, 2 H), 3.33–3.61 (br.s, 1 H), 2.91 (s, 3 H), 2.40 (s, 3 H), 2.35 (t, 2 H), 1.90 (m, 2 H); MS (ESI) m/z 575 (M+H$^+$).

EXAMPLE 117

5-(3-{4-[(benzyl{2-methyl-3-[(methylsulfonyl)amino]phenyl}amino)methyl]phenoxyl}phenoxy)pentanoic acid

EXAMPLE 117A ethyl 5-[3-(4-{[benzyl(2-methyl-3-nitrophenyl)amino]methyl}phenoxy)phenoxy]pentanoate The product from Example 61F and ethyl 5-bromovalerate were processed as described in Example 116A to provide the title compound.

EXAMPLE 117B 5-(3-{4-[(benzyl{2-methyl-3-[(methylsulfonyl)amino]phenyl}amino)methyl]phenoxy}phenoxy)pentanoic acid The product from Example 117A was processed as described in Examples 6C, 6D and 50 to provide the title compound. $^1$H NMR (300 M, CDCL$_3$) δ7.06–7.37 (m, 8 H), 6.99 (d, 1 H), 6.89 (d, 2 H), 6.61 (ddd, 1 H), 6.50 (m, 2 H), 6.45 (t, 2 H), 3.99–4.25 (m, 4 H), 3.89 (m, 4 H), 2.89 (s, 3 H), 2.44 (m, 2 H), 2.29 (s, 3 H), 1.67–1.89 (m, 4 H); MS (ESI) m/z 589 (M+H$^+$).

EXAMPLE 118

N-[3-(4-{4-[(benzyl{2-methyl-3-[(methylsulfonyl)amino]phenyl}amino)methyl]phenoxy}phenyl)propanoyl]-N-methylglycine The product from Example 104A and sarcosine ethyl ester hydrochloride were processed as described in Example 104B to provide the title compound. $^1$H NMR (300 MHz, DMSO-$d_6$) δ8.97 (s, 1 H), 7.15–7.38 (m, 8 H), 7.02 (m, 4 H), 6.87 (m, 4 H), 4.12 (s, 1 H), 4.06 (s, 2 H), 4.01 (s, 2 H), 3.99 (s, 1 H), 2.99 (s, 2 H), 2.91 (s, 3 H), 2.82 (s, 1 H), 2.76 (m, 2 H), 2.62 (m, 2 H), 2.39 (s, 3 H); MS (ESI) m/z 616 (M+H$^+$).

EXAMPLE 119

N-[4-(4-{4-[(benzyl{2-methyl-3-[(methylsulfonyl)amino]phenyl}amino)methyl]phenoxy}phenyl)butanoyl]-N-methylglcine The product from Example 100 and sarcosine ethyl ester hydrochloride was processed as described in Example 104B to provide the title compound. $^1$H NMR (300 MHz, DMSO-$d_6$) δ8.97 (s, 1 H), 7.12–7.36 (m, 8 H), 7.02 (m, 4 H), 6.89 (m, 4 H), 4.08 (s, 1 H), 4.06 (s, 2 H), 4.02 (s, 2 H), 3.98 (s, 1 H), 2.97 (s, 2 H), 2.91 (s, 3 H), 2.81 (s, 1 H), 2.58 (m, 2 H), 2.39 (s, 3 H), 2.33 (m, 2 H), 2.22 (m, 1 H), 1.66–1.88 (m, 2 H); MS (ESI) m/z 630 (M+H$^+$).

EXAMPLE 120

4-(3-{4-[((2,4-difluorobenzyl){2-methyl-3-[(methylsulfonyl)amino]phenyl}amino)methyl]phenoxy}phenoxy)butanoic acid

EXAMPLE 120A

N-{4-[3-(allyloxy)phenoxy]benzyl}-N-(2,4-difluorobenzyl)-N-(2-methyl-3-nitrophenyl)amine The product from Example 61D and 2,4-difluorobenzyl bromide were processed as described in Example 6B to provide the title compound.

EXAMPLE 120B 3-(4-{[(2,4-difluorobenzyl)(2-methyl-3-nitrophenyl)amino]methyl}phenoxy)phenol The product from Example 120A was processed as described in Example 33A to provide the title compound.

EXAMPLE 120C ethyl 4-[3-(4-{[(2,4-difluorobenzyl)(2-methyl-3-nitrophenyl)amino]methyl}phenoxy)phenoxy]butanoate The product from Example 120B and ethyl 4-bromobutyrate were processed as described in Example 116A to provide the title compound.

EXAMPLE 120D 4-(3-{4-[((2,4-difluorobenzyl){2-methyl-3-[(methylsulfonyl)amino]phenyl}amino)methyl]phenoxy}phenoxy)butanoic acid The product from Example 120C was processed as described in Examples 6C, 6D and 50 to provide the title compound. $^1$H NMR (300 MHz, DMSO-d$_6$) δ8.97 (s, 1 H), 7.28 (m, 4 H), 6.86–7.19 (m, 7 H), 6.69 (m, 1 H), 6.49 (m, 2 H), 4.08 (s, 2 H), 4.06 (s, 2 H), 3.94 (t, 2 H), 2.90 (s, 3 H), 2.38 (m, 2 H), 2.33 (s, 3 H), 1.91 (m, 2 H); MS (APCI) m/z 611 (M+H$^+$).

EXAMPLE 121

5-(3-{4-[((2,4-difluorobenzyl){2-methyl-3-[(methylsulfonyl)amino]phenyl}amino)methyl]phenoxy}phenoxy)pentanoic acid

EXAMPLE 121A ethyl 5-[3-(4-{[(2,4-difluorobenzyl)(2-methyl-3-nitrophenyl)amino]methyl}phenoxy)phenoxy]pentanoate The product from Example 120B and ethyl 5-bromovalerate were processed as described in Example 116A to provide the title compound.

EXAMPLE 121B 5-(3-{4-[((2,4-difluorobenzyl){2-methyl-3-[(methylsulfonyl)amino]phenyl}amino)methyl]phenoxy}phenoxy)pentanoic acid The product from Example 121A was processed as described in Examples 6C, 6D and 50 to provide the title compound. $^1$H NMR (300 MHz, DMSO-d$_6$) δ8.97 (s, 1 H), 7.28 (m, 4 H), 6.85–7.20 (m, 7 H), 6.69 (dd, 1 H), 6.47 (m, 2 H), 4.08 (s, 2 H), 4.06 (s, 2 H), 3.92 (t, 2 H), 2.90 (s, 3 H), 2.33 (s, 3 H), 2.26 (t, 2 H), 1.48–1.81 (m, 4 H); MS (ESI) m/z 625 (M+H$^+$).

EXAMPLE 122

N-[(3-{4-[(benzyl{2-methyl-3-[(methylsulfonyl)amino]phenyl}amino)methyl]phenoxy}phenoxy)acetyl]glycine The product from Example 62C was processed as described in Example 104B to provide the title compound. $^1$H NMR (300 MHz, DMSO-d$_6$) δ8.97 (s, 1 H), 8.37 (t, 1 H), 7.13–7.35 (m, 8 H), 6.88–7.09 (m, 5 H), 6.73 (ddd, 1 H), 6.60 (t, 1 H), 6.54 (ddd, 1 H), 4.50 (s, 2 H), 4.06 (s, 2 H), 4.03 (s, 2 H), 3.79 (d, 2 H), 2.91 (s, 3 H), 2.40 (s, 3 H); MS (APCI) Mn/z 604 (M+H$^+$).

EXAMPLE 123

N-[(3-{4-[(benzyl{2-methyl-3-[(methylsulfonyl)amino]phenyl}amino)methyl]phenoxy}phenoxy)acetyl]-beta-alanine The product from Example 62C and β-alanine ethyl ester hydrochloride were processed as described in Example 104B to provide the title compound. $^1$H NMR (300 MHz, DMSO-d$_6$) δ8.97 (s, 1 H), 8.10 (t, 1 H), 7.24 (m, 8 H), 6.99 (m, 5 H), 6.71 (m, 1 H), 6.55 (m, 2 H), 4.43 (s, 2 H), 4.06 (s, 2 H), 4.03 (s, 2 H), 3.31 (dd, 2 H), 2.88 (s, 3 H), 2.40 (t, 4 H), 2.07 (s, 2 H); MS (APCI) m/z 618 (M+H$^+$).

EXAMPLE 124

N-[(3-{4-[(benzyl{2-methyl-3-[(methylsulfonyl)amino]phenyl}amino)methyl]phenoxy}phenoxy)acetyl]-N-methylglycine The product from Example 62C and sarcosine ethyl ester hydrochloride were processed as described in Example 104B to provide the title compound. $^1$H NMR (300 MHz, DMSO-d$_6$) δ8.97 (s, 1 H), 7.24 (m, 8 H), 6.89–7.09 (m, 5 H), 6.66 (m, 1 H), 6.54 (t, 1 H), 6.47 (m, 1 H), 4.85 (s, 1 H), 4.70 (s, 1 H), 4.14 (s, 1 H), 4.06 (s, 2 H), 4.02 (s, 2 H), 3.99 (s, 1 H), 3.91 (br.s, 2 H), 3.01 (s, 2 H), 2.91 (s, 2 H), 2.82 (s, 2 H), 2.40 (s, 2 H); MS (APCI) m/z 618 (M+H$^+$).

EXAMPLE 125

4-{[(3-{4-[(benzyl{2-methyl-3-[(methylsulfonyl)amino]phenyl}amino)methyl]phenoxy}phenoxy)acetyl]amino}butanoic acid The product from Example 62C and ethyl 4-aminobutyrate hydrochloride were processed as described in Example 104B to provide the title compound. $^1$H NMR (300 MHz, DMSO-d$_6$) δ8.97 (s, 1 H), 8.10 (t, 1 H), 7.24 (m, 8 H), 6.88–7.10 (m, 5 H), 6.71 (dd, 1 H), 6.55 (m, 2 H), 4.43 (s, 2 H), 4.06 (s, 2 H), 4.03 (s, 2 H), 3.12 (dd, 2 H), 2.92 (s, 3 H), 2.40 (s, 3 H), 2.18 (t, 2 H), 1.63 (m, 2 H); MS (APCI) m/z 632 (M+H$^+$).

EXAMPLE 126 ethyl 4-(3-{4-[(benzyl{2-methyl-3-[(methylsulfonyl)amino]phenyl}amino)methyl]phenoxy}phenoxy)butanoate The product from Example 116A was processed as described in Examples 6C and 6D to provide the title compound. $^1$H NMR (300 MHz, CDCL$_3$) δ7.07–7.31 (m, 10 H), 6.90 (m, 3 H), 6.62 (m, 1 H), 6.54 (m, 1 H), 6.50 (t, 1 H), 6.14 (s, 1 H), 4.13 (q, 2 H), 4.07 (s, 2 H), 4.04 (s, 2 H), 3.96 (t, 2 H), 2.94 (s, 3 H), 2.49 (t, 2 H), 2.34 (s, 3 H), 2.08 (m, 2 H), 1.24 (t, 3 H); MS (APCI) m/z 603 (M+H$^+$).

EXAMPLE 127 ethyl 5-(3-{4-[(benzyl{2-methyl-3-[(methylsulfonyl)amino]phenyl}amino)methyl]phenoxy}phenoxy)pentanoate The product from Example 117A was processed as described in Examples 6C and 6D to provide the title compound. $^1$H NMR (300 MHz, CDCL$_3$) δ7.07–7.31 (m, 10 H), 6.91 (m, 3 H), 6.61 (ddd, 1 H), 6.54 (ddd, 1 H), 6.49 (t, 1 H), 6.14 (s, 1 H), 4.12 (dd, 2 H), 4.06 (s, 2 H), 4.02 (s, 2 H), 3.92 (m, 2 H), 2.94 (s, 3 H), 2.38 (m, 2 H), 2.33 (s, 3 H), 1.80 (m, 4 H), 1.25 (t, 3 H); MS (APCI) m/z 617 (M+H$^+$).

EXAMPLE 128

N-[4-(3-{4-[(benzyl{2-methyl-3-[(methylsulfonyl)amino]phenyl}amino)methyl]phenoxy}phenoxy)butanoyl]glycine The product from Example 116B was processed as described in Example 104B to provide the title compound. $^1$H NMR (300 MHz, DMSO-d$_6$) δ8.97 (s, 1 H), 8.18 (t, 1 H), 7.14–7.34 (m, 8 H), 6.88–7.09 (m, 5 H), 6.68 (ddd, 1 H), 6.49 (m, 2 H), 4.06 (s, 2 H), 4.02 (s, 2 H), 3.93 (t, 2 H), 3.82 (br.s, 1 H), 3.72 (d, 2 H), 2.91 (s, 3 H), 2.40 (s, 3 H), 2.27 (t, 2 H), 1.91 (m, 2 H); MS (APCI) m/z 630 (M–H$^-$).

EXAMPLE 129

N-[4-(3-{4-[(benzyl{2-methyl-3-[(methylsulfonyl)amino]phenyl}amino)methyl]phenoxy}phenoxy)butanoyl]-beta-alanine The product from Example 116B and β-alanine ethyl ester hydrochloride were processed as described in Example 104B to provide the title compound. $^1$H NMR (300 MHz, DMSO-d$_6$) δ8.97 (s, 1 H), 7.90 (t, 1 H), 7.14–7.36 (m, 8 H), 6.85–7.12 (m, 5 H), 6.67 (ddd, 1 H), 6.48 (m, 2 H), 4.06 (s, 2 H), 4.02 (s, 2 H), 3.90 (t, 2 H), 3.80 (br.s, 1 H), 3.22 (dd, 2 H), 2.91 (s, 3 H), 2.40 (s, 3 H), 2.35 (t, 2 H), 2.19 (t, 2 H), 1.76–1.98 (m, 2 H); MS (APCI) m/z 646 (M+H$^+$).

EXAMPLE 130

4-{[4-(3-{4-[(benzyl{2-methyl-3-[(methylsulfonyl)amino]phenyl}amino)methyl]phenoxy}phenoxy)butanoyl]amino}butanoic acid The product from Example 116B and ethyl 4-aminobutyrate hydrochloride were processed as described in Example 104B to provide the title compound. $^1$H NMR (300 MHz, DMSO-d$_6$) δ8.97 (s, 1 H), 7.83 (t, 1 H), 7.13–7.34 (m, 8 H), 6.87–7.09 (m, 5 H), 6.67 (m, 1 H), 6.47 (m, 2 H), 4.27–4.62 (br.s, 1 H), 4.06 (s, 2 H), 4.03 (s, 2 H), 3.91 (t, 2 H), 3.03 (dd, 2 H), 2.91 (s, 3 H), 2.40 (s, 3 H), 2.19 (t, 4 H), 1. 88 (m, 2 H), 1.59 (m, 2 H); MS (APCI) m/z 660 (M+H$^+$).

EXAMPLE 131

N-[5-(3-{4-[(benzyl{2-methyl-3-[(methylsulfonyl)amino]phenyl}amino)methyl]phenoxy}phenoxy)pentanoyl]glycine The product from Example 117B was processed as described in Example 104B to provide the title compound. $^1$H NMR (300 MHz, DMSO-d$_6$) δ8.97 (s, 1 H), 8.12 (t, 1 H), 7.23 (m, 8 H), 6.87–7.08 (m, 5 H), 6.68 (m, 1 H), 6.48 (m, 2 H), 4.06 (s, 2 H), 4.02 (s, 2 H), 3.91 (t, 2 H), 3.90–4.23 (br.s, 1 H), 3.72 (d, 2 H), 2.91 (s, 3 H), 2.40 (s, 3 H), 2.17 (t, 2 H), 1.52–1.77 (m, 4 H); MS (APCI) m/z 646 (M+H$^+$).

EXAMPLE 132

N-[5-(3-{4-[(benzyl{2-methyl-3-[(methylsulfonyl)amino]phenyl}amino)methyl]phenoxy}phenoxy)pentanoyl]-beta-alanine The product from Example 117B and β-alanine ethyl ester hydrochloride were processed as described in Example 104B to provide the title compound. $^1$H NMR (300 MHz, DMSO-d$_6$) δ ppm 8.97 (s, 1 H), 7.86 (t, 1 H), 7.23 (m, 8 H), 6.88–7.08 (m, 5 H), 6.67 (m, 1 H), 6.48 (m, 2 H), 4.06 (s, 2 H), 4.03 (s, 2 H), 3.91 (t, 2 H), 3.35 (br.s, 1 H), 3.22 (dd, 2 H), 2.91 (s, 3 H), 2.40 (s, 3 H), 2.35 (t, 2 H), 2.09 (t, 2 H), 1.50–1.74 (m, 4 H); MS (APCI) m/z 658 (M−H$^-$).

EXAMPLE 133

4-{[5-(3-{4-[(benzyl{2-methyl-3-[(methylsulfonyl)amino]phenyl}amino)methyl]phenoxy}phenoxy)pentanoyl]amino}butanoic acid The product from Example 117B and ethyl 4-aminobutyrate hydrochloride was processed as described in Example 104B to provide the title compound. $^1$H NMR (300 MHz, DMSO-d$_6$) δ ppm 8.97 (s, 1 H), 7.79 (t, 1 H), 7.24 (m, 8 H), 6.87–7.09 (m, 5 H), 6.68 (dd, 1 H), 6.48 (m, 2 H), 4.06 (s, 2 H), 4.03 (s, 2 H), 3.91 (t, 2 H), 3.27–3.53 (m, 1 H), 3.03 (dd, 2 H), 2.91 (s, 3 H), 2.40 (s, 3 H), 2.20 (t, 2 H), 2.10 (t, 2 H), 1.49–1.74 (m, 6 H); MS (APCI) m/z 674 (M+H$^+$).

EXAMPLE 134

N-[3-(benzyl{4-[3-(2-hydroxyethoxy)phenoxy]benzyl}amino)-2-methylphenyl]methanesulfonamide The product from Example 92B was processed as described in Example 6C, 6D, and 50 to provide the title compound. $^1$H NMR (300 MHz, DMSO-d$_6$) δ8.97 (s, 1 H), 7.24 (m, 8 H), 6.88–7.08 (m, 5 H), 6.70 (m, 1 H), 6.49 (m, 2 H), 4.06 (s, 2 H), 4.03 (s, 2 H), 3.94 (t, 2 H), 3.67 (t, 2 H), 3.35 (br.s, 1 H), 2.92 (s, 3 H), 2.40 (s, 3 H); MS (APCI) m/z 533 (M+H$^+$).

EXAMPLE 135

[2-(3-{4-[(benzyl{2-methyl-3-[(methylsulfonyl)amino]phenyl}amino)methyl]phenoxy}phenoxy)ethoxy]acetic acid

EXAMPLE 135A ethyl {2-[3-(4-{[benzyl(2-methyl-3-nitrophenyl)amino]methyl}phenoxy)phenoxy]ethoxy}acetate The product from Example 92B and ethyl iodoacetate were processed as described in Example 116A to provide the title compound.

EXAMPLE 135B

[2-(3-{4-[(benzyl{2-methyl-3-[(methylsulfonyl)amino]phenyl}amino)methyl]phenox}phenoxy)ethoxy]acetic acid The product from Example 135A was processed as described in Example 6C, 6D, and 50 to provide the title compound. $^1$H NMR (300 MHz, DMSO-d$_6$) δ8.97 (s, 1 H), 7.24 (m, 8 H), 6.88–7.09 (m, 5 H), 6.70 (m, 1 H), 6.50 (m, 2 H), 4.07 (s, 2 H), 4.06 (s, 2 H), 4.03 (s, 2 H), 3.94 (t, 1 H), 3.78 (m, 2 H), 3.67 (t, 1 H), 3.36 (br.s, 1 H), 2.92 (s, 3 H), 2.40 (s, 3 H); MS (APCI) m/z 591 (M+H$^+$).

EXAMPLE 136

2,4-dideoxy-6-O-(3-{4-[((2,4-difluorobenzyl){2-methyl-3-[(methylsulfonyl)amino]phenyl}amino)methyl]phenoxy}phenyl)-D-erythro-hexonic acid

EXAMPLE 136A tert-butyl 2,4-dideoxy-6-O-[3-(4-{[(2,4-difluorobenzyl)(2-methyl-3-nitrophenyl)amino]methyl}phenoxy)phenyl]-3,5-O-(1-methylethylidene)-D-erythro-hexonate The product from Example 120B was processed as described in Example 60F to provide the title compound.

EXAMPLE 136B tert-butyl 2,4-dideoxy-6-O-(3-{4-[((2,4-difluorobenzyl){2-methyl-3-[(methylsulfonyl)amino]phenyl}amino)methyl]phenoxy}phenyl)-3,5-O-(1-methylethylidene)-D-erythro-hexonate The product from Example 136A was processed as described in Examples 6C and D to provide the title compound.

EXAMPLE 136C 2,4-dideoxy-6-O-(3-{4-[((2,4-difluorobenzyl){2-methyl-3-[(methylsulfonyl)amino]phenyl}amino)methyl]phenoxy}phenyl)-D-erythro-hexonic acid The product from Example 136B was processed as described in Example 60H to provide the title compound. $^1$H NMR (300 MHz, CDCL$_3$) δ7.00–7.21 (m, 7 H), 6.92 (m, 1

H), 6.83 (m, 2 H), 6.71 (m, 2 H), 6.53 (m, 2 H), 6.42 (s, 1 H), 4.30 (br.s, 1 H), 4.16 (br.s, 1 H), 4.05 (s, 2 H), 4.00 (s, 2 H), 3.62–3.87 (br.s, 4 H), 2.88 (s, 3 H), 2.33–2.58 (br.s, 2 H), 2.25 (s, 3 H), 2.08 (s, 1 H), 1.71 (br.s, 2 H); MS (ESI) m/z 671 (M+H$^+$).

EXAMPLE 137

(3-{4-[((2-bromobenzyl){2-methyl-3-[(methylsulfonyl)amino]phenyl}amino)methyl] phenoxy}phenoxy)acetic acid

EXAMPLE 137A ethyl (3-(4-(((2-bromobenzyl)(2-methyl-3-((methylsulfonyl)amino)phenyl)amino)methyl) phenoxy)phenoxy)acetate The product from Example 83B and 2-bromobenzyl bromide were processed as described in Example 6B–D to provide the title compound.

EXAMPLE 137B

The product from Example 137A was treated with 2:1:1 2N aqueous sodium hydroxide:tetrahydrofuran:water overnight. The mixture was acidified with 2N aqueous hydrochloric acid and extracted with ethyl acetate. The ethyl acetate phase was dried over sodium sulfate, filtered and the filtrate concentrated under reduced pressure to provide the title compound. $^1$H NMR (500 MHz, DMSO-d6) δ8.93 (s, 1 H), 7.55 (d, 1 H), 7.42 (d, 1 H), 7.27 (m, 4 H), 7.15 (t, 1 H), 7.07 (m, 1 H), 7.00 (m, 2 H), 6.92 (d, 2 H), 6.66 (d, 1 H), 6.51 (m, 2 H), 4.64 (s, 2 H), 4.17 (s, 2 H), 4.11 (s, 2 H), 2.89 (s, 3 H), 2.32 (s, 3 H); MS (ESI+) m/z 625 (M+H)$^+$.

EXAMPLE 138

N-{3-[(4-benzoylbenzyl)(benzyl)amino]-2-methylphenyl}methanesulfonamide

The product from Example 6A and 4-(bromomethyl) benzophenone were processed as described in Examples 6B, 6C, and 6D to provide the title compound. $^1$H NMR (300 Mz, CDCl$_3$) δ7.75 (m, 7 H), 7.60 (m, 2 H), 7.50 (m, 2 H), 7.35 (dd, 1 H), 6.25 (m, 2 H), 7.10 (t, 2H), 6.9 (d, 2H), 4.15 (s, 2H), 4.10 (s, 2H), 2.97 (s, 3H), 2.39 (s, 3H); MS (ESI+) m/z 485 (M+H)$^+$.

EXAMPLE 139

N-(3-{benzyl[4-(phenylthio)benzyl]amino}-2-methylphenyl)methanesulfonamide

EXAMPLE 139A

N-benzyl-N-(2-methyl-3-nitrophenyl)-N-[4-(phenylthio)benzyl]amine 4-thiophenoxybenzaldehyde was processed as described in Example 6A to provide the title compound.

EXAMPLE 139B

N-(3-{benzyl[4-(phenylthio)benzyl]amino}-2-methylphenyl)methanesulfonamide

The product from Example 139A and benzyl bromide were processed as described in Examples 6B, 6C, and 6D to provide the title compound. 1H NMR (300 MHz, CDCl3) δ7.33 (m, 2H), 7.21 (m, 6H), 7.14 (m, 4H), 6.90 (m, 3H), 6.88 (d, 2H), 6.13 (s, 1H), 4.08 (d, 2H), 4.02 (d, 2H), 2.94 (s, 3H), 2.34 (s, 3H); MS (ESI+) m/z 487 (M+H)+.

EXAMPLE 140

N-{3-[[4-(3-acetylphenoxy)benzyl](2,4-difluorobenzyl)amino]-2-methylphenyl}methanesulfonamide The product from Example 33A and 3-acetylphenylboronic acid were processed as described in Examples 48A, 6C, and 6D to provide the title compound. $^1$H NMR (MeOH, 500 MHz) δ7.72 (m, 1 H), 7.49 (m, 1 H), 7.46 (d, 1 H), 7.28 (m, 2 H), 7.21 (m, 2 H), 7.09 (m, 2 H), 7.02 (m, 1 H), 6.91 (m, 2 H), 6.82 (m, 2 H), 4.15 (s, 2 H), 4.12 (s, 2 H), 2.88 (s, 3 H), 2.55 (s, 3 H), 2.36 (s, 3 H); MS(ESI, +Q1MS) m/e 551.

EXAMPLE 141

N-(3-{(2,4-difluorobenzyl)[4-(3,4-dimethoxyphenoxy)benzyl]amino}-2-methylphenyl) methanesulfonamide The product from Example 33A and 3,4-dimethoxyphenylboronic acid were processed as described in Examples 48A, 6C, and 6D to provide the title compound. $^1$H NMR (MeOH, 500 MHz) δ7.22 (m, 3 H), 7.08 (m, 2 H), 6.99 (m, 1 H), 6.91 (d, 1 H), 6.83 (m, 4 H), 6.64 (d, 1 H), 6.48 (dd, 1 H), 4.12 (s, 2 H), 4.08 (s, 2 H), 3.81 (s, 3 H), 3.76 (s, 3 H), 2.88 (s, 3 H), 2.35 (s, 3 H); MS(ESI, +Q1MS) m/e 569.

EXAMPLE 142

N-{3-[(2,4-difluorobenzyl)(4-ethoxybenzyl)amino]-2-methylphenyl}methanesulfonamide

EXAMPLE 142A

N-(2,4-difluorobenzyl)-N-(4-ethoxybenzyl)-N-(2-methyl-3-nitrophenyl)amine

The product from Example 33A(39 mg, 0.1 mmole) and di-t-butylazo dicarboxylate (35 mg, 0.15 mmole) in tetrahydrofuran (1.5 ml) were added to PPh3 on resin (70 mg, 0.3 mmole: loading 3 mmole/g) followed by ethanol (5.7 mg, 0.125 mmole) in 50 microliter tetrahydrofuran. Reaction mixture was shaken at room temperature overnight. Filtered off and solvent removed. Solaris 530 organic synthesis system from PE Biosystems was used to do this reaction. The residue purified by HPLC (CH$_3$CN:0.1 TFA in H$_2$O) on a YMC ODS guardpak column.

EXAMPLE 142B

The product from Example 142A processed as described in Example 6C–D to provide the title compound. $^1$H NMR (500 MHz, CDCL$_3$) δ7.22 (d, 1 H), 7.14 (m, 4 H), 6.94 (d, 1 H), 6.78 (d, 2 H), 6.72 (m, 2 H), 6.08 (s, 1 H), 4.14 (s, 2 H), 4.06 (s, 2 H), 3.99 (q, 2 H), 2.91 (s, 3 H), 2.25 (s, 3 H), 1.39 (t, 3 H); MS (ESI+) m/z 461 (M+H)$^+$.

EXAMPLE 143

N-(3-{(2,4-difluorobenzyl)[4-(pent-3-ynyloxy) benzyl]amino}-2-methylphenyl)methanesulfonamide The product from Example 33A and 3-pentyn-1-ol were processed as described in Examples 142A, 6C, and 6D to provide the title compound. $^1$H NMR (500 MHz, CDCl$_3$)

δ7.20 (d, 1 H), 7.11 (m, 4 H), 6.89 (d, 1 H), 6.80 (d, 2 H), 6.72 (m, 2 H), 6.06 (s, 1 H), 4.05 (s, 2 H), 4.01 (m, 4 H), 2.93 (s, 3 H), 2.58 (m, 2 H), 2.29 (s, 3 H), 1.79 (t, 3 H); MS (ESI+) m/z 499 (M+H)$^+$.

EXAMPLE 144

N-(3-{(4-chloro-2-fluorobenzyl)[4-(methylthio) benzyl]amino}-2-methylphenyl)methanesulfonamide

EXAMPLE 144A

2-Methyl-3-nitroaniline (3.65 g, 24 mmoles) and 2-fluoro-4-chlorobenzaldehyde (6.47 g, 40.8 mmoles) were processed as described in example 6A to provide the product.

EXAMPLE 144B

The product from Example 144A and 4-Methylthio-1-(iodomethyl)benzene prepared as in Example 32A were processed as described in Example 6B–D to provide the title compound. $^1$NMR (500 MHz, DMSO-D$_6$) δ8.97 (s, 1 H), 7.33 (dd, 1 H), 7.25 (t, 1 H), 7.18 (m, 5 H), 7.04 (t, 1 H), 6.98 (d, 1 H), 6.92 (d, 1 H), 4.08 (s, 2 H), 4.04 (s, 2 H), 2.90 (s, 3 H), 2.43 (s, 3 H), 2.33 (s, 3 H); MS (ESI+) m/z 479 (M+H)$^+$.

EXAMPLE 145

N-{3-[(4-chloro-2-fluorobenzyl)(2-fluorobenzyl) amino]-2-methylphenyl}methanesulfonamide The product from Example 144A and 2-fluoro-1-(bromomethyl)benzene were processed as described in Examples 6B–D to provide the title compound. $^1$H NMR (500 MHz, DMSO-D$_6$) δ8.96 (s, 1 H), 7.33 (dd, 1 H), 7.26 (m, 3 H), 7.19 (dd, 1 H), 7.11 (m, 2 H), 7.05 (t, 1 H), 7.00 (d, 1 H), 6.96 (d, 1 H), 4.13 (d, 4 H), 2.87 (s, 3 H), 2.28 (s, 3 H); MS (ESI+) m/z 451 (M+H)$^+$.

EXAMPLE 146

N-(3-{benzyl[(2'-cyano-1,1'-biphenyl-4-yl)methyl] amino}-2-methylphenyl)methanesulfonamide The product from Example 6A and 4'-bromomethyl-2-cyanobiphenyl were processed as described in Examples 6B–D to provide the title compound. $^1$H NMR (500 MHz, DMSO-D$_6$) δ ppm 8.97 (s, 1 H), 7.92 (d, 1 H), 7.76 (t, 1 H), 7.60 (d, 1 H), 7.56 (td, 1 H), 7.51 (d, 2 H), 7.45 (d, 2 H), 7.29 (d, 4 H), 7.21 (m, 1 H), 7.04 (m, 2 H), 6.98 (d, 1 H), 4.15 (s, 2 H), 4.10 (s, 2 H), 2.92 (s, 3 H), 2.44 (s, 3 H); MS (ESI–) m/z 480 (M–H).

EXAMPLE 147

3-(4-{4-[(benzyl{2-methyl-3-[(metbylsulfonyl) amino]phenyl}amino)methyl]phenoxy}phenyl)-N-(2-morpholin-4-ylethyl)propanamide Dicyclohexylcarbodiimide on resin (70 mg) was added to a Robbin's Organic Synthesis Block (Robbins Scientific Corporation) followed by the product from Example 104A (375 microliter of 0.13 M solution) in 20% dimethylacetamide in 1,2-dichloroethane. Then HOAt (375 micolitre of 0.23 M solution in 20% DME in DCE and 4-(2-aminoethyl) morpholine (375 microliter of 0.2 M solution in 20% DME/ DCE) were added using Gilson Liquid Handler. Reaction block was covered and shaken gently at room temperature overnight. Trisamine resin (57 mg, 4.3 mmole/g loading) was added and shaken two hours. Filtered it off in a Robbin's Collection Block and washed with CH$_2$Cl$_2$ (4×0.5 ml). Filtrates concentrated. Residue purified by HPLC to provide the title compound. $^1$H NMR (500 MHz, DMSO-D$_6$) δ8.95 (s, 1 H), 8.11 (t, 1 H), 7.26 (m, 6 H), 7.20 (m, 3 H), 7.04 (t, 1 H), 6.97 (m, 2 H), 6.89 (m, 4 H), 4.04 (d, 4 H), 3.96 (s, 4 H), 3.63 (s, 4 H), 3.14 (t, 2 H), 3.10 (s, 2 H), 2.92 (s, 3 H), 2.81 (t, 2 H), 2.41 (m, 5 H); MS (ESI+) m/z 657 (M+H)$^+$.

EXAMPLE 148

3-(4-{4-[(benzyl{2-methyl-3-[(methylsulfonyl) amino]phenyl}amino)methyl]phenoxy}phenyl)-N-[3-(2-oxopyrrolidin-1-yl)propyl]propanamide The product from Example 104A and 1-(3-aminopropyl)-2-pyrrolidinone were processed as described in Example 147 to provide the title compound. $^1$H NMR (500 MHz, CDCL$_3$) δ7.26 (m, 2 H), 7.19 (m, 6 H), 7.11 (m, 3 H), 6.88 (m, 5 H), 6.79 (m, 1 H), 6.16 (s, 1 H), 4.04 (d, 4 H), 3.38 (t, 2 H), 3.22 (t, 2 H), 3.16 (dd, 2 H), 2.95 (m, 5 H), 2.51 (t, 2 H), 2.42 (t, 2 H), 2.33 (s, 3 H), 2.06 (m, 2 H), 1.62 (m, 2 H); MS (ESI+) m/z 669 (M+H)$^+$.

EXAMPLE 149

3-(4-{4-[(benzyl{2-methyl-3-[(methylsulfonyl) amino]phenyl}amino)methyl]phenoxy}phenyl)-N-(5-hydroxypentyl)propanamide The product from Example 104A and 5-amino-1-pentanol were processed as described in Example 147 to provide the title compound. $^1$H NMR (500 MHz, DMSO-D$_6$) δ8.95 (s, 1 H), 7.73 (t, 1 H), 7.26 (m, 6 H), 7.19 (m, 3 H), 7.04 (t, 1 H), 6.96 (m, 2 H), 6.87 (m, 4 H), 4.03 (d, 4 H), 3.35 (m, 2 H), 3.00 (dd, 2 H), 2.91 (s, 3 H), 2.78 (t, 2 H), 2 H), 2.39 (s, 3 H), 2.33 (t, 2 H), 1.37 (m, 4 H), 1.23 (m, 2 H); MS (ESI+) m/z 630 (M+H)$^+$.

EXAMPLE 150

3-(4-{4-[(benzyl{2-methyl-3-[(methylsulfonyl) amino]phenyl}amino)methyl]phenoxy}phenyl)-N-(4-hydroxybutyl)propanamide The product from Example 104A and 4-amino-1-butanol were processed as described in Example 147 to provide the title compound. 1H NMR (500 MHz, DMSO-d6) δ8.95 (s, 1 H), 7.74 (t, 1 H), 7.26 (m, 6 H), 7.19 (m, 3 H), 7.04 (t, 1 H), 6.96 (m, 2 H), 6.86 (m, 4 H), 4.03 (d, 4 H), 3.35 (m, 2 H), 3.03 (m, 2 H), 2.91 (s, 3 H), 2.78 (t, 2 H), 2.39 (s, 3 H), 2.34 (m, 2 H), 1.37 (m, 4 H); MS (ESI+) m/z 616 (M+H)+.

EXAMPLE 151

3-(4-{4-[(benzyl{2-methyl-3-[(methylsulfonyl) amino]phenyl}amino)methyl]phenoxy}phenyl)-N-(3-hydroxypropyl)propanamide The product from Example 104A and 3-amino-1-propanol were processed as described in Example 147 to provide the title compound. $^1$H NMR (500 MHz, DMSO-D$_6$) δ ppm 8.95 (s, 1 H), 7.75 (t, 1 H), 7.26 (m, 6 H), 7.19 (m, 3 H), 7.04 (t, 1 H), 6.96 (m, 2 H), 6.87 (m, 4 H), 4.05 (s, 2 H), 4.01 (s, 2 H), 3.35 (m, 2 H), 3.07 (dd, 2 H), 2.91 (s, 3 H), 2.78 (t, 2 H), 2.39 (s, 3 H), 2.34 (t, 2 H), 1.50 (m, 2 H); MS (ESI+) m/z 602 (M+H)$^+$.

EXAMPLE 152

3-(4-{4-[(benzyl{2-methyl-3-[(methylsulfonyl) amino]phenyl}amino)methyl]phenoxy}phenyl)-N-(2-hydroxyethyl)propanamide The product from Example 104A and ethanolamine were processed as described in Example 147 to provide the title compound. ¹H NMR (500 MHz, DMSO-D₆) δ8.95 (s, 1 H), 7.78 (t, 1 H), 7.26 (m, 6 H), 7.19 (m, 3 H), 7.04 (t, 1 H), 6.97 (m, 2 H), 6.87 (m, 4 H), 4.03 (d, 4 H), 3.35 (m, 2 H), 3.10 (dd, 2 H), 2.91 (s, 3 H), 2.78 (t, 2 H), 2.39 (s, 3 H), 2.36 (m, 2 H); MS (ESI+) m/z 588 (M+H)⁺.

EXAMPLE 153

3-(4-{4-[(benzyl{2-methyl-3-[(methlsulfonyl)amino]phenyl}amino)methyl]phenoxy}phenyl)-N-(6-hydroxyhexyl)propanamide The product from Example 104A and 6-amino-1-hexanol processed as described in Example 147 to provide the title compound. ¹H NMR (500 MHz, DMSO-D) δ8.95 (s, 1 H), 7.73 (t, 1 H), 7.26 (m, 6 H), 7.19 (m, 3 H), 7.04 (t, 1 H), 6.96 (m, 2 H), 6.87 (m, 4 H), 4.03 (d, 4 H), 3.35 (m, 2 H), 3.00 (dd, 2 H), 2.91 (s, 3 H), 2.78 (t, 2 H), 2.39 (s, 3 H), 2.33 (t, 2 H), 1.37 (m, 4 H), 1.23 (m, 4 H); MS (APCI+) m/z 645 (M+H)⁺.

EXAMPLE 154

N-(3-{(2,4-difluorobenzyl)[4-(3-furylmethoxy)benzyl]amino}-2-methylphenyl)methanesulfonamide The product from Example 33A and 3-furanmethanol were processed as described in Examples 142A, 6C, and 6D to provide the title compound. ¹H NMR (500 MHz, CDCl₃) δ7.49 (m, 1 H), 7.43 (t, 1 H), 7.21 (d, 1 H), 7.12 (m, 4 H), 6.91 (d, 1 H), 6.86 (d, 2 H), 6.73 (m, 2 H), 6.47 (d, 1 H), 6.08 (s, 1 H), 4.91 (s, 2 H), 4.07 (s, 2 H), 4.01 (s, 2 H), 2.94 (s, 3 H), 2.29 (s, 3 H); MS (APCI−) m/z 511 (M−H).

EXAMPLE 155

N-(3-{(2,4-difluorobenzyl)[4-(2-furylmethoxy)benzyl]amino}-2-methylphenyl)methanesulfonamide The product from Example 33A and furfurylalcohol were processed as described in Examples 142A, 6C, and 6D to provide the title compound. ¹H NMR (500 MHz, CDCl₃) δ7.44 (m, 1 H), 7.21 (d, 1 H), 7.13 (m, 4 H), 6.92 (d, 1 H), 6.87 (d, 2 H), 6.72 (m, 2 H), 6.41 (d, 1 H), 6.38 (m, 1 H), 6.05 (s, 1 H), 4.96 (s, 2 H), 3.96–4.18 (m, 4 H), 2.90 (s, 3 H), 2.26 (s, 3H); MS (APCI−) m/z 511 (M−H).

EXAMPLE 156

N-{3-[[4-(1,3-benzodioxol-5-ylmethoxy)benzyl](2,4-difluorobenzyl)amino]-2-methylphenyl}methanesulfonamide The product from Example 33A and piperonylalcohol were processed as described in Examples 142A, 6C, and 6D to provide the title compound. ¹H NMR (500 MHz, CDCl₃) δ7.21 (d, 1 H), 7.13 (m, 4 H), 6.92 (m, 2 H), 6.85 (m, 3 H), 6.80 (d, 1 H), 6.72 (m, 2 H), 6.05 (s, 1 H), 5.96 (s, 2 H), 4.92 (s, 2 H), 4.11 (s, 2 H), 4.03 (s, 2 H), 2.91 (s, 3 H), 2.27 (s, 3 H); MS (APCI−) m/z 565 (M−H).

EXAMPLE 157

N-{3-[{4-[(6-chloro-1,3-benzodioxol-5-yl)methoxy]benzyl}(2,4-difluorobenzyl)amino]-2-methylphenyl}methanesulfonamide The product from Example 33A and 6-chloropiperonylalcohol were processed as described in Examples 142A, 6C, and 6D to provide the title compound. ¹H NMR (500 MHz, CDCL₃) δ7.22 (d, 1 H), 7.14 (m, 3 H), 6.97 (s, 1 H), 6.94 (d, 1 H), 6.85 (d, 3 H), 6.72 (m, 2 H), 6.06 (s, 1 H), 5.97 (s, 2 H), 5.03 (s, 2 H), 4.11 (s, 2 H), 4.05 (s, 2 H), 2.91 (s, 3 H), 2.26 (s, 3 H); MS (APCI−) m/z 599 (M−H).

EXAMPLE 158

N-(3-{(2,4-difluorobenzyl)[4-(2-phenylethoxy)benzyl]amino}-2-methylphenyl)methanesulfonamide The product from Example 33A and 2-phenylethylalcohol were processed as described in Examples 142A, 6C, and 6D to provide the title compound. ¹H NMR (500 MHz, CDCL₃) δ7.26 (m, 6 H), 7.11 (d, 4 H), 6.90 (d, 1 H), 6.78 (d, 2 H), 6.72 (m, 2 H), 6.04 (s, 1 H), 4.13 (t, 2 H), 4.07 (s, 2 H), 4.01 (s, 2 H), 3.08 (t, 2 H), 2.89 (s, 3 H), 2.27 (s, 3 H); MS (APCI−) m/z 535 (M−H).

EXAMPLE 159

N-(3-{benzyl[4-(3-isopropoxyphenoxy)benzyl]amino}-2-methylphenyl)methanesulfonamide

EXAMPLE 159A

The product from Example 61F (40 mg, 0.09 mmole) and di-t-butylazo dicarboxylate (33.6 mg, 0.14 mmole) in tetrahydrofuran (1.5 ml) were added to PPh3 on resin (63 mg, 0.19 mmole: loading 3 mmole/g) followed by isopropanol (6.8 mg, 0.113 mmole) in 50 microliter tetrahydrofuran. Reaction mixture was shaken at room temperature overnight. Filtered off and solvent removed. The residue purified by HPLC.

EXAMPLE 159B

The product from Example 159A processed as described in Example 6C–D to provide the title compound. ¹H NMR (500 MHz, CDCl₃) δ7.10–7.32 (m, 10 H), 6.97 (br.s, 1 H), 6.89 (d, 2 H), 6.62 (m, 1 H), 6.51 (m, 2 H), 6.09 (s, 1 H), 4.49 (m, 1 H), 4.00–4.24 (br.s, 4 H), 2.90 (s, 3 H), 2.30 (s, 3 H), 1.32 (s, 3 H), 1.30 (s, 3 H); MS (ESI+) m/z 531 (M+H)⁺.

EXAMPLE 160

N-[3-(benzyl{4-[3-(cyclobutyloxy)phenoxy]benzyl}amino)-2-methylphenyl]methanesulfonamide The product from Example 61F and cyclobutanol were processed as described in Examples 159A, 6C, and 6D to provide the title compound. ¹H NMR (500 MHz, CDCl₃) δ7.11–7.36 (m, 10 H), 7.00 (s, 1 H), 6.88 (d, 2 H), 6.53 (m, 2 H), 6.40 (s, 1 H), 6.07 (s, 1 H), 4.59 (m, 1 H), 4.21 (Br.S., 4 H), 2.85 (s, 3 H), 2.40 (m, 2 H), 2.27 (s, 3 H), 2.15 (m, 2 H), 1.86 (m, 1 H), 1.67 (m, 1 H); MS (ESI+) m/z 543 (M+H)⁺.

EXAMPLE 161

N-(3-{benzyl[4-(3-sec-butoxyphenoxy)benzyl]amino}-2-methylphenyl)methanesulfonamide The product from Example 61F and 2-butanol were processed as described in Examples 159A, 6C, and 6D to provide the title compound. ¹H NMR (500 MHz, CDCl₃) δ1H NMR (500 MHz, CDCL3) δ ppm 7.20 (m, 10 H), 6.97 (s, 1 H), 6.90 (d, 2 H), 6.63 (m, 1 H), 6.51 (m, 2 H), 6.10 (s, 1 H), 4.24 (m, 1 H), 4.14 (s, 4 H), 2.90 (s, 3 H), 2.30 (s, 3 H), 1.73 (m, 1 H), 1.59 (m, 1 H), 1.27 (d, 3 H), 0.95 (t, 3 H; MS (ESI+) m/z 545 (M+H)⁺.

EXAMPLE 162

N-[3-(benzyl{4-[3-(cyclopentyloxy)phenoxy] benzy}amino)-2-methylphenyl]methanesulfonamide The product from Example 61F and cyclopentanol were processed as described in Examples 159A, 6C, and 6D to provide the title compound. $^1$H NMR (500 MHz, CDCl$_3$) δ ppm 7.12–7.34 (m, 10 H), 7.01 (s, 1 H), 6.88 (s, 2 H), 6.62 (m, 1 H), 6.49 (m, 2 H), 6.07 (s, 1 H), 4.67 (m, 1 H), 4.22 (s, 4 H), 2.86 (s, 3 H), 2.28 (s, 3 H), 1.73–1.93 (m, 6 H); MS (ESI+) m/z 557 (M+H)$^+$.

EXAMPLE 163

N-[3-(benzyl{4-[3-(1-methylbutoxy)phenoxy] benzyl}amino)-2-methylphenyl]methanesulfonamide The product from Example 61F and 2-pentanol were processed as described in Example 159A to provide the title compound. 1H NMR (500 MHz, CDCl3) δ7.12–7.33 (m, 10 H), 6.99 (s, 1 H), 6.89 (d, 2 H), 6.62 (m, 1 H), 6.50 (m, 2 H), 6.08 (s, 1 H), 4.31 (m, 1 H), 4.15 (s, 4 H), 2.88 (s, 3 H), 2.30 (s, 3 H), 1.71 (m, 1 H), 1.40 (m, 3 H), 1.27 (d, 3 H), 0.92 (t, 3 H); MS (ESI+) m/z 559 (M+H)+.

EXAMPLE 164

N-[3-(benzyl{4-[3-(2-methoxy-1-methylethoxy) phenoxy]benzyl}amino)-2-methylphenyl] methanesulfonamide The product from Example 61F and 1-methoxy-2-propanol were processed as described in Examples 159A, 6C, and 6D to provide the title compound. $^1$H NMR (500 MHz, CDCl$_3$) 7.18 (m, 9 H), 6.97 (br.s, 1 H), 6.89 (d, 2 H), 6.66 (m, 1 H), 6.54 (m, 2 H), 6.14 (s, 1 H), 4.47 (m, 1 H), 4.10 (s, 4 H), 3.56 (m, 1 H), 3.46 (m, 1 H), 3.39 (s, 3 H), 2.90 (s, 3 H), 2.31 (s, 3 H), 1.28 (d, 3 H); MS (ESI+) m/z 561 (M+H)$^+$.

EXAMPLE 165

N-[3-(benzyl{4-[3-(cyclohexyloxy)phenoxy] benzyl}amino)-2-methylphenyl]methanesulfonamide The product from Example 61F and cyclohexanol were processed as described in Examples 159A, 6C, and 6D to provide the title compound. $^1$H NMR (500 MHz, CDCl$_3$) δ7.19 (m, 9 H), 6.98 (br.s, 1 H), 6.89 (d, 2 H), 6.65 (m, 1 H), 6.64 (dd, 1 H), 6.50 (m, 2 H), 6.11 (s, 1 H), 4.05–4.30 (m, 5 H), 2.89 (s, 3 H), 2.29 (s, 3 H), 1.97 (m, 2 H), 1.70–1.91 (m, 2 H), 1.55 (m, 3 H), 1.33 (m, 3 H); MS (ESI+) m/z 571 (M+H)$^+$.

EXAMPLE 166

N-{3-[benzyl(4-{3-[(3-methylcyclopentyl)oxy] phenoxy}benzyl)amino]-2-methylphenyl}methanesulfonamide The product from Example 61F and 3-methylcyclopentanol were processed as described in Examples 159A, 6C, and 6D to provide the title compound. $^1$H NMR (500 MHz, CDCl$_3$) δ7.19 (m, 9 H), 6.99 (br.s, 1 H), 6.89 (d, 2 H), 6.59 (m, 1 H), 6.48 (m, 2 H), 6.08 (s, 1 H), 4.68 (m, 1 H), 4.02–4.32 (br.s, 4 H), 2.88 (s, 3 H), 2.25 (m, 4 H), 1.74–2.15 (m, 4 H), 1.38 (m, 1 H), 1.13 (m, 1 H), 1.06 (d, 1 H), 1.00 (d, 2 H); MS (ESI+) m/z 571 (M+H)$^+$.

EXAMPLE 167

N-[3-(benzyl{4-[3-(2-ethoxy-1-methylethoxy) phenoxy]benzyl}amino)-2-methylphenyl] methanesulfonamide The product from Example 61F and 1-ethoxy-2-propanol were processed as described in Examples 159A, 6C, and 6D to provide the title compound. $^1$H NMR (500 MHz, CDCl$_3$) δ7.18 (m, 9 H), 6.97 (br.s, 1 H), 6.89 (d, 2 H), 6.67 (m, 1 H), 6.54 (m, 2 H), 6.13 (s, 1 H), 4.46 (m, 1 H), 3.98–4.24 (br.s, 4 H), 3.60 (m, 1 H), 3.53 (m, 2 H), 3.47 (m, 1 H), 2.90 (s, 3 H), 2.31 (s, 3 H), 1.29 (d, 3 H), 1.18 (t, J=7.0 Hz, 3 H); MS (ESI+) m/z 575 (M+H)$^+$.

EXAMPLE 168

N-{3-[benzyl(4-{3-[(4-methylcyclohexyl)oxy] phenoxy}benzyl)amino]-2-methylphenyl}methanesulfonamide The product from Example 61F and 4-methylcyclohexanol were processed as described in Examples 159A, 6C, and 6D to provide the title compound. $^1$H NMR (500 MHz, CDCl$_3$) δ7.18 (m, 9 H), 6.99 (br.s, 1 H), 6.88 (d, 2 H), 6.65 (m, 1 H), 6.51 (m, 2 H), 6.09 (s, 1 H), 4.43 (m, 1 H), 4.04–4.32 (br.s, 4 H), 2.88 (s, 3 H), 2.29 (s, 3 H), 1.97 (m, 2 H), 1.65–1.87 (m, 2 H), 1.23–1.59 (m, 4 H), 1.02 (m, 1 H), 0.93 (d, 2 H), 0.90 (d, 1 H); MS (ESI+) m/z 585 (M+H)$^+$.

EXAMPLE 169

N-[3-(benzyl{4-[3-(cycloheptyloxy)phenoxy] benzyl}amino)-2-methyphenyl]methanesulfonamide The product from Example 61F and cycloheptanol were processed as described in Examples 159A, 6C, and 6D to provide the title compound. $^1$H NMR (500 MHz, CDCl$_3$) δ7.19 (m, 9 H), 6.98 (br.s, 1 H), 6.89 (d, 2 H), 6.60 (m, 1 H), 6.49 (m, 2 H), 6.10 (s, 1 H), 4.35 (m, 1 H), 3.99–4.28 (br.s, 4 H), 2.89 (s, 3 H), 2.29 (s, 3 H), 1.99 (m, 2 H), 1.74 (m, 8 H), 1.43 (m, 2 H); MS (ESI+) m/z 585 (M+H)$^+$.

EXAMPLE 170

N-(3-{benzyl[4-(3-methoxyphenoxy)benzyl]amino}-2-methylphenyl)methanesulfonamide The product from Example 61F and methanol were processed as described in Examples 159A, 6C, and 6D to provide the title compound. $^1$H NMR (500 MHz, CDCl$_3$) δ7.10–7.35 (m, 9 H), 7.01 (br.s, 1 H), 6.88 (d, 2 H), 6.64 (dd, 1 H), 6.54 (dd, 1 H), 6.47 (s, 1 H), 6.09 (s, 1 H), 3.98–4.40 (br.s, 4 H), 3.77 (s, 3 H), 2.84 (s, 3 H), 2.28 (s, 3 H); MS (ESI+) m/z 503 (M+H)$^+$.

EXAMPLE 171

N-(3-{benzyl[4-(3-ethoxyphenoxy)benzyl]amino}-2-methylphenyl)methanesulfonamide

The product from Example 61F and ethanol were processed as described in Examples 159A, 6C, and 6D to provide the title compound. $^1$H NMR (500 MHz, CDCl$_3$) δ7.20 (m, 9 H), 7.00 (br.s, 1 H), 6.88 (d, 2 H), 6.63 (dd, 1 H), 6.52 (dd, 1 H), 6.49 (t, 1H), 6.10 (s, 1 H), 4.08–4.35 (br.s, 4 H), 3.99 (dd, 2 H), 2.87 (s, 3 H), 2.27 (s, 3 H), 1.38 (t, 3 H); MS (ESI−) m/z 515 (M−H)$^−$.

EXAMPLE 172

N-(3-{benzyl[4-(3-propoxyphenoxy)benzyl]amino}-2-methylphenyl)methanesulfonamide The product from Example 61F and propanol were processed as described in Examples 159A, 6C, and 6D to provide the title compound. $^1$H NMR (500 MHz, CDCl$_3$)

δ7.20 (m, 9 H), 7.00 (br.s, 1 H), 6.88 (d, 2 H), 6.64 (dd, 1 H), 6.52 (m, 2 H), 6.10 (s, 1 H), 4.06–4.32 (br.s, 4 H), 3.88 (t, 2 H), 2.88 (s, 3 H), 2.28 (s, 3 H), 1.70–1.93 (m, 2 H), 1.01 (t, 3 H); MS (ESI+) m/z 531 (M+H)$^+$.

EXAMPLE 173

N-[3-(benzyl{4-[3-(cyclopropylmethoxy)phenoxy]benzyl}amino)-2-methylphenyl]methanesulfonamide The product from Example 61F and cyclopropylmethanol were processed as described in Examples 159A, 6C, and 6D to provide the title compound. $^1$H NMR (500 MHz, CDCl$_3$) δ7.19 (m, 9 H), 6.98 (br.s, 1 H), 6.89 (d, 2 H), 6.63 (dd, 1 H), 6.52 (m, 2 H), 6.10 (s, 1 H), 4.00–4.32 (br.s, 4 H), 3.76 (d, 2 H), 2.88 (s, 3 H), 2.29 (s, 3 H), 1.25 (m, 1 H), 0.63 (m, 2 H), 0.32 (m, 2 H); MS (ESI–) m/z 541 (M–H)$^-$.

EXAMPLE 174

N-(3-{benzyl[4-(3-butoxyphenoxy)benzyl]amino}-2-methlphenyl)methanesulfonamide

The product from Example 61F and 1-butanol were processed as described in Example 159A to provide the title compound. $^1$H NMR (500 MHz, CDCl$_3$) δ7.18 (m, 9 H), 6.99 (br.s, 1 H), 6.89 (d, 2 H), 6.64 (dd, 1 H), 6.52 (m, 2 H), 6.10 (s, 1 H), 4.06–4.38 (br.s, 4 H), 3.92 (t, 2 H), 2.88 (s, 3 H), 2.28 (s, 3 H), 1.65–1.96 (m, 2 H), 1.46 (m, 2 H), 0.96 (t, 3 H; MS (ESI+) m/z 545 (M+H)$^+$.

EXAMPLE 175

N-(3-{benzyl[4-(3-isobutoxyphenoxy)benzyl]amino}-2-methylphenyl)methanesulfonamide The product from Example 61F and isobutyl alcohol were processed as described in Examples 159A, 6C, and 6D to provide the title compound. $^1$H NMR (500 MHz, CDCl$_3$) δ7.11–7.34 (m, 9 H), 7.00 (br.s, 1 H), 6.88 (d, 2 H), 6.64 (dd, 1 H), 6.50 (m, 2 H), 6.07 (s, 1 H), 3.99–4.39 (br.s, 4 H), 3.67 (d, 2 H), 2.86 (s, 3 H), 2.28 (s, 3 H), 2.07 (m, 1 H), 1.00 (d, 6 H); MS (ESI+) m/z 545 (M+H)$^+$.

EXAMPLE 176

N-[3-(benzyl{4-[3-(pent-3-ynyloxy)phenoxy]benzyl}amino)-2-methylphenyl]methanesulfonamide The product from Example 61F and 3-pentyn-1-ol were processed as described in Examples 159A, 6C, and 6D to provide the title compound. $^1$H NMR (500 MHz, CDCL$_3$) δ7.08–7.46 (m, 7 H), 6.84 (m, 3 H), 6.65 (m, 2 H), 6.52 (m, 2 H), 6.46 (s, 1 H), 6.04 (s, 1 H), 3.91–4.18 (m, 6 H), 2.76 (s, 3 H), 2.59 (m, 2 H), 2.21 (s, 3 H), 1.78 (t, 2 H); MS (ESI–) m/z 553 (M–H)$^-$.

EXAMPLE 177

N-{3-[benzyl(4-{3-[(2E)-pent-2-enyloxy]phenoxy}benzyl)amino]-2-methylphenyl}methanesulfonamide The product from Example 61F and 2-pentyn-1-ol were processed as described in Examples 159A, 6C, and 6D to provide the title compound. $^1$H NMR (500 MHz, CDCl$_3$) δ7.20 (m, 9 H), 7.04 (br.s, 1 H), 6.88 (s, 2 H), 6.65 (dd, 1 H), 6.51 (m, 2 H), 6.06 (s, 1 H), 5.63 (m, 2 H), 4.54 (d, 2 H), 3.98–4.42 (br.s, 4 H), 2.84 (s, 3 H), 2.27 (s, 3 H), 2.10 (m, 2 H), 1.00 (m, 3 H); MS (ESI+) m/z 557 (M+H)$^+$.

EXAMPLE 178

N-{3-[benzyl(4-{3-[(1-methylcyclopropyl)methoxy]phenoxy}benzyl)amino]-2-methylphenyl}methanesulfonamide The product from Example 61F and 2-methylcyclopropanemethanol were processed as described in Examples 159A, 6C, and 6D to provide the title compound. $^1$H NMR (500 MHz, CDCl$_3$) δ7.19 (m, 9 H), 7.01 (br.s, 1 H), 6.88 (d, 2 H), 6.63 (dd, 1 H), 6.52 (dd, 1 H), 6.49 (t, 1 H), 6.11 (s, 1 H), 4.05–4.42 (br.s, 4 H), 3.79 (m, 1 H), 3.72 (m, 1 H), 2.86 (s, 3 H), 2.26 (s, 3 H), 1.08 (d, 3 H), 0.94 (m, 1 H), 0.73 (m, 1 H), 0.47 (m, 1 H), 0.37 (m, 1 H); MS (ESI–) m/z 555 (M–H)$^-$.

EXAMPLE 179

N-[3-(benzyl{4-[3-(cyclobutylmethoxy)phenoxy]benzyl}amino)-2-methylphenyl]methanesulfonamide The product from Example 61F and cyclobutylmethanol were processed as described in Examples 159A, 6C, and 6D to provide the title compound. $^1$H NMR (500 M, CDCl$_3$) δ7.12–7.33 (m, 9 H), 7.01 (br.s, 1 H), 6.88 (d, 2 H), 6.64 (m, 1 H), 6.51 (m, 2 H), 6.08 (s, 1 H), 3.98–4.50 (br.s, 4 H), 3.88 (d, 2 H), 2.85 (s, 3 H), 2.74 (m, 1 H), 2.27 (s, 3 H), 2.13 (m, 2 H), 1.78–2.02 (m, 4 H); MS (ESI–) m/z 555 (M–H)$^-$.

EXAMPLE 180

N-[3-(benzyl{4-[3-(2-cyclopropylethoxy)phenoxy]benzyl}amino)-2-methylphenyl]methanesulfonamide The product from Example 61F and 2-cyclopropylethanol were processed as described in Examples 159A, 6C, and 6D to provide the title compound. $^1$H NMR (500 MHz, CDCl$_3$) δ7.22 (m, 9 H), 7.00 (br.s, 1 H), 6.88 (d, 2 H), 6.66 (m, 1 H), 6.51 (m, 2 H), 6.09 (s, 1 H), 4.03–4.39 (br.s, 4 H), 3.99 (t, 2 H), 2.86 (s, 3 H), 2.28 (s, 3 H), 1.65 (dd, 2 H), 0.83 (m, 1 H), 0.47 (m, 2 H), 0.10 (dd, 2 H); MS (ESI+) m/z 557 (M+H)$^+$.

EXAMPLE 181

N-[3-(benzyl{4-[3-(phenyloxy)phenoxy]benzyl}amino)-2-methylphenyl]methanesulfonamide The product from Example 61F and 1-pentanol were processed as described in Examples 159A, 6C, and 6D to provide the title compound. $^1$H NMR (500 MHz, CDCl$_3$) δ7.18 (m, 9 H), 6.99 (br.s, 1 H), 6.89 (d, 2 H), 6.64 (m, 1 H), 6.52 (m, 2 H), 6.09 (s, 1 H), 3.99–4.33 (br.s, 4 H), 3.91 (t, 2 H), 2.88 (s, 3 H), 2.30 (s, 3 H), 1.76 (m, 2 H), 1.37 (m, 4 H), 0.92 (t, 3 H); MS (ESI–) m/z 557 (M–H)$^-$.

EXAMPLE 182

N-[3-(benzyl{4-[3-(2-methylbutoxy)phenoxy]benzyl}amino)-2-methylphenyl]methanesulfonamide The product from Example 61F and 2-methyl-1-butanol were processed as described in Examples 159A, 6C, and 6D to provide the title compound. $^1$H NMR (500 MHz, CDCl$_3$) δ7.19 (m, 9 H), 7.00 (br.s, 1 H), 6.88 (d, 2 H), 6.64 (m, 1 H), 6.51 (m, 2H), 6.09 (s, 1 H), 3.97–4.40 (br.s, 4 H), 3.78 (m, 1 H), 3.68 (m, 1 H), 2.87 (s, 3 H), 2.29 (s, 3 H), 1.84 (m, 1 H), 1.25 (m, 2 H), 0.99 (d, 3 H), 0.93 (t, 3 H); MS (ESI+) m/z 559 (M+H)$^+$.

EXAMPLE 183

N-[3-(benzyl{4-[3-(3-methylbutoxy)phenoxy]benzyl}amino)-2-methylphenyl]methanesulfonamide The product from Example 61F and isoamyl alcohol were processed as described in Examples 159A, 6C, and 6D to provide the title compound. $^1$H NMR (500 MHz, CDCl$_3$) δ7.19 (m, 9 H), 7.00 (br.s, 1 H), 6.88 (d, 2 H), 6.64 (m, 1 H), 6.51 (m, 2 H), 6.10 (s, 1 H), 4.00–4.40 (br.s, 4 H), 3.94 (t, 2 H), 2.87 (s, 3 H), 2.28 (s, 3 H), 1.82 (m, 1 H), 1.65 (q, 2 H), 0.94 (d, 6 H); MS (ESI+) m/z 559 (M+H)$^+$.

EXAMPLE 184

N-[3-(benzyl{4-[3-(2-ethoxyethoxy)phenoxy]benzyl}amino)-2-methylphenyl]methanesulfonamide The product from Example 61F and 2-ethoxyethanol were processed as described in Examples 159A, 6C, and 6D to provide the title compound. $^1$H NMR (500 MHz, CDCl$_3$) δ7.16 (m, 9 H), 6.96 (br.s, 1 H), 6.89 (d, 2 H), 6.66 (d, 1 H), 6.55 (d, 1 H), 6.52 (s, 1 H), 6.14 (s, 1 H), 4.07 (t, 2 H), 3.94–4.25 (br.s, 4 H), 3.76 (t, 2 H), 3.58 (q, 2 H), 2.90 (s, 3 H), 2.31 (s, 3 H), 1.22 (t, 3 H); MS (ESI+) m/z 561 (M+H)$^+$.

EXAMPLE 185

N-{3-[benzyl(4-{3-[2-(methylthio)ethoxy]phenoxy}benzyl)amino]-2-methylphenyl}methanesulfonamide The product from Example 61F and 2-(methylthio)ethanol were processed as described in Examples 159A, 6C, and 6D to provide the title compound. $^1$H NMR (500 MHz, CDCl$_3$) δ7.14–7.34 (m, 9 H), 7.05 (br.s, 1 H), 6.87 (d, 2 H), 6.64 (d, 1 H), 6.54 (d, 1 H), 6.48 (s, 1 H), 6.12 (s, 1 H), 4.17–4.45 (br.s, 4 H), 4.11 (t, 2 H), 2.85 (m, 5 H), 2.24 (s, 3 H), 2.20 (s, 3 H); MS (ESI+) m/z 563 (M+H)$^+$.

EXAMPLE 186

N-[3-(benzyl{4-[3-(cyclopentymethoxy)phenoxy]benzyl}amino)-2-methylphenyl]methanesulfonamide The product from Example 61F and cyclopentylmethanol were processed as described in Examples 159A, 6C, and 6D to provide the title compound. $^1$H NMR (500 MHz, CDCl$_3$) δ7.23 (m, 9 H), 7.00 (br.s, 1 H), 6.88 (d, 2 H), 6.64 (d, 1 H), 6.51 (m, 2 H), 6.09 (s, 1 H), 3.95–4.44 (br.s, 4 H), 3.78 (d, 2 H), 2.86 (s, 3 H), 2.33 (m, 1 H), 2.27 (s, 3 H), 1.81 (m, 2 H), 1.60 (m, 4 H), 1.33 (m, 2 H); MS (ESI+) m/z 571 (M+H)$^+$.

EXAMPLE 187

N-[3-(benzyl{4-[3-(tetrahydrofuran-2-ylmethoxy)phenoxylbenzyl}amino)-2-methylphenyl]methanesulfonamide The product from Example 61F and tetrahydro-2-furanmethanol were processed as described in Examples 159A, 6C, and 6D to provide the title compound. $^1$H NMR (500 MHz, CDCl$_3$) δ7.11–7.39 (m, 9 H), 7.06 (br.s, 1 H), 6.87 (d, 2 H), 6.65 (dd, 1 H), 6.55 (dd, 1 H), 6.42 (br.s, 1 H), 6.27 (br.s, 1 H), 4.07–4.37 (m, 4 H), 3.91 (m, 4 H), 3.81 (m, 1 H), 2.80 (s, 3 H), 2.25 (s, 3 H), 2.06 (m, 1 H), 1.92 (m, 2 H), 1.74 (m, 1 H); MS (ESI+) m/z 573 (M+H)$^+$.

EXAMPLE 188

N-[3-(benzyl{4-[3-(tetrahydrofuran-3-ylmethoxy)phenoxy]benzyl}amino)-2-methylphenyl]methanesulfonamide The product from Example 61F and tetrahydro-3-furanmethanol were processed as described in Examples 159A, 6C, and 6D to provide the title compound. $^1$H NMR (500 MHz, CDCl$_3$) δ7.22 (m, 9 H), 7.01 (br.s, 1 H), 6.88 (d, 2 H), 6.63 (dd, 1 H), 6.54 (dd, 1 H), 6.49 (s, 1 H), 6.14 (s, 1 H), 4.00–4.42 (br.s, 4 H), 3.87 (m, 4 H), 3.77 (dd, 1 H), 3.68 (m, 1 H), 2.87 (s, 3 H), 2.72 (m, 1 H), 2.28 (s, 3 H), 2.10 (m, 1 H), 1.72 (m, 1 H); MS (ESI+) m/z 573 (M+H)$^+$.

EXAMPLE 189

N-[3-(benzyl{4-[3-(hexyloxy)phenoxy]benzyl}amino)-2-methylphenyl]methanesulfonamide The product from Example 61F and 1-hexanol were processed as described in Examples 159A, 6C, and 6D to provide the title compound. $^1$H NMR (500 MHz, CDCl$_3$) δ7.09–7.31 (m, 9 H), 6.99 (br.s, 1 H), 6.89 (d, 2 H), 6.63 (d, 1 H), 6.52 (m, 2 H), 6.10 (s, 1 H), 3.96–4.37 (br.s, 4 H), 3.91 (t, 2 H), 2.89 (s, 3 H), 2.29 (s, 3 H), 1.76 (m, 2 H), 1.43 (m, 2 H), 1.31 (m, 4 H), 0.89 (t, , 3 H); MS (ESI+) m/z 574 (M+H)$^+$.

EXAMPLE 190

N-[3-(benzyl{4-[3-(3,3-dimethylbutoxy)phenoxy]benzyl}amino)-2-methylphenyl]methanesulfonamide The product from Example 61F and 3,3-dimethylbutanol were processed as described in Examples 159A, 6C, and 6D to provide the title compound. $^1$H NMR (500 MHz, CDCl$_3$) δ7.19 (m, 9 H), 6.99 (br.s, 1 H), 6.89 (d, 2 H), 6.64 (m, 1 H), 6.51 (m, 2 H), 6.10 (s, 1 H), 4.04–4.39 (br.s, 4 H), 3.98 (t, 2 H), 2.88 (s, 3 H), 2.28 (s, 3 H), 1.70 (t, 2 H), 0.97 (s, 9 H); MS (ESI+) m/z 573 (M+H)$^+$.

EXAMPLE 191

N-[3-(benzyl{4-[3-(2-isopropoxyethoxy)phenoxy]benzyl}amino)-2-methylphenyl]methanesulfonamide The product from Example 61F and 2-isopropoxyethanol were processed as described in Examples 159A, 6C, and 6D to provide the title compound. $^1$H NMR (500 MHz, CDCl$_3$) δ7.18 (m, 9 H), 7.00 (br.s, 1 H), 6.87 (d, 2 H), 6.66 (dd, 1 H), 6.54 (dd, 1 H), 6.51 (m, 1 H), 6.13 (s, 1 H), 4.09–4.35 (br.s, 4 H), 4.05 (m, 2 H), 3.75 (t, 2 H), 3.67 (m, 1 H), 2.87 (s, 3 H), 2.27 (s, 3 H), 1.18 (d, 6 H); MS (ESI+) m/z 575 (M+H)$^+$.

EXAMPLE 192

N-[3-(benzyl{4-[3-(cyclohexylmethoxy)phenoxy]benzyl}amino)-2-methylphenyl]methanesulfonamide The product from Example 61F and cyclohexylmethanol were processed as described in Examples 159A, 6C, and 6D to provide the title compound. $^1$H NMR (500 MHz, CDCl$_3$) δ7.12–7.36 (m, 9 H), 7.03 (m, 1 H), 6.87 (d, 2 H), 6.64 (br.S., 1 H), 6.50 (m, 2 H), 6.07 (s, 1 H), 4.00–4.55 (br.S., 4 H), 3.70 (d, 2 H), 2.84 (s, 3 H), 2.26 (s, 3 H), 1.84 (m, 5 H), 1.14–1.36 (m, 4 H), 1.03 (m, 2 H); MS (ESI+) m/z 586 (M+H)$^+$.

EXAMPLE 193

N-[3-(benzyl{4-[3-(3-methoxy-3-methylbutoxy)phenoxy]benzyl}amino)-2-methylphenyl]methanesulfonamide The product from Example 61F and 3-methoxy-3-methyl-1-butanol were processed as described in Example 159A, 6C and 6D to provide the title compound. $^1$H NMR (500 MHz, CDCL$_3$) δ7.13–7.35 (m, 9 H), 7.04 (br.s, 1 H), 6.87 (s, 2 H), 6.64 (d, 1 H), 6.52 (d, 1 H), 6.49 (s, 1 H), 6.14 (s, 1 H), 4.06–4.44 (br.s, 4 H), 4.01 (t, 2 H), 3.20 (s, 3 H), 2.84 (s, 3 H), 2.27 (s, 3 H), 1.97 (t, 2 H), 1.22 (s, 6 H); MS (ESI+) m/z 589 (M+H)$^+$.

EXAMPLE 194

1-(4-ethoxy-6-propylpyrimidin-2-yl)isoquinoline

The product from Example 61F and 3-pentyn-1-ol were processed as described in Examples 159A, 6C, and 6D to provide the title compound. $^1$H NMR (500 MHz, CDCl$_3$) δ7.10–7.36 (m, 9 H), 6.99 (br.s, 1 H), 6.89 (d, 2 H), 6.64 (dd, 1 H), 6.52 (m, 2 H), 6.08 (s, 1 H), 5.61 (m, 1 H), 5.46 (m, 1 H), 3.97–4.29 (br.s, 4 H), 3.92 (t, 2 H), 2.89 (s, 3 H), 2.52 (dd, 2 H), 2.30 (s, 3 H), 1.64 (d, 3 H); MS (ESI–) m/z 555 (M–H)$^-$.

EXAMPLE 195

N-[3-(benzyl{4-[3-(3-furylmethoxy)phenoxy] benzyl}amino)-2-methylphenyl]methanesulfonamide The product from Example 61F and 3-furanmethanol were processed as described in Examples 159A, 6C, and 6D to provide the title compound. $^1$H NMR (500 MHz, CDCl$_3$) δ7.46 (m, 1 H), 7.42 (m, 1 H), 7.07–7.33 (m, 9 H), 6.92 (m, 3 H), 6.70 (m, 1 H), 6.57 (m, 2 H), 6.46 (m, 1 H), 6.09 (m, 1 H), 4.89 (s, 2 H), 4.07 (d, 4 H), 2.93 (s, 3 H), 2.33 (s, 3 H); MS (ESI+) m/z 569 (M+H)$^+$.

EXAMPLE 196

N-[3-(benzyl{4-[3-(2-furylmethoxy)phenoxy] benzyl}amino)-2-methylphenyl]methanesulfonamide The product from Example 61F and furfuryl alcohol were processed as described in Examples 159A, 6C, and 6D to provide the title compound. $^1$H NMR (500 MHz, CDCl3) δ7.43 (dd, 1 H), 7.24 (m, 3 H), 7.12 (m, 5 H), 6.91 (m, 4 H), 6.71 (m, 1 H), 6.59 (m, 2 H), 6.40 (m, 1 H), 6.36 (m, 1 H), 6.09 (s, 1 H), 4.95 (s, 2 H), 4.04 (d, 4 H), 2.94 (s, 3 H), 2.34 (s, 3 H); MS (ESI+) m/z 569 (M+H)$^+$.

EXAMPLE 197

N-[3-(benzyl{4-[3-(thien-3-ylmethoxy)phenoxy] benzyl}amino)-2-methylphenyl]methanesulfonamide The product from Example 61F and 3-thiophenemethanol were processed as described in Examples 159A, 6C, and 6D to provide the title compound. $^1$H NMR (500 MHz, CDCl$_3$) δ7.32 (m, 1 H), 7.24 (m, 7 H), 7.13 (m, 4 H), 6.91 (m, 3 H), 6.70 (m, 1 H), 6.57 (m, 2 H), 6.10 (s, 1 H), 5.02 (s, 2 H), 4.06 (d, 4 H), 2.93 (s, 3 H), 2.33 (s, 3 H); MS (ESI+) m/z 585 (M+H)$^+$.

EXAMPLE 198

N-[3-(benzyl{4-[3-(2-thien-3-ylethoxy)phenoxy] benzyl}amino)-2-methylphenyl]methanesulfonamide The product from Example 61F and 2-(3-thienyl)ethanol were processed as described in Examples 159A, 6C, and 6D to provide the title compound. $^1$H NMR (500 MHz, CDCl$_3$) δ7.26 (m, 2 H), 7.20 (m, 5 H), 7.13 (m, 3 H), 7.06 (d, 1 H), 7.01 (dd, 1 H), 6.91 (m, 3 H), 6.65 (dd, 1 H), 6.54 (m, 2 H), 6.09 (s, 1 H), 4.13 (t, 2 H), 4.05 (d, 4 H), 3.10 (t, 2 H), 2.93 (s, 3 H), 2.32 (s, 3 H); MS (ESI+) m/z 599 (M+H)$^+$.

EXAMPLE 199

N-[3-(benzyl{4-[3-(thien-2-ylmethoxy)phenoxy] benzyl}amino)-2-methylphenyl]methanesulfonamide The product from Example 61F and thiophene-2-methanol were processed as described in Examples 159A, 6C, and 6D to provide the title compound. $^1$H NMR (500 MHz, CDCl$_3$) δ7.31 (dd, 1 H), 7.27 (m, 1 H), 7.21 (m, 5 H), 7.13 (m, 3 H), 7.07 (m, 1 H), 6.99 (m, 1 H), 6.91 (m, 3 H), 6.72 (m, 1 H), 6.59 (m, 2 H), 6.09 (s, 1 H), 5.17 (s, 2 H), 4.06 (d, 4 H), 2.93 (s, 3 H), 2.33 (s, 3 H); MS (ESI+) m/z 585 (M+H)$^+$.

EXAMPLE 200

N-[3-(benzyl{4-[3-(2-thien-2-ylethoxy)phenoxy] benzyl}amino)-2-methylphenyl]methanesulfonamide The product from Example 61F and 2-(2-thienyl)ethanol were processed as described in Examples 159A, 6C, and 6D to provide the title compound. $^1$H NMR (500 MHz, CDCl$_3$) δ7.27 (m, 1 H), 7.20 (m, 5 H), 7.13 (m, 4 H), 6.91 (m, 5 H), 6.66 (m, 1 H), 6.55 (m, 2 H), 6.09 (s, 1 H), 4.15 (t, 2 H), 4.04 (d, 4 H), 3.28 (t, 2 H), 2.94 (s, 3 H), 2.33 (s, 3 H); MS (ESI+) m/z 599 (M+H)$^+$.

EXAMPLE 201

N-{3-[benzyl(4-{3-[2-(4-methyl-1,3-thiazol-5-yl) ethoxy]phenoxy}benzyl)amino]-2-methylphenyl}methanesulfonamide The product from Example 61F and 4-methyl-5-thiazoleethanol were processed as described in Examples 159A, 6C, and 6D to provide the title compound. $^1$H NMR (500 MHz, CDCl$_3$) δ8.77 (s, 1 H), 7.27 (m, 1 H), 7.21 (m, 5 H), 7.13 (m, 3 H), 6.91 (m, 3 H), 6.63 (dd, 1 H), 6.57 (dd, 1 H), 6.52 (t, 1 H), 6.17 (s, 1 H), 4.11 (t, 2 H), 4.05 (d, 4 H), 3.23 (t, 2 H), 2.95 (s, 3 H), 2.45 (s, 3 H), 2.33 (s, 3 H); MS (ESI+) m/z 614 (M+H)$^+$.

EXAMPLE 202

N-{3-[benzyl(4-{3-[2-(2-oxopyrrolidin-1-yl)ethoxy] phenoxy}benzyl)amino]-2-methylphenyl}methanesulfonamide The product from Example 61F and N-(2-hydroxyethyl)-2-pyrrolidone were processed as described in Examples 159A, 6C, and 6D to provide the title compound. $^1$H NMR (500 MHz, CDCl$_3$) δ7.24 (m, 6 H), 7.13 (m, 3 H), 6.96 (d, 1 H), 6.89 (d, 2 H), 6.59 (m, 2 H), 6.45 (s, 1 H), 6.42 (t, 1 H), 4.03 (m, 6 H), 3.65 (t, 2 H), 3.55 (t, 2 H), 2.93 (s, 3 H), 2.39 (t, 2 H), 2.32 (s, 3 H), 2.01 (m, 2 H); MS (ESI+) m/z 600 (M+H)$^+$.

EXAMPLE 203

N-[3-(benzyl{4-[3-(2-morpholin-4-ylethoxy) phenoxy]benzyl}amino)-2-methylphenyl] methanesulfonamide The product from Example 61F and N-(2-hydroxyethyl) morpholine were processed as described in Examples 159A, 6C, and 6D to provide the title compound. $^1$H NMR (500 MHz, CDCl$_3$) δ7.20 (m, 9 H), 7.07 (m, 1 H), 6.87 (d, 2 H), 6.79 (s, 1 H), 6.66 (dd, 1 H), 6.57 (dd, 1 H), 6.28 (t, 1 H), 4.26 (m, 2 H), 4.22 (s, 2 H), 4.17 (s, 2 H), 3.99 (s, 2 H), 3.70 (d, 2 H), 3.52 (m, 2 H), 3.05 (br.s, 2 H), 2.89 (s, 3 H), 2.33–2.66 (br.s, 2 H), 2.21 (s, 3 H); MS (ESI+) m/z 602 (M+H)$^+$.

EXAMPLE 204

N-[3-(benzyl{4-[3-(2-phenylethoxy)phenoxy]benzyl}amino)-2-methylphenyl]methanesulfonamide The product from Example 61F and 2-phenylethanol were processed as described in Examples 159A, 6C, and 6D to provide the title compound. $^1$H NMR (500 MHz, CDCl$_3$) δ7.25 (m, 11 H), 7.12 (m, 3 H), 6.90 (m, 3 H), 6.64 (dd, 1 H), 6.54 (m, 2 H), 6.09 (s, 1 H), 4.13 (t, 2 H), 4.05 (d, 4 H), 3.07 (t, 2 H), 2.94 (s, 3 H), 2.32 (s, 3 H); MS (ESI+) m/z 593 (M+H)$^+$.

EXAMPLE 205

N-{3-[{4-[3-(1,3-benzodioxol-5-ylmethoxy)phenoxy]benzyl}(benzyl)amino]-2-methylphenyl}methanesulfonamide The product from Example 61F and piperonyl alcohol were processed as described in Examples 159A, 6C, and 6D to provide the title compound. $^1$H NMR (500 MHz, CDCl$_3$) δ7.23 (m, 5 H), 7.13 (m, 4 H), 6.91 (m, 4 H), 6.84 (m, 1 H), 6.78 (d, 1 H), 6.69 (dd, 1 H), 6.57 (m, 2 H), 6.10 (s, 1 H), 5.95 (s, 2 H), 4.90 (s, 2 H), 4.08 (d, 4 H), 2.93 (s, 3 H), 2.32 (s, 3 H); MS (ESI+) m/z 623 (M+H)$^+$.

EXAMPLE 206

N-[3-(benzyl{4-[3-(benzyloxy)phenoxy]benzyl}amino)-2-methylphenyl]methanesulfonamide The product from Example 61F and benzyl alcohol were processed as described in Examples 159A, 6C, and 6D to provide the title compound. $^1$H NMR (500 MHz, CDCl$_3$) δ7.35 (m, 5 H), 7.26 (m, 6 H), 7.13 (m, 3 H), 6.91 (m, 3 H), 6.71 (dd, 1 H), 6.60 (t, 1 H), 6.57 (dd, 1 H), 6.09 (s, 1 H), 5.02 (s, 2 H), 4.05 (d, 4 H), 2.93 (s, 3 H), 2.33 (s, 3 H); MS (ESI+) m/z 579 (M+H)$^+$.

EXAMPLE 207

(3-{4-[((2-methylbenzyl){2-methyl-3-[(methylsulfonyl)amino]phenyl}amino)methyl]phenoxy}phenoxy)acetic acid The product from Example 83B and 2-methylbenzyl bromide were processed as described in Examples 6B, 6C, 6D, and 137B to provide the title compound. $^1$H NMR (500 MHz, DMSO-D$_6$) δ8.93 (s, 1 H), 7.25 (m, 4 H), 7.08 (m, 5 H), 6.99 (m, 1 H), 6.92 (d, 2 H), 6.66 (m, 1 H), 6.50 (m, 2 H), 4.58 (s, 2 H), 4.06 (s, 4 H), 2.87 (s, 3 H), 2.27 (s, 3 H), 2.17 (s, 3 H); MS (ESI)$^-$ m/z 559 (M−H)$^-$.

EXAMPLE 208

(3-{4-[((4-methylbenzyl){2-methyl-3-[(methylsulfonyl)amino]phenyl}amino)methyl]phenoxy}phenoxy)acetic acid The product from Example 83B and 4-methylbenzyl bromide were processed as described in Examples 6B, 6C, 6D, and 137B to provide the title compound. $^1$H NMR (500 MHz, DMSO-D$_6$) δ8.94 (s, 1 H), 7.25 (m, 3 H), 7.13 (m, 2 H), 7.07 (m, 2 H), 7.02 (d, 1 H), 6.94 (m, 4 H), 6.66 (m, 1 H), 6.51 (m, 2 H), 4.64 (s, 2 H), 4.01 (s, 4 H), 2.91 (s, 3 H), 2.39 (s, 3 H), 2.24 (s, 3 H); MS (ESI+) m/z 562 (M+H)$^+$.

EXAMPLE 209

(3-{4-[((2,4-dichlorobenzyl){2-methyl-3-[(methylsulfonyl)amino]phenyl}amino)methyl]phenoxy}phenoxy)acetic acid The product from Example 83B and 2,4-dichlorolbenzyl bromide were processed as described in Examples 6B, 6C, 6D, and 137B to provide the title compound. $^1$H NMR (500 MHz, DMSO-D$_6$) δ8.94 (s, 1 H), 7.52 (d, 1 H), 7.39 (d, 1 H), 7.32 (dd, 1 H), 7.25 (m, 3 H), 7.08 (t, 1 H), 7.01 (m, 2 H), 6.92 (d, 2 H), 6.67 (m, 1 H), 6.51 (m, 2 H), 4.64 (s, 2 H), 4.17 (s, 2 H), 4.09 (s, 2 H), 2.89 (s, 3 H), 2.30 (s, 3 H); MS (ESI+) m/z 615 (M+H)$^+$.

EXAMPLE 210

(3-{4-[((2-chloro-4-fluorobenzol){2-methyl-3-[(methylsulfonyl)amino]phenyl}amino)methyl]phenoxy}phenoxy)acetic acid The product from Example 83B and 2-chloro-4-fluorobenzyl bromide were processed as described in Examples 6B, 6C, 6D, and 137B to provide the title compound. $^1$H NMR (500 MHz, DMSO-D$_6$) δ8.93 (s, 1 H), 7.39 (m, 1 H), 7.33 (m, 1 H), 7.25 (m, 3 H), 7.10 (m, 2 H), 7.01 (m, 2 H), 6.92 (d, 2 H), 6.67 (m, 1 H), 6.50 (m, 2 H), 4.64 (s, 2 H), 4.16 (s, 2 H), 4.09 (s, 2 H), 2.89 (s, 3 H), 2.30 (s, 3 H); MS (ESI+) m/z 599 (M+H)$^+$.

EXAMPLE 211

(3-{4-[((4-benzoylbenzyl){2-methyl-3-[(methylsulfonyl)amino]phenyl}amino)methyl]phenoxy}phenoxy)acetic acid The product from Example 83B and 4-benzoylbenzyl bromide were processed as described in Examples 6B, 6C, 6D, and 137B to provide the title compound. $^1$H NMR (500 MHz, DMSO-D$_6$) δ9.00 (s, 1 H), 7.68 (m, 4 H), 7.54 (t, 2 H), 7.47 (d, 2 H), 7.28 (d, 2 H), 7.24 (t, 1 H), 7.03 (m, 4 H), 6.93 (d, 2 H), 6.65 (d, 1 H), 6.50 (m, 2 H), 4.58 (s, 2 H), 4.18 (s, 2 H), 4.07 (s, 2 H), 2.92 (s, 3 H), 2.41 (s, 3 H); MS (ESI+) m/z 651 (M+H)$^+$.

EXAMPLE 212

(3-{4-[((3,4-difluorobenzyl){2-methyl-3-[(methylsulfonyl)amino]phenyl}amino)methyl]phenoxy}phenoxy)acetic acid The product from Example 83B and 3,4-difluorobenzyl bromide were processed as described in Examples 6B, 6C, 6D, and 137B to provide the title compound. $^1$H NMR (500 MHz, DMSO-D$_6$) δ8.97 (s, 1 H), 7.27 (m, 5 H), 7.07 (m, 2 H), 6.95 (m, 4 H), 6.66 (d, 1 H), 6.51 (m, 2 H), 4.63 (s, 2 H), 4.05 (d, 4 H), 2.92 (s, 3 H), 2.38 (s, 3 H); MS (ESI+) m/z 583 (M+H)$^+$.

EXAMPLE 213

N-[3-(benzyl{4-[4-(4-hydrazino-4-oxobutyl)phenoxy]benzyl}amino)-2-methylphenyl]methanesulfonamide

EXAMPLE 213A tert-butyl 2-(4-(4-(4-((benzyl(2-methyl-3-((methylsulfonyl)amino)phenyl)amino)methyl)phenoxy)phenyl)butanoyl)hydrazecarboxylate The product from Example 100 (56 mg, 0.1 mmole), 1-[3-(dimethylamino)propyl]-1-ethylcarbodiimide hydrochloride (27 mg, 0.14 mmole) and 1-hydroxybenzotriazole hydrate (19 mg, 0.14 mmole) were dissolved in N,N-dimethylformamide (1.5 mL) and let stand for 15 minutes at room temperature. Tert-butyl carbazate (26 mg, 0.2 mmole) and N,N-diisopropylethylamine (35 μL, 0.2 mmole) in N,N- dimethylformamide (0.5 mL) were added to the reaction mixture and stirred overnight at room temperature. The reaction mixture was acidified with 1N aqueous hydrochloric acid (3 mL) and extracted with dichloromethane (3 mL). The organic layer was washed with saturated $NaHCO_3$ solution (3 mL) and brine (3 mL), dried ($Na_2SO_4$), and concentrated under reduced pressure. The crude product was purified using HPLC.

EXAMPLE 213B

N-[3-(benzyl{4-[4-(4-hydrazino-4-oxobutyl)phenoxy]benzyl}amino)-2-methylphenyl]methanesulfonamide The purified product from Example 213A was hydrolyzed with 10% trifluoroacetic acid in dichloromethane (2 mL) at room temperature for 2 hours and concentrated under reduced pressure. The crude product was purified using HPLC to provide the title compound. $^1$H NMR (500 MHz, DMSO-$d_6$) δ10.71 (s, 1 H), 8.95 (s, 1 H), 7.26 (m, 6 H), 7.19 (m, 3 H), 7.04 (m, 1 H), 6.96 (m, 2 H), 6.89 (m, 4 H), 4.06 (s, 2 H), 4.02 (s, 2 H), 2.92 (s, 3 H), 2.58 (m, 2 H), 2.39 (s, 3 H), 2.22 (m, 2 H), 1.82 (m, 2 H); MS (APCI+) m/z 573 (M+H)$^+$.

EXAMPLE 214

N~2~-[4-(4-{4-[(benzyl{2-methyl-3-[(methylsulfonyl)amino]phenyl}amino)methyl]phenoxy}phenyl)butanoyl]-L-asparagine The product from Example 100 (56 mg, 0.1 mmole) and H-Asn-OtBu (38 mg, 0.2 mmole) were processed as in Example 213A–B to provide the title compound. $^1$H NMR (500 MHz, DMSO-$d_6$) δ12.11–12.80 (br.s, 1 H), 8.94 (s, 1 H), 7.99 (s, 1 H), 7.28 (m, 7 H), 7.18 (m, 3 H), 7.03 (m, 1 H), 6.96 (m, 2 H), 6.87 (m, 5 H), 4.50 (m, 1 H), 4.05 (s, 2 H), 4.01 (s, 2 H), 2.91 (s, 3 H), 2.55 (m, 2 H), 2.44 (m, 2 H), 2.39 (s, 3 H), 2.11 (t, 2 H), 1.76 (m, 2 H); MS (APCI+) m/z 673 (M+H)$^+$.

EXAMPLE 215

N-[4-(4-{4-[(benzyl{2-methyl-3-[(methylsulfonyl)amino]phenyl}amino)methyl]phenoxy}phenyl)butanoyl]-D-valine The product from Example 100 (56 mg, 0.1 mmole) and H-D-Val-OtBu (42 mg, 0.2 mmole) were processed as in Example 213A–B to provide the title compound. $^1$H NMR (500 MHz, DMSO-$d_6$) δ11.75–13.22 (br.s, 1 H), 8.95 (s, 1 H), 7.92 (d, 1 H), 7.26 (m, 6 H), 7.18 (m, 3 H), 7.04 (m, 1 H), 6.97 (m, 2 H), 6.88 (m, 4 H), 4.15 (dd, 1 H), 4.06 (s, 2 H), 4.02 (s, 2 H), 2.91 (s, 3 H), 2.54 (t, 2 H), 2.39 (s, 3 H), 2.19 (m, 2 H), 2.03 (t, 1 H), 1.78 (m, 2 H), 0.89 (s, 3 H), 0.87 (s, 3 H); MS (APCI+) m/z 659 (M+H)$^+$.

EXAMPLE 216

N-[4-(4-{4-[(benzyl{2-methyl-3-[(methylsulfonyl)amino]phenyl}amino)methyl]phenoxy}phenyl)butanoyl]-L-tyrosine The product from Example 100 (56 mg, 0.1 mmole) and H-Tyr-OtBu (47 mg, 0.2 mmole) were processed as in Example 213A–B to provide the title compound. $^1$H NMR (500 MHz, DMSO-$d_6$) δ11.81–13.15 (br.s, 1 H), 8.95 (s, 1 H), 8.69–9.58 (br.s, 1 H), 8.03 (d, 1 H), 7.26 (m, 6 H), 7.19 (m, 1 H), 7.12 (d, 2 H), 7.00 (m, 5 H), 6.88 (m, 4 H), 6.64 (d, 2 H), 4.36 (m, 1 H), 4.05 (s, 2 H), 4.02 (s, 2 H), 2.94 (d, 1 H), 2.91 (s, 3 H), 2.72 (d, 1 H), 2.44 (t, 2 H), 2.39 (s, 3 H), 2.06 (m, 2 H), 1.69 (m, 2 H); MS (APCI+) m/z 723 (M+H)$^+$.

EXAMPLE 217

N-[4-(4-{4-[(benzyl{2-methyl-3-[(methylsulfonyl)amino]phenyl}amino)methyl]phenoxy}phenyl)butanoyl]-L-methionine The product from Example 100 (56 mg, 0.1 mmole) and H-Met-OtBu HCl (48 mg, 0.2 mmole) were processed as in Example 213A–B to provide the title compound. $^1$H NMR (500 MHz, DMSO-$d_6$) δ11.65–13.33 (br.s, 1 H), 8.95 (s, 1 H), 8.07 (d, 1 H), 7.26 (m, 6 H), 7.19 (m, 3 H), 7.04 (m, 1 H), 6.97 (m, 2 H), 6.89 (m, 4 H), 4.30 (m, 1 H), 4.05 (s, 2 H), 4.02 (s, 2 H), 2.91 (s, 3 H), 2.55 (m, 2 H), 2.46 (m, 2 H), 2.39 (s, 3 H), 2.14 (m, 2 H), 2.03 (s, 3 H), 1.95 (m, 1 H), 1.80 (m, 3 H); MS (APCI+) m/z 646 (M+H)$^+$.

EXAMPLE 218

N~2~-[4-(4-{4-[(benzyl{2-methyl-3-[(methylsulfonyl)amino]phenyl}amino)methyl]phenoxy}phenyl)butanoyl]-L-lysine The product from Example 100 (56 mg, 0.1 mmole) and H-Lys(Boc)-OtBu HCl (68 mg, 0.2 mmole) were processed as in Example 213A–B to provide the title compound. 1H NMR (500 MHz, DMSO-$d_6$) δ11.68–13.46 (br.s, 1 H), 8.95 (s, 1 H), 8.04 (d, 1 H), 7.50–7.74 (br.s, 2 H), 7.27 (m, 6 H), 7.19 (m, 3 H), 7.04 (m, 1 H), 6.97 (m, 2 H), 6.89 (m, 4 H), 4.18 (m, 1 H), 4.06 (s, 2 H), 4.02 (s, 2 H), 2.92 (s, 3 H), 2.75 (m, 2 H), 2.55 (t, 2 H), 2.39 (s, 3 H), 2.14 (t, 2 H), 1.64–1.85 (m, 3 H), 1.43–1.63 (m, 3 H), 1.22–1.43 (m, 2 H); MS (APCI+) m/z 687 (M+H)$^+$.

EXAMPLE 219

N-[4-(4-{4-[(benzyl{2-methyl-3-[(methylsulfonyl)amino]phenyl}amino)methyl]phenoxy}phenyl)butanoyl]-L-serine The product from Example 100 (56 mg, 0.1 mmole) and H-Ser(tBu)-OtBu (51 mg, 0.2 mmole) were processed as in Example 213A–B to provide the title compound. $^1$H NMR (500 MHz, DMSO-$d_6$) δ11.72–13.24 (br.s, 1 H), 8.95 (s, 1 H), 8.28–8.51 (br.s, 1 H), 7.91 (d, 1 H), 7.26 (m, 6 H), 7.19 (m, 3 H), 7.04 (m, 1 H), 6.96 (m, 2 H), 6.88 (m, 4 H), 4.27 (m, 1 H), 4.06 (s, 2 H), 4.02 (s, 2 H), 3.64 (m, 2 H), 2.91 (s, 3 H), 2.56 (m, 2 H), 2.39 (s, 3 H), 2.17 (m, 2 H), 1.78 (m, 2 H); MS (APCI+) m/z 646 (M+H)$^+$.

EXAMPLE 220

N-[4-(4-{4-[(benzyl{2-methyl-3-[(methylsulfonyl)amino]phenyl}amino)methyl]phenoxy}phenyl)butanoyl]-L-phenylalanine The product from Example 100 (56 mg, 0.1 mmole) and H-Phe-OtBu HCl (52 mg, 0.2 mmole) were processed as in Example 213A–B to provide the title compound. $^1$H NMR (500 MHz, DMSO-$d_6$) δ12.22–12.98 (br.s, 1 H), 8.95 (s, 1 H), 8.10 (d, 1 H), 7.22 (m, 12 H), 7.10 (d, 2 H), 7.04 (t, 1 H), 6.96 (m, 2 H), 6.87 (m, 4 H), 4.45 (m, 1 H), 4.06 (s, 2 H), 4.02 (s, 2 H), 3.06 (dd, 1 H), 2.91 (s, 3 H), 2.84 (dd, 1 H), 2.42 (t, 2 H), 2.39 (s, 3 H), 2.06 (m, 2 H), 1.68 (m, 2 H); MS (APCI+) m/z 706 (M+H)$^+$.

EXAMPLE 221

N-[4-(4-{4-[(benzyl{2-methyl-3-[(methylsulfonyl)amino]phenyl}amino)methyl]phenoxy}phenyl)butanoyl]-D-tyrosine The product from Example 100 (56 mg, 0.1 mmole) and H-D-Tyr-OtBu (47 mg, 0.2 mmole) were processed as in Example 213A–B to provide the title compound. $^1$H NMR (500 MHz, DMSO-d$_6$) δ11.78–13.25 (br.s, 1 H), 8.95 (s, 1 H), 8.64–9.80 (br.s, 1 H), 8.03 (d, 1 H), 7.26 (m, 6 H), 7.19 (m, 1 H), 7.12 (d, 2 H), 7.00 (m, 5 H), 6.88 (m, 4 H), 6.64 (d, 2 H), 4.35 (m, 1 H), 4.06 (s, 2 H), 4.02 (s, 2 H), 2.94 (d, 1 H), 2.91 (s, 3 H), 2.72 (dd, 1 H), 2.44 (t, 2 H), 2.39 (s, 3 H), 2.06 (m, 2 H), 1.69 (m, 2 H); MS (APCI+) m/z 723 (M+H)$^+$.

EXAMPLE 222

N~2~-[4-(4-{4-[(benzyl{2-methyl-3-[(methylsulfonyl)amino]phenyl}amino)methyl]phenoxy}phenyl)butanoyl]-L-glutamine The product from Example 100 (56 mg, 0.1 mmole) and H-Gln-OtBu HCl (48 mg, 0.2 mmole) were processed as in Example 213A–B to provide the title compound. $^1$H NMR (500 MHz, DMSO-d$_6$) δ11.53–13.22 (br.s, 1 H), 8.95 (s, 1 H), 8.06 (d, 1 H), 7.26 (m, 6 H), 7.18 (m, 3 H), 7.04 (m, 1 H), 6.96 (m, 2 H), 6.88 (m, 4 H), 6.73 (br.s, 2 H), 4.15 (m, 1 H), 4.06 (s, 2 H), 4.02 (s, 2 H), 2.91 (s, 3 H), 2.54 (t, 2 H), 2.39 (s, 3 H), 2.13 (m, 4 H), 1.93 (m, 1 H), 1.75 (m, 3 H); MS (APCI+) m/z 687 (M+H)$^+$.

EXAMPLE 223

N-[4-(4-{4-[(benzyl{2-methyl-3-[(methylsulfonyl)amino]phenyl}amino)methyl]phenoxy}phenyl)butanoyl]-L-isoleucine The product from Example 100 (56 mg, 0.1 mmole) and H-Ile-OtBu HCl (45 mg, 0.2 mmole) were processed as in Example 213A–B to provide the title compound. $^1$H NMR (500 MHz, DMSO-d$_6$) δ11.81–12.98 (br.s, 1 H), 8.95 (s, 1 H), 7.93 (d, 1 H), 7.26 (m, 6 H), 7.18 (m, 3 H), 7.04 (t, 1 H), 6.96 (m, 2 H), 6.88 (d, 4 H), 4.19 (dd, 1 H), 4.05 (s, 2 H), 4.02 (s, 2 H), 2.91 (s, 3 H), 2.53 (t, 2 H), 2.39 (s, 3 H), 2.18 (m, 2 H), 1.76 (m, 3 H), 1.39 (m, 1 H), 1.20 (m, 1 H), 0.83 (m, 6 H); MS (APCI+) m/z 673 (M+H)$^+$.

EXAMPLE 224

N-[4-(4-{4-[(benzyl{2-methyl-3-[(methylsulfonyl)amino]phenyl}amino)methyl]phenoxy}phenyl)butanoyl]-L-glutamic acid

EXAMPLE 224A

The product from Example 100 (56 mg, 0.1 mmole) and L-glutamic acid dimethyl ester hydrochloride (42 mg, 0.2 mmole) were processed as in Example 213A to give the methyl ester intermediate.

EXAMPLE 224B

The product from example 224A was hydrolyzed with a mixture of 2N aqueous sodium hydroxide solution (1 mL), ethyl alcohol (0.5 mL) and tetrahydrofuran (0.5 mL) with stirring overnight at room temperature. The reaction mixture was acidified with 2N aqueous hydrochloric acid to pH 2~3 and extracted with ethyl acetate (3 mL). The organic layer was washed with brine, dried over sodium sulfate, filtered, and concentrated under reduced pressure. The crude product was purified using HPLC to give the title compound. $^1$H NMR (500 MHz, DMSO-d$_6$) δ11.54–13.13 (br.s, 2 H), 8.95 (s, 1 H), 8.05 (d, 1 H), 7.26 (m, 6 H), 7.19 (m, 3 H), 7.04 (m, 1 H), 6.96 (m, 2 H), 6.89 (d, 4 H), 4.21 (m, 1 H), 4.04 (d, 4 H), 2.91 (s, 3 H), 2.54 (m, 2 H), 2.39 (s, 3 H), 2.28 (m, 2 H), 2.14 (t, 2 H), 1.96 (m, 1 H), 1.78 (m, 3 H); MS (APCI+) m/z 689 (M+H)$^+$.

EXAMPLE 225

N-[4-(4-{4-[(benzyl{2-methyl-3-[(methylsulfonyl)amino]phenyl}amino)methy]phenoxy}phenyl)butanoy]-D-histidine The product from Example 100 (56 mg, 0.1 mmole) and H-D-His-OMe.2HCl (48 mg, 0.2 mmole) were processed as in Examples 213A and 224B to provide the title compound. $^1$H NMR (500 MHz, DMSO-d$_6$) δ13.88–14.43 (m, 1 H), 8.96 (d, 2 H), 8.20 (d, 1 H), 7.38 (s, 1 H), 7.26 (m, 5 H), 7.20 (m, 1 H), 7.13 (d, 4 H), 7.04 (m, 1 H), 6.96 (m, 2 H), 6.88 (m, 4 H), 4.43–4.70 (m, 1 H), 4.04 (d, 4 H), 3.14 (m, 1 H), 2.98 (m, 1 H), 2.92 (s, 3 H), 2.39 (s, 3 H), 2.36 (m, 2 H), 2.09 (m, 2 H), 1.71 (m, 2 H); MS (APCI+) m/z 696 (M+H)$^+$.

EXAMPLE 226

1-[4-(4-{4-[(benzyl{2-methyl-3-[(methylsulfonyl)amino]phenyl}amino)methyl]phenoxy}phenyl)butanoyl]-L-proline The product from Example 100 (56 mg, 0.1 mmole) and L-Proline methyl ester hydrochloride (33 mg, 0.2 mmole) were processed as in Examples 213A and 224B to provide the title compound. $^1$H NMR (500 MHz, DMSO-d$_6$) δ11.66–13.14 (br.s, 1 H), 8.95 (s, 1 H), 7.26 (m, 6 H), 7.18 (m, 3 H), 7.04 (m, 1 H), 6.96 (m, 2 H), 6.88 (m, 4 H), 4.22 (dd, 1 H), 4.03 (d, 4 H), 3.46 (m, 2 H), 2.91 (s, 3 H), 2.58 (t, 2 H), 2.39 (s, 3 H), 2.27 (t, 2 H), 1.97–2.24 (m, 2 H), 1.70–1.95 (m, 4 H); MS (APCI+) m/z 656 (M+H)$^+$.

EXAMPLE 227

N-[4-(4-{4-[(benzyl{2-methyl-3-[(methylsulfonyl)amino]phenyl}amino)methyl]phenoxy}phenyl)butanoyl]-L-valine The product from Example 100 (56 mg, 0.1 mmole) and L-Valine methyl ester hydrochloride (34 mg, 0.2 mmole) were processed as in Examples 213A and 224B to provide the title compound. $^1$H NMR (500 MHz, DMSO-d$_6$) δ12.28–12.62 (br.s, 1 H), 8.94 (s, 1 H), 7.92 (d, 1 H), 7.26 (m, 6 H), 7.18 (m, 3 H), 7.04 (m, 1 H), 6.96 (m, 2 H), 6.88 (m, 4 H), 4.15 (dd, 1 H), 4.05 (s, 2 H), 4.01 (s, 2 H), 2.91 (s, 3 H), 2.54 (t, 2 H), 2.39 (s, 3 H), 2.19 (td, 2 H), 2.02 (m, 1 H), 1.78 (m, 2 H), 0.88 (s, 3 H), 0.87 (s, 3 H); MS (APCI+) m/z 658 (M+H)$^+$.

EXAMPLE 228

N-[4-(4-{4-[(benzyl{2-methyl-3-[(methylsulfonyl)amino]phenyl}amino)methyl]phenoxy}phenyl)butanoyl]-L-aspartic acid The product from Example 100 (56 mg, 0.1 mmole) and L-Aspartic acid dimethyl ester hydrochloride (40 mg, 0.2 mmole) were processed as in Examples 213A and 224B to provide the title compound. $^1$H NMR (500 MHz, DMSO-d$_6$) δ11.46–13.35 (br.s, 2 H), 8.95 (s, 1 H), 8.13 (d, 1 H), 7.26 (m, 6 H), 7.18 (m, 3 H), 7.03 (m, 1 H), 6.96 (m, 2 H), 6.88 (m, 4 H), 4.54 (m, 1 H), 4.05 (s, 2 H), 4.01 (s, 2 H), 2.91 (s, 3 H), 2.69 (m, 1 H), 2.55 (m, 3 H), 2.39 (s, 3 H), 2.12 (t, 2 H), 1.76 (m, 2 H); MS (APCI+) m/z 674 (M+H)$^+$.

EXAMPLE 229

4-{[4-(4-{4-[(benzyl{2-methyl-3-[(methylsulfonyl)amino]phenyl}amino)metbyl]phenoxy}phenyl)butanoyl]amino}-1-methyl-1H-pyrrole-2-carboxylic acid The product from Example 100 (56 mg, 0.1 mmole) and 4-Amino-1-methyl-1H-pyrrole-2-carboxylic acid methyl ester hydrochloride (38 mg, 0.2 mmole) were processed as in Examples 213A and 224B to provide the title compound. $^1$H NMR (500 MHz, DMSO-$d_6$) δ11.62–12.57 (br.s, 1 H), 9.74 (s, 1 H), 8.95 (s, 1 H), 7.24 (m, 10 H), 7.04 (m, 1 H), 6.96 (m, 2 H), 6.89 (m, 4 H), 6.65 (d, 1 H), 4.05 (s, 2 H), 4.02 (s, 2 H), 3.79 (s, 3 H), 2.91 (s, 3 H), 2.57 (t, 2 H), 2.39 (s, 3 H), 2.23 (t, 2H), 1.84 (m, 2 H); MS (APCI+) m/z 681 (M+H)$^+$.

EXAMPLE 230

4-(4-{4-[(benzyl{2-methyl-3-[(methylsulfonyl)amino]phenyl}amino)methyl]phenoxy}phenyl)-N-(2-oxotetrahydrofuran-3-yl)butanamide The product from Example 100 (56 mg, 0.1 mmole) and α-Amino-γ-butyrolactone hydrobromide (36 mg, 0.2 mmole) were processed as in Examples 213A and 224B to provide the title compound. $^1$H NMR (500 MHz, DMSO-$d_6$) δ8.95 (s, 1 H), 8.31 (d, 1 H), 7.26 (m, 6 H), 7.18 (m, 3 H), 7.04 (m, 1 H), 6.97 (m, 2 H), 6.88 (m, 4 H), 4.53 (dd, 1 H), 4.34 (t, 1 H), 4.20 (m, 1 H), 4.06 (s, 2 H), 4.02 (s, 2 H), 3.17 (s, 3 H), 2.91 (s, 3 H), 2.55 (t, 2 H), 2.39 (m, 2 H), 2.13 (t, 2 H), 1.67–1.90 (m, 2 H); MS (APCI+) m/z 642 (M+H)$^+$.

EXAMPLE 231

N-(3-((2,4-difluorobenzyl)(4-(3-(((2S,4R)-6-oxo-4-hydroxytetrahydro-2H-pyran-2-yl)methoxy)phenoxy)benzyl)amino)-2-methylphenyl)methanesulfonamide A solution of the product from Example 136B (0.2098 g, 0.274 mmoles) and 3N HCl (0.1 mL) in THF (0.68 mL) and EtOH (1.4 mL) was stirred for 16 h at room temperature. The reaction mixture was diluted with pH 7 buffer (10 mL) and extracted with EtOAc (24 mL). The organic layer was rinsed with brine, dried over $Na_2SO_4$, and concentrated in vacuo. The crude products were dissolved in $CH_2Cl_2$ (0.55 mL), cooled to 0° C., and treated with TFA (0.15 mL). After warming to room temperature and stirring for 2 h, the reaction was cooled to 0° C. and quenched with $NaHCO_3$ (0.136 g). The crude products were diluted with EtOAc, extracted with pH 7 buffer, rinsed with brine, and dried over $Na_2SO_4$. After concentration in vacuo, purification by preparative HPLC ($CH_3CN$:10 mM $NH_4OAc$ in $H_2O$) on a YMC ODS Guardpak column yielded the titled compound (0.1321 g, 74%) as a white solid. $^1$H NMR (400 MHz, $CDCL_3$) δ7.16 (m, 5 H), 6.96 (m, 1 H), 6.90 (m, 2 H), 6.74 (m, 2 H), 6.61 (dt, 2 H), 6.43 (t, 1 H), 6.30 (s, 1 H), 5.04 (m, 1 H), 4.47 (m, 1 H), 4.09 (s, 2 H), 4.07 (m, 2 H), 4.04 (s, 2 H), 2.91 (s, 3 H), 2.76 (dd, 1 H), 2.67 (m, 1 H), 2.27 (s, 3 H), 2.04 (m, 2 H), 1.60 (br.s, 2 H); MS (ESI) m/z 653 (M+H$^+$).

434889 EXAMPLE 232 JAMES LINK ethyl 4-(4-{4-[(benzyl{2-methyl-3-[(methylsulfonyl)amino]phenyl}amino)methyl]phenoxy}phenoxy)butanoate

EXAMPLE 232A ethyl 4-(4-(4-((benzyl(2-methyl-3-nitrophenyl)amino)methyl)phenoxy)phenoxy)butanoate The product from Example 60E was processed as described in Example 116A to provide the titled compound.

EXAMPLE 232B ethyl 4-(4-{4-[(benzyl{2-methyl-3-[(methylsulfonyl)amino]phenyl}amino)methyl]phenoxy}phenoxy)butanoate The product from Example 232A was processed as described in Examples 6C and 6D to provide the titled compound. $^1$H NMR (300 MHz, $CDCL_3$) δ7.21 (m, 5 H), 7.10 (m, 3 H), 6.87 (m, 8 H), 6.10 (s, 1 H), 4.15 (q, 2 H), 4.05 (s, 2 H), 4.00 (s, 2 H), 3.98 (t, 2 H), 2.94 (s, 3 H), 2.52 (t, 2 H), 2.33 (s, 3 H), 2.11 (m, 2 H), 1.26 (t, 3 H); MS (ESI) m/z 603 (M+H$^+$).

EXAMPLE 233

4-(4-{4-[(benzyl{2-methyl-3-[(methylsulfonyl)amino]phenyl}amino)methyl]phenoxy}phenoxy)butanoic acid The product from Example 232B was processed as described in Example 50 to provide the titled compound. $^1$H NMR (300 MHz, $CDCL_3$) δ7.05–7.30 (m, 9 H), 6.76–6.97 (m, 7 H), 6.23 (s, 1 H), 3.88–4.19 (m, 7 H), 2.91 (s, 3H), 2.59 (t, 2 H), 2.31 (s, 3 H), 2.13 (m, 2 H); MS (ESI) m/z 575 (M+H$^+$).

EXAMPLE 234

5-(4-{4-[(benzyl{2-methyl-3-[(methylsulfonyl)amino]phenyl}amino)methyl]phenoxy}phenoxy)pentanoic acid

EXAMPLE 234A ethyl 5-(4-(4-((benzyl(2-methyl-3-nitrophenyl)amino)methyl)phenoxy)phenoxy)pentanoate The product from Example 60E and ethyl-5-bromovalerate was processed as described in Example 116A to provide the titled compound.

EXAMPLE 234B 5-(4-{4-[(benzyl{2-methyl-3-[(methylsulfonyl)amino]phenyl}amino)methyl]phenoxy}phenoxy)pentanoic acid The product from Example 234A was processed as described in Examples 6C, 6D, and 50 to provide the titled compound. $^1$H NMR (300 MHz, $CDCL_3$) δ7.22 (m, 8 H), 7.11 (m, 2 H), 6.92 (m, 2 H), 6.82 (m, 4 H), 6.15 (s, 1 H), 4.11 (s, 2 H), 4.06 (s, 2 H), 3.95 (m, 2 H), 2.92 (s, 3 H), 2.46 (m, 2 H), 2.36 (br.s, 1 H), 2.29 (s, 3 H), 1.85 (m, 4 H); MS (APCI) m/z 589 (M+H$^+$).

EXAMPLE 235

N-(3-(benzyl(4-(4-(((2S, 4R)-6-oxo-4hydroxytetrahydro-2H-pyran-2-yl)methoxy)phenoxy)benzyl)amino)-2-methylphenyl)methanesulfonamide The product from Example 60G was processed as described in Example 231 to provide the titled compound. $^1$H NMR (400 MHz, $CDCL_3$) δ7.23 (m, 7 H), 7.10 (m, 3 H), 6.88 (m, 6 H), 6.28 (s, 1 H), 5.05 (m, 1 H), 4.16 (dd, 1 H), 4.09 (dd, 1 H), 4.04 (s, 2 H), 4.00 (s, 2 H), 2.94 (s, 3 H), 2.77 (dd, 1 H), 2.68 (dd, 1 H), 2.34 (s, 3 H), 2.09 (dd, 2 H), 1.99 (s, 1 H), 1 (m, 1 H); MS (ESI) m/z 617 (M+H$^+$).

EXAMPLE 236

(5-{4-[((2,4-difluorobenzyl){2-methyl-3-[(methylsulfonyl)amino]phenyl}amino)methyl]phenoxy}-2-ethylphenoxy)acetic acid

EXAMPLE 236A 3-(allyloxy)-4-ethylphenyl 4-methylbenzenesulfonate

4-Ethyl resorcinol was processed as described in Example 63A.

EXAMPLE 236B 3-(allyloxy)-4-ethylphenol

The product from Example 236A was processed as described in Example 63B.

EXAMPLE 236C 4-(3-(allyloxy)-4-ethylphenoxy)benzaldehyde

The product from Example 236B and 4-fluorobenzaldehyde were processed as in Example 61C to provide the titled compound. MS (DCI) m/z 289 (M+H)$^+$.

EXAMPLE 236D

N-(4-(3-(allyloxy)-4-ethylphenoxy)benzyl)-N-(2-methyl-3-nitrophenyl)amine

The product from Example 236C and 2-methyl-3-nitroaniline were processed as in Example 6A to provide the titled compound. MS (ESI–) m/z 423 (M–H)$^-$.

EXAMPLE 236E

The product from Example 236D and 2,4-difluorobenzyl bromide were processed as described in Example 6B to provide the titled compound. MS (ESI+) m/z 573 (M+H)$^+$.

EXAMPLE 236F

The product from Example 236E was processed as described in Example 33A to provide the titled compound.

EXAMPLE 236G

The product from Example 236F and ethyl glycolate were processed as described in Example 62A to provide the titled compound. MS (ESI+) m/z 597 (M+H)$^+$.

EXAMPLE 236H

The product from Example 236G was processed as described in Example 6C and D to provide the titled compound.

EXAMPLE 236I (5-{4-[((2,4-difluorobenzyl){2-methyl-3-[(methylsulfonyl)amino]phenyl}amino)methyl]phenoxy}-2-ethyylphenoxy) acetic acid The product from Example 236H was processed as described in Example 50 to provide the titled compound. $^1$H NMR (300 MHz, CDCl$_3$) δ7.10–7.40 (m, 5 H), 6.95 (m, 3 H), 6.77 (d, J=8.5 Hz, 2 H), 6.65 (m, 3 H), 6.43 (d, J=2.4 Hz, 1 H), 4.60 (s, 2 H), 4.31 (s, 2 H), 4.13 (s, 2 H), 2.90 (s, 3 H), 2.50–2.80 (m, 2 H), 1.99 (s, 3 H), 1.21 (t, J=7.5 Hz, 3 H); MS (ESI+) m/z 611 (M+H)$^+$.

EXAMPLE 237 ethyl 4-{[4-(3-{4-[(benzy{2-methyl-3-[(methylsulfonyl)amino]phenyl}amino)methyl]phenoxy}phenoxy)butanoyl]amino}butanoate The product from Example 116B and ethyl 4-aminobutyrate hydrochloride were processed as described in Example 68D to provide the titled compound. $^1$H NMR (500 MHz, CDCl$_3$) δ7.25 (m, 7 H), 7.15 (m, 3 H), 6.94 (d, 1 H), 6.89 (d, 2 H), 6.61 (dd, 1 H), 6.56 (dd, 1 H), 6.45 (t, 1 H), 6.31 (s, 1 H), 5.77 (s, 1 H), 4.12 (q, 2 H), 4.06 (s, 2 H), 4.02 (s, 2 H), 3.93 (t, 2 H), 3.28 (dd, 2 H), 2.93 (s, 3 H), 2.35 (m, 4 H), 2.33 (s, 3 H), 2.05 (m, 2 H), 1.80 (m, 2 H), 1.24 (t, 3 H); MS (ESI+) m/z 688 (M+H)$^+$.

EXAMPLE 238

(5-{4-[((2,4-difluorobenzyl){2-methyl-3-[(methylsulfonyl)amino]phenyl}amino)methyl]phenoxy}-2-hexylphenoxy)acetic acid

EXAMPLE 238A 3-(allyloxy)-4-hexylphenyl 4-methylbenzenesulfonate

4-Hexylresorcinol was processed as described in Example 63A.

EXAMPLE 238B 3-(allyloxy)-4-hexylphenol

The product from Example 238A was processed as described in Example 63B.

EXAMPLE 238C 4-(3-(allyloxy)-4-hexnlphenoxy)benzaldehyde

The product from Example 238B and 4-fluorobenzaldehyde were processed as in Example 61C to provide the titled compound. MS (DCI) m/z 289 (M+H)$^+$.

EXAMPLE 238D (2-hexyl-5-(4-(((2-methyl-3-nitrophenyl)amino)methyl)phenoxy)phenoxy)acetic acid The product from Example 238C and 2-methyl-3-nitroaniline were processed as in Example 6A to provide the titled compound. MS (ESI–) m/z 423 (M–H)$^-$.

EXAMPLE 238E

N-(4-(3-(allyloxy)-4-hexylphenoxy)benzyl)-N-(2,4-difluorobenzyl)-N-(2-methyl-3-nitrophenyl)amine The product from Example 238D and 2,4-difluorobenzyl bromide were processed as described in Example 6B to provide the titled compound. MS (ESI+) m/z 573 (M+H)$^+$.

EXAMPLE 238F 5-(4-(((2,4-difluorobenzyl)(2-methyl-3-nitrophenyl)amino)methyl)phenoxy)-2-hexylphenol The product from Example 238E was processed as described in Example 33A to provide the titled compound.

EXAMPLE 238G ethyl (5-(4-(((2,4-difluorobenzyl)(2-methyl-3-nitrophenyl)amino)methyl)phenoxy)-2-hexylphenoxy)acetate The product from Example 238F and ethyl glycolate were processed as described in Example 62A to provide the titled compound. MS (ESI+) m/z 597 (M+H)$^+$.

EXAMPLE 238H ethyl (5-(4-(((2,4-difluorobenzyl)(2-methyl-3-((methylsulfonyl)amino)phenyl)amino)methyl)phenoxy)-2-hexylphenoxy)acetate The product from Example 238G was processed as described in Example 6C and D to provide the titled compound.

EXAMPLE 238I (5-{4-[((2,4-difluorobenzyl){2-methyl-3-[(methylsulfonyl)amino]phenyl}amino)methyl]phenoxy}-2-hexylphenoxy)acetic acid The product from Example 238H was processed as described in Example 50 to provide the titled compound. $^1$H NMR (500 MHz, CDCl$_3$) δ7.25 (m, 2 H), 7.17 (t, 1 H), 7.09 (d, 2 H), 7.03 (d, 2 H), 6.80 (d, 2 H), 6.75 (m, 3 H), 6.60 (dd, 1 H), 6.42 (d, 1 H), 4.59 (s, 2 H), 4.23 (s, 2 H), 4.10 (s, 2 H), 2.90 (s, 3 H), 2.60 (t, 2 H), 2.08 (s, 3 H), 1.55 (m, 2 H), 1.30 (m, 6 H), 0.88 (t, 3 H); MS (ESI+) m/z 667 (M+H)$^+$.

EXAMPLE 239 ethyl N-[4-(3-{4-[(benzyl{2-methyl-3-[(methylsulfonyl)amino]phenyl}amino)methyl]phenoxy}phenoxy)butanoyl]-N-methylglycinate The product from Example 116B and sarcosine hydrochloride were processed as described in Example 68D to provide the titled compound. $^1$H NMR (500 MHz, CDCl$_3$) δ7.25 (m, 7 H), 7.15 (m, 3 H), 6.95 (m, 1 H), 6.90 (d, 2 H), 6.63 (dd, 1 H), 6.55 (dd, 1 H), 6.50 (m, 1 H), 6.32 (s, 1 H), 4.17 (q, 2 H), 4.06 (s, 2 H), 4.05 (m, 2 H), 4.02 (s, 2 H), 3.95 (m, 2 H), 3.07 (s, 3 H), 2.93 (s, 3 H), 2.57 (t, 2 H), 2.34 (s, 3 H), 2.15 (m, 2 H), 1.26 (t, 3 H)); MS (ESI+) m/z 674 (M+H)$^+$.

EXAMPLE 240

N-[4-(3-{4-[(benzyl{2-methyl-3-[(methylsulfonyl)amino]phenyl}amino)methyl]phenoxy}phenoxy)butanoyl]-N-methylglycine The product from Example 239 was processed as described in Example 50 to provide the titled compound. $^1$H NMR (500 MHz, CDCl$_3$) δ7.32 (d, 1 H), 7.25 (m, 9 H), 7.15 (m, 2 H), 6.86 (d, 2 H), 6.60 (m, 2 H), 6.26 (t, 1 H), 4.47 (br.s, 4 H), 4.05 (s, 2 H), 3.82 (t, 2 H), 3.07 (s, 3 H), 2.75 (s, 3 H), 2.57 (t, 2 H), 2.10 (m, 2 H), 2.08 (s, 3 H); MS (ESI+) m/z 646 (M+H)$^+$.

EXAMPLE 241 ethyl (2-chloro-5-{4-[((2,4-difluorobenzyl){2-methyl-3-[(methylsulfonyl)amino]phenyl}amino)methyl]phenoxy}phenoxy)acetate The product from Example 91G was processed as described in Example 6C and D to provide the titled compound. $^1$H NMR (500 MHz, CDCl$_3$) δ7.29 (d, 1 H), 7.20 (m, 3 H), 7.10 (m, 2 H), 6.91 (d, 1 H), 6.91 (d, 2 H), 6.75 (m, 2 H), 6.50 (m, 2 H), 6.22 (s, 1 H), 4.63 (s, 2 H), 4.23 (q, 2 H), 4.07 (s, 2 H), 4.04 (s, 2 H), 2.95 (s, 3 H), 2.31 (s, 3 H), 1.25 (t, 3 H); MS (ESI+) m/z 645 (M+H)$^+$.

EXAMPLE 242

N-[3-(benzyl{4-[3-(2-cyclopropylethoxy)benzoyl]benzyl}amino)-2-methylphenyl]methanesulfonamide

EXAMPLE 242A

N-di-(3-(benzyl(4-(3-(2-cyclopropylethoxy)benzoyl)benzyl)amino)-2-methylphenyl)methanesulfonamide The product from Example 88F (50 mg, 0.087 mmoles) in anhydrous tetrahydrofuran (0.5 ml) was treated with triphenylphosphine (46 mg, 0.174 mmoles) in anhydrous tetrahydrofuran (0.1 ml), di-t-butylazodicarboxylate (30 mg, 0.131 mmoles) in anhydrous tetrahydrofuran (0.1 ml), 2-cyclopropylethanol (9.26 mg, 0.109 mmoles) in anhydrous tetrahydrofuran (0.109 ml) at room temperature overnight. Di-t-butylazodicarboxylate (30 mg, 0.131 mmoles) in anhydrous tetrahydrofuran (0.1 ml) and 2-cyclopropylethanol (9.26 mg, 0.109 mmoles) in anhydrous tetrahydrofuran (0.109 ml) were added and reaction was continued at room temperature overnight. Reaction mixture was diluted with ethyl acetate and washed with water and brine, dried over sodium sulfate, filtered and the filtrate concentrated in vaccuo. The residue was purified by HPLC to provide the titled compound.

EXAMPLE 242B

N-[3-(benzyl{4-[3-(2-cyclopropylethoxy)benzoyl]benzyl}amino)-2-methylphenyl]methanesulfonamide The product from Example 242A was treated with 2 2N aqueous sodium hydroxide: 1 tetrahydrofuran: 1 ethanol (4 ml) at room temperature overnight. The reaction mixture acidified with 1N hydrochloric acid, extracted with ethyl acetate. The organic layer dried over anhydrous sodium sulfate, filtered and the filtrate concentrated in vaccuo. The residue purified by HPLC to provide the titled compound. $^1$H NMR (500 MHz, DMSO-d$_6$) δ8.96 (s, 1 H), 7.66 (d, 2 H), 7.45 (m, 3 H), 7.28 (d, 4 H), 7.21 (m, 4 H), 7.01 (m, 3 H), 4.17 (s, 2 H), 4.09 (s, 2 H), 4.07 (t, 2 H), 2.92 (s, 3 H), 2.42 (s, 3 H), 1.63 (dd, 2 H), 0.83 (m, 1 H), 0.42 (m, 2 H), 0.11 (m, 2 H); MS (ESI+) m/z 569 (M+H)$^+$.

EXAMPLE 243

N-[3-(benzyl{4-[3-(cyclopentylmethoxy)benzoyl]benzyl}amino)-2-methylphenyl]methanesulfonamide The product from Example 88F and cyclopentylmethanol were processed as described in Example 242A and B to provide the titled compound. $^1$H NMR (500 MHz, DMSO-d$_6$) δ8.96 (s, 1 H), 7.65 (d, 2 H), 7.45 (m, 3 H), 7.28 (d, 4 H), 7.20 (m, 4 H), 7.01 (m, 3 H), 4.17 (s, 2 H), 4.09 (s, 2 H), 3.89 (d, 2 H), 2.92 (s, 3 H), 2.42 (s, 3 H), 2.29 (m, 1 H), 1.77 (m, 2 H), 1.47–1.68 (m, 4 H), 1.33 (m, 2 H); MS (ESI+) m/z 583 (M+H)$^+$.

EXAMPLE 244

N-[3-(benzyl{4-[3-(tetrahydrofuran-2-ylmethoxy)benzoyl]benzyl}amino)-2-methylphenyl]methanesulfonamide The product from Example 88F and tetrahydro-2-furanmethanol were processed as described in Example 242A and B to provide the titled compound. $^1$H NMR (500 MHz, DMSO-d$_6$) δ8.95 (s, 1 H), 7.66 (d, 2 H), 7.45 (m, 3 H), 7.29 (d, 4 H), 7.22 (m, 4 H), 7.01 (m, 3 H), 4.17 (s, 2 H), 4.14 (m, 1 H), 4.09 (s, 2 H), 3.99 (m, 2 H), 3.77 (m, 2 H), 2.92 (s, 3 H), 2.42 (s, 3 H), 1.99 (m, 1 H), 1.85 (m, 2 H), 1.68 (m, 1 H); MS (ESI+) m/z 585 (M+H)$^+$.

EXAMPLE 245

N-[3-(benzyl{4-[3-(tetrahydrofuran-3-ylmethoxy)benzoyl]benzyl}amino)-2-methylphenyl]methanesulfonamide The product from Example 88F and tetrahydro-3-furanmethanol were processed as described in Example 242A and B to provide the titled compound. $^1$H NMR (500

MHz, DMSO-$d_6$) δ8.96 (s, 1 H), 7.66 (d, 2 H), 7.45 (m, 3 H), 7.29 (d, 4 H), 7.22 (m, 4 H), 7.01 (m, 3 H), 4.17 (s, 2 H), 4.09 (s, 2 H), 3.71–4.05 (m, 4 H), 3.64 (m, 1 H), 3.53 (m, 1 H), 2.92 (s, 3 H), 2.66 (m, 1 H), 2.42 (s, 3 H), 2.01 (m, 1 H), 1.66 (m, 1 H); MS (ESI+) m/z 585 (M+H)$^+$.

EXAMPLE 246

N-[3-(benzyl{4-[3-(2-phenylethoxy)benzoyl] benzyl}amino)-2-methylphenyl]methanesulfonamide The product from Example 88F and 2-phenyl ethanol were processed as described in Example 242A and B to provide the titled compound. $^1$H NMR (500 MHz, DMSO-$d_6$) δ8.96 (s, 1 H), 7.65 (d, 2 H), 7.44 (m, 3 H), 7.30 (m, 8 H), 7.20 (m, 5 H), 7.01 (m, 3 H), 4.25 (t, 2 H), 4.16 (s, 2 H), 4.09 (s, 2 H), 3.04 (t, 2 H), 2.91 (s, 3 H), 2.41 (s, 3 H); MS (ESI+) m/z 605 (M+H)$^+$.

EXAMPLE 247

N-[3-(benzyl{4-[3-(benzyloxy)benzoyl] benzyl}amino)-2-methylphenyl]methanesulfonamide The product from Example 88F and benzyl alcohol were processed as described in Example 242A and B to provide the titled compound. $^1$H NMR (500 MHz, DMSO-$d_6$) δ8.96 (s, 1 H), 7.62 (d, 2 H), 7.45 (m, 5 H), 7.39 (m, 2 H), 7.31 (m, 7 H), 7.22 (m, 2 H), 7.01 (m, 3 H), 5.17 (s, 2 H), 4.17 (s, 2 H), 4.09 (s, 2 H), 2.92 (s, 3 H), 2.42 (s, 3 H); MS (ESI+) m/z 591 (M+H)$^+$.

EXAMPLE 248

N-{3-[benzyl(4-{3-[2-(2-oxopyrrolidin-1-yl)ethoxy] benzoyl}benzyl)amino]-2-methylphenyl}methanesulfonamide The product from Example 88F and N-(2-hydroxyethyl)-2-pyrrolidone were processed as described in Example 242A and B to provide the titled compound. $^1$H NMR (500 MHz, DMSO-$d_6$) δ8.96 (s, 1 H), 7.66 (d, 2 H), 7.45 (m, 3 H), 7.28 (d, 4 H), 7.21 (m, 4 H), 7.01 (m, 3 H), 4.17 (s, 2 H), 4.13 (t, 2 H), 4.09 (s, 2 H), 3.55 (t, 2 H), 3.44 (t, 2 H), 2.92 (s, 3 H), 2.42 (s, 3 H), 2.20 (t, 2 H), 1.90 (m, 2 H); MS (ESI+) m/z 612 (M+H)$^+$.

EXAMPLE 249

N-{3-[benzyl(4-{3-[2-(4-methyl-1,3-thiazol-5-yl) ethoxy]benzoyl}benzyl)amino]-2-methylphenyl}methanesulfonamide The product from Example 88F and 4-methyl-5-thiazoleethanol were processed as described in Example 242A and B to provide the titled compound. $^1$H NMR (500 MHz, DMSO-$d_6$) δ8.96 (s, 1 H), 8.82 (s, 1 H), 7.65 (d, 2 H), 7.45 (m, 3 H), 7.28 (d, 4 H), 7.21 (m, 4 H), 7.01 (m, 3 H), 4.20 (t, 2 H), 4.17 (s, 2 H), 4.09 (s, 2 H), 3.23 (t, 2 H), 2.92 (s, 3 H), 2.42 (s, 3 H), 2.34 (s, 3 H); MS (ESI+) m/z 626 (M+H)$^+$.

EXAMPLE 250

N-(3-{benzyl[4-(4-{[(2R)-2,3-dihydroxypropyl] oxy}benzoyl)benzyl]amino}-2-methylphenyl) methanesulfonamide

EXAMPLE 250A 1-(allyloxy)-4-bromobenzene

4-Bromophenol was processed as described in Example 88C to provide the title compound.

EXAMPLE 250B

N-(3-((4-(4-(allyloxy)benzoyl)benzyl)(benzyl) amino)-2-methylphenyl)methanesulfonamide The product Example 88B was processed as described in Example 88D using the product from Example 250A instead of 1-(allyloxy)-3-bromobenzene to provide the title compound.

EXAMPLE 250C di-N-(3-((4-(4-(allyloxy)benzoyl)benzyl)(benzyl) amino)-2-methylphenyl)methanesulfonamide The product from Example 250B was processed as described in Example 6D to provide the title compound.

EXAMPLE 250D

The product from Example 250C was processed as described in Example 33A to provide the title compound.

EXAMPLE 250E

N-(3-{benzyl[4-(4-{[(2R)-2,3-dihydroxypropyl] oxy}benzoyl)benzyl]amino}-2-methylphenyl) methanesulfonamide The product from Example 250D (50 mg, 0.087 mmole), (4S)-2,2-dimethyl-1,3-dioxolane-4-methanol (79.3 mg, 0.6 mmole), di-tert-butyl azodicarboxylate (30 mg, 0.13 mmole), and triphenyiphosphine (45 mg, 0.17 mmole) were dissolved in tetrahydrofuran (2 mL) in a capped test-tube and shaked at room temperature overnight. Ethyl acetate (2 mL) was added to dilute the reaction mixture. Then, the diluted organic solution was washed with water (2 mL) and brine (2 mL), dried ($Na_2SO_4$), concentrated in vaccuo, and purified by HPLC to give the ethylene glycol protected compound. To the ethylene glycol protected compound was added 2N NaOH solution (2 mL), tetrahydrofuran (1 mL), and ethyl alcohol (1 mL). The mixture was shaken at room temperature overnight. Then 1N HCl solution was used to adjust the PH to 2~3. Ethyl acetate (4 mL) was used to extract the product. The extraction solution was concentrated in vaccuo and purified by HPLC to provide the titled compound. $^1$H NMR (500 M, DMSO-$d_6$) δ ppm 8.96 (s, 1 H), 7.70 (m, 2 H), 7.60 (m, 2 H), 7.44 (m, 2 H), 7.28 (m, 4 H), 7.21 (m, 1 H), 7.03 (m, 5 H), 4.17 (s, 2 H), 4.11 (m, 1 H), 4.10 (s, 2 H), 3.97 (dd, 1 H), 3.82 (m, 1 H), 3.46 (d, 2 H), 2.92 (s, 3 H), 2.42 (s, 3 H); MS (APCI+) m/z 575 (M+H)$^+$.

EXAMPLE 251

N-[4-(4-{4-[(benzyl{2-methyl-3-[(methylsulfonyl) amino]phenyl}amino)methyl]phenoxy}phenoxy) butanoyl]glycine

EXAMPLE 251A methyl N-(4-(4-(4-((benzyl(2-methyl-3-((methylsulfonyl)amino)phenyl)amino)methyl) phenoxy)phenoxy)butanoyl)glycinate The product from Example 233 (28.7 mg, 0.05 mmoles) in anhydrous dimethylformamide (0.5 ml) was treated with 1-[3-(dimethylamino)propyl]-3-ethylcarbodiimide hydrochloride (14 mg, 0.07 mmoles) and 1-hydroxybenzotriazole hydrate (10 mg, 0.07 mmoles) at room temperature for 15 minutes. A mixture of glycine methyl ester hydrochloride (12.6 mg, 0.1 mmole) and N,N-diisopropylethylamine (0.014 ml, 0.1 mmole) in anhydrous dimethylformamide (0.235 ml) was added to the reaction and shaken at room temperature overnight. The reacton mixture was acidified with 1N aqueous hydrochloric acid and extracted with dichloromethane. The organic layer was washed with saturated aqueous sodium bicarbonate solution and brine, dried over anhydrous sodium sulfate, filtered and filtrate concentrated in vacuo. The residue purified by HPLC to provide the titled compound.

EXAMPLE 251B

N-[4-(4-{4-[(benzyl{2-methyl-3-[(methylsulfonyl) amino]phenyl}amino)methyl]phenoxy}phenoxy) butanoyl]glycine The product from Example 251A was treated with 22N aqueous sodium hydroxide: 1 tetrahydrofuran: 1 ethanol (2 ml) at room temperature overnight. The reaction mixture acidified with 1N hydrochloric acid to pH 3–4, extracted with ethyl acetate. The organic layer was dried over anhydrous sodium sulfate, filtered and the filtrate concentrated in vacuo. The residue purified by HPLC to provide the titled compound. $^1$H NMR (500 MHz, DMSO-d$_6$) δ12.13–12.81 (br.s, 1 H), 8.94 (s, 1 H), 8.18 (t, 1 H), 7.14–7.34 (m, 7 H), 6.98 (m, 7 H), 6.82 (d, 2 H), 4.05 (s, 2 H), 4.00 (s, 2 H), 3.95 (t, 2 H), 3.74 (d, 2 H), 2.91 (s, 3 H), 2.38 (s, 3 H), 2.30 (t, 2 H), 1.93 (m, 2 H); MS (ESI+) m/z 632 (M+H)$^+$.

EXAMPLE 252

N-[4-(4-{4-[(benzyl{2-methyl-3-[(methylsulfonyl) amino]phenyl}amino)methyl]phenoxy}phenoxy) butanoyl]-beta-alanine The product from Example 233 and beta-alanine ethyl ester hydrochloride were processed as described in Example 251A and B to provide the titled compound. $^1$H NMR (500 MHz, DMSO-d$_6$) δ11.91–12.41 (br.s, 1 H), 8.94 (s, 1 H), 7.90 (m, 1 H), 7.22 (m, 7 H), 6.88–7.09 (m, 7 H), 6.82 (d, 2 H), 4.04 (s, 2 H), 4.00 (s, 2 H), 3.92 (t, 2 H), 3.24 (dd, 2 H), 2.91 (s, 3 H), 2.38 (s, 3 H), 2.37 (t, 2 H), 2.21 (t, 2 H), 1.91 (m, 2 H); MS (ESI+) m/z 646 (M+H)$^+$.

EXAMPLE 253

4-{[4-(4-{4-[(benzyl{2-methyl-3-[(methylsulfonyl) amino]phenyl}amino)methyl]phenoxy}phenoxy) butanoyl]amino}butanoic acid The product from Example 233 and ethyl 4-aminobutyrate hydrochloride were processed as described in Example 251A and B to provide the titled compound. $^1$H NMR (500 MHz, DMSO-d$_6$) δ11.75–12.25 (br.s, 1 H), 8.94 (s, 1 H), 7.83 (t, 1 H), 7.24 (m, 7 H), 6.98 (m, 7 H), 6.82 (d, 2 H), 4.04 (s, 2 H), 4.00 (s, 2 H), 3.93 (t, 2 H), 3.05 (dd, 2 H), 2.91 (s, 3 H), 2.39 (s, 3 H), 2.20 (m, 4 H), 1.91 (m, 2 H), 1.62 (m, 2 H); MS (ESI+) m/z 660 (M+H)$^+$.

EXAMPLE 254

N-[4-(4-{4-[(benzyl{2-methyl-3-[(methylsulfonyl) amino]phenyl}amino)methyl]phenoxy}phenoxy) butanoyl]-N-methylglycine The product from Example 233 and N-methylglycine ethyl ester hydrochloride were processed as described in Example 251A and B to provide the titled compound. $^1$H NMR (500 MHz, DMSO-d$_6$) δ12.13–13.26 (br.s, 1 H), 8.94 (s, 1 H), 7.23 (m, 7 H), 6.99 (m, 7 H), 6.82 (d, J=8.7 Hz, 2 H), 4.12 (s, 1 H), 4.04 (s, 2 H), 3.96 (m, 5 H), 3.01 (s, 3 H), 3.01 (s, 2 H), 2.82 (s, 1 H), 2.50 (m, 1 H), 2.37 (m, 4 H), 1.92 (m, 2 H); MS (ESI+) m/z 646 (M+H)$^+$.

EXAMPLE 255

N-[4-(4-{4-[(benzyl{2-methyl-3-[(methylsulfonyl) amino]phenyl}amino)methyl]phenoxy}phenoxy) butanoyl]-L-glutamic acid The product from Example 233 and L-glutamic acid dimethyl ester hydrochloride were processed as described in Example 251A and B to provide the titled compound. $^1$H NMR (500 MHz, DMSO-d$_6$) δ12.33–12.71 (br.s, 1 H), 11.89–12.26 (br.s, 1 H), 8.94 (s, 1 H), 8.12 (d, 1 H), 7.23 (m, 7 H), 6.99 (m, 7 H), 6.82 (d, 2 H), 4.22 (m, 1 H), 4.04 (s, 2 H), 4.00 (s, 2 H), 3.94 (t, 2 H), 2.91 (s, 3 H), 2.39 (s, 3 H), 2.28 (m, 4 H), 1.95 (m, 3 H), 1.77 (m, 1 H); MS (ESI+) m/z 704 (M+H)$^+$.

EXAMPLE 256

N-[4-(4-{4-[(benzyl{2-methyl-3-[(methylsulfonyl) amino]phenyl}amino)methyl]phenoxy}phenoxy) butanoyl]-L-valine The product from Example 233 and L-valine methyl ester hydrochloride were processed as described in Example 251A and B to provide the titled compound. $^1$H NMR (500 MHz, DMSO-d$_6$) δ12.18–12.73 (br.s, 1 H), 8.94 (s, 1 H), 7.98 (d, 1 H), 7.23 (m, 7 H), 6.97 (m, 7 H), 6.82 (d, 2 H), 4.14 (m, 1 H), 4.04 (s, 2 H), 4.00 (s, 2 H), 3.94 (t, 2 H), 2.91 (s, 3 H), 2.39 (s, 3 H), 2.34 (m, 2 H), 2.03 (m, 1 H), 1.92 (m, 2 H), 0.87 (dd, 6 H); MS (ESI+) m/z 674 (M+H)$^+$.

EXAMPLE 257

4-{[4-(4-{4-[(benzyl{2-methyl-3-[(methylsulfonyl) amino]phenyl}amino)methyl]phenoxy}phenoxy) butanoyl]amino}-1-methyl-1H-pyrrole-2-carboxylic acid The product from Example 233 and 4-amino-1-methyl-1H-pyrrole-2-carboxylic acid methyl ester hydrochloride were processed as described in Example 251A and B to provide the titled compound. $^1$H NMR (500 MHz, DMSO-d$_6$) δ11.89–12.33 (br.s, 1 H), 9.81 (s, 1 H), 8.94 (s, 1 H), 7.24 (m, 8 H), 6.98 (m, 7 H), 6.82 (d, 2 H), 6.65 (d, 1 H), 4.04 (s, 2 H), 4.00 (s, 2 H), 3.97 (t, 2 H), 3.79 (s, 3 H), 2.91 (s, 3 H), 2.38 (m, 5 H), 1.99 (m, 2 H); MS (ESI+) m/z 697 (M+H)$^+$.

EXAMPLE 258

N-[4-(4-{4-[(benzyl{2-methyl-3-[(methylsulfonyl) amino]phenyl}amino)methyl]phenoxy}phenoxy) butanoyl]-L-serine

EXAMPLE 258A tert-butyl N-(4-(4-(4-((benzyl(2-methyl-3-((methylsulfonyl)amino)phenyl)amino)methyl) phenoxy)phenoxy)butanoyl)-L-serinate The product from Example 233 and O-tert-butyl L-serine tert-butyl ester hydrochloride were processed as described in Example 251A to provide the titled compound.

EXAMPLE 258B

N-[4-(4-{4-[(benzyl{2-methyl-3-[(methylsulfonyl) amino]phenyl}amino)methyl]phenoxy}phenoxy) butanoyl]-L-serine The product from Example 258A was treated with 10% trifluoroacetic acid in dichloromethane (2 ml) for 5 hours at room temperature and concentrated in vacuo. Residue purified by HPLC to provide the titled compound. $^1$H NMR (500 MHz, DMSO-d$_6$) δ12.04–12.95 (br.s, 1 H), 8.94 (s, 1 H), 8.00 (d, 1 H), 7.24 (m, 7 H), 6.88–7.09 (m, 7 H), 6.82 (d, 2 H), 4.29 (m, 1 H), 4.05 (s, 2 H), 4.00 (s, 2 H), 3.95 (t, 2 H), 3.65 (m, 2 H), 2.91 (s, 3 H), 2.38 (s, 3 H), 2.32 (m, 2 H), 1.94 (m, 2 H); MS (ESI+) m/z 662 (M+H)$^+$.

EXAMPLE 259

N-[4-(4-{4-[(benzyl{2-methyl-3-[(methylsulfonyl)amino]phenyl}amino)methyl]phenoxy}phenoxy)butanoyl]-L-isoleucine The product from Example 233 and L-isoleucine tert-butyl ester hydrochloride were processed as described in Example 251A and 258B to provide the titled compound. $^1$H NMR (500 MHz, DMSO-d$_6$) δ12.06–12.82 (br.s, 1 H), 8.94 (s, 1 H), 7.99 (d, 1 H), 7.23 (m, 7 H), 6.87–7.09 (m, 7 H), 6.82 (d, 2 H), 4.19 (dd, 1 H), 4.04 (s, 2 H), 4.00 (s, 2 H), 3.93 (m, 2 H), 2.91 (s, 3 H), 2.38 (s, 3 H), 2.33 (m, 2 H), 1.92 (m, 2 H), 1.76 (m, 1 H), 1.40 (m, 1 H), 1.18 (m, 1 H), 0.83 (m, 6 H); MS (ESI+) m/z 688 (M+H)$^+$.

EXAMPLE 260

N~2~-[4-(4-{4-[(benzyl{2-methyl-3-[(methylsulfonyl)amino]phenyl}amino)methyl]phenoxy}phenoxy)butanoyl]-L-glutamine The product from Example 233 and L-glutamine tert-butyl ester hydrochloride were processed as described in Example 251A and 258B to provide the titled compound. $^1$H NMR (500 MHz, DMSO-d$_6$) δ12.00–12.89 (br.s, 1 H), 8.94 (s, 1 H), 8.13 (d, 1 H), 7.24 (m, 8 H), 6.98 (m, 7 H), 6.82 (d, 2 H), 6.73 (s, 1 H), 4.16 (m, 1 H), 4.05 (s, 2 H), 4.00 (s, 2 H), 3.95 (m, 2 H), 2.91 (s, 3 H), 2.39 (s, 3 H), 2.29 (t, 2 H), 2.12 (m, 2 H), 1.94 (m, 3 H), 1.74 (m, 1 H), MS (ESI+) m/z 703 (M+H)$^+$.

EXAMPLE 261

N-[5-(4-{4-[(benzyl{2-methyl-3-[(methylsulfonyl)amino]phenyl}amino)methyl]phenoxy}phenoxy)pentanoyl]glycine The product from Example 234B and glycine methyl ester hydrochloride were processed as described in Example 251A and B to provide the titled compound. $^1$H NMR (500 MHz, DMSO-d$_6$) δ12.13–12.77 (br.s, 1 H), 8.94 (s, 1 H), 8.12 (t, 1 H), 7.24 (m, 7 H), 7.03 (t, 1 H), 6.94 (m, 6 H), 6.82 (d, 2 H), 4.04 (s, 2 H), 4.00 (s, 2 H), 3.93 (t, 2 H), 3.73 (d, 2 H), 2.91 (s, 3 H), 2.39 (s, 3 H), 2.19 (t, 2 H), 1.55–1.79 (m, 4 H); MS (ESI+) m/z 646 (M+H)$^+$.

EXAMPLE 262

N-[5-(4-{4-[(benzyl{2-methyl-3-[(methylsulfonyl)amino]phenyl}amino)methyl]phenoxy}phenoxy)pentanoyl]-beta-alanine The product from Example 234B and beta-alanine ethyl ester hydrochloride were processed as described in Example 251A and B to provide the titled compound. $^1$H NMR (500 MHz, DMSO-d$_6$) δ11.84–12.51 (br.s, 1 H), 8.94 (s, 1 H), 7.85 (t, 1 H), 7.22 (m, 7 H), 7.03 (t, J=7.8 Hz, 1 H), 6.94 (m, 6 H), 6.82 (d, 2 H), 4.04 (s, 2 H), 4.00 (s, 2 H), 3.92 (t, 2 H), 3.23 (dd, 2 H), 2.91 (s, 3 H), 2.39 (s, 3 H), 2.36 (t, 2 H), 2.11 (t, 2 H), 1.64 (m, 4 H); MS (ESI+) m/z 660 (M+H)$^+$.

EXAMPLE 263

4-{[5-(4-{4-[(benzyl{2-methyl-3-[(methylsulfonyl)amino]phenyl}amino)methyl]phenoxy}phenoxy)pentanoyl]amino}butanoic acid The product from Example 234B and ethyl 4-aminobutyrate hydrochloride were processed as described in Example 251A and B to provide the titled compound. $^1$H NMR (500 MHz, DMSO-d$_6$) δ11.33–12.51 (br.s, 1 H), 8.94 (s, 1 H), 7.79 (t, 1 H), 7.23 (m, 7 H), 7.03 (t, 1 H), 6.94 (m, 6 H), 6.82 (d, 2 H), 4.04 (s, 2 H), 4.00 (s, 2 H), 3.93 (t, 2 H), 3.04 (dd, 2 H), 2.91 (s, 3 H), 2.38 (s, 3 H), 2.21 (t, 2 H), 2.12 (t, 2 H), 1.63 (m, 6 H); MS (ESI+) m/z 674 (M+H)$^+$.

EXAMPLE 264

N-[5-(4-{4-[(benzyl{2-methyl-3-[(methylsulfonyl)amino]phenyl}amino)methyl]phenoxy}phenoxy)pentanoyl]-N-methylglycine The product from Example 234B and N-methylglycine ethyl ester hydrochloride were processed as described in Example 251A and B to provide the titled compound. $^1$H NMR (500 MHz, DMSO-d$_6$) δ12.20–13.15 (br.s, 1 H), 8.94 (s, 1 H), 7.23 (m, 7 H), 7.03 (t, 1 H), 6.95 (m, 6 H), 6.82 (d, 2 H), 4.12 (s, 1 H), 4.04 (s, 2 H), 4.00 (s, 2 H), 3.94 (m, 3 H), 3.01 (s, 2 H), 2.91 (s, 3 H), 2.81 (s, 1 H), 2.40 (m, 4 H), 2.27 (t, 1 H), 1.58–1.79 (m, 4 H); MS (ESI+) m/z 660 (M+H)$^+$.

EXAMPLE 265

N-[5-(4-{4-[(benzyl{2-methyl-3-[(methylsulfonyl)amino]phenyl}amino)methyl]phenoxy}phenoxy)pentanoyl]-L-glutamic acid The product from Example 234B and L-glutamic acid dimethyl ester hydrochloride were processed as described in Example 251A and B to provide the titled compound. $^1$H NMR (500 MHz, DMSO-d$_6$) δ11.60–13.04 (br.s, 2 H), 8.94 (s, 1 H), 8.06 (d, 1 H), 7.23 (m, 7 H), 7.03 (t, 1 H), 6.95 (m, 6 H), 6.82 (d, 2 H), 4.21 (m, 1 H), 4.04 (s, 2 H), 4.00 (s, 2 H), 3.93 (t, 2 H), 2.91 (s, 3 H), 2.39 (s, 3 H), 2.28 (m, 2 H), 2.19 (t, 2 H), 1.96 (m, 1 H), 1.60–1.82 (m, 5 H); MS (ESI+) m/z 718 (M+H)$^+$.

EXAMPLE 266

N-[5-(4-{4-[(benzyl{2-methyl-3-[(methylsulfonyl)amino]phenyl}amino)methyl]phenoxy}phenoxy)pentanoyl]-L-valine The product from Example 234B and L-valine methyl ester hydrochloride were processed as described in Example 251A and B to provide the titled compound. $^1$H NMR (500 MHz, DMSO-d$_6$) δ12.15–12.77 (br.s, 1 H), 8.94 (s, 1 H), 7.92 (d, 1 H), 7.23 (m, 7 H), 7.03 (t, 1 H), 6.94 (m, 6 H), 6.82 (d, 2 H), 4.15 (dd, 1 H), 4.04 (s, 2 H), 4.00 (s, 2 H), 3.94 (t, 2 H), 2.91 (s, 3 H), 2.38 (s, 3 H), 2.23 (m, 2 H), 2.04 (m, 1 H), 1.67 (m, 4 H), 0.88 (dd, 6 H); MS (ESI+) m/z 688 (M+H)$^+$.

EXAMPLE 267

1-[5-(4-{4-[(benzyl{2-methyl-3-[(methylsulfonyl)amino]phenyl}amino)methyl]phenoxy}phenoxy)pentanoyl]-L-proline The product from Example 234B and L-proline methyl ester hydrochloride were processed as described in Example 251A and B to provide the titled compound. $^1$H NMR (500 MHz, DMSO-d$_6$) δ11.95–13.15 (br.s, 1 H), 8.94 (s, 1 H), 7.23 (m, 7 H), 7.03 (t, 1 H), 6.95 (m, 6 H), 6.82 (d, 2 H), 4.21 (dd, 1 H), 4.04 (s, 2 H), 4.00 (s, 2 H), 3.93 (m, 2 H), 3.52 (m, 2 H), 2.91 (s, 3 H), 2.39 (s, 3 H), 2.34 (t, 2 H), 1.99–2.27 (m, 2 H), 1.87 (m, 2 H), 1.68 (m, 4 H; MS (ESI+) m/z 686 (M+H)$^+$.

EXAMPLE 268

5-(4-{4-[(benzyl{2-methyl-3-[(methylsulfonyl)
amino]phenyl}amino)methyl]phenoxy}phenoxy)-N-
(2-oxotetrahydrofuran-3-yl)pentanamide The product from Example 234B and alpha-amino-gamma-butyrolactone hydrobromide were processed as described in Example 251A to provide the titled compound. $^1$H NMR (500 MHz, DMSO-d$_6$) δ8.94 (s, 1 H), 8.33 (d, 1 H), 7.23 (m, 7 H), 7.03 (t, 1 H), 6.94 (m, 6 H), 6.82 (d, 2 H), 4.53 (dd, 1 H), 4.34 (t, 1 H), 4.20 (m, 1 H), 4.04 (s, 2 H), 4.00 (s, 2 H), 3.94 (t, 2 H), 3.44 (m, 1 H), 2.91 (s, 3 H), 2.39 (s, 3 H), 2.16 (m, 3 H), 1.55–1.78 (m, 4 H); MS (ESI+) m/z 672 (M+H)$^+$.

EXAMPLE 269

N-[5-(4-{4-[(benzyl{2-methyl-3-[(methylsulfonyl)
amino]phenyl}amino)methyl]phenoxy}phenoxy)
pentanoyl]-L-serine The product from Example 234B and O-tert-butyl L-serine tert-butyl ester hydrochloride were processed as described in Example 251A and 258B to provide the titled compound. $^1$H NMR (500 MHz, DMSO-d$_6$) δ11.98–13.00 (br.s, 1 H), 8.95 (s, 1 H), 7.93 (d, 1 H), 7.23 (m, 7 H), 7.03 (t, 1 H), 6.94 (m, 6 H), 6.82 (d, 2 H), 4.27 (m, 1 H), 4.05 (s, 2 H), 4.00 (s, 2 H), 3.94 (t, 2 H), 3.65 (m, 2 H), 2.91 (s, 3 H), 2.38 (s, 3 H), 2.22 (m, 2 H), 1.66 (m, 4 H); MS (ESI+) m/z 676 (M+H)$^+$.

EXAMPLE 270

N-[5-(4-{4-[(benzyl{2-methyl-3-[(methylsulfonyl)
amino]phenyl}amino)methyl]phenoxy}phenoxy)
pentanoyl]-L-isoleucine The product from Example 234B and L-isoleucine tert-butyl ester hydrochloride were processed as described in Example 251A and 258B to provide the titled compound. $^1$H NMR (500 MHz, DMSO-d$_6$) δ12.09–12.71 (br.s, 1 H), 8.94 (s, 1 H), 7.93 (d, 1 H), 7.23 (m, 7 H), 7.03 (t, 1 H), 6.94 (m, 6 H), 6.82 (d, 2 H), 4.19 (dd, 1 H), 4.04 (s, 2 H), 4.00 (s, 2 H), 3.93 (t, 2 H), 2.91 (s, 3 H), 2.38 (s, 3 H), 2.21 (m, 2 H), 1.59–1.80 (m, 5 H), 1.39 (m, 1 H), 1.20 (m, 1 H), 0.84 (m, 6 H); MS (ESI+) m/z 702 (M+H)$^+$.

EXAMPLE 271

4-{[(4-{4-[(benzyl{2-methyl-3-[(methylsulfonyl)
amino]phenyl}amino)methyl]phenoxy}phenoxy)
acetyl]amino}butanoic acid The product from Example 95C and ethyl 4-aminobutyrate hydrochloride were processed as described in Example 251A and B to provide the titled compound. $^1$H NMR (500 MHz, DMSO-d$_6$) δ11.69–12.36 (br.s, 1 H), 8.94 (s, 1 H), 8.09 (t, 1 H), 7.23 (m, 7 H), 7.03 (t, 1 H), 6.96 (m, 6 H), 6.83 (d, 2 H), 4.43 (s, 2 H), 4.05 (s, 2 H), 4.00 (s, 2 H), 3.15 (m, 2 H), 2.91 (s, 3 H), 2.39 (s, 3 H), 2.20 (t, 2 H), 1.66 (m, 2H); MS (ESI+) m/z 632 (M+H)$^+$.

EXAMPLE 272

N-[(4-{4-[(benzyl{2-methyl-3-[(methylsulfonyl)
amino]phenyl}amino)methyl]phenoxy}phenoxy)
acetyl]-N-methylglycine The product from Example 95C and N-methylglycine ethyl ester hydrochloride were processed as described in Example 251A and B to provide the titled compound. $^1$H NMR (500 MHz, DMSO-d$_6$) δ12.40–13.15 (br.s, 1 H), 8.94 (s, 1 H), 7.23 (m, 7 H), 7.03 (t, 1 H), 6.93 (m, 6 H), 6.82 (dd, 2 H), 4.84 (s, 1 H), 4.69 (s, 1 H), 4.17 (s, 1 H), 4.05 (s, 2 H), 4.00 (m, 3 H), 3.04 (s, 2 H), 2.91 (s, 3 H), 2.85 (s, 1 H), 2.39 (s, 3 H); MS (ESI+) m/z 618 (M+H)$^+$.

EXAMPLE 273

N-[(4-{4-[(benzyl{2-methyl-3-[(methylsulfonyl)
amino]phenyl}amino)methyl]phenoxy}phenoxy)
acetyl]-L-valine The product from Example 95C and L-valine methyl ester hydrochloride were processed as described in Example 251A and B to provide the titled compound. $^1$H NMR (500 MHz, DMSO-d$_6$) δ12.36–13.13 (br.s, 1 H), 8.94 (s, 1 H), 7.99 (d, 1 H), 7.23 (m, 7 H), 7.03 (t, 1 H), 6.95 (m, 6 H), 6.82 (d, 2 H), 4.58 (d, 2 H), 4.21 (dd, 1 H), 4.05 (s, 2 H), 4.00 (s, 2 H), 2.91 (s, 3 H), 2.39 (s, 3 H), 2.10 (m, 1 H), 0.87 (dd, 6 H); MS (ESI+) m/z 646 (M+H)$^+$.

EXAMPLE 274

2-(4-{4-[(benzyl{2-methyl-3-[(methylsulfonyl)
amino]phenyl}amino)methyl]phenoxy}phenoxy)-N-
(2-oxotetrahydrofuran-3-yl)acetamide The product from Example 95C and alpha-amino-gamma-butyrolactone hydrobromide were processed as described in Example 251A to provide the titled compound. $^1$H NMR (500 MHz, DMSO-d$_6$) δ8.94 (s, 1 H), 8.62 (d, 1 H), 7.23 (m, 7 H), 7.00 (m, 7 H), 6.84 (d, 2 H), 4.69 (dd, 1 H), 4.52 (d, 2 H), 4.36 (m, 1 H), 4.23 (dd, 1 H), 4.05 (s, 2 H), 4.00 (s, 2 H), 2.91 (s, 3 H), 2.39 (m, 4 H), 2.27 (m, 1 H); MS (ESI+) m/z 630 (M+H)$^+$.

EXAMPLE 275

N-[(4-{4-[(benzyl{2-methyl-3-[(methylsulfonyl)
amino]phenyl}amino)methyl]phenoxy}phenoxy)
acetyl]-L-serine The product from Example 95C and O-tert-butyl L-serine tert-butyl ester hydrochloride were processed as described in Example 251A and 258B to provide the titled compound. $^1$H NMR (500 MHz, DMSO-d$_6$) δ12.26–13.13 (br.s, 1 H), 8.94 (s, 1 H), 8.01 (d, 1 H), 7.23 (m, 7 H), 7.00 (m, 7 H), 6.84 (d, 2 H), 4.54 (s, 2 H), 4.36 (m, 1 H), 4.05 (s, 2 H), 4.00 (s, 2 H), 3.78 (m, 1 H), 3.68 (m, 1 H), 2.91 (s, 3 H), 2.39 (s, 3 H); MS (ESI+) m/z 634 (M+H)$^+$.

EXAMPLE 276

N~2~-[(4-{4-[(benzyl{2-methyl-3-[(methylsulfonyl)
amino]phenyl}amino)methyl]phenoxy}phenoxy)
acetyl]-L-asparagine The product from Example 95C and L-aspargine tert-butyl ester hydrochloride were processed as described in Example 251A and 258B to provide the titled compound. $^1$H NMR (500 MHz, DMSO-d$_6$) δ12.18–13.09 (br.s, 1 H), 8.94 (s, 1 H), 8.28 (d, 1 H), 7.39 (s, 1 H), 7.23 (m, 7 H), 7.03 (t, 1 H), 6.94 (m, 6 H), 6.91 (s, 1 H), 6.84 (d, 2 H), 4.60 (dd, 1 H), 4.49 (s, 2 H), 4.05 (s, 2 H), 4.00 (s, 2 H), 2.91 (s, 3 H), 2.60 (d2 H), 2.39 (s, 3 H); MS ((ESI+) m/z 661 (M+H)$^+$.

EXAMPLE 277

N-[3-(benzyl{4-[4-(2-hydrazino-2-oxoethoxy)
phenoxy]benzyl}amino)-2-methylphenyl]
methanesulfonamide The product from Example 95C and tert-butyl carbazate were processed as described in Example 251A and 258B to provide the titled compound. $^1$H NMR (500 MHz, DMSO-$d_6$) δ8.94 (s, 1 H), 7.22 (m, 7 H), 6.99 (m, 7 H), 6.83 (d, 2 H), 4.64 (m, 2 H), 4.05 (s, 2 H), 4.01 (s, 2 H), 2.91 (s, 3 H), 2.39 (s, 3 H); MS (ESI+) m/z 561 (M+H)$^+$.

EXAMPLE 278

N-(3-{benzyl[4-(3-{[(2S)-5-oxopyrrolidin-2-yl]methoxy}phenoxy)benzyl]amino}-2-methylphenyl)methanesulfonamide

EXAMPLE 278A (5S)-5-((3-(4-((benzyl(2-methyl-3-nitrophenyl)amino)methyl)phenoxy)phenoxy)methyl)pyrrolidin-2-one The product from Example 61F (88 mg, 0.2 mmole), (S)-5-(hydroxymethyl)-2-pyrrolidinone (58 mg, 0.5 mmole), di-tert-butyl azodicarboxylate (69 mg, 0.3 mmole), and triphenylphosphine (77 mg, 0.3 mmole) were dissolved in tetrahydrofuran (1.5 mL) in a capped test-tube and shaked at room temperature overnight. Ethyl acetate (2 mL) was added to dilute the reaction mixture. Then, the diluted organic solution was washed with water (2 mL) and saturated sodium chloride solution (2 mL), dried in vaccuo, and purified by HPLC to give the pure intermediate.

EXAMPLE 278B (5S)-5-((3-(4-(((3-amino-2-methylphenyl)(benzyl)amino)methyl)phenoxy)phenoxy)methyl)pyrrolidin-2-one To the product from Example 278A in a capped test-tube were added iron powder (78.4 mg, 1.4 mmoles), NH$_4$Cl (7.5 mg, 1.4 mmoles), ethyl alcohol (3 mL) and water (1 mL). The reaction mixture was shaken violently at 80° C. overnight. CH$_2$Cl$_2$ (4 mL) was added to extract the product. Then, the reaction mixture was filtered. The CH$_2$Cl$_2$ layer was separated and dried in vaccuo.

EXAMPLE 278C

N-(3-{benzyl[4-(3-{[(2S)-5-oxopyrrolidin-2-yl]methoxy}phenoxy)benzyl]amino}-2-methylphenyl)methanesulfonamide The dried product from example 278B was dissolved in anhydrous pyridine (3 mL) at 0° C. for 30 minutes. Then methanesulfonyl chloride (50 μL, 6 mmoles) was injected. The reaction mixture was let to stand at room temperature for 3 hours. Then the reaction mixture was dried in vaccuo, dissolved in CH$_2$Cl$_2$ (4 mL), filtered and dried in vaccuo. The final residue was purified by HPLC to provide the titled compound. $^1$H NMR (500 MHz, DMSO-$d_6$) δ8.95 (s, 1 H), 7.76 (s, 1 H), 7.27 (m, 7 H), 7.20 (m, 1 H), 7.04 (m, 1 H), 6.95 (m, 4 H), 6.71 (m, 1 H), 6.53 (m, 2 H), 4.06 (s, 2 H), 4.03 (s, 2 H), 3.92 (m, 1 H), 3.82 (m, 2 H), 2.91 (s, 3 H), 2.39 (s, 3 H), 2.04–2.29 (m, 3 H), 1.80 (m, 1 H); MS (APCI+) m/z 586 (M+H)$^+$.

EXAMPLE 279

1-[4-(3-{4-[(benzyl{2-methyl-3-[(methylsulfonyl)amino]phenyl}amino)methyl]phenoxy}phenoxy)butanoyl]piperidine-3-carboxylic acid

EXAMPLE 279A ethyl 1-(4-(3-(4-((benzyl(2-methyl-3-((methylsulfonyl)amino)phenyl)amino)methyl)phenoxy)phenoxy)butanoyl)piperidine-3-carboxylate The product from Example 116 (57 mg, 0.10 mmole), 1-[3-(dimethylainino)propyl]-1-ethylcarbodiimide hydrochloride (27 mg, 0.14 mmole), and 1-hydroxybenzotriazole hydrate (19 mg, 0.14 mmole) were dissolved in N,N-dimethylformamide (1.5 mL) and let stand for 15 minutes at room temperature. Ethyl nipecotate (31 mg, 0.20 mmole) and N,N-diisopropylethyl amine (35 μL, 0.20 mmole) in N,N-diinethylformamide (0.5 ml) were added. The reaction mixture was shaken at room temperature overnight. Then the reaction mixture was acidified with 1N hydrochloric acid (3 mL) and extracted with dichloromethane (3 mL). The organic layer was washed with saturated NaHCO$_3$ solution (3 mL) and brine (3mL), dried (MgSO$_4$), and concentrated in vaccuo. The crude product was purified using HPLC to provide the ester compound.

EXAMPLE 279B

1-[4-(3-{4-[(benzyl{2-methyl-3-[(methylsulfonyl)amino]phenyl}amino)methyl]phenoxyl}phenoxy)butanoyl]piperidine-3-carboxylic acid The product from Example 279A was treated with 2N NaOH aqueous solution (1 mL), ethyl alcohol (0.5 mL) and tetrahydrofuran (0.5 mL) at room temperature overnight. 1N hydrochloric acid was dropped to the reaction mixture until pH=2~3. Ethyl acetate (3 mL) was used to extract the product. The organic layer was separated, dried (Na$_2$SO$_4$), concentrated in vaccuo, and purified by HPLC to provide the titled compound. $^1$H NMR (500 MHz, DMSO-$d_6$) δ12.03–12.70 (br.s, 1 H), 8.95 (s, 1 H), 7.24 (m, 8 H), 7.04 (m, 1 H), 6.94 (m, 4 H), 6.69 (m, 1 H), 6.49 (m, 2 H), 4.06 (s, 2 H), 4.03 (s, 2 H), 3.94 (t, J=6.4 Hz, 2 H), 3.82 (m, 1 H), 3.72 (m, 1 H), 3.31 (dd, J=13.6, 9.2 Hz, 1 H), 2.98 (t, J=11.1 Hz, 1 H), 2.91 (s, 3 H), 2.38 (m, 5 H), 2.24 (m, 1 H), 1.90 (m, 3 H), 1.65 (m, 1 H), 1.52 (m, 1 H), 1.34 (m, 1 H); MS (APCI+) m/z 686.1 (M+H)$^+$.

EXAMPLE 280

1-[4-(3-{4-[(benzyl{2-methyl-3-[(methylsulfonyl)amino]phenyl}amino)methyl]phenoxy}phenoxy)butanoyl]piperidine-4-carboxylic acid The product from Example 116B (57 mg, 0.10 mmole) and ethyl isonipecotate (31 mg, 0.20 mmole) were processed as in Example 279A and B to provide the titled compound. $^1$H NMR (500 MHz, DMSO-$d_6$ δ12.05–12.35 (br.s, 1 H), 8.95 (s, 1 H), 7.23 (m, 8 H), 7.03 (m, 1 H), 6.94 (m, 4 H), 6.69 (dd, 1 H), 6.49 (m, 2 H), 4.20 (d, 1 H), 4.06 (s, 2 H), 4.03 (s, 2 H), 3.94 (t, 2 H), 3.77 (d, 1 H), 3.05 (t, 1 H), 2.91 (s, 3 H), 2.70 (t, 1 H), 2.47 (m, 1 H), 2.43 (m, 2 H), 2.39 (s, 3 H), 1.90 (m, 2 H), 1.79 (m, 2 H), 1.45 (m, 1 H), 1.34 (m, 1 H); MS (APCI+) m/z 686.4 (M+H)$^+$.

EXAMPLE 281

1-[4-(3-{4-[(benzyl{2-methyl-3-[(methylsulfonyl)amino]phenyl}amino)methyl]phenoxy}phenoxy)butanoyl]piperidine-2-carboxylic acid The product from Example 116B (57 mg, 0.10 mmole) and ethyl pipecolinate (31 mg, 0.20 mmole) were processed as in Example 279A and B to provide the titled compound. $^1$H NMR (500 MHz, DMSO-$d_6$) δ12.29–13.30 (br.s, 1 H), 8.95 (s, 1 H), 7.24 (m, 8 H), 7.04 (m, 1 H), 6.95 (m, 4 H), 6.69 (m, 1 H), 6.49 (m, 2 H), 5.07 (d, 1 H), 4.06 (s, 2 H), 4.03 (s, 2 H), 3.94 (m, 2 H), 3.77 (d, 1 H), 3.09 (m, 1 H), 2.91 (s, 3 H), 2.49 (m, 2 H), 2.40 (s, 3 H), 2.12 (m, 1 H), 1.90 (m, 2 H), 1.62 (m, 2 H), 1.49 (m, 1 H), 1.35 (m, 1 H), 1.21 (m, 1 H); MS (APCI+) m/z 685.9 (M+H)$^+$.

EXAMPLE 282

1-[4-(3-{4-[(benzyl{2-methyl-3-[(methylsulfonyl)amino]phenyl}amino)methyl]phenoxy}phenoxy)butanoyl]proline The product from Example 116B (57 mg, 0.10 mmole) and H-PRO-OME hydrochloride (33 mg, 0.20 mmole) were processed as in Example 279A and B to provide the titled compound. $^1$H NMR (500 MHz, DMSO-d$_6$) δ11.66–13.20 (br.s, 1 H), 8.95 (s, 1 H), 7.24 (m, 8 H), 7.04 (m, 1 H), 6.95 (m, 4 H), 6.69 (m, 1 H), 6.50 (m, 2 H), 4.46 (m, 0 H), 4.22 (m, 1 H), 4.06 (s, 2 H), 4.03 (s, 2 H), 3.93 (m, 2 H), 3.50 (m, 2 H), 2.91 (s, 3 H), 2.40 (s, 3 H), 2.39 (m, 2 H), 1.98–2.25 (m, 2 H), 1.76–1.97 (m, 4 H); MS (APCI+) m/z 672.5 (M+H)$^+$.

EXAMPLE 283

N-{3-[benzyl(4-{3-[(3-methyloxetan-3-yl)methoxy]phenoxy}benzyl)amino]-2-methylphenyl}methanesulfonamide The product from Example 61F (88 mg, 0.2 mmole) and 3-methyl-3-oxetanemethanol (51 mg, 0.5 mmole) were processed as in Example 278A–C to provide the titled compound. $^1$H NMR (500 MHz, DMSO-d$_6$) δ8.95 (s, 1 H), 7.23 (m, 8 H), 7.04 (m, 1 H), 6.94 (m, 4 H), 6.72 (m, 1 H), 6.53 (m, 2 H), 4.45 (d, 1 H), 4.27 (d, 1 H), 4.06 (s, 2 H), 4.03 (s, 2 H), 4.01 (s, 1 H), 3.78 (dd, 1 H), 3.64 (dd, 1 H), 3.38 (d, 1 H), 2.91 (s, 3 H), 2.40 (s, 3 H), 1.33 (s, 2 H), 0.99 (s, 1 H); MS (APCI+) m/z 573 (M+H)$^+$.

EXAMPLE 284

2-[(3-{4-[(benzyl{2-methyl-3-[(methylsulfonyl)amino]phenyl}amino)methyl]phenoxy}phenoxy)methyl]cyclopropanecarboxylic acid

EXAMPLE 284A ethyl 2-((3-(4-((benzyl(2-methyl-3-((methylsulfonyl)amino)phenyl)amino)methyl)phenoxy)phenoxy)methyl)cyclopropanecarboxylate The product from Example 61F (88 mg, 0.2 mmole) and ethyl 2-hydroxymethyl-1-cyclopropanecarboxylate (51 mg, 0.5 mmole) were processed as in Example 278A–C to provide the ester compound.

EXAMPLE 284B

2-[(3-{4-[(benzyl{2-methyl-3-[(methylsulfonyl)amino]phenyl}amino)methyl]phenoxy}phenoxy)methyl]cyclopropanecarboxylic acid To the product from Example 284A was added 2N hydrochloric acid (1 mL), tetrahydrofuran (0.5 mL) and water (0.5 mL). The reaction mixture was stirred at room temperature overnight. Water (2 mL) was added. The solution was neutralized with 1N hydrochloric aid until pH=2~3. The product was extracted with ethyl acetate (2 mL), dried in vaccuo, and purified by HPLC to provide the titled compound. $^1$H NMR (500 MHz, DMSO-d$_6$) δ12.01–12.29 (br.s, 1 H), 8.95 (s, 1 H), 7.23 (m, 8 H), 7.03 (m, 1 H), 6.94 (m, 4 H), 6.69 (m, 1 H), 6.50 (m, 2 H), 4.06 (s, 2 H), 4.03 (s, 2 H), 3.94 (m, 1 H), 3.80 (m, 1 H), 2.91 (s, 3 H), 2.40 (s, 3 H), 1.67 (m, 1 H), 1.57 (m, 1 H), 1.05 (m, 1 H), 0.92 (m, 1 H); MS (APCI+) m/z 587.1 (M+H)$^+$.

EXAMPLE 285

N-(3-{benzyl[4-(3-{[(2R)-2,3-dihydroxypropyl]oxy}phenoxy)benzyl]amino}-2-methylphenyl)methanesulfonamide

EXAMPLE 285A

N-(3-(benzyl(4-(3-(((4S)-2,2-dimethyl-1,3-dioxolan-4-yl)methoxy)phenoxy)benzyl)amino)-2-methylphenyl)methanesulfonamide The product from Example 61F (88 mg, 0.2 mmole) and (S)-(+)-2,2-dimethyl-1,3-dioxolane-4-methanol (66 mg, 0.5 mmole) were processed as in Example 278A–C to provide the titled compound.

EXAMPLE 285B

N-(3-{benzyl[4-(3-{[(2R)-2,3-dihydroxypropyl]oxy}phenoxy)benzyl]amino}-2-methylphenyl)methanesulfonamide The product from Example 285A was treated with tetrafluoroacetic acid (0.20 mL) and dichloromethane (1.8 mL). The reaction mixture was stirred for 3 hours at room temperature, then dried in vaccuo, and purified by HPLC to provide the titled compound. $^1$H NMR (500 MHz, DMSO-d$_6$) δ8.95 (s, 1 H), 7.23 (m, 8 H), 7.04 (m, 1 H), 6.94 (m, 4 H), 6.69 (m, 1 H), 6.49 (m, 2 H), 4.06 (s, 2 H), 4.03 (s, 2 H), 3.95 (m, 1 H), 3.81 (m, 1 H), 3.75 (m, 1 H), 3.41 (m, 2 H), 2.91 (s, 3 H), 2.40 (s, 3 H); MS (APCI+) m/z 563.2 (M+H)$^+$.

EXAMPLE 286

4-(3-{4-[(benzyl{2-methyl-3-[(methylsulfonyl)amino]phenyl}amino)methyl]phenoxy}phenoxy)cyclohexanecarboxylic acid The product from Example 61F (88 mg, 0.2 mmole) and ethyl 4-hydroxycyclohexanecarboxylate (86 mg, 0.5 mmole) were processed as in Example 278 A–C and 284B to provide the title compound. $^1$H NMR (500 MHz, DMSO-d$_6$) δ11.88–12.20 (m, 1 H), 8.95 (s, 1 H), 7.23 (m, 8 H), 7.03 (m, 1 H), 6.94 (m, 4 H), 6.69 (m, 1 H), 6.52 (m, 1 H), 6.46 (m, 1 H), 4.20–4.52 (m, 1 H), 4.06 (s, 2 H), 4.03 (s, 2 H), 2.91 (s, 3 H), 2.40 (s, 3 H), 2.17–2.38 (m, 1 H), 1.85–2.06 (m, 3 H), 1.57–1.83 (m, 2 H), 1.29–1.55 (m, 3 H); MS (APCI+) m/z 615.1 (M+H)$^+$.

EXAMPLE 287

N-[3-(benzyl{4-[3-(tetrahydro-2H-pyran-4-yloxy)phenoxy]benzyl}amino)-2-methylphenyl]methanesulfonamide The product from Example 61F (88 mg, 0.2 mmole) and tetrahydro-2H-pyran-4-ol (51 mg, 0.5 mmole) were processed as in Example 278A–C to provide the titled compound. $^1$H NMR (500 MHz, DMSO-d$_6$) δ8.95 (s, 1 H), 7.24 (m, 8 H), 7.04 (m, 1 H), 6.95 (m, 4 H), 6.73 (dd, 1 H), 6.56 (m, 1 H), 6.48 (dd, 1 H), 4.53 (m, 1 H), 4.06 (s, 2 H), 4.03 (s, 2 H), 3.81 (m, 2 H), 3.45 (m, 2 H), 2.91 (s, 3 H), 2.40 (s, 3 H), 1.92 (m, 2 H), 1.55 (m, 2 H); MS (APCI+) m/z 573.7 (M+H)$^+$.

EXAMPLE 288

N-[3-(benzyl{4-[3-(tetrahydrofuran-3-yloxy)phenoxy]benzyl}amino)-2-methylphenyl]methanesulfonamide The product from Example 61F (88 mg, 0.2 mmole) and 3-hydroxytetrahydrofuran (44 mg, 0.5 mmole) were processed as in Example 278A–C to provide the titled compound. $^1$H NMR (500 MHz, DMSO-d$_6$) δ8.95 (s, 1 H), 7.24 (m, 8 H), 6.99 (m, 5 H), 6.67 (m, 1 H), 6.50 (m, 2 H), 4.97 (m, 1 H), 4.06 (s, 2 H), 4.03 (s, 2 H), 3.79 (m, 4 H), 2.91 (s, 3 H), 2.39 (s, 3 H), 2.17 (m, 1 H), 1.93 (m, 1 H); MS (APCI+) m/z 559.6 (M+H)$^+$.

EXAMPLE 289

N-(3-{benzyl[4-(3-{[(2S)-1-methylpyrrolidin-2-yl]methoxy}phenoxy)benzyl]amino}-2-methylphenyl)methanesulfonamide The product from Example 61F (88 mg, 0.2 mmole) and (S)-(−)-2-hydroxymethyl-1-methylpyrrolidine (58 mg, 0.5 mmole) were processed as in Example 278A–C to provide the titled compound. $^1$H NMR (500 MHz, DMSO-d$_6$) δ8.95 (s, 1 H), 7.25 (m, 8 H), 7.04 (t, 1 H), 6.95 (m, 4 H), 6.79 (d, 1 H), 6.64 (dd, 1 H), 6.58 (dd, 1 H), 4.31 (dd, 1 H), 4.16 (dd, 2 H), 4.06 (s, 2 H), 4.04 (s, 2 H), 2.93 (d, 2 H), 2.92 (s, 3 H), 2.77 (d, 2 H), 2.50 (s, 3 H), 2.40 (s, 3 H), 1.86 (m, 2 H); MS (APCI+) m/z 586 (M+H)$^+$.

EXAMPLE 290

N-[3-(benzyl{4-[3-(pyridin-3-ylmethoxy)phenoxy]benzyl}amino)-2-methylphenyl]methanesulfonamide The product from Example 61F (88 mg, 0.2 mmole) and pyridine-3-methanol (55 mg, 0.5 mmole) were processed as in Example 278A–C to provide the titled compound. $^1$H NMR (500 MHz, DMSO-d$_6$) δ8.95 (s, 1 H), 8.81 (s, 1 H), 8.71 (d, 1 H), 8.20 (d, 1 H), 7.73 (dd, 1 H), 7.28 (m, 7 H), 7.20 (m, 1 H), 7.03 (m, 1 H), 6.94 (m, 4 H), 6.81 (dd, 1 H), 6.66 (t, 1 H), 6.55 (dd, 1 H), 5.21 (s, 2 H), 4.07 (s, 2 H), 4.04 (s, 2 H), 2.91 (s, 3 H), 2.40 (s, 3 H); MS (APCI+) m/z 580 (M+H)$^+$.

EXAMPLE 291

N-{3-[benzyl(4-{3-[(2S)-pyrrolidin-2-ylmethoxy]phenoxy}benzyl)amino]-2-methylphenyl}methanesulfonamide The product from Example 61F (88 mg, 0.2 mmole) and 1-methyl-3-pyrrolidinol (51 mg, 0.5 mmole) were processed as in Example 278A–C and 285B to provide the title compound processed as in Example 278A–C and 285B to provide the title compound. $^1$H NMR (500 MHz, DMSO-d$_6$) δ8.96 (s, 1 H), 7.28 (m, 7 H), 7.20 (m, 1 H), 7.04 (m, 1 H), 6.95 (m, 4 H), 6.75 (m, 1 H), 6.58 (m, 2 H), 4.23 (m, 1 H), 4.06 (s, 2 H), 4.04 (s, 2 H), 4.03 (m, 1 H), 3.89 (m, 1 H), 3.20 (m, 2 H), 2.92 (s, 3 H), 2.40 (s, 3 H), 2.10 (m, 1 H), 1.92 (m, 2 H), 1.70 (m, 1 H); MS (APCI+) m/z 572 (M+H)$^+$.

EXAMPLE 292

N-{3-[benzyl(4-{3-[(1-methylpyrrolidin-3-yl)oxy]phenoxy}benzyl)amino]-2-methylphenyl}methanesulfonamide The product from Example 61F (88 mg, 0.2 mmole) and 1-methyl-3-pyrrolidinol (51 mg, 0.5 mmole) were processed as in Example 278A–C to provide the titled compound. $^1$H NMR (500 MHz, DMSO-d$_6$) δ8.95 (s, 1 H), 7.29 (m, 7 H), 7.20 (m, 1 H), 7.04 (m, 1 H), 6.95 (m, 4 H), 6.72 (m, 1 H), 6.56 (m, 2 H), 5.12 (m, 1 H), 4.06 (s, 2 H), 4.04 (s, 2 H), 3.33 (m, 1 H), 3.23 (m, 1 H), 3.11 (m, 1 H), 2.92 (s, 3 H), 2.85 (m, 3 H), 2.57 (m, 1 H), 2.40 (s, 3 H), 2.24 (m, 1 H), 2.03 (m, 1 H); MS (APCI+) m/z 572.6 (M+H)$^+$.

EXAMPLE 293

N-{3-[benzyl(4-chloro-2-fluorobenzyl)amino]-2-methylphenyl}methanesulfonamide

The product from Example 6A and 2-flouro-4-chloro-1-(bromomethyl)benzene were processed as described in Example 6B–D to provide the titled compound. $^1$H NMR (500 MHz, DMSO-d$_6$) δ8.95 (s, 1 H), 7.25 (m, 8 H), 7.04 (t, 1 H), 6.99 (d, 1 H), 6.94 (d, 1 H), 4.08 (s, 4 H), 2.89 (s, 3 H), 2.34 (s, 3 H); MS (APCI+) m/z 433 (M+H)$^+$.

EXAMPLE 294

N-[4-(3-{4-[(benzyl{2-methyl-3-[(methylsulfonyl)amino]phenyl}amino)methyl]phenoxy}phenoxy)butanoyl]-L-glutamic acid The product from Example 116B (57 mg, 0.10 mmole) and H-GLU(OME)-OME hydrochloride (42 mg, 0.20 mmole) were processed as in Example 279 A and B to provide the titled compound. $^1$H NMR (500 MHz, DMSO-d$_6$) δ12.32–12.71 (br.s, 1 H), 11.89–12.32 (br.s, 1 H), 8.95 (s, 1 H), 8.10 (d, 1 H), 7.24 (m, 8 H), 7.04 (m, 1 H), 6.95 (m, 4 H), 6.68 (dd, 1 H), 6.49 (m, 2 H), 4.20 (m, 1 H), 4.06 (s, 2 H), 4.03 (s, 2 H), 3.93 (t, 2 H), 2.91 (s, 3 H), 2.40 (s, 3 H), 2.26 (m, 4 H), 1.93 (m, 3 H), 1.75 (m, 1 H); MS (APCI+) m/z 703.9 (M+H)$^+$.

EXAMPLE 295

4-(3-{4-[(benzyl{2-methyl-3-[(methylsulfonyl)amino]phenyl}amino)methyl]phenoxy}phenoxy)-N-(2-oxotetrahydrofuran-3-yl)butanamide The product from Example 116B (57 mg, 0.10 mmole) and (α-Amino-γ-butyrolactone hydrobromide (36 mg, 0.20 mmole) were processed as in Example 279A to provide the titled compound. $^1$H NMR (500 M/z, DMSO-d$_6$) δ8.95 (s, 1 H), 8.36 (d, 1 H), 7.23 (m, 8 H), 7.04 (m, 1 H), 6.94 (m, 4 H), 6.69 (dd, 1 H), 6.50 (m, 2 H), 4.53 (d, 1 H), 4.33 (d, 1 H), 4.19 (ddd, 1 H), 4.06 (s, 2 H), 4.03 (s, 2 H), 3.94 (t, 2 H), 2.91 (s, 3 H), 2.40 (s, 3 H), 2.35 (m, 1 H), 2.27 (m, 2 H), 2.13 (m, 1 H), 1.91 (m, 2 H); MS (APCI+) m/z 702.9 (M+H)$^+$.

EXAMPLE 296

N-[4-(3-{4-[(benzyl{2-methyl-3-[(methylsulfonyl)amino]phenyl}amino)methyl]phenoxy}phenoxy)butanoyl]-L-leucine The product from Example 116B (57 mg, 0.10 mmole) and L-leucine methyl ester hydrochloride (36 mg, 0.20 mmole) were processed as in Example 279A and B to provide the titled compound. $^1$H NMR (500 MHz, DMSO-d$_6$) δ12.22–12.61 (br.s, 1 H), 8.95 (s, 1 H), 8.06 (d, 1 H), 7.24 (m, 8 H), 7.03 (m, 1 H), 6.94 (m, 4 H), 6.67 (dd, 1 H), 6.49 (m, 2 H), 4.22 (m, 1 H), 4.06 (s, 2 H), 4.03 (s, 2 H), 3.91 (m, 2 H), 2.91 (s, 3 H), 2.40 (s, 3 H), 2.26 (m, 2 H), 1.90 (m, 2 H), 1.60 (m, 1 H), 1.47 (m, 2 H), 0.85 (d, 3 H), 0.81 (d, 3 H); MS (APCI+) m/z 688.7 (M+H)$^+$.

EXAMPLE 297

N-[4-(3-{4-[(benzyl{2-methyl-3-[(methylsulfonyl)amino]phenyl}amino)methyl]phenoxy}phenoxy)butanoyl]-L-aspartic acid The product from Example 116B (57 mg, 0.10 mmole) and H-ASP(OME)-OME hydrocloride (36 mg, 0.20 mmole) were processed as in Example 279A and B to provide the titled compound. $^1$H NMR (500 MHz, DMSO-d$_6$) δ11.68–13.28 (br.s, 2 H), 8.95 (s, 1 H), 8.18 (d, 1 H), 7.24 (m, 8 H), 7.04 (m, 1 H), 6.95 (m, 4 H), 6.68 (dd, 1 H), 6.49 (m, 2 H), 4.53 (m, 1 H), 4.06 (s, 2 H), 4.03 (s, 2 H), 3.92 (m, 2 H), 2.91 (s, 3 H), 2.68 (m, 1 H), 2.55 (m, 1 H), 2.39 (s, 3 H), 2.24 (m, 2 H), 1.89 (m, 2 H); MS (APCI+) m/z 690.7 (M+H)$^+$.

EXAMPLE 298

N-[4-(3-{4-[(benzyl{2-methyl-3-[(methylsulfonyl)amino]phenyl}amino)methyl]phenoxy}phenoxy)butanoyl]-L-valine The product from Example 116B (57 mg, 0.10 mmole) and L-valine methyl ester hydrochloride (34 mg, 0.20 mmole) were processed as in Example 279A and B to provide the titled compound. $^1$H NMR (500 MHz, DMSO-d$_6$) δ12.03–12.85 (br.s, 1 H), 8.95 (s, 1 H), 7.96 (d, 1 H), 7.23 (m, 8 H), 7.04 (m, 1 H), 6.94 (m, 4 H), 6.68 (dd, 1 H), 6.49 (m, 2 H), 4.14 (dd, 1 H), 4.06 (s, 2 H), 4.03 (s, 2 H), 3.92 (t, 2 H), 2.91 (s, 3 H), 2.40 (s, 3 H), 2.31 (m, 2 H), 2.02 (m, 1 H), 1.90 (m, 2 H), 0.86 (s, 3 H), 0.85 (s, 3 H); MS (APCI+) m/z 674.7 (M+H)$^+$.

EXAMPLE 299

1-[(2-chloro-5-{4-[((2,4-difluorobenzyl){2-methyl-3-[(methylsulfonyl)amino]phenyl}amino)methyl]phenoxy}phenoxy)acetyl]piperidine-4-carboxamide The product from Example 91 (62 mg, 0.1 mmoles) in anhydrous dimethylformamide (1.0 ml) was treated with 1-[3-(dimethylamino)propyl]-3-ethylcarbodiimide hydrochloride (27 mg, 0.14 mmoles) and 1-hydroxybenzotriazole hydrate (19 mg, 0.14 mmoles) at room temperature for 15 minutes. A mixture of isonipecotamide (24.4 mg, 0.21 mmole) and N,N-diisopropylethylamine (0.056 ml, 0.4 mmoles) in anhydrous dimethylformamide (0.2 ml) was added to the reaction and shaken at room temperature overnight. The reaction mixture was acidified with 1N aqueous hydrochloric acid and extracted with dichloromethane. The organic layer was washed with saturated aqueous sodium bicarbonate solution and brine, dried over anhydrous sodium sulfate, filtered and filtrate concentrated in vacuo. The residue purified by HPLC to provide the titled compound. $^1$H NMR (500 MHz, DMSO-d$_6$) δ8.94 (s, 1 H), 7.37 (d, 1 H), 7.26 (m, 4 H), 7.09 (m, 2 H), 6.96 (m, 5 H), 6.78 (d, 1 H), 6.75 (s, 1 H), 6.45 (dd, 1 H), 4.92 (m, 2 H), 4.23 (d, 1 H), 4.07 (d, 4 H), 3.79 (d, 1 H), 3.00 (t, 1 H), 2.90 (s, 3 H), 2.64 (m, 1 H), 2.32 (m, 4 H), 1.71 (m, 2 H), 1.51 (m, 1 H), 1.33 (m, 1 H); MS (ESI+) m/z 727 (M+H)$^+$.

EXAMPLE 300

2-(2-chloro-5-{4-[((2,4-difluorobenzyl){2-methyl-3-[(methylsulfonyl)amino]phenyl}amino)methyl]phenoxy}phenoxy)-N-[3-(2-oxopyrrolidin-1-yl)propyl]acetamide The product from Example 91 and 1-(3-aminopropyl)-2-pyrrolidinone were processed as described in Example 299 to provide the titled compound. $^1$H NMR (500 MHz, DMSO-d$_6$) δ8.94 (s, 1 H), 7.92 (t, 1 H), 7.40 (d, 1 H), 7.26 (m, 3 H), 7.09 (m, 2 H), 6.96 (m, 5 H), 6.74 (d, 1 H), 6.51 (dd, 1 H), 4.56 (s, 2 H), 4.07 (d, 4 H), 3.27 (m, 2 H), 3.13 (t, 2 H), 3.07 (dd, 2 H), 2.90 (s, 3 H), 2.33 (s, 3 H), 2.18 (t, 2 H), 1.88 (m, 2 H), 1.56 (m, 2 H); MS (ESI+) m/z 741 (M+H)$^+$.

EXAMPLE 301

2-(2-chloro-5-{4-[((2,4-difluorobenzyl){2-methyl-3-[(methylsulfonyl)amino]phenyl}amino)methyl]phenoxy}phenoxy)-N-(1,3-thiazol-5-ylmethyl)acetamide The product from Example 91 and 5-(aminomethyl)thiazole were processed as described in Example 299 to provide the titled compound. $^1$H NMR (500 MHz, DMSO-d$_6$) δ9.02 (s, 1 H), 8.95 (s, 1 H), 8.47 (t, 1 H), 7.39 (m, 2 H), 7.27 (m, 3 H), 7.09 (m, 2 H), 6.96 (m, 5 H), 6.79 (d, 1 H), 6.50 (dd, 1 H), 4.66 (s, 2 H), 4.46 (d, 2 H), 4.07 (d, 4 H), 2.90 (s, 3 H), 2.33 (s, 3 H); MS (ESI+) m/z 713 (M+H)$^+$.

EXAMPLE 302

2-(2-chloro-5-{4-[((2,4-difluorobenzyl){2-methyl-3-[(methylsulfonyl)amino]phenyl}amino)methyl]phenoxy}phenoxy)-N-(3-morpholin-4-ylpropyl)acetamide The product from Example 91 and N-(3-aminopropyl)morpholine were processed as described in Example 299 to provide the titled compound. $^1$H NMR (500 MHz, DMSO-d$_6$) δ8.95 (s, 1 H), 8.08 (t, 1 H), 7.41 (d, 1 H), 7.26 (m, 3 H), 7.10 (m, 2 H), 6.96 (m, 5 H), 6.79 (d, 1 H), 6.50 (dd, 1 H), 4.59 (s, 2 H), 4.07 (d, 4 H), 3.96 (d, 2 H), 3.61 (m, 2 H), 3.39 (d, 2 H), 3.20 (dd, 2 H), 3.05 (m, 4 H), 2.90 (s, 3 H), 2.33 (s, 3 H), 1.82 (m, 2 H); MS (ESI+) m/z 743 (M+H)$^+$.

EXAMPLE 303

N-[4-(3-{4-[(benzyl{2-methyl-3-[(methylsulfonyl)amino]phenyl}amino)methyl]phenoxy}phenoxy)butanoyl]-L-serine

EXAMPLE 303A

The product from Example 116 (57 mg, 0.10 mmole) and O-tert-butyl-L-serine tert-butyl ester hydrochloride (60 mg, 0.20 mmole) were processed as in Example 279A to provide the titled compound.

EXAMPLE 303B

The product from example 303A was treated with trifluoroacetic acid (0.2 mL) and dichloromethane (1.8 mL) at room temperature for about 4 hours with shaking. Saturated NaHCO$_3$ solution (2 mL) was added to neutralize the reaction mixture 1N hydrochloric acid was used to adjust the pH value to 2~3. The organic layer was separated, dried (MgSO$_4$), concentrated in vaccuo, and purified by HPLC to provide the titled compound. $^1$H NMR (500 MHz, DMSO-d$_6$) δ11.94–12.89 (br.s, 1 H), 8.95 (s, 1 H), 7.98 (d, 1 H), 7.24 (m, 8 H), 7.03 (m, 1 H), 6.94 (m, 4 H), 6.68 (dd, 1 H), 6.49 (m, 2 H), 4.27 (m, 1 H), 4.06 (s, 2 H), 4.03 (s, 2 H), 3.94 (t, 2 H), 3.67 (dd, 1 H), 3.61 (dd, 1 H), 2.91 (s, 3 H), 2.39 (s, 3 H), 2.30 (t, 2 H), 1.90 (m, 2 H); MS (APCI+) m/z 662.1 (M+H)$^+$.

EXAMPLE 304

N~2~-[4-(3-{4-[(benzyl{2-methyl-3-[(methylsulfonyl)amino]phenyl}amino)methyl]phenoxy}phenoxy)butanoyl]-L-glutamine The product from Example 116 (57 mg, 0.10 mmole) and L-glutamine tert-butyl ester hydrochloride (26 mg, 0.20 mmole) were processed as in Example 303A and B to provide the titled compound. $^1$H NMR (500 MHz, DMSO-d$_6$) δ12.07–12.91 (br.s, 1 H), 8.95 (s, 1 H), 8.11 (d, 1 H), 7.23 (m, 9 H), 7.05 (m, 1 H), 6.95 (m, 4 H), 6.71 (m, 2 H), 6.49 (m, 2 H), 4.15 (m, 1 H), 4.06 (s, 2 H), 4.03 (s, 2 H), 3.93 (t, 2 H), 2.91 (s, 3 H), 2.40 (s, 3 H), 2.27 (t, 2 H), 2.11 (t, 2 H), 1.92 (m, 1 H), 1.90 (t, 2 H), 1.73 (m, 1 H); MS (APCI+) m/z 703.7 (M+H)$^+$.

EXAMPLE 305

(5-(4-(((2,4-difluorobenzyl)(2-methyl-3-((methylsulfonyl)amino)phenyl)amino)methyl)phenoxy)-2-fluorophenoxy)acetic acid

EXAMPLE 305A 4-fluorobenzene-1,3-diol

[1-(Chloromethyl)-4-fluoro-1,4-diazoniabicyclo[2.2.2]octane bis(tetrafluoroborate)] (SELECTFLUOR) (1.61 g., 4.54 mmoles) in anhydrous acetonitrile (50 mL) was treated with resorcinol (0.500 g., 4.54 mmoles) and heated at 100° C. overnight. The reaction was diluted with diethyl ether, washed with H$_2$O (2x), saturated NaHCO$_3$ (2x), brine, dried (Na$_2$SO$_4$), filtered, and the filtrate concentrated under reduced pressure. MS (DCI) m/z 129 (M+H)$^+$.

EXAMPLE 305B 3-(allyloxy)-4-fluorophenyl 4-methylbenzenesulfonate

The product from Example 305A was processed as described in Example 63A. MS (DCI) m/z 300 (M+NH$_4$)$^+$.

EXAMPLE 305C 3-(allyloxy)-4-fluorophenol

The product from Example 305B was processed as described in Example 63B. MS (DCI) m/z 168 (M+H)$^+$.

EXAMPLE 305D 4-(3-(allyloxy)-4-fluorophenoxy)benzaldehyde

The product from Example 305C and 4-fluorobenzaldehyde were processed as in Example 61C to provide the title compound.

EXAMPLE 305E

N-(4-(3-(allyloxy)-4-fluorophenoxy)benzyl)-N-(2-methyl-3-nitrophenyl)amine

The product from Example 305D and 2-methyl-3-nitroaniline were processed as in Example 6A to provide the title compound. MS (ESI–) m/z 407 (M–H)$^+$.

EXAMPLE 305F

N-(4-(3-(allyloxy)-4-fluorophenoxy)benzyl)-N-(2,4-difluorobenzyl)-N-(2-methyl-3-nitrophenyl)amine The product from Example 305E and 2,4-difluorobenzyl bromide were processed as described in Example 6B to provide the title compound. MS (ESI+) m/z 535 (M+H)$^+$.

EXAMPLE 305G 5-(4-(((2,4-difluorobenzyl)(2-methyl-3-nitrophenyl)amino)methyl)phenoxy)-2-fluorophenol The product from Example 305F was processed as described in Example 33A to provide the title compound.

EXAMPLE 305H ethyl (5-(4-(((2,4-difluorobenzyl)(2-methyl-3-nitrophenyl)amino)methyl)phenoxy)-2-fluorophenoxy)acetate The product from Example 305G and ethyl glycolate were processed as described in Example 62A to provide the title compound.

EXAMPLE 305I ethyl (5-(4-(((2,4-difluorobenzyl)(2-methyl-3-((methylsulfonyl)amino)phenyl)amino)methyl)phenoxy)-2-fluorophenoxy)acetate The product from Example 305H was processed as described in Example 6C and D to provide the title compound.

EXAMPLE 305J (5-(4-(((2,4-difluorobenzyl)(2-methyl-3-((methylsulfonyl)amino)phenyl)amino)methyl)phenoxy)-2-fluorophenoxy)acetic acid The product from Example 305I was processed as described in Example 50 to provide the title compound. $^1$H NMR (500 MHz, DMSO) δ8.95 (s, 1 H), 7.26 (d, 2 H), 7.21 (m, 2 H), 7.11 (m, 1 H), 7.05 (d, 1 H), 7.00 (d, 1 H), 6.95 (m, 2 H), 6.88 (d, 2 H), 6.82 (m, 1 H), 6.48 (m, 1 H), 4.75 (s, 2 H), 4.07 (s, 2 H), 4.05 (s, 2 H), 2.90 (s, 3 H), 2.33 (s, 3 H); MS (ESI+) m/z 601 (M+H)$^+$.

EXAMPLE 306

(2-chloro-5-(4-(((2-fluorobenzyl)(2-methyl-3-((methylsulfonyl)amino)phenyl)amino)methyl)phenoxy)phenoxy)acetic acid

EXAMPLE 306A ethyl (2-chloro-5-(4-(((2-methyl-3-nitrophenyl)amino)methyl)phenoxy)phenoxy)acetate The product from Example 91D was processed as in Examples 33A and 62A to provide the title compound.

EXAMPLE 306B ethyl (2-chloro-5-(4-(((2-fluorobenzyl)(2-methyl-3-nitrophenyl)amino)methyl)phenoxy)phenoxy)acetate The product from Example 306A (86 mg, 0.18 mmoles) in anhydrous dimethylformamide (1 mL) was treated with Hunig's base (0.107 mL, 0.5 mmoles) and 1-(bromomethyl)-2-fluorobenzene (0.198 mL, 0.9 mmoles) in anhydrous dimethylformamide (1 mL) and heated at 90° C. for 72 hours. The reaction was diluted with ether, washed with saturated NH$_4$Cl, water, brine, dried (Na$_2$SO$_4$), filtered, and filtrate concentrated under reduced pressure. The residue purified by using ethyl acetate and hexane gradient on 10 g silica column to provide the title compound.

EXAMPLE 306C ethyl (5-(4-(((3-amino-2-methylphenyl)(2-fluorobenzyl)amino)methyl)phenoxy)-2-chlorophenoxy)acetate The product from Example 306B in ethanol (1.2 mL) and H$_2$O (0.6 mL) was treated with iron powder (100 mg, 1.8 mmoles) and NH$_4$Cl (10 mg, 0.18 mmoles) at 80° C. overnight. The reaction mixture filtered, residue washed with methanol and dichloromethane, the filtrate concentrated in vacuo to provide the title compound.

EXAMPLE 306D ethyl (2-chloro-5-(4-(((2-fluorobenzyl)(2-methyl-3-((methylsulfonyl)amino)phenyl)amino)methyl)phenoxy)phenoxy)acetate compound with ethane (1:1)

The product from Example 306C in anhydrous pyridine (1.5 mL) was cooled at 0° C. and treated with methane sulfonyl chloride (0.042 mL, 0.54 mmoles) at 0° C. for 1 hour, then room temperature for 1 hour. The reaction mixture concentrated in vacuo, residue dissolved in dichloromethane, filtered and filtrate concentrated in vacuo to provide the title compound.

EXAMPLE 306E

The product from Example 306D was treated with 2M aqueous NaOH (2 mL), tetrahydrofuran (1 mL) and ethanol (1 mL) at room temperature overnight. The reaction was acidified with 1 M aqueous hydrochloric acid to pH 3–4, extracted with ethyl acetate, dried (Na$_2$SO$_4$), filtered and filtrate concentrated in vacuo. The residue was purified by HPLC to provide the title compound. $^1$H NMR (500 MHz, DMSO-d6) δ ppm 12.76–13.43 (br.s, 1 H), 8.94 (s, 1 H), 7.38 (d, 1 H), 7.26 (m, 4 H), 7.07 (m, 3 H), 6.95 (m, 4 H), 6.77 (d, 1 H) 6.47 (dd, 1 H), 4.78 (s, 2 H), 4.11 (s, 2 H), 4.07 (s, 2 H), 2.90 (s, 3 H), 2.35 (s, 3 H); MS (ESI+) m/z 599 (M+H).

EXAMPLE 307

(5-(4-(((2-bromobenzyl)(2-methyl-3-((methylsulfonyl)amino)phenyl)amino)methyl)phenoxy)-2-chlorophenoxy)acetic acid The product from Example 306A and 1-bromo-2-(bromomethyl)benzene were processed as described in Example 306B–E to provide the title compound. $^1$H NMR (500 MHz, DMSO-d6) δ ppm 8.93 (s, 1 H), 7.55 (d, 1 H), 7.42 (d, 1 H), 7.38 (d, 1 H), 7.28 (m, 3 H), 7.15 (m, 1 H), 7.15 (br.s, 1 H), 7.07 (t, 1 H), 7.00 (t, 2 H), 6.93 (d, 2 H), 6.76 (d, 1 H), 6.46 (dd, 1 H), 4.78 (s, 2 H), 4.17 (s, 2 H), 4.11 (s, 2 H), 2.89 (s, 3 H), 2.32 (s, 3 H); MS (ESI+) m/z 681 (M+22).

EXAMPLE 308

(5-(4-(((4-bromobenzyl)(2-methyl-3-((methylsulfonyl)amino)phenyl)amino)methyl)phenoxy)-2-chlorophenoxy)acetic acid The product from Example 306A and 1-bromo-4-(bromomethyl)benzene were processed as described in Example 306B–E to provide the title compound. $^1$H NMR (500 MHz, DMSO-d6) δ ppm 12.84–13.29 (br.s, 1 H), 8.95 (s, 1 H), 7.45 (d, 2 H), 7.38 (d, 1 H), 7.26 (d, J=8.7 Hz, 2 H), 7.20 (d, 2 H), 7.04 (t, 1 H), 6.95 (m, 4 H), 6.76 (d, 1 H), 6.48 (dd, 1 H), 4.78 (s, 2 H), 4.03 (d, 4 H), 2.92 (s, 3 H), 2.38 (s, 3 H); MS (ESI+) m/z 661 (M+H).

EXAMPLE 309

(2-chloro-5-(4-(((2,4-dichlorobenzyl)(2-methyl-3-((methylsulfonyl)amino)phenyl)amino)methyl)phenoxy)phenoxy)acetic acid The product from Example 306A and 2,4-dichloro-1-(iodomethyl)benzene were processed as described in Example 306B–E to provide the title compound. $^1$H NMR (500 MHz, DMSO-d6) δ ppm 12.78–13.45 (br.s, 1 H), 8.94 (s, 1 H), 7.52 (d, 1 H), 7.38 (d, 2 H), 7.32 (dd, 1 H), 7.26 (d, 2 H), 7.07 (t, 1 H), 7.00 (d, 2 H), 6.93 (d, 2 H), 6.76 (d, 1 H), 6.46 (dd, 1 H), 4.78 (s, 2 H), 4.16 (s, 2 H), 4.09 (s, 2 H), 2.90 (s, 3 H), 2.30 (s, 3 H); MS (ESI+) m/z 651 (M+H).

EXAMPLE 310

(2-chloro-5-(4-(((4-chloro-2-fluorobenzyl)(2-methyl-3-((methylsulfonyl)amino)phenyl)amino)methyl)phenoxy)phenoxy)acetic acid The product from Example 306A and 2-fluoro-4-chloro-1-(bromomethyl)benzene were processed as described in Example 306B–E to provide the title compound. $^1$H NMR (500 MHz, DMSO-d6) δ ppm 12.86–13.21 (br.s, 1 H), 8.95 (s, 1 H), 7.38 (d, 1 H), 7.28 (m, 4 H), 7.17 (d, 1 H), 7.06 (t, 1 H), 6.96 (m, 4 H), 6.77 (d, 1 H), 6.47 (dd, 1 H), 4.78 (s, 2 H), 4.07 (d, 4 H), 2.90 (s, 3 H), 2.33 (s, 3 H); MS (ESI+) m/z 633 (M+H).

EXAMPLE 311

(2-chloro-5-(4-(((2-chloro-4-fluorobenzyl)(2-methyl-3-((methylsulfonyl)amino)phenyl)amino)methyl)phenoxy)phenoxy)acetic acid The product from Example 306A and 2-chloro-4-fluoro-1-(bromomethyl)benzene were processed as described in Example 306B–E to provide the title compound. $^1$H NMR (500 MHz, DMSO-d6) δ ppm 12.86–13.32 (br.s, 1 H), 8.93 (s, 1 H), 7.39 (m, 2 H), 7.34 (dd, 1 H), 7.26 (d, 2 H), 7.11 (t, 1 H), 7.07 (d, 1 H), 7.01 (t, 2 H), 6.93 (d, 2 H), 6.76 (d, 1 H), 6.46 (dd, 1 H), 4.78 (s, 2 H), 4.15 (s, 2 H), 4.09 (s, 2 H), 2.89 (s, 3 H), 2.30 (s, 3 H); MS (ESI+) m/z 633 (M+H).

EXAMPLE 312

(5-(4-(((2-bromo-4-chlorobenzyl)(2-methyl-3-((methylsulfonyl)amino)phenyl)amino)methyl)phenoxy)-2-chlorophenoxy)acetic acid The product from Example 306A and 2-bromo-4-chloro-1-(bromomethyl)benzene were processed as described in Example 306B–E to provide the title compound. $^1$H NMR (500 MHz, DMSO-d6) δ ppm 12.84–13.32 (br.s, 1 H), 8.96 (s, 1 H), 7.67 (s, 1 H), 7.38 (m, 3 H), 7.24 (d, 2 H), 7.07 (d, 1 H), 7.00 (d, 2 H), 6.92 (d, 2 H), 6.74 (s, 1 H), 6.46 (dd, 1 H), 4.75 (s, 2 H), 4.15 (s, 2 H), 4.10 (s, 2 H), 2.90 (s, 3 H), 2.30 (s, 3 H); MS (ESI+) m/z 695 (M+H).

EXAMPLE 313

(2-chloro-5-(4-(((3,4-difluorobenzyl)(2-methyl-3-((methylsulfonyl)amino)phenyl)amino)methyl)phenoxy)phenoxy)acetic acid The product from Example 306A and 3,4-difluoro-1-(bromomethyl)benzene were processed as described in Example 306B–E to provide the title compound. $^1$H NMR (500 MHz, DMSO-d6) δ ppm 12.91–13.25 (br.s, 1 H), 8.96 (s, 1 H), 7.38 (d, 1 H), 7.27 (m, 4 H), 7.08 (m, 2 H), 6.95 (m, 4 H), 6.76 (d, 1 H), 6.47 (dd, 1 H), 4.78 (s, 2 H), 4.05 (d, 4 H), 2.92 (s, 3 H), 2.38 (s, 3 H); MS (ESI–) m/z 695 (M+79).

EXAMPLE 314

(5-(4-(((4-benzoylbenzyl)(2-methyl-3-((methylsulfonyl)amino)phenyl)amino)methyl)phenoxy)-2-chlorophenoxy)acetic acid The product from Example 306A and 4-(bromomethyl)benzophenone were processed as described in Example 306B–E to provide the title compound. $^1$H NMR (500 MHz, DMSO-d6) δ ppm 12.76–13.43 (br.s, 1 H), 8.97 (s, 1 H), 7.67 (m, 5 H), 7.55 (t, 2 H), 7.46 (d, 2 H), 7.38 (d, 1 H), 7.29 (d, 2 H), 7.06 (t, 1 H), 7.00 (t, 2 H), 6.94 (d, 2 H), 6.76 (d, 1 H), 6.48 (dd, 1 H), 4.78 (s, 2 H), 4.18 (s, 2 H), 4.07 (s, 2 H), 2.92 (s, 3 H), 2.41 (s, 3 H); MS (ESI–) m/z 685 (M+79).

EXAMPLE 315

(5-(4-(((4-bromo-2-fluorobenzyl)(2-methyl-3-((methylsulfonyl)amino)phenyl)amino)methyl)phenoxy)-2-chlorophenoxy)acetic acid The product from Example 306A and 2-fluoro-4-bromo-1-(bromomethyl)benzene were processed as described in Example 306B–E to provide the title compound. $^1$H NMR (500 MHz, DMSO-d6) δ ppm 12.67–13.36 (br.s, 1 H), 8.95 (s, 1 H), 7.43 (dd, 1H), 7.39 (d, 1 H), 7.29 (t, 3 H), 7.18 (t, 1 H), 7.06 (t, 1 H), 7.00 (d, 1 H), 6.96 (d, 1H), 6.93 (d, 2 H), 6.76 (d, 1 H), 6.47 (dd, 1 H), 4.78 (s, 2 H), 4.07 (d, 4 H), 2.90 (s, 3 H), 2.33 (s, 3 H); MS (ESI–) m/z 679 (M+H).

EXAMPLE 316

N-((2-chloro-5-(4-(((2,4-difluorobenzyl)(2-methyl-3-((methylsulfonyl)amino)phenyl)amino)methyl)phenoxy)phenoxy)acetyl)glycine The product from Example 911 was processed as described in Example 104B to provide the title compound.

¹H NMR (300 MHz, DMSO-$d_6$) δ8.97 (s, 1 H), 8.18 (t, 1 H), 7.40 (d, 1 H), 6.90–7.33 (m, 11 H), 6.82 (d, 1 H), 6.49 (dd, 1 H), 4.62 (s, 2 H), 4.08 (s, 2 H), 4.06 (s, 2 H), 3.83 (d, 2 H), 2.90 (s, 3 H), 2.33 (s, 3 H); MS (ESI) m/z 674 (M+H⁺).

EXAMPLE 317

N-((2-chloro-5-(4-(((2,4-difluorobenzyl)(2-methyl-3-((methylsulfonyl)amino)phenyl)amino)methyl)phenoxy)phenoxy)acetyl)-beta-alanine The product from Example 91I and β-alanine ethyl ester hydrochloride was processed as described in Example 104B to provide the title compound. ¹H NMR (300 MHz, DMSO-$d_6$) δ8.97 (s, 1 H), 7.94 (t, 1 H), 7.40 (d, 1 H), 6.87–7.35 (m, 10 H), 6.76 (d, 1 H), 6.50 (dd, 1 H), 4.56 (s, 2 H), 4.08 (s, 2 H), 4.06 (s, 2 H), 3.32 (q, 2 H), 2.90 (s, 3 H), 2.39 (t, 3 H), 2.33 (s, 3 H); MS (ESI) m/z 688 (M+H⁺).

EXAMPLE 318

4-(((2-chloro-5-(4-(((2,4-difluorobenzyl)(2-methyl-3-((methylsulfonyl)amino)phenyl)amino)methyl)phenoxy)phenoxy)acetyl)amino)butanoic acid The product from Example 91I and ethyl 4-aminobutyrate hydrochloride was processed as described in Example 104B to provide the title compound. ¹H NMR (300 MHz, DMSO-$d_6$) δ8.96 (s, 1 H), 7.97 (t, 1 H), 7.39 (d, 1 H), 6.88–7.33 (m, 11 H), 6.72 (d, 1 H), 6.49 (dd, 1 H), 4.55 (s, 2 H), 4.07 (s, 2 H), 4.05 (s, 2 H), 3.11 (q, 2 H), 2.90 (s, 3 H), 2.33 (s, 3 H), 2.19 (t, 2 H), 1.61 (m, 2 H); MS (ESI) m/z 702 (M+H⁺).

EXAMPLE 319

4-((4-(5-(4-((benzyl(2-methyl-3-((methylsulfonyl)amino)phenyl)amino)methyl)phenoxy)-2-chlorophenoxy)butanoyl)amino)butanoic acid

EXAMPLE 319A

N-(4-(3-(allyloxy)-4-chlorophenoxy)benzyl)-N-benzyl-N-(2-methyl-3-nitrophenyl)amine The product from Example 91D and benzyl bromide was processed as described in Example 6B to provide the title compound.

EXAMPLE 319B ethyl 4-(5-(4-((benzyl(2-methyl-3-nitrophenyl)amino)methyl)phenoxy)-2-chlorophenoxy)butanoate The product from Example 319A was processed as described in Examples 33A and 116A to provide the title compound.

EXAMPLE 319C 4-(5-(4-((benzyl(2-methyl-3-((methylsulfonyl)amino)phenyl)amino)methyl)phenoxy)-2-chlorophenoxy)butanoic acid The product from Example 319B was processed as described in Examples 6C, 6D, and 50 to provide the title compound.

EXAMPLE 319D 4-((4-(5-(4-((benzyl(2-methyl-3-((methylsulfonyl)amino)phenyl)amino)methyl)phenoxy)-2-chlorophenoxy)butanoyl)amino)butanoic acid The product from Example 319C and ethyl 4-aminobutyrate hydrochloride was processed as described in Example 104B to provide the title compound. ¹H NMR (300 MHz, DMSO-$d_6$) δ8.97 (s, 1 H), 7.84 (t, 1 H), 7.36 (d, 1 H), 7.24 (m, 7 H), 6.99 (m, 5 H), 6.83 (d, 1 H), 6.45 (dd, 1 H), 4.06 (s, 2 H), 4.03 (s, 2 H), 3.99 (t, 2 H), 3.04 (dd, 2 H), 2.92 (s, 3 H), 2.40 (s, 3 H), 2.22 (m, 5 H), 1.92 (m, 2 H), 1.60 (m, 2 H); MS (ESI) m/z 694 (M+H⁺.

EXAMPLE 320

4-((4-(2-chloro-5-(4-(((2,4-difluorobenzyl)(2-methyl-3-((methylsulfonyl)amino)phenyl)amino)methyl)phenoxy)phenoxy)butanoyl)amino)butanoic acid

EXAMPLE 320A ethyl 4-(2-chloro-5-(4-(((2,4-difluorobenzyl)(2-methyl-3-nitrophenyl)amino)methyl)phenoxy)phenoxy)butanoate The product from Example 91F was processed as described in Example 116A to provide the title compound.

EXAMPLE 320B 4-(2-chloro-5-(4-(((2,4-difluorobenzyl)(2-methyl-3-((methylsulfonyl)amino)phenyl)amino)methyl)phenoxy)phenoxy)butanoic acid The product from Example 320A was processed as described in Examples 6C, 6D, and 50 to provide the title compound.

EXAMPLE 320C 4-((4-(2-chloro-5-(4-(((2,4-difluorobenzyl)(2-methyl-3-((methylsulfonyl)amino)phenyl)amino)methyl)phenoxy)phenoxy)butanoyl)amino)butanoic acid The product from Example 320B and ethyl 4-aminobutyrate hydrochloride was processed as described in Example 104B to provide the title compound. ¹H NMR (300 MHz, DMSO-$d_6$) δ12.03 (s, 1 H), 8.97 (s, 1 H), 7.85 (t, 1 H), 7.37 (d, 1 H), 6.89–7.33 (m, 10 H), 6.83 (d, 1 H), 6.45 (dd, 1 H), 4.08 (s, 2 H), 4.06 (s, 2 H), 3.99 (t, 2 H), 3.04 (m, 2 H), 2.90 (s, 3 H), 2.33 (s, 3 H), 2.21 (m, 4 H), 1.91 (m, 2 H), 1.60 (m, 2 H); MS (ESI) m/z 730 (M+H⁺).

EXAMPLE 321

(2R)-2-(2-chloro-5-(4-(((2,4-difluorobenzyl)(2-methyl-3-((methylsulfonyl)amino)phenyl)amino)methyl)phenoxy)phenoxy)propanoic acid

EXAMPLE 321A methyl (2R)-2-(2-chloro-5-(4-(((2,4-difluorobenzyl)(2-methyl-3-nitrophenyl)amino)methyl)phenoxy)phenoxy)propanoate The product from Example 91F and methyl-(R)-lactate was processed as described in Example 62A to provide the title compound.

EXAMPLE 321B (2R)-2-(2-chloro-5-(4-(((2,4-difluorobenzyl)(2-methyl-3-((methylsulfonyl)amino)phenyl)amino)methyl)phenoxy)phenoxy)propanoic acid The product from Example 321A was processed as described in Examples 6C, 6D and 50 to provide the title compound. $^1$H NMR (300 MHz, DMSO-d$_6$) δ13.12 (s, 1 H), 8.97 (s, 1 H), 7.38 (d, 1 H), 6.82–7.34 (m, 10 H), 6.66 (d, 1 H), 6.47 (dd, 1 H), 4.90 (q, 1 H), 4.07 (s, 2 H), 4.05 (s, 2 H), 2.90 (s, 3 H), 2.33 (s, 3 H), 1.51 (d, 3 H); MS (ESI) m/z 631 (M+H$^+$).

EXAMPLE 322

N-(3-((4-(4-chloro-3-hydroxyphenoxy)benzyl)(2,4-difluorobenzyl)amino)-2-methylphenyl)methanesulfonamide The product from Example 91F was processed as described in Examples 6C and 6D to provide the title compound. $^1$H NMR (300 MHz, CDCl$_3$) δ7.07–7.29 (m, 5 H), 6.91 (m, 3 H), 6.73 (m, 3 H), 6.59 (d, 1 H), 6.52 (dd, 1 H), 6.10 (s, 1 H), 5.57 (s, 1 H), 4.09 (s, 2 H), 4.06 (s, 2 H), 2.95 (s, 3 H), 2.29 (s, 3 H); MS (ESI) m/z 559 (M+H$^+$).

EXAMPLE 323

(2-bromo-5-(4-(((2,4-difluorobenzyl)(2-methyl-3-((methylsulfonyl)amino)phenyl)amino)methyl)phenoxy)phenoxy)acetic acid

EXAMPLE 323A

N-(4-(3-(allyloxy)-4-bromophenoxy)benzyl)-N-(2,4-difluorobenzyl)-N-(2-methyl-3-nitrophenyl)amine The product from Example 63D and 2,4-difluorobenzyl bromide were processed as described in Example 6B to provide the title compound. MS (ESI+) m/z 597 (M+H)$^+$.

EXAMPLE 323B 2-bromo-5-(4-(((2,4-difluorobenzyl)(2-methyl-3-nitrophenyl)amino)methyl)phenoxy)phenol The product from Example 323A was processed as described in Example 33A to provide the title compound. MS (ESI+) m/z 557 (M+H)$^+$.

EXAMPLE 323C ethyl (2-bromo-5-(4-(((2,4-difluorobenzyl)(2-methyl-3-nitrophenyl)amino)methyl)phenoxy)phenoxy)acetate The product from Example 323B and ethyl glycolate were processed as described in Example 62A to provide the title compound. MS (ESI+) m/z 641 (M+H)$^+$.

EXAMPLE 323D ethyl (2-bromo-5-(4-(((2,4-difluorobenzyl)(2-methyl-3-((methylsulfonyl)amino)phenyl)amino)methyl)phenoxy)phenoxy)acetate The product from Example 323C was processed as described in Example 6C and D to provide the title compound. MS (ESI+) m/z 689 (M+H)$^+$.

EXAMPLE 323E (2-bromo-5-(4-(((2,4-difluorobenzyl)(2-methyl-3-((methylsulfonyl)amino)phenyl)amino)methyl)phenoxy)phenoxy)acetic acid The product from Example 323D was processed as described in Example 50 to provide the title compound. $^1$H NMR (500 MHz, CDCl$_3$) δ7.48 (d, 1 H), 7.35 (dd, 1 H), 7.28 (dd, 1 H), 7.21 (m, 2 H), 7.09 (s, 1 H), 7.03 (d, 2 H), 7.03 (d, 2 H), 6.78 (d, 1 H), 6.73 (m, 1 H), 6.63 (dd, 1 H), 6.55 (d, 1 H), 4.64 (s, 2 H), 4.35 (s, 2 H), 4.20 (s, 2 H), 2,89 (s, 3 H), 2.01 (s, 3 H) ); MS (ESI+) m/z 663 (M+H)$^+$.

EXAMPLE 324

N-(4-(3-(4-(((2,4-difluorobenzyl)(2-methyl-3-((methylsulfonyl)amino)phenyl)amino)methyl)phenoxy)phenoxy)butanoyl)-beta-alanine The product from Example 120D and β-alanine ethyl ester hydrochloride was processed as described in Example 104B to provide the title compound. $^1$H NMR (300 MHz, DMSO-d$_6$) δ8.97 (s, 1 H), 7.90 (t, 1 H), 6.87–7.35 (m, 11 H), 6.68 (m, 1 H), 6.48 (m, 2 H), 4.08 (s, 2 H), 4.05 (s, 2 H), 3.90 (t, 2 H), 3.64 (s, 1 H), 3.22 (dd, 2 H), 2.90 (s, 3 H), 2.35 (m, 2 H), 2.33 (s, 3 H), 2.19 (t, , 2 H), 1.87 (m, 2 H); MS (ESI) m/z 682 (M+H$^+$).

EXAMPLE 325

4-((4-(3-(4-(((2,4-difluorobenzyl)(2-methyl-3-((methylsulfonyl)amino)phenyl)amino)methyl)phenoxy)phenoxy)butanoyl)amino)butanoic acid The product from Example 120D and ethyl 4-aminobutyrate hydrochloride was processed as described in Example 104B to provide the title compound. $^1$H NMR (300 MHz, DMSO-d$_6$) δ8.96 (s, 1 H), 7.83 (t, 1 H), 6.88–7.32 (m, 11 H), 6.68 (m, 1 H), 6.49 (m, 2 H), 4.08 (s, 2 H), 4.05 (s, 2 H), 3.91 (t, 2 H), 3.03 (dd, 2 H), 2.90 (s, 3 H), 2.33 (s, 3 H), 2.19 (t, 4 H), 2.07 (s, 1 H), 1.89 (m, 2 H), 1.59 (m, 2 H); MS (ESI) m/z 696 (M+H$^+$).

EXAMPLE 326

N-(4-(3-(4-(((2,4-difluorobenzyl)(2-methyl-3-((methylsulfonyl)amino)phenyl)amino)methyl)phenoxy)phenoxy)butanoyl)-N-methylglycine The product from Example 120D and sarcosine ethyl ester hydrochloride was processed as described in Example 104B to provide the title compound. $^1$H NMR (300 MHz, DMSO-d$_6$) δ8.96 (s, 1 H), 6.85–7.34 (m, 11 H), 6.69 (m, 1 H), 6.49 (m, 2 H), 4.08 (s, 2 H), 4.05 (s, 2 H), 3.94 (m, 4 H), 2.98 (s, 3 H), 2.89 (s, 3 H), 2.80 (s, 1 H), 2.50 (m, 2 H), 2.33 (s, 3 H), 1.90 (m, 2 H); MS (ESI) m/z 682 (M+H$^+$).

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13–30. The present invention contemplates various stereoisomers and mixtures thereof and are specifically included within the scope of this invention. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can also exist in the compounds of the present invention. The present invention contemplates the various geometric isomers and mixtures thereof resulting from the arrangement of substituents around a carbon-carbon double bond or arrangement of substituents around a ring. Substituents around a carbon-carbon double bond are designated as being in the Z or E configuration where the term "Z" represents substituents on the same side of the carbon-carbon double bond and the term "E" represents substituents on opposite sides of the carbon-carbon double bond. The arrangement of substituents around a ring are designated as cis or trans where the term "cis" represents substituents on the same side of the plane of the ring and the term "trans" represents substituents on opposite sides of the plane of the ring. Mixtures of compounds where the substitutients are disposed on both the same and opposite sides of plane of the ring are designated cis/trans.

The term "pharmaceutically acceptable prodrugs" represents those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug" represents compounds which are rapidly transformed in vivo to a compound of formula (I–IV), for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987.

The term "pharmaceutically acceptable salt" represents those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66:1–19 (1977). The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The present invention also provides pharmaceutical compositions, which comprise compounds of the present invention formulated together with one or more non-toxic pharmaceutically acceptable carriers. The pharmaceutical compositions may be specially formulated for oral administration in solid or liquid form, for parenteral injection, or for rectal administration.

Further included within the scope of the present invention are pharmaceutical compositions comprising one or more of the compounds of formula (I–IV) prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other animals orally, rectally, parenterally, intracistemally, intravaginally, intraperitoneally, topically (as by powders, ointments, or drops), bucally, or as an oral or nasal spray. The term "parenteral" administration refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. Conversely, reduced particle size may maintain biological activity.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally, dosage levels of about 1 to about 50 mg/kg/day, more preferably of about 5 to about 25 mg/kg/day of active compound are administered orally to a mammalian patient. If desired, the effective daily dose may be divided into multiple doses for purposes of administration, e.g. two to four separate doses per day.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound having formula (I)

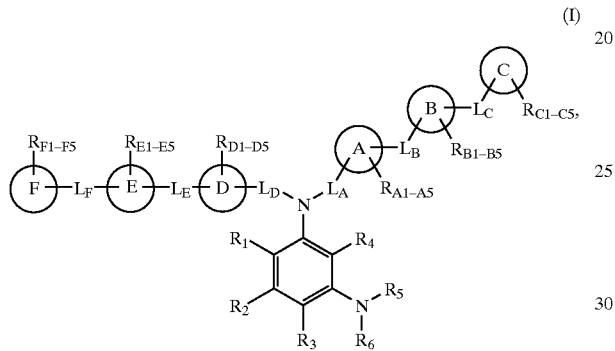

(I)

or a pharmaceutically acceptable salt or prodrug thereof, wherein $L_A$ is a covalent bond or $C(X_{A1})(X_{A2})$;

$L_D$ is a covalent bond or $C(X_{D1})(X_{D2})$;

$X_{A1}$ is selected from the group consisting of hydrogen, alkoxy, alkoxycarbonyl, alkoxyalkyl, alkyl, alkylcarbonyl, cyano, halogen, hydroxy, hydroxyalkyl, nitro and $(NR_{10}R_{11})$carbonyl;

$X_{A2}$ is selected from the group consisting of hydrogen and alkyl;

or $X_{A1}$ and $X_{A2}$ together are oxo;

$X_{D1}$ is selected from the group consisting of hydrogen, alkoxy, alkoxycarbonyl, alkoxyalkyl, alkyl, alkylcarbonyl, cyano, halogen, hydroxy, hydroxyalkyl, nitro and $(NR_{10}R_{11})$carbonyl;

$X_{D2}$ is selected from the group consisting of hydrogen and alkyl;

or $X_{D1}$ and $X_{D2}$ together are oxo;

$L_B$ is absent or selected from the group consisting of a covalent bond, alkenylene, alkylene, alkynylene, $-(CH_2)_mC(O)(CH_2)_n-$, $-(CH_2)_mC(O)(CH_2)_nCH=CH-$, $-(CH_2)_mC(O)(CH_2)_nC\equiv C-$, $-(CH_2)_mCH(OH)(CH_2)_n-$, $-(CH_2)_mCH(OH)(CH_2)_nCH_2CH=CH-$, $-(CH_2)_mCH(OH)(CH_2)_nCH_2C\equiv C-$, $-(CH_2)_mO(CH_2)_n-$, $-(CH_2)_mO(CH_2)_nCH_2CH=CH-$, $-(CH_2)_mO(CH_2)_nCH_2C\equiv C-$, $-(CH_2)_mS(CH_2)_n-$, $-(CH_2)_mS(O)(CH_2)_n-$, $-(CH_2)_mS(O)_2(CH_2)_n-$, $-(CH_2)_mN(R_7)(CH_2)_n-$, $-(CH_2)_mN(R_7)C(O)(CH_2)_n-$, $-(CH_2)_mC(O)N(R_7)(CH_2)_n-$, $-O(CH_2)_mC(O)N(R_7)(CH_2)_n-$, $-(CH_2)_mC(O)O(CH_2)_n-$, $-O(CH_2)_mC(O)(CH_2)_n-$, $-(CH_2)_mN(R_7)S(O)_2(CH_2)_n-$, $-(CH_2)_mS(O)_2N(R_7)(CH_2)_n-$, $-(CH_2)_mS(O)_2O(CH_2)_n-$ and $-(CH_2)_mOS(O)_2(CH_2)_n-$ wherein each group is inserted as drawn with the left end attached to A and the right end attached to B;

m is an integer of 0–6;

n is an integer of 0–6;

$L_C$ is absent or selected from the group consisting of a covalent bond, alkenylene, alkylene, alkynylene, $-(CH_2)_pC(O)(CH_2)_q-$, $-(CH_2)_pC(O)(CH_2)_qCH=CH-$, $-(CH_2)_pC(O)(CH_2)_qC\equiv C-$, $-(CH_2)_pCH(OH)(CH_2)_q-$, $-(CH_2)_pCH(OH)(CH_2)_qCH_2CH=CH-$, $-(CH_2)_pCH(OH)(CH_2)_qCH_2C\equiv C-$, $-(CH_2)_pO(CH_2)_q-$, $-(CH_2)_pO(CH_2)_qCH_2CH=CH-$, $-(CH_2)_pO(CH_2)_qCH_2C\equiv C-$, $-(CH_2)_pS(CH_2)_q-$, $-(CH_2)_pS(O)(CH_2)_q-$, $-(CH_2)_pS(O)_2(CH_2)_q-$, $-(CH_2)_pN(R_7)(CH_2)_q-$, $-(CH_2)_pN(R_7)C(O)(CH_2)_q-$, $-(CH_2)_pC(O)N(R_7)(CH_2)_q-$, $-O(CH_2)_pC(O)N(R_7)(CH_2)_q-$, $-(CH_2)_pC(O)O(CH_2)_q-$, $-O(CH_2)_pC(O)(CH_2)_q-$, $-(CH_2)_pN(R_7)S(O)_2(CH_2)_q-$, $-(CH_2)_pS(O)_2N(R_7)(CH_2)_q-$, $-(CH_2)_pS(O)_2O(CH_2)_q-$ and $-(CH_2)_pOS(O)_2(CH_2)_q-$ wherein each group is inserted as drawn with the left end attached to B and the right end attached to C;

p is an integer of 0–6;

q is an integer of 0–6;

$L_E$ is absent or selected from the group consisting of a covalent bond, alkenylene, alkylene, alkynylene, $-(CH_2)_rC(O)(CH_2)_s-$, $-(CH_2)_rC(O)(CH_2)_sCH=CH-$, $-(CH_2)_rC(O)(CH_2)_sC\equiv C-$, $-(CH_2)_rCH(OH)(CH_2)_s-$, $-(CH_2)_rCH(OH)(CH_2)_sCH_2CH=CH-$, $-(CH_2)_rCH(OH)(CH_2)_sCH_2C\equiv C-$, $-(CH_2)_rO(CH_2)_s-$, $-(CH_2)_rO(CH_2)_sCH_2CH=CH-$, $-(CH_2)_rO(CH_2)_sCH_2C\equiv C-$, $-(CH_2)_rS(CH_2)_s-$, $-(CH_2)_rS(O)(CH_2)_s-$, $-(CH_2)_rS(O)_2(CH_2)_s-$, $-(CH_2)_rN(R_7)(CH_2)_s-$, $-(CH_2)_rN(R_7)C(O)(CH_2)_s-$, $-(CH_2)_rC(O)N(R_7)(CH_2)_s-$, $-O(CH_2)_rC(O)N(R_7)(CH_2)_s-$, $-(CH_2)_rC(O)O(CH_2)_s-$, $-O(CH_2)_rC(O)(CH_2)_s-$, $-(CH_2)_rN(R_7)S(O)_2(CH_2)_s-$, $-(CH_2)_rS(O)_2N(R_7)(CH_2)_s-$, $-(CH_2)_rS(O)_2O(CH_2)_s-$ and $-(CH_2)_rOS(O)_2(CH_2)_s-$ wherein each group is inserted as drawn with the left end attached to D and the right end attached to E;

r is an integer of 0–6;

s is an integer of 0–6;

$L_F$ is absent or selected from the group consisting of a covalent bond, alkenylene, alkylene, alkynylene, $-(CH_2)_uC(O)(CH_2)_v-$, $-(CH_2)_uC(O)(CH_2)_vCH=CH-$, $-(CH_2)_uC(O)(CH_2)_vC\equiv C-$, $-(CH_2)_uCH(OH)(CH_2)_v-$, $-(CH_2)_uCH(OH)(CH_2)_vCH_2CH=CH-$, $-(CH_2)_uCH(OH)(CH_2)_vCH_2C\equiv C-$, $-(CH_2)_uO(CH_2)_v-$, $-(CH_2)_uO(CH_2)_vCH_2CH=CH-$, $-(CH_2)_uO(CH_2)_vCH_2C\equiv C-$, $-(CH_2)_uS(CH_2)_v-$, $-(CH_2)_uS(O)(CH_2)_v-$, $-(CH_2)_uS(O)_2(CH_2)_v-$, $-(CH_2)_uN(R_7)(CH_2)_v-$, $-(CH_2)_uN(R_7)C(O)(CH_2)_v-$, $-(CH_2)_uC(O)N(R_7)(CH_2)_v-$, $-O(CH_2)_uC(O)N(R_7)(CH_2)_v-$, $-(CH_2)_uC(O)O(CH_2)_v-$, $-O(CH_2)_uC(O)(CH_2)_v-$, $-(CH_2)_uN(R_7)S(O)_2(CH_2)_v-$, $-(CH_2)_uS(O)_2N(R_7)(CH_2)_v-$, $-(CH_2)_uS(O)_2O(CH_2)_v-$ and $-(CH_2)_uOS(O)_2(CH_2)_v-$ wherein each group is inserted as drawn with the left end attached to E and the right end attached to F;

u is an integer of 0–6;

v is an integer of 0–6;

A and D are each independently selected from the group consisting of aryl, cycloalkyl and heterocycle;

B, C, F and F are each independently absent or each independently selected from the group consisting of aryl, cycloalkyl and heterocycle;

$R_{A1}$, $R_{A2}$, $R_{A3}$, $R_{A4}$, $R_{A5}$, $R_{B1}$, $R_{B2}$, $R_{B3}$, $R_{B4}$, $R_{B5}$, $R_{C1}$, $R_{C2}$, $R_{C3}$, $R_{C4}$, $R_{C5}$, $R_{D1}$, $R_{D2}$, $R_{D3}$, $R_{D4}$, $R_{D5}$, $R_{E1}$, $R_{E2}$, $R_{E3}$, $R_{E4}$, $R_{E5}$, $R_{F1}$, $R_{F2}$, $R_{F3}$, $R_{F4}$ and $R_{F5}$ are each independently absent or each independently selected from the group consisting of hydrogen, alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkylcarbonylalkyl, alkylcarbonylalkylthio, alkylcarbonyl($NR_{11}$)sulfonylalky, alkylcarbonyloxy, alkylcarbonylthio, alkylsulfinyl, alkylsulfinylalkyl, alkylsulfonyl, alkylsulfonylalkyl, alkylsulfonyl($NR_{10}$)carboxyalkyl, alkylsulfonyl($NR_{10}$)carboxyalkoxy, alkylsulfonyl($NR_{10}$)alkyl($NR_{11}$)—, alkylthio, alkylthioalkyl, alkylthioalkoxy, alkynyl, alkynyloxy, alkynylthio, carboxy, carboxyalkoxy, carboxyalkoxyalkoxy, carboxyalkyl, cyano, cyanoalkoxy, cyanoalkyl, cyanoalkylthio, cycloalkylalkoxy, cycloalkyloxy, ethylenedioxy, formyl, formylalkoxy, formylalkyl, haloalkenyl, haloalkenyloxy, haloalkoxy, haloalkyl, haloalkynyl, haloalkynyloxy, halogen, hydroxy, hydroxyalkoxy, hydroxyalkyl, mercapto, mercaptoalkoxy, mercaptoalkyl, methylenedioxy, nitro, —$NR_8R_9$, ($NR_8R_9$)alkoxy, ($NR_8R_9$)alkyl, ($NR_8R_9$)carbonyl, ($NR_8R_9$)carbonylalkoxy, ($NR_8R_9$)carbonylalkyl, ($NR_{10}R_{11}$)sulfonyl, ($NR_{10}R_{11}$)sulfonylalkyl, —$NR_{10}S(O)_2R_{12}$, —$NR_{10}S(O)_2NR_{13}R_{14}$, and —$S(O)_2OH$;

$R_1$, $R_2$, and $R_3$ are each independently selected from the group consisting of hydrogen, alkoxycarbonyl, alkoxy, alkoxyalkyl, alkyl, alkylcarbonyl, carboxy, halogen, hydroxyalkyl, —$NR_{10}R_{11}$ and ($NR_{10}R_{11}$)alkyl;

$R_4$ is selected from the group consisting of alkenyl, alkoxy, alkoxyalkenyl, alkoxyalkoxy, alkoxyalkyl, alkoxyalkynyl, alkoxycarbonyl, alkoxycarbonylalkoxy, alkoxycarbonylalkenyl, alkoxycarbonylalkyl, alkoxycarbonylalkynyl, alkyl, alkylcarbonyl, alkylcarbonylalkenyl, alkylcarbonylalkoxy, alkylcarbonylalkyl, alkylcarbonylalkynyl, alkynyl, carboxy, carboxyalkenyl, carboxyalkyl, carboxyalkynyl, haloalkoxy, haloalkyl, haloalkenyl, haloalkynyl, halogen, hydroxyalkyl, —$NR_{10}R_{11}$, ($NR_{10}R_{11}$)alkyl, ($NR_{10}R_{11}$)carbonyl, ($NR_{10}R_{11}$)carbonylalkyl, ($NR_{10}R_{11}$)carbonylalkenyl and ($NR_{10}R_{11}$)carbonylalkynyl;

$R_5$ is selected from the group consisting of hydrogen and alkyl;

$R_6$ is selected from the group consisting of hydrogen, alkoxycarbonyl, alkoxysulfonyl, alkyl, alkylcarbonyl, alkylsulfonyl, arylalkoxycarbonyl, arylalkylcarbonyl, arylalkylsulfonyl, arylcarbonyl, arylsulfonyl, cycloalkylcarbonyl, cycloalkylalkylcarbonyl, cycloalkylsulfonyl, cycloalkylalkylsulfonyl, heterocyclecarbonyl, heterocyclealkylcarbonyl, heterocyclesulfonyl, heterocyclealkylsulfonyl, ($NR_{13}R_{14}$)carbonyl and ($NR_{13}R_{14}$)sulfonyl;

$R_8$ and $R_9$ are each independently selected from the group consisting of hydrogen, alkenyl, alkoxyalkyl, alkoxycarbonyl, alkoxycarbonylalkyl, alkyl, alkylcarbonyl, alkylsulfonyl, alkynyl, carboxyalkylcarbonyl; cyanoalkyl, formyl, hydroxy, hydroxyalkyl, —$NR_{10}R_{11}$, ($NR_{10}R_{11}$)carbonyl and carboxyalkyl wherein the alkyl portion of carboxyalkyl is optionally substituted with one or two substituents selected from the group consisting of alkylthio, aryl, heterocycle, hydroxy, carboxy, —$NR_{10}R_{11}$ and ($NR_{10}R_{11}$)carboxy;

$R_{10}$ and $R_{11}$ are each independently selected from the group consisting of hydrogen and alkyl;

$R_{12}$ is selected from the group consisting of alkoxy, alkyl, aryl, arylalkyl, cycloalkyl, cycloalkylalkyl, heterocycle and heterocyclealkyl; and $R_{13}$ and $R_{14}$ are each independently selected from the group consisting of hydrogen, alkyl, aryl, arylalkyl, cycloalkyl, cycloalkylalkyl, heterocycle and heterocyclealkyl.

2. A compound according to claim 1 wherein
$L_A$ is a covalent bond;
$L_D$ is a covalent bond;
A is aryl; and
D is aryl.

3. A compound according to claim 1 wherein
$L_A$ is a covalent bond;
$L_D$ is a covalent bond;
A is heterocycle; and
D is aryl.

4. A compound according to claim 1 wherein
$L_A$ is a covalent bond;
$L_D$ is a covalent bond;
A is heterocycle; and
D is heterocycle.

5. A compound according to claim 1 wherein
$L_A$ is $C(X_{A1})(X_{A2})$;
$L_D$ is a covalent bond;
A is aryl; and
D is aryl.

6. A compound according to claim 1 wherein
$L_A$ is $C(X_{A1})(X_{A2})$;
$L_D$ is a covalent bond;
A is heterocycle; and
D is aryl.

7. A compound according to claim 1 wherein
$L_A$ is $C(X_{A1})(X_{A2})$;
$L_D$ is a covalent bond;
A is heterocycle; and
D is heterocycle.

8. A compound according to claim 1 wherein
$L_A$ is $C(X_{A1})(X_{A2})$;
$L_D$ is a covalent bond;
A is aryl; and
D is heterocycle.

9. A compound according to claim 1 wherein
$L_A$ is $C(X_{A1})(X_{A2})$;
$L_D$ is $C(X_{D1})(X_{D2})$;
A is heterocycle; and
D is heterocycle.

10. A compound according to claim 1 wherein
$L_A$ is $C(X_{A1})(X_{A2})$;
$L_D$ is $C(X_{D1})(X_{D2})$;
A is aryl; and
D is heterocycle.

11. A compound according to claim 1 wherein
$L_A$ is $C(X_{A1})(X_{A2})$;
$L_D$ is $C(X_{D1})(X_{D2})$;
A is aryl; and
D is aryl.

12. A compound according to claim 1 of formula (II)

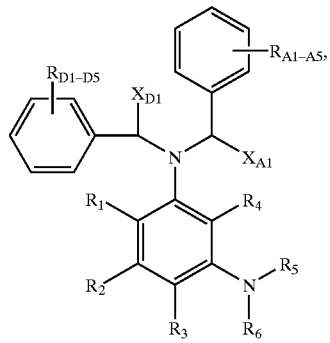

(II)

or a pharmaceutically acceptable salt or prodrug thereof.

13. A compound according to claim 12 wherein
$R_1$, $R_2$, $R_3$, $R_5$, $X_{A1}$ and $X_{D1}$ are each hydrogen;
$R_4$ is alkyl; and
$R_6$ is alkylsulfonyl.

14. A compound according to claim 13 selected from the group consisting of
N-{3-[bis(2-bromobenzyl)amino]-2-methylphenyl}methanesulfonamide;
N-[3-(dibenzylamino)-2-methylpheny]methanesulfonamide;
N-[3-(dibenzylamino)-2-methylphenyl]ethanesulfonamide;
N-[3-(dibenzylamino)-2-methylphenyl]-2-propanesulfonamide;
N-{3-[benzyl(4-methoxycarbonylbenzyl)amino]-2-methylphenyl}methanesulfonamide;
N-{3-[benzyl(2-bromobenzyl)amino]-2-methylphenyl}methanesulfonamide;
N-{3-[benzyl(4-nitrobenzyl)amino]-2-methylphenyl}methanesulfonamide;
N-{3-[benzyl(4-fluorobenzyl)amino]-2-methylphenyl}methanesulfonamide;
N-{3-[benzyl(2,4-difluorobenzyl)amino]-2-methylphenyl}methanesulfonamide;
N-{3-[benzyl(2-cyanobenzyl)amino]-2-methylphenyl}methanesulfonamide;
N-{3-[benzyl(4-methoxybenzyl)amino]-2-methylphenyl}methanesulfonamide;
N-{3-[benzyl(4-bromobenzyl)amino]-2-methylphenyl}methanesulfonamide;
N-{3-[benzyl(3-methoxybenzyl)amino]-2-methylphenyl}methanesulfonamide;
N-{3-[(1,3-benzodioxol-5-ylmethyl)(benzyl)amino]-2-methylphenyl}methanesulfonamide;
N-{3-[benzyl(2,3-dihydro-1,4-benzodioxin-6-ylmethyl)amino]-2-methylphenyl}methanesulfonamide;
N-{3-[benzyl(2-chlorobenzyl)amino]-2-methylphenyl}methranesulfonamide;
N-{3-[benzyl(2-fluorobenzyl)amino]-2-methylphenyl}methanesulfonamide;
N-{3-[[4-(allyloxy)benzyl](benzyl)amino]-2-methylphenyl}methanesulfonamide;
N-{3-[[4-(allyloxy)benzyl](2,4-difluorobenzyl)amino]-2-methylphenyl}methanesulfonamide;
N-{3-[(2-cyanobenzyl)(2-fluoro-4-methoxybenzyl)amino]-2-methylphenyl}methanesulfonamide;
N-{3-[(2,4-difluorobenzyl)(4-methoxybenzyl)amino]-2-methylphenyl}methanesulfonamide;
N-{3-[(2,4-difluorobenzyl)(2-fluorobenzyl)amino]-2-methylphenyl}methanesulfonamide;
N-{3-[bis(2,4-difluorobenzyl)amino]-2-methylphenyl}methanesulfonamide;
N-{3-[(2-cyanobenzyl)(2,4-difluorobenzyl)amino]-2-methylphenyl}methanesulfonamide;
N-{3-[benzyl(4-phenoxybenzyl)amino]-2-methylphenyl}methanesulfonamide;
N-{3-[benzyl(2-methylbenzyl)amino]-2-methylphenyl}methanesulfonamide;
N-{3-[benzyl(4-methylbenzyl)amino]-2-methylphenyl}methanesulfonamide;
N-{3-[benzyl(4-chlorobenzyl)amino]-2-methylphenyl}methanesulfonamide;
N-(3-{benzyl[4-(trifluoromethyl)benzyl]amino}-2-methylphenyl)methanesulfonamide;
N-(3-{benzyl[2-fluoro-4-(trifluoromethyl)benzyl]amino}-2-methylphenyl)methanesulfonamide;
N-{3-[benzyl(2,4-dichlorobenzyl)amino]-2-methylphenyl}methanesulfonamide;
N-{3-[benzyl(4-{[3-bromo-2-propenyl]oxy}benzyl)amino]-2-methylphenyl}methanesulfonamide;
N-(3-{benzyl[4-(methoxymethyl)benzyl]amino}-2-methylphenyl)methanesulfonamide;
N-(3-{benzyl[4-(hydroxymethyl)benzyl]amino}-2-methylphenyl)methanesulfonamide;
N-(3-{benzyl[4-(2-hydroxyethoxy)benzyl]amino}-2-methylphenyl)methanesulfonamide;
N-{3-[(2,4-difluorobenzyl)(4-propoxybenzyl)amino]-2-methylphenyl}methanesulfonamide;
N-[3-(dibenzylamino)-2-ethylphenyl]methanesulfonamide;
N-{3-[benzyl(4-bromo-2-fluorobenzyl)amino]-2-methylphenyl}methanesulfonamide;
N-{3-[benzyl(2-chloro-4-fluorobenzyl)amino]-2-methylphenyl}methanesulfonamide;
N-{3-[benzyl(4-{[(2Z)-3-bromoprop-2-enyl]oxy}benzyl)amino]-2-methylphenyl}methanesulfonamide;
N-{3-[(2,4-difluorobenzyl)(4-ethoxybenzyl)amino]-2-methylphenyl}methanesulfonamide; and
N-{3-[benzyl(4-chloro-2-fluorobenzyl)amino]-2-methylphenyl}methanesulfonamide.

15. A compound according to claim 12 wherein
$R_1$, $R_2$, $R_3$, $R_5$, $X_{A1}$ and $X_{D1}$ are each hydrogen;
$R_4$ is alkyl; and
$R_6$ is $(NR_{12}R_{13})$sulfonyl.

16. A compound according to claim 15 that is N'-[3-(dibenzylamino)-2-methylphenyl]-N,N-dimethylsulfamide.

17. A compound according to claim 12 wherein
$R_2$, $R_3$, $R_4$, $R_5$, $X_{A1}$ and $X_{D1}$ are each hydrogen;
$R_1$ is alkoxy; and
$R_6$ is alkylsulfonyl.

18. A compound according to claim 17 that is N-{3-[bis(2-bromobenzyl)amino]-4-methoxyphenyl}methanesulfonamide.

19. A compound according to claim 12 wherein
$X_{A1}$ is cyano;
$R_1$, $R_2$, $R_3$, $R_5$ and $X_{D1}$ are each hydrogen;
$R_4$ is alkyl; and
$R_6$ is alkylsulfonyl.

20. A compound according to claim 19 that is N-(3-{(2-bromobenzyl)[cyano(phenyl)methyl]amino}-2-methylphenyl)methanesulfonamide.

21. A compound according to claim 12 wherein
$R_1$, $R_2$, $R_3$, $R_5$, $X_{A1}$ and $X_{D1}$ are each hydrogen;
$R_4$ is selected from the group consisting of alkenyl, alkoxyalkyl, alkoxycarbonylalkenyl and hydroxyalkyl; and
$R_6$ is alkylsulfonyl.

22. A compound according to claim 21 selected from the group consisting of
N-[3-(dibenzylamino)-2-((E)-3-ethoxy-3-oxo-1-propenyl)phenyl]methanesulfonamide;
N-[3-(dibenzylamino)-2-(hydroxymethyl)phenyl]methanesulfonamide;
N-[3-(dibenzylamino)-2-vinylphenyl]methanesulfonamide;
N-[3-(dibenzylamino)-2-(methoxymethyl)phenyl]methanesulfonamide; and
N-[3-(dibenzylamino)-2-(ethoxymethyl)phenyl]methanesulfonamide.

23. A compound according to claim 1 of formula (III)

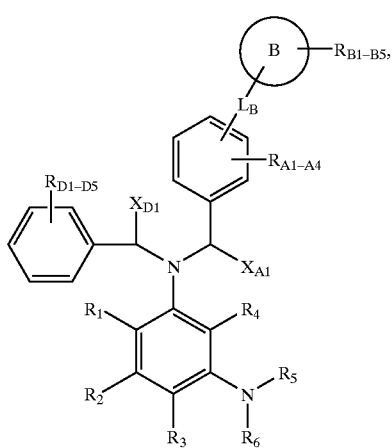

(III)

or a pharmaceutically acceptable salt or prodrug thereof.

24. A compound according to claim 23 wherein
B is aryl wherein said aryl is phenyl;
$L_B$ is —$(CH_2)_m O(CH_2)_n$—;
m and n are each 0;
$R_1$, $R_2$, $R_3$, $R_5$, $X_{A1}$ and $X_{D1}$ are each hydrogen;
$R_4$ is alkyl; and
$R_6$ is alkylsulfonyl.

25. A compound according to claim 24 selected from the group consisting of
N-{3-[[4-(4-bromophenoxy)benzyl](2,4-difluorobenzyl)amino]-2-methylphenyl}methanesulfonamide;
N-{3-[(4-(4-(3-ethoxy-3-oxopropyl)phenoxy)benzyl)(2,4-difluorobenzyl)amino]-2-methylphenyl}methanesulfonamide;
N-{3-[(4-(4-(2-carboxyethyl)phenoxy)benzyl)(2,4-difluorobenzyl)amino]-2-methylphenyl}methanesulfonamide;
N-{3-[(2,4-difluorobenzyl)(4-phenoxybenzyl)amino]-2-methylphenyl}methanesulfonamide;
methyl 4-{4-[((2,4-difluorobenzyl){2-methyl-3-[(methylsulfonyl)amino]phenyl}amino)methyl]phenoxy}benzoate;
N-{3-[(2,4-difluorobenzyl)(2-fluoro-4-phenoxybenzyl)amino]-2-methylphenyl}methanesulfonamide;
N-(3-{(2,4-difluorobenzyl)[4-(3-methoxyphenoxy)benzyl]amino}-2-methylphenyl)methanesulfonamide;
N-{3-[(2-fluorobenzyl)(4-phenoxybenzyl)amino]-2-methylphenyl}methanesulfonamide;
N-{3-[(4-methoxybenzyl)(4-phenoxybenzyl)amino]-2-methylphenyl}methanesulfonamide;
3-(4-{4-[((2,4-difluorobenzyl){2-methyl-3-[(methylsulfonyl)amino]phenyl}amino)methyl]phenoxy}phenyl)propanoic acid;
N-[3-(benzyl{4-[3-(2-methoxyethoxy)phenoxy]benzyl}amino)-2-methylphenyl]methanesulfonamide;
(3-{4-[(benzyl{2-methyl-3-[(methylsulfonyl)amino]phenyl}amino)methyl]phenoxy}phenoxy)acetic acid;
4-[4-{4-[(benzyl{2-methyl-3-[(methylsulfonyl)amino]phenyl}amino)methyl]phenoxy}-2-(2-methoxyethoxy)phenyl]butanoic acid;
ethyl 4-(4-{4-[(benzyl{2-methyl-3-[(methylsulfonyl)amino]phenyl}amino)methyl]phenoxy}phenyl)butanoate;
N-[3-(benzyl{4-[3-(3-hydroxypropyl)phenoxy]benzyl}amino)-2-methylphenyl]methanesulfonamide;
methyl 4-{4-[(benzyl{2-methyl-3-[(methylsulfonyl)amino]phenyl}amino)methyl]phenoxy}benzoate;
ethyl N-(4-{4-[((2,4-difluorobenzyl){2-methyl-3-[(methylsulfonyl)amino]phenyl}amino)methyl]phenoxy}benzoyl)-beta-alaninate;
methyl 3-{4-[((2,4-difluorobenzyl){2-methyl-3-[(methylsulfonyl)amino]phenyl}amino)methyl]phenoxy}benzoate;
N-{3-[benzyl(4-{3-[2-(2-methoxyethoxy)ethoxy]phenoxy}benzyl)amino]-2-methylphenyl}methanesulfonamide;
N-[3-(3-{4-[(benzyl{2-methyl-3-[(methylsulfonyl)amino]phenyl}amino)methyl]phenoxy}phenoxy)propyl]acetamide;
N-[3-(3-{4-[(benzyl{2-methyl-3-[(methylsulfonyl)amino]phenyl}amino)methyl]phenoxy}phenoxy)propyl]methanesulfonamide;
N-{3-[benzyl(4-{3-[3-(dimethylamino)propoxy]phenoxy}benzyl)amino]-2-methylphenyl}methanesulfonamide;
4-(4-{4-[((2,4-difluorobenzyl){2-methyl-3-[(methylsulfonyl)amino]phenyl}amino)methyl]phenoxy}phenyl)butanoic acid;
3-(4-{4-[((2-bromobenzyl){2-methyl-3-[(methylsulfonyl)amino]phenyl}amino)methyl]phenoxy}phenyl)propanoic acid;
(5-{4-[(benzyl{2-methyl-3-[(methylsulfonyl)amino]phenyl}amino)methyl]phenoxy}-2-bromophenoxy)acetic acid;
4-{[2-(3-{4-[(benzyl{2-methyl-3-[(methylsulfonyl)amino]phenyl}amino)methyl]phenoxy}phenoxy)ethyl]amino}-4-oxobutanoic acid;
5-{[2-(3-{4-[(benzyl{2-methyl-3-[(methylsulfonyl)amino]phenyl}amino)methyl]phenoxy}phenoxy)ethyl]amino}-5-oxopentanoic acid;
N-[2-(3-{4-[(benzyl{2-methyl-3-[(methylsulfonyl)amino]phenyl}amino)methyl]phenoxy}phenoxy)ethyl]acetamide;
N-[2-(3-{4-[(benzyl{2-methyl-3-[(methylsulfonyl)amino]phenyl}amino)methyl]phenoxy}phenoxy)ethyl]methanesulfonamide;
methyl 2-(3-{4-[(benzyl{2-methyl-3-[(methylsulfonyl)amino]phenyl}amino)methyl]phenoxy}phenoxy)ethylcarbamate;
(3-{4-[((4-chloro-2-fluorobenzyl){2-methyl-3-[(methylsulfonyl)amino]phenyl}amino)methyl]phenoxy}phenoxy)acetic acid;
3-(4-{4-[((2-fluorobenzyl){2-methyl-3-[(methylsulfonyl)amino]phenyl}amino)methyl]phenoxy}phenyl)propanoic acid;
3-(4-{4-[((4-fluorobenzyl){2-methyl-3-[(methylsulfonyl)amino]phenyl}amino)methyl]phenoxy}phenyl)propanoic acid;

3-(4-{4-[((4-chloro-2-fluorobenzyl){2-methyl-3-[(methylsulfonyl)amino]phenyl}amino)methyl]phenoxy}phenyl)propanoic acid;

(3-{4-[((2,4-difluorobenzyl){2-ethyl-3-[(methylsulfonyl)amino]phenyl}amino)methyl]phenoxy}phenoxy)acetic acid;

(3-{4-[((2,4-difluorobenzyl){2-methyl-3-[(methylsulfonyl)amino]phenyl}amino)methyl]phenoxy}-5-methylphenoxy)acetic acid;

(3-{4-[((2,4-difluorobenzyl){2-methyl-3-[(methylsulfonyl)amino]phenyl}amino)methyl]phenoxy}-5-methoxyphenoxy)acetic acid;

(2-chloro-5-{4-[((2,4-difluorobenzyl){2-methyl-3-[(methylsulfonyl)amino]phenyl}amino)methyl]phenoxy}phenoxy)acetic acid;

(4-{4-[(benzyl{2-methyl-3-[(methylsulfonyl)amino]phenyl}amino)methyl]phenoxy}phenoxy)acetic acid;

4-{4-[(benzyl{2-methyl-3-[(methylsulfonyl)amino]phenyl}amino)methyl]phenoxy}benzoic acid;

N-[3-(benzyl{4-[4-(methoxymethoxy)phenoxy]benzyl}amino)-2-methylphenyl]methanesulfonamide;

N-[3-(benzyl{4-[4-(3-hydroxypropyl)phenoxy]benzyl}amino)-2-methylphenyl]methanesulfonamide;

4-(4-{4-[(benzyl{2-methyl-3-[(methylsulfonyl)amino]phenyl}amino)methyl]phenoxy}phenyl)butanoic acid;

N-[3-(benzyl{4-[4-(4-hydroxybutyl)phenoxy]benzyl}amino)-2-methylphenyl]methanesulfonamide;

N-{3-[(3-bromobenzyl)(4-phenoxybenzyl)amino]-2-methylphenyl}methanesulfonamide

N-{3-[(4-bromobenzyl)(4-phenoxybenzyl)amino]-2-methylphenyl}methanesulfonamide;

N-[3-(4-{4-[(benzyl{2-methyl-3-[(methylsulfonyl)amino]phenyl}amino)methyl]phenoxy}phenyl)propanoyl]glycine;

N-[3-(4-{4-[(benzyl{2-methyl-3-[(methylsulfonyl)amino]phenyl}amino)methyl]phenoxy}phenyl)propanoyl]-beta-alanine;

4-{[3-(4-{4-[(benzyl{2-methyl-3-[(methylsulfonyl)amino]phenyl}amino)methyl]phenoxy}phenyl)propanoyl]amino}butanoic acid;

N-[4-(4-{4-[(benzyl{2-methyl-3-[(methylsulfonyl)amino]phenyl}amino)methyl]phenoxy}phenyl)butanoyl]glycine;

N-[4-(4-{4-[(benzyl{2-methyl-3-[(methylsulfonyl)amino]phenyl}amino)methyl]phenoxy}phenyl)butanoyl]-beta-alanine;

4-{[4-(4-{4-[(benzyl{2-methyl-3-[(methylsulfonyl)amino]phenyl}amino)methyl]phenoxy}phenyl)butanoyl]amino}butanoic acid;

(3-{4-[((2,4-difluorobenzyl){2-methyl-3-[(methylsulfonyl)amino]phenyl}amino)methyl]phenoxy}phenoxy)acetic acid;

2-(3-{4-[(benzyl{2-methyl-3-[(methylsulfonyl)amino]phenyl}amino)methyl]phenoxy}phenoxy)propanoic acid;

2-(3-{4-[(benzyl{2-methyl-3-[(methylsulfonyl)amino]phenyl}amino)methyl]phenoxy}phenoxy)-4-hydroxybutanoic acid;

N-(3-{benzyl[4-(3-hydroxyphenoxy)benzyl]amino}-2-methylphenyl)methanesulfonamide;

4-(3-{4-[(benzyl{2-methyl-3-[(methylsulfonyl)amino]phenyl}amino)methyl]phenoxy}phenoxy)butanoic acid;

5-(3-{4-[(benzyl{2-methyl-3-[(methylsulfonyl)amino]phenyl}amino)methyl]phenoxy}phenoxy)pentanoic acid;

N-[3-(4-{4-[(benzyl{2-methyl-3-[(methylsulfonyl)amino]phenyl}amino)methyl]phenoxy}phenyl)propanoyl]-N-methylglycine;

N-[4-(4-{4-[(benzy{2-methyl-3-[(methylsulfonyl)amino]phenyl}amino)methyl]phenoxy}phenyl)butanoyl]-N-methylglycine;

4-(3-{4-[((2,4-difluorobenzyl){2-methyl-3-[(methylsulfonyl)amino]phenyl}amino)methyl]phenoxy}phenoxy)butanoic acid;

5-(3-{4-[((2,4-difluorobenzyl){2-methyl-3-[(methylsulfonyl)amino]phenyl}amino)methyl]phenoxy}phenoxy)pentanoic acid;

N-[(3-{4-[(benzyl{2-methyl-3-[(methylsulfonyl)amino]phenyl}amino)methyl]phenoxy}phenoxy)acetyl]glycine;

N-[(3-{4-[(benzyl{2-methyl-3-[(methylsulfonyl)amino]phenyl}amino)methyl]phenoxy}phenoxy)acetyl]-beta-alanine;

N-[(3-{4-[(benzyl{2-methyl-3-[(methylsulfonyl)amino]phenyl}amino)methyl]phenoxy}phenoxy)acetyl]-N-methylglycine;

4-{[(3-{4-[(benzyl{2-methyl-3-[(methylsulfonyl)amino]phenyl}amino)methyl]phenoxy}phenoxy)acetyl]amino}butanoic acid;

ethyl 4-(3-{4-[(benzyl{2-methyl-3-[(methylsulfonyl)amino]phenyl}amino)methyl]phenoxy}phenoxy)butanoate;

ethyl 5-(3-{4-[(benzyl{2-methyl-3-[(methylsulfonyl)amino]phenyl}amino)methyl]phenoxy}phenoxy)pentanoate;

N-[4-(3-{4-[(benzyl{2-methyl-3-[(methylsulfonyl)amino]phenyl}amino)methyl]phenoxy}phenoxy)butanoyl]glycine;

N-[4-(3-{4-[(benzyl{2-methyl-3-[(methylsulfonyl)amino]phenyl}amino)methyl]phenoxy}phenoxy)butanoyl]-beta-alanine;

4-{[4-(3-{4-[(benzyl{2-methyl-3-[(methylsulfonyl)amino]phenyl}amino)methyl]phenoxy}phenoxy)butanoyl]amino}butanoic acid;

N-[5-(3-{4-[(benzyl{2-methyl-3-[(methylsulfonyl)amino]phenyl}amino)methyl]phenoxy}phenoxy)pentanoyl]glycine;

N-[5-(3-{4-[(benzyl{2-methyl-3-[(methylsulfonyl)amino]phenyl}amino)methyl]phenoxy}phenoxy)pentanoyl]-beta-alanine;

4-{[5-(3-{4-[(benzyl{2-methyl-3-[(methylsulfonyl)amino]phenyl}amino)methyl]phenoxy}phenoxy)pentanoyl]amino}butanoic acid;

N-[3-(benzyl{4-[3-(2-hydroxyethoxy)phenoxy]benzyl}amino)-2-methylphenyl]methanesulfonamide;

[2-(3-{4-[(benzyl{2-methyl-3-[(methylsulfonyl)amino]phenyl}amino)methyl]phenoxy}phenoxy)ethoxy]acetic acid;

2,4-dideoxy-6-O-(3-{4-[((2,4-difluorobenzyl){2-methyl-3-[(methylsulfonyl)amino]phenyl}amino)methyl]phenoxy}phenyl)-D-erythro-hexonic acid;

(3-{4-[((2-bromobenzyl){2-methyl-3-[(methylsulfonyl)amino]phenyl}amino)methyl]phenoxy}phenoxy)acetic acid;

N-{3-[[4-(3-acetylphenoxy)benzyl](2,4-difluorobenzyl)amino]-2-methylphenyl}methanesulfonamide;

N-(3-{(2,4-difluorobenzyl)[4-(3,4-dimethoxyphenoxy)benzyl]amino}-2-methylphenyl)methanesulfonamide;

N-(3-{(2,4-difluorobenzyl)[4-(pent-3-ynyloxy)benzyl]amino}-2-methylphenyl)methanesulfonamide;

N-(3-{(4-chloro-2-fluorobenzyl)[4-(methylthio)benzyl]amino}-2-methylphenyl)methanesulfonamide;

N-{3-[(4-chloro-2-fluorobenzyl)(2-fluorobenzyl)amino]-2-methylphenyl}methanesulfonamide;

N-(3-{benzyl[(2'-cyano-1,1'-biphenyl-4-yl)methyl]amino}-2-methylphenyl)methanesulfonamide;

3-(4-{4-[(benzyl{2-methyl-3-[(methylsulfonyl)amino]phenyl}amino)methyl]phenoxy}phenyl)-N-(5-hydroxypentyl)propanamide;

3-(4-{4-[(benzyl{2-methyl-3-[(methylsulfonyl)amino]phenyl}amino)methyl]phenoxy}phenyl)-N-(4-hydroxybutyl)propanamide;

3-(4-{4-[(benzyl{2-methyl-3-[(methylsulfonyl)amino]phenyl}amino)methyl]phenoxy}phenyl)-N-(3-hydroxypropyl)propanamide;

3-(4-{4-[(benzyl{2-methyl-3-[(methylsulfonyl)amino]phenyl}amino)methyl]phenoxy}phenyl)-N-(2-hydroxyethyl)propanamide;

3-(4-{4-[(benzyl{2-methyl-3-[(methylsulfonyl)amino]phenyl}amino)methyl]phenoxy}phenyl)-N-(6-hydroxyhexyl)propanamide;

N-(3-{benzyl[4-(3-isopropoxyphenoxy)benzyl]amino}-2-methylphenyl)methanesulfonamide;

N-[3-(benzyl{4-[3-(cyclobutyloxy)phenoxy]benzyl}amino)-2-methylphenyl]methanesulfonamide;

N-(3-{benzyl[4-(3-sec-butoxyphenoxy)benzyl]amino}-2-methylphenyl)methanesulfonamide;

N-[3-(benzyl{4-[3-(cyclopentyloxy)phenoxy]benzyl}amino)-2-methylphenyl]methanesulfonamide;

N-[3-(benzyl{4-[3-(1-methylbutoxy)phenoxy]benzyl}amino)-2-methylphenyl]methanesulfonamide;

N-[3-(benzyl{4-[3-(2-methoxy-1-methylethoxy)phenoxy]benzyl}amino)-2-methylphenyl]methanesulfonamide;

N-[3-(benzyl{4-[3-(cyclohexyloxy)phenoxy]benzyl}amino)-2-methylphenyl]methanesulfonamide;

N-{3-[benzyl(4-{3-[(3-methylcyclopentyl)oxy]phenoxy}benzyl)amino]-2-methylphenyl}methanesulfonamide;

N-[3-(benzyl{4-[3-(2-ethoxy-1-methylethoxy)phenoxy]benzyl}amino)-2-methylphenyl]methanesulfonamide;

N-{3-[benzyl(4-{3-[(4-methylcyclohexyl)oxy]phenoxy}benzyl)amino]-2-methylphenyl}methanesulfonamide;

N-[3-(benzyl{4-[3-(cycloheptyloxy)phenoxy]benzyl}amino)-2-methylphenyl]methanesulfonamide;

N-(3-{benzyl[4-(3-methoxyphenoxy)benzyl]amino}-2-methylphenyl)methanesulfonamide;

N-(3-{benzyl[4-(3-ethoxyphenoxy)benzyl]amino}-2-methylphenyl)methanesulfonamide;

N-(3-{benzyl[4-(3-propoxyphenoxy)benzyl]amino}-2-methylphenyl)methanesulfonamide;

N-[3-(benzyl{4-[3-(cyclopropylmethoxy)phenoxy]benzyl}amino)-2-methylphenyl]methanesulfonamide;

N-(3-{benzyl[4-(3-butoxyphenoxy)benzyl]amino}-2-methylphenyl)methanesulfonamide;

N-(3-{benzyl[4-(3-isobutoxyphenoxy)benzyl]amino}-2-methylphenyl)methanesulfonamide;

N-[3-(benzyl{4-[3-(pent-3-ynyloxy)phenoxy]benzyl}amino)-2-methylphenyl]methanesulfonamide;

N-{3-[benzyl(4-{3-[(2E)-pent-2-enyloxy]phenoxy}benzyl)amino]-2-methylphenyl}methanesulfonamide;

N-{3-[benzyl(4-{3-[(1-methylcyclopropyl)methoxy]phenoxy}benzyl)amino]-2-methylphenyl}methanesulfonamide;

N-[3-(benzyl{4-[3-(cyclobutylmethoxy)phenoxy]benzyl}amino)-2-methylphenyl]methanesulfonamide;

N-[3-(benzyl{4-[3-(2-cyclopropylethoxy)phenoxy]benzyl}amino)-2-methylphenyl]methanesulfonamide;

N-[3-(benzyl{4-[3-(pentyloxy)phenoxy]benzyl}amino)-2-methylphenyl]methanesulfonamide;

N-[3-(benzyl{4-[3-(2-methylbutoxy)phenoxy]benzyl}amino)-2-methylphenyl]methanesulfonamide;

N-[3-(benzyl{4-[3-(3-methylbutoxy)phenoxy]benzyl}amino)-2-methylphenyl]methanesulfonamide;

N-[3-(benzyl{4-[3-(2-ethoxyethoxy)phenoxy]benzyl}amino)-2-methylphenyl]methanesulfonamide;

N-{3-[benzyl(4-{3-[2-(methylthio)ethoxy]phenoxy}benzyl)amino]-2-methylphenyl}methanesulfonamide;

N-[3-(benzyl{4-[3-(cyclopentylmethoxy)phenoxy]benzyl}amino)-2-methylphenyl]methanesulfonamide;

N-[3-(benzyl{4-[3-(hexyloxy)phenoxy]benzyl}amino)-2-methylphenyl]methanesulfonamide;

N-[3-(benzyl{4-[3-(3,3-dimethylbutoxy)phenoxy]benzyl}amino)-2-methylphenyl]methanesulfonamide;

N-[3-(benzyl{4-[3-(2-isopropoxyethoxy)phenoxy]benzyl}amino)-2-methylphenyl]methanesulfonamide;

N-[3-(benzyl{4-[3-(cyclohexylmethoxy)phenoxy]benzyl}amino)-2-methylphenyl]methanesulfonamide;

N-[3-(benzyl{4-[3-(3-methoxy-3-methylbutoxy)phenoxy]benzyl}amino)-2-methylphenyl]methanesulfonamide;

(3-{4-[((2-methylbenzyl){2-methyl-3-[(methylsulfonyl)amino]phenyl}amino)methyl]phenoxy}phenoxy)acetic acid;

(3-{4-[((4-methylbenzyl){2-methyl-3-[(methylsulfonyl)amino]phenyl}amino)methyl]phenoxy}phenoxy)acetic acid;

(3-{4-[((2,4-dichlorobenzyl){2-methyl-3-[(methylsulfonyl)amino]phenyl}amino)methyl]phenoxy}phenoxy)acetic acid;

(3-{4-[((2-chloro-4-fluorobenzyl){2-methyl-3-[(methylsulfonyl)amino]phenyl}amino)methyl]phenoxy}phenoxy)acetic acid;

(3-{4-[((3,4-difluorobenzyl){2-methyl-3-[(methylsulfonyl)amino]phenyl}amino)methyl]phenoxy}phenoxy)acetic acid;

N-[3-(benzyl{4-[4-(4-hydrazino-4-oxobutyl)phenoxy]benzyl}amino)-2-methylphenyl]methanesulfonamide;

N~2~-[4-(4-{4-[(benzyl{2-methyl-3-[(methylsulfonyl)amino]phenyl}amino)methyl]phenoxy}phenyl)butanoyl]-L-asparagine;

N-[4-(4-{4-[(benzyl{2-methyl-3-[(methylsulfonyl)amino]phenyl}amino)methyl]phenoxy}phenyl)butanoyl]-D-valine;

N-[4-(4-{4-[(benzyl{2-methyl-3-[(methylsulfonyl)amino]phenyl}amino)methyl]phenoxy}phenyl)butanoyl]-L-tyrosine;

N-[4-(4-{4-[(benzyl{2-methyl-3-[(methylsulfonyl)amino]phenyl}amino)methyl]phenoxy}phenyl)butanoyl]-L-methionine;

N~2~-[4-(4-{4-[(benzyl{2-methyl-3-[(methylsulfonyl)amino]phenyl}amino)methyl]phenoxy}phenyl)butanoyl]-L-lysine;

N-[4-(4-{4-[(benzyl{2-methyl-3-[(methylsulfonyl)amino]phenyl}amino)methyl]phenoxy}phenyl)butanoyl]-L-serine;

N-[4-(4-{4-[(benzyl{2-methyl-3-[(methylsulfonyl)amino]phenyl}amino)methyl]phenoxy}phenyl)butanoyl]-L-phenylalanine;

N-[4-(4-{4-[(benzyl{2-methyl-3-[(methylsulfonyl)amino]phenyl}amino)methyl]phenoxy}phenyl)butanoyl]-D-tyrosine;

N~2~-[4-(4-{4-[(benzyl{2-methyl-3-[(methylsulfonyl)amino]phenyl}amino)methyl]phenoxy}phenyl)butanoyl]-L-glutamine;

N-[4-(4-{4-[(benzyl{2-methyl-3-[(methylsulfonyl)amino]phenyl}amino)methyl]phenoxy}phenyl)butanoyl]-L-isoleucine;

N-[4-(4-{4-[(benzyl{2-methyl-3-[(methylsulfonyl)amino]phenyl}amino)methyl]phenoxy}phenyl)butanoyl]-D-glutamic acid;

N-[4-(4-{4-[(benzyl{2-methyl-3-[(methylsulfonyl)amino]phenyl}amino)methyl]phenoxy}phenyl)butanoyl]-D-histidine;

N-[4-(4-{4-[(benzyl{2-methyl-3-[(methylsulfonyl)amino]phenyl}amino)methyl]phenoxy}phenyl)butanoyl]-L-valine;

N-[4-(4-{4-[(benzyl{2-methyl-3-[(methylsulfonyl)amino]phenyl}amino)methyl]phenoxy}phenyl)butanoyl]-L-aspartic acid;

ethyl 4-(4-{4-[(benzyl{2-methyl-3-[(methylsulfonyl)amino]phenyl}amino)methyl]phenoxy}phenoxy)butanoate;
4-(4-{4-[(benzyl{2-methyl-3-[(methylsulfonyl)amino]phenyl}amino)methyl]phenoxy}phenoxy)butanoic acid;
5-(4-{4-[(benzyl{2-methyl-3-[(methylsulfonyl)amino]phenyl}amino)methyl]phenoxy}phenoxy)pentanoic acid;
(5-{4-[((2,4-difluorobenzyl){2-methyl-3-[(methylsulfonyl)amino]phenyl}amino)methyl]phenoxy}-2-ethylphenoxy)acetic acid;
ethyl 4-{[4-(3-{4-[(benzyl{2-methyl-3-[(methylsulfonyl)amino]phenyl}amino)methyl]phenoxy}phenoxy)butanoyl]amino}butanoate;
(5-{4-[((2,4-difluorobenzyl){2-methyl-3-[(methylsulfonyl)amino]phenyl}amino)methyl]phenoxy}-2-hexylphenoxy)acetic acid;
ethyl N-[4-(3-{4-[(benzyl{2-methyl-3-[(methylsulfonyl)amino]phenyl}amino)methyl]phenoxy}phenoxy)butanoyl]-N-methylglycinate;
N-[4-(3-{4-[(benzyl{2-methyl-3-[(methylsulfonyl)amino]phenyl}amino)methyl]phenoxy}phenoxy)butanoyl]-N-methylglycine;
ethyl (2-chloro-5-{4-[((2,4-difluorobenzyl){2-methyl-3-[(methylsulfonyl)amino]phenyl}amino)methyl]phenoxy}phenoxy)acetate;
N-[4-(4-{4-[(benzyl{2-methyl-3-[(methylsulfonyl)amino]phenyl}amino)methyl]phenoxy}phenoxy)butanoyl]glycine;
N-[4-(4-{4-[(benzyl{2-methyl-3-[(methylsulfonyl)amino]phenyl}amino)methyl]phenoxy}phenoxy)butanoyl]-beta-alanine;
4-{[4-(4-{4-[(benzyl{2-methyl-3-[(methylsulfonyl)amino]phenyl}amino)methyl]phenoxy}phenoxy)butanoyl]amino}butanoic acid;
N-[4-(4-{4-[(benzyl{2-methyl-3-[(methylsulfonyl)amino]phenyl}amino)methyl]phenoxy}phenoxy)butanoyl]-N-methylglycine;
N-[4-(4-{4-[(benzyl{2-methyl-3-[(methylsulfonyl)amino]phenyl}amino)methyl]phenoxy}phenoxy)butanoyl]-L-glutamic acid;
N-[4-(4-{4-[(benzyl{2-methyl-3-[(methylsulfonyl)amino]phenyl}amino)methyl]phenoxy}phenoxy)butanoyl]-L-valine;
N-[4-(4-{4-[(benzyl{2-methyl-3-[(methylsulfonyl)amino]phenyl}amino)methyl]phenoxy}phenoxy)butanoyl]-L-serine;
N-[4-(4-{4-[(benzyl{2-methyl-3-[(methylsulfonyl)amino]phenyl}amino)methyl]phenoxy}phenoxy)butanoyl]-L-isoleucine;
N~2~-[4-(4-{4-[(benzyl{2-methyl-3-[(methylsulfonyl)amino]phenyl}amino)methyl]phenoxy}phenoxy)butanoyl]-L-glutamine;
N-[5-(4-{4-[(benzyl{2-methyl-3-[(methylsulfonyl)amino]phenyl}amino)methyl]phenoxy}phenoxy)pentanoyl]glycine;
N-[5-(4-{4-[(benzyl{2-methyl-3-[(methylsulfonyl)amino]phenyl}amino)methyl]phenoxy}phenoxy)pentanoyl]-beta-alanine;
4-{[5-(4-{4-[(benzyl{2-methyl-3-[(methylsulfonyl)amino]phenyl}amino)methyl]phenoxy}phenoxy)pentanoyl]amino}butanoic acid;
N-[5-(4-{4-[(benzyl{2-methyl-3-[(methylsulfonyl)amino]phenyl}amino)methyl]phenoxy}phenoxy)pentanoyl]-N-methylglycine;
N-[5-(4-{4-[(benzyl{2-methyl-3-[(methylsulfonyl)amino]phenyl}amino)methyl]phenoxy}phenoxy)pentanoyl]-L-glutamic acid;
N-[5-(4-{4-[(benzyl{2-methyl-3-[(methylsulfonyl)amino]phenyl}amino)methyl]phenoxy}phenoxy)pentanoyl]-L-valine;
N-[5-(4-{4-[(benzyl{2-methyl-3-[(methylsulfonyl)amino]phenyl}amino)methyl]phenoxy}phenoxy)pentanoyl]-L-serine;
N-[5-(4-{4-[(benzyl{2-methyl-3-[(methylsulfonyl)amino]phenyl}amino)methyl]phenoxy}phenoxy)pentanoyl]-L-isoleucine;
4-{[(4-{4-[(benzyl{2-methyl-3-[(methylsulfonyl)amino]phenyl}amino)methyl]phenoxy}phenoxy)acetyl]amino}butanoic acid;
N-[(4-{4-[(benzyl{2-methyl-3-[(methylsulfonyl)amino]phenyl}amino)methyl]phenoxy}phenoxy)acetyl]-N-methylglycine;
N-[(4-{4-[(benzyl{2-methyl-3-[(methylsulfonyl)amino]phenyl}amino)methyl]phenoxy}phenoxy)acetyl]-L-valine;
N-[(4-{4-[(benzyl{2-methyl-3-[(methylsulfonyl)amino]phenyl}amino)methyl]phenoxy}phenoxy)acetyl]-L-serine;
N~2~-[(4-{4-[(benzyl{2-methyl-3-[(methylsulfonyl)amino]phenyl}amino)methyl]phenoxy}phenoxy)acetyl]-L-asparagine;
N-[3-(benzyl{4-[4-(2-hydrazino-2-oxoethoxy)phenoxy]benzyl}amino)-2-methylphenyl]methanesulfonamide;
N-(3-{benzyl[4-(3-{[(2R)-2,3-dihydroxypropyl]oxy}phenoxy)benzyl]amino}-2-methylphenyl)methanesulfonamide;
N-[4-(3-{4-[(benzyl{2-methyl-3-[(methylsulfonyl)amino]phenyl}amino)methyl]phenoxy}phenoxy)butanoyl]-L-glutamic acid;
N-[4-(3-{4-[(benzyl{2-methyl-3-[(methylsulfonyl)amino]phenyl}amino)methyl]phenoxy}phenoxy)butanoyl]-L-leucine;
N-[4-(3-{4-[(benzyl{2-methyl-3-[(methylsulfonyl)amino]phenyl}amino)methyl]phenoxy}phenoxy)butanoyl]-L-aspartic acid;
N-[4-(3-{4-[(benzyl{2-methyl-3-[(methylsulfonyl)amino]phenyl}amino)methyl]phenoxy}phenoxy)butanoyl]-L-valine;
N-[4-(3-{4-[(benzyl{2-methyl-3-[(methylsulfonyl)amino]phenyl}amino)methyl]phenoxy}phenoxy)butanoyl]-L-serine;
N~2~-[4-(3-{4-[(benzyl{2-methyl-3-[(methylsulfonyl)amino]phenyl}amino)methyl]phenoxy}phenoxy)butanoyl]-L-glutamine;
(5-(4-(((2,4-difluorobenzyl)(2-methyl-3-((methylsulfonyl)amino)phenyl)amino)methyl)phenoxy)-2-fluorophenoxy)acetic acid;
(2-chloro-5-(4-(((2-fluorobenzyl)(2-methyl-3-((methylsulfonyl)amino)phenyl)amino)methyl)phenoxy)phenoxy)acetic acid;
(5-(4-(((2-bromobenzyl)(2-methyl-3-((methylsulfonyl)amino)phenyl)amino)methyl)phenoxy)-2-chlorophenoxy)acetic acid;
(5-(4-(((4-bromobenzyl)(2-methyl-3-((methylsulfonyl)amino)phenyl)amino)methyl)phenoxy)-2-chlorophenoxy)acetic acid;
(2-chloro-5-(4-(((2,4-dichlorobenzyl)(2-methyl-3-((methylsulfonyl)amino)phenyl)amino)methyl)phenoxy)phenoxy)acetic acid;
(2-chloro-5-(4-(((4-chloro-2-fluorobenzyl)(2-methyl-3-((methylsulfonyl)amino)phenyl)amino)methyl)phenoxy)phenoxy)acetic acid;
(2-chloro-5-(4-(((2-chloro-4-fluorobenzyl)(2-methyl-3-((methylsulfonyl)amino)phenyl)amino)methyl)phenoxy)phenoxy)acetic acid;
(5-(4-(((2-bromo-4-chlorobenzyl)(2-methyl-3-((methylsulfonyl)amino)phenyl)amino)methyl)phenoxy)-2-chlorophenoxy)acetic acid;

(2-chloro-5-(4-(((3,4-difluorobenzyl)(2-methyl-3-((methylsulfonyl)amino)phenyl)amino)methyl)phenoxy)phenoxy)acetic acid;

(5-(4-(((4-bromo-2-fluorobenzyl)(2-methyl-3-((methylsulfonyl)amino)phenyl)amino)methyl)phenoxy)-2-chlorophenoxy)acetic acid;

N-((2-chloro-5-(4-(((2,4-difluorobenzyl)(2-methyl-3-((methylsulfonyl)amino)phenyl)amino)methyl)phenoxy)phenoxy)acetyl)glycine;

N-((2-chloro-5-(4-(((2,4-difluorobenzyl)(2-methyl-3-((methylsulfonyl)amino)phenyl)amino)methyl)phenoxy)phenoxy)acetyl)-beta-alanine;

4-(((2-chloro-5-(4-(((2,4-difluorobenzyl)(2-methyl-3-((methylsulfonyl)amino)phenyl)amino)methyl)phenoxy)phenoxy)acetyl)amino)butanoic acid;

4-((4-(5-(4-((benzyl(2-methyl-3-((methylsulfonyl)amino)phenyl)amino)methyl)phenoxy)-2-chlorophenoxy)butanoyl)amino)butanoic acid;

4-((4-(2-chloro-5-(4-(((2,4-difluorobenzyl)(2-methyl-3-((methylsulfonyl)amino)phenyl)amino)methyl)phenoxy)phenoxy)butanoyl)amino)butanoic acid;

(2R)-2-(2-chloro-5-(4-(((2,4-difluorobenzyl)(2-methyl-3-((methylsulfonyl)amino)phenyl)amino)methyl)phenoxy)phenoxy)propanoic acid;

N-(3-((4-(4-chloro-3-hydroxyphenoxy)benzyl)(2,4-difluorobenzyl)amino)-2-methylphenyl)methanesulfonamide;

(2-bromo-5-(4-(((2,4-difluorobenzyl)(2-methyl-3-((methylsulfonyl)amino)phenyl)amino)methyl)phenoxy)phenoxy)acetic acid;

N-(4-(3-(4-(((2,4-difluorobenzyl)(2-methyl-3-((methylsulfonyl)amino)phenyl)amino)methyl)phenoxy)butanoyl)-beta-alanine;

4-((4-(3-(4-(((2,4-difluorobenzyl)(2-methyl-3-((methylsulfonyl)amino)phenyl)amino)methyl)phenoxy)butanoyl)amino)butanoic acid; and N-(4-(3-(4-(((2,4-difluorobenzyl)(2-methyl-3-((methylsulfonyl)amino)phenyl)amino)methyl)phenoxy)butanoyl)-N-methylglycine.

26. A compound according to claim 23 wherein
B is aryl wherein said aryl is phenyl;
$L_B$ is —$(CH_2)_mO(CH_2)_n$—;
m is 0;
n is 1–6;
$R_1$, $R_2$, $R_3$, $R_5$, $X_{A1}$ and $X_{D1}$ are each hydrogen;
$R_4$ is alkyl; and
$R_6$ is alkylsulfonyl.

27. A compound according to claim 26 selected from the group consisting of
N-{3-[[4-(benzyloxy)benzyl](2,4-difluorobenzyl)amino]-2-methylphenyl}methanesulfonamide; and
N-(3-{(2,4-difluorobenzyl)[4-(2-phenylethoxy)benzyl]amino}-2-methylphenyl)methanesulfonamide.

28. A compound according to claim 23 wherein
B is heterocycle;
$L_B$ is —$(CH_2)_mO(CH_2)_n$—;
m is 0;
n is 1–6;
$R_1$, $R_2$, $R_3$, $R_5$, $X_{A1}$ and $X_{D1}$ are each hydrogen;
$R_4$ is alkyl; and
$R_6$ is alkylsulfonyl.

29. A compound according to claim 28 selected from the group consisting of
N-(3-{(2,4-difluorobenzyl)[4-(3-furylmethoxy)benzyl]amino}-2-methylphenyl)methanesulfonamide;

N-(3-{(2,4-difluorobenzyl)[4-(2-furylmethoxy)benzyl]amino}-2-methylphenyl)methanesulfonamide;

N-{3-[[4-(1,3-benzodioxol-5-ylmethoxy)benzyl](2,4-difluorobenzyl)amino]-2-methylphenyl}methanesulfonamide; and N-{3-[{4-[(6-chloro-1,3-benzodioxol-5-yl)methoxy]benzyl}(2,4-difluorobenzyl)amino]-2-methylphenyl}methanesulfonamide.

30. A compound according to claim 23 wherein
B is aryl wherein said aryl is phenyl;
$L_B$ is —$(CH_2)_mO(CH_2)_nCH_2CH=CH$—
m is 0;
$R_1$, $R_2$, $R_3$, $R_5$, $X_{A1}$ and $X_{D1}$ are each hydrogen;
$R_4$ is alkyl; and
$R_6$ is alkylsulfonyl.

31. A compound according to claim 30 that is N-{3-[(2,4-difluorobenzyl)(4-{[3-phenyl-2-propenyl]oxy}benzyl)amino]-2-methylphenyl}methanesulfonamide.

32. A compound according to claim 23 wherein
B is aryl wherein said aryl is phenyl;
$L_B$ is —$(CH_2)_mC(O)(CH_2)_n$—;
m and n are each 0;
$R_1$, $R_2$, $R_3$, $R_5$, $X_{A1}$ and $X_{D1}$ are each hydrogen;
$R_4$ is alkyl; and
$R_6$ is alkylsulfonyl.

33. A compound according to claim 32 selected from the group consisting of
(3-{4-[(benzyl{2-methyl-3-[(methylsulfonyl)amino]phenyl}amino)methyl]benzoyl}phenoxy)acetic acid;

N-{3-[(4-benzoylbenzyl)(benzyl)amino]-2-methylphenyl}methanesulfonamide;

N-[3-(benzyl{4-[3-(2-cyclopropylethoxy)benzoyl]benzyl}amino)-2-methylphenyl]methanesulfonamide;

N-[3-(benzyl{4-[3-(cyclopentylmethoxy)benzoyl]benzyl}amino)-2-methylphenyl]methanesulfonamide; and N-(3-{benzyl[4-(4-{[(2R)-2,3-dihydroxypropyl]oxy}benzoyl)benzyl]amino}-2-methylphenyl)methanesulfonamide.

34. A compound according to claim 23 wherein
B is aryl wherein said aryl is phenyl;
$L_B$ is —$(CH_2)_mS(CH_2)_n$—;
m and n are each 0;
$R_1$, $R_2$, $R_3$, $R_5$, $X_{A1}$ and $X_{D1}$ are each hydrogen;
$R_4$ is alkyl; and
$R_6$ is alkylsulfonyl.

35. A compound according to claim 34 that is N-(3-{benzyl[4-(phenylthio)benzyl]amino}-2-methylphenyl)methanesulfonamide.

36. A compound according to claim 23 wherein
B is aryl wherein said aryl is phenyl;
$L_B$ is alkylene;
$R_1$, $R_2$, $R_3$, $R_5$, $X_{A1}$ and $X_{D1}$ are each hydrogen;
$R_4$ is alkyl; and
$R_6$ is alkylsulfonyl.

37. A compound according to claim 23 wherein
B is aryl wherein said aryl is phenyl;
$L_B$ is —$(CH_2)_mC(OH)(CH_2)_n$—;
$R_1$, $R_2$, $R_3$, $R_5$, $X_{A1}$ and $X_{D1}$ are each hydrogen;
$R_4$ is alkyl; and
$R_6$ is alkylsulfonyl.

38. A compound according to claim 23 wherein
B is cycloalkyl;
$L_B$ is $-(CH_2)_mO(CH_2)_n-$;
$R_1$, $R_2$, $R_3$, $R_5$, $X_{A1}$ and $X_{D1}$ are each hydrogen;
$R_4$ is alkyl; and
$R_6$ is alkylsulfonyl.

39. A compound according to claim 23 wherein
B is heterocycle;
$L_B$ is $-(CH_2)_mC(O)(CH_2)_n-$;
$R_1$, $R_2$, $R_3$, $R_5$, $X_{A1}$ and $X_{D1}$ are each hydrogen;
$R_4$ is alkyl; and
$R_6$ is alkylsulfonyl.

40. A compound according to claim 1 of formula (IV)

(IV)

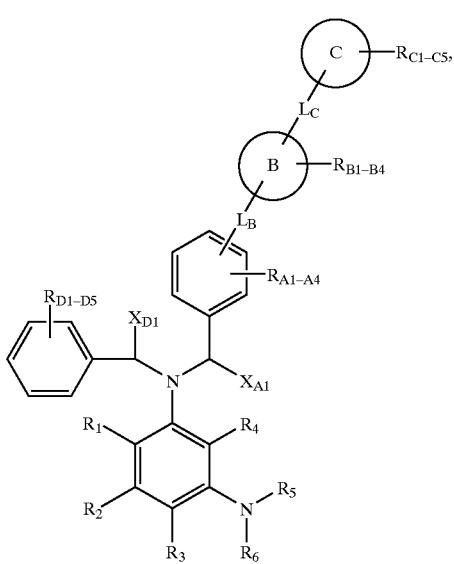

or a pharmaceutically acceptable salt or prodrug thereof.

41. A compound according to claim 40 wherein
B is aryl wherein said aryl is phenyl;
C is aryl wherein said aryl is phenyl;
$L_B$ is $-(CH_2)_mO(CH_2)_n-$;
m and n are each 0;
$L_C$ is $-(CH_2)_pO(CH_2)_q-$;
p is 0;
$R_1$, $R_2$, $R_3$, $R_5$, $X_{A1}$ and $X_{D1}$ are each hydrogen;
$R_4$ is alkyl; and
$R_6$ is alkylsulfonyl.

42. A compound according to claim 41 selected from the group consisting of
N-[3-(benzyl{4-[3-(2-phenylethoxy)phenoxy]benzyl}amino)-2-methylphenyl]methanesulfonamide;
N-{3-[{4-[3-(1,3-benzodioxol-5-ylmethoxy)phenoxy]benzyl}(benzyl)amino]-2-methylphenyl}methanesulfonamide; and
N-[3-(benzyl{4-[3-(benzyloxy)phenoxy]benzyl}amino)-2-methylphenyl]methanesulfonamide.

43. A compound according to claim 40 wherein
B is aryl wherein said aryl is phenyl;
C is aryl wherein said aryl is phenyl;
$L_B$ is $-(CH_2)_mO(CH_2)_n-$;
m and n are each 0;
$L_C$ is $-(CH_2)_pO(CH_2)_q-$;
p and q are each 0;
$R_1$, $R_2$, $R_3$, $R_5$, $X_{A1}$ and $X_{D1}$ are each hydrogen;
$R_4$ is alkyl; and
$R_6$ is alkylsulfonyl.

44. A compound according to claim 40 wherein
B is aryl wherein said aryl is phenyl;
C is heterocycle;
$L_B$ is $-(CH_2)_mO(CH_2)_n-$;
m and n are each 0;
$L_C$ is $-(CH_2)_pO(CH_2)_q-$;
p is 0;
$R_1$, $R_2$, $R_3$, $R_5$, $X_{A1}$ and $X_{D1}$ are each hydrogen;
$R_4$ is alkyl; and
$R_6$ is alkylsulfonyl.

45. A compound according to claim 44 selected from the group consisting of
N-[3-(benzyl{4-[3-(3-morpholin-4-ylpropoxy)phenoxy]benzyl}amino)-2-methylphenyl]methanesulfonamide;
1-[2-(3-{4-[(benzyl{2-methyl-3-[(methylsulfonyl)amino]phenyl}amino)methyl]phenoxy}phenoxy)ethyl]piperidine-2-carboxylic acid;
N-{3-[benzyl(4-{3-[(1-methylpyrrolidin-3-yl)methoxy]phenoxy}benzyl)amino]-2-methylphenyl}methanesulfonamide;
N-{3-[(4-{3-[(1-acetylpyrrolidin-3-yl)methoxy]phenoxy}benzyl)(benzyl)amino]-2-methylphenyl}methanesulfonamide;
N-{3-[benzyl(4-{3-[(2-oxotetrahydrofuran-3-yl)oxy]phenoxy}benzyl)amino]-2-methylphenyl}methanesulfonamide;
N-[3-(benzyl{4-[3-(tetrahydrofuran-2-ylmethoxy)phenoxy]benzyl}amino)-2-methylphenyl]methanesulfonamide;
N-[3-(benzyl{4-[3-(tetrahydrofuran-3-ylmethoxy)phenoxy]benzyl}amino)-2-methylphenyl]methanesulfonamide;
N-[3-(benzyl{4-[3-(3-furylmethoxy)phenoxy]benzyl}amino)-2-methylphenyl]methanesulfonamide;
N-[3-(benzyl{4-[3-(2-furylmethoxy)phenoxy]benzyl}amino)-2-methylphenyl]methanesulfonamide;
N-[3-(benzyl{4-[3-(thien-3-ylmethoxy)phenoxy]benzyl}amino)-2-methylphenyl]methanesulfonamide;
N-[3-(benzyl{4-[3-(2-thien-3-ylethoxy)phenoxy]benzyl}amino)-2-methylphenyl]methanesulfonamide;
N-[3-(benzyl{4-[3-(thien-2-ylmethoxy)phenoxy]benzyl}amino)-2-methylphenyl]methanesulfonamide;
N-[3-(benzyl{4-[3-(2-thien-2-ylethoxy)phenoxy]benzyl}amino)-2-methylphenyl]methanesulfonamide;
N-{3-[benzyl(4-{3-[2-(4-methyl-1,3-thiazol-5-yl)ethoxy]phenoxy}benzyl)amino]-2-methylphenyl}methanesulfonamide;
N-{3-[benzyl(4-{3-[2-(2-oxopyrrolidin-1-yl)ethoxy]phenoxy}benzyl)amino]-2-methylphenyl}methanesulfonamide;
N-[3-(benzyl{4-[3-(2-morpholin-4-ylethoxy)phenoxy]benzyl}amino)-2-methylphenyl]methanesulfonamide;
N-(3-((2,4-difluorobenzyl)(4-(3-(((2S,4R)-6-oxo-4-hydroxytetrahydro-2H-pyran-2-yl)methoxy)phenoxy)benzyl)amino)-2-methylphenyl)methanesulfonamide;
N-(3-(benzyl(4-(4-(((2S, 4R)-6-oxo-4hydroxytetrahydro-2H-pyran-2-yl)methoxy)phenoxy)benzyl)amino)-2-methylphenyl)methanesulfonamide;
N-(3-{benzyl[4-(3-{[(2S)-5-oxopyrrolidin-2-yl]methoxy}phenoxy)benzyl]amino}-2-methylphenyl)methanesulfonamide;
N-{3-[benzyl(4-{3-[(3-methyloxetan-3-yl)methoxy]phenoxy}benzyl)amino]-2-methylphenyl}methanesulfonamide;

N-[3-(benzyl{4-[3-(tetrahydro-2H-pyran-4-yloxy)phenoxy]
benzyl}amino)-2-methylphenyl]methanesulfonamide;
N-[3-(benzyl{4-[3-(tetrahydrofuran-3-yloxy)phenoxy]
benzyl}amino)-2-methylphenyl]methanesulfonamide;
N-(3-{benzyl[4-(3-{[(2S)-1-methylpyrrolidin-2-yl]
methoxy}phenoxy)benzyl]amino}-2-methylphenyl)
methanesulfonamide;
N-[3-(benzyl{4-[3-(pyridin-3-ylmethoxy)phenoxy]
benzyl}amino)-2-methylphenyl]methanesulfonamide;
N-{3-[benzyl(4-{3-[(2S)-pyrrolidin-2-ylmethoxy]
phenoxy}benzyl)amino]-2-
methylphenyl}methanesulfonamide; and
N-{3-[benzyl(4-{3-[(1-methylpyrrolidin-3-yl)oxy]
phenoxy}benzyl)amino]-2-
methylphenyl}methanesulfonamide.

46. A compound according to claim 40 wherein
B is aryl wherein said aryl is phenyl;
C is cycloalkyl;
$L_B$ is —$(CH_2)_mO(CH_2)_n$—;
m and n are each 0;
$L_C$ is —$(CH_2)_pO(CH_2)_q$—;
p is 0;
$R_1$, $R_2$, $R_3$, $R_5$, $X_{A1}$ and $X_{D1}$ are each hydrogen;
$R_4$ is alkyl; and
$R_6$ is alkylsulfonyl.

47. A compound according to claim 46 selected from the group consisting of
2-[(3-{4-[(benzyl{2-methyl-3-[(methylsulfonyl)amino]
phenyl}amino)methyl]phenoxy}phenoxy)methyl]
cyclopropanecarboxylic acid; and
4-(3-{4-[(benzyl{2-methyl-3-[(methylsulfonyl)amino]
phenyl}amino)methyl]phenoxy}phenoxy)
cyclohexanecarboxylic acid.

48. A compound according to claim 40 wherein
B is aryl wherein said aryl is phenyl;
C is aryl wherein said aryl is phenyl;
$L_B$ is —$(CH_2)_mO(CH_2)_n$—;
m and n are each 0;
$L_C$ is —$(CH_2)_pC(O)O(CH_2)_q$—;
$R_1$, $R_2$, $R_3$, $R_5$, $X_{A1}$ and $X_{D1}$ are each hydrogen;
$R_4$ is alkyl; and
$R_6$ is alkylsulfonyl.

49. A compound according to claim 48 that is
benzyl 3-(4-{4-[(benzyl{2-methyl-3-[(methylsulfonyl)
amino]phenyl}amino)methyl]phenoxy}phenyl)
propanoate.

50. A compound according to claim 40 wherein
B is aryl wherein said aryl is phenyl;
C is heterocycle;
$L_B$ is —$(CH_2)_mO(CH_2)_n$—;
m and n are each 0;
$L_C$ is —$(CH_2)_pC(O)(CH_2)_q$—;
q is 0;
$R_1$, $R_2$, $R_3$, $R_5$, $X_{A1}$ and $X_{D1}$ are each hydrogen;
$R_4$ is alkyl; and
$R_6$ is alkylsulfonyl.

51. A compound according to claim 50 that is
1-[4-(4-{4-[(benzyl{2-methyl-3-[(methylsulfonyl)amino]
phenyl}amino)methyl]phenoxy}phenyl)butanoyl]-L-
proline.

52. A compound according to claim 40 wherein
B is aryl wherein said aryl is phenyl;
C is heterocycle;
$L_B$ is —$(CH_2)_mO(CH_2)_n$—;
m and n are each 0;
$L_C$ is —$O(CH_2)_pC(O)(CH_2)_q$—;
q is 0;
$R_1$, $R_2$, $R_3$, $R_5$, $X_{A1}$ and $X_{D1}$ are each hydrogen;
$R_4$ is alkyl; and
$R_6$ is alkylsulfonyl.

53. A compound according to claim 52 selected from the group consisting of
1-[5-(4-{4-[(benzyl{2-methyl-3-[(methylsulfonyl)amino]
phenyl}amino)methyl]phenoxy}phenoxy)pentanoyl]-L-
proline;
1-[4-(3-{4-[(benzyl{2-methyl-3-[(methylsulfonyl)amino]
phenyl}amino)methyl]phenoxy}phenoxy)butanoyl]
piperidine-3-carboxylic acid;
1-[4-(3-{4-[(benzyl{2-methyl-3-[(methylsulfonyl)amino]
phenyl}amino)methyl]phenoxy}phenoxy)butanoyl]
piperidine-4-carboxylic acid;
1-[4-(3-{4-[(benzyl{2-methyl-3-[(methylsulfonyl)amino]
phenyl}amino)methyl]phenoxy}phenoxy)butanoyl]
piperidine-2-carboxylic acid;
1-[4-(3-{4-[(benzyl{2-methyl-3-[(methylsulfonyl)amino]
phenyl}amino)methyl]phenoxy}phenoxy)butanoyl]
proline; and
1-[(2-chloro-5-{4-[((2,4-difluorobenzyl){2-methyl-3-
[(methylsulfonyl)amino]phenyl}amino)methyl]
phenoxy}phenoxy)acetyl]piperidine-4-carboxamide.

54. A compound according to claim 40 wherein
B is aryl wherein said aryl is phenyl;
C is aryl wherein said aryl is phenyl;
$L_B$ is —$(CH_2)_mO(CH_2)_n$—;
$L_C$ is —$(CH_2)_pC(O)N(R_7)(CH_2)_q$—;
$R_1$, $R_2$, $R_3$, $R_5$, $X_{A1}$ and $X_{D1}$ are each hydrogen;
$R_4$ is alkyl; and
$R_6$ is alkylsulfonyl.

55. A compound according to claim 40 wherein
B is aryl wherein said aryl is phenyl;
C is heterocycle;
$L_B$ is —$(CH_2)_mO(CH_2)_n$—;
m and n are each 0;
$L_C$ is —$(CH_2)_pC(O)N(R_7)(CH_2)_q$—;
$R_1$, $R_2$, $R_3$, $R_5$, $X_{A1}$ and $X_{D1}$ are each hydrogen;
$R_4$ is alkyl; and
$R_6$ is alkylsulfonyl.

56. A compound according to claim 55 selected from the group consisting of
4-(4-{4-[((2,4-difluorobenzyl){2-methyl-3-
[(methylsulfonyl)amino]phenyl}amino)methyl]
phenoxy}phenyl)-N-[3-(2-oxopyrrolidin-1-yl)propyl]
butanamide;
3-(4-{4-[(benzyl{2-methyl-3-[(methylsulfonyl)amino]
phenyl}amino)methyl]phenoxy}phenyl)-N-(2-
morpholin-4-ylethyl)propanamide;
3-(4-{4-[(benzyl{2-methyl-3-[(methylsulfonyl)amino]
phenyl}amino)methyl]phenoxy}phenyl)-N-[3-(2-
oxopyrrolidin-1-yl)propyl]propanamide;
4-{[4-(4-{4-[(benzyl{2-methyl-3-[(methylsulfonyl)amino]
phenyl}amino)methyl]phenoxy}phenyl)butanoyl]
amino}-1-methyl-1H-pyrrole-2-carboxylic acid; and
4-(4-{4-[(benzyl{2-methyl-3-[(methylsulfonyl)amino]
phenyl}amino)methyl]phenoxy}phenyl)-N-(2-
oxotetrahydrofuran-3-yl)butanamide.

57. A compound according to claim 40 wherein
B is aryl wherein said aryl is phenyl;
C is heterocycle;
$L_B$ is —$(CH_2)_mO(CH_2)_n$—;
m and n are each 0;
$L_C$ is —$O(CH_2)_pC(O)N(R_7)(CH_2)_q$—;
$R_1$, $R_2$, $R_3$, $R_5$, $X_{A1}$ and $X_{D1}$ are each hydrogen;
$R_4$ is alkyl; and
$R_6$ is alkylsulfonyl.

58. A compound according to claim 57 selected from the group consisting of
2-(3-{4-[(benzyl{2-methyl-3-[(methylsulfonyl)amino]phenyl}amino)methyl]phenoxy}phenoxy)-N-[3-(2-oxopyrrolidin-1-yl)propyl]acetamide;
4-{[4-(4-{4-[(benzyl{2-methyl-3-[(methylsulfonyl)amino]phenyl}amino)methyl]phenoxy}phenoxy)butanoyl]amino}-1-methyl-1H-pyrrole-2-carboxylic acid;
5-(4-{4-[(benzyl{2-methyl-3-[(methylsulfonyl)amino]phenyl}amino)methyl]phenoxy}phenoxy)-N-(2-oxotetrahydrofuran-3-yl)pentanamide;
2-(4-{4-[(benzyl{2-methyl-3-[(methylsulfonyl)amino]phenyl}amino)methyl]phenoxy}phenoxy)-N-(2-oxotetrahydrofuran-3-yl)acetamide;
4-(3-{4-[(benzyl{2-methyl-3-[(methylsulfonyl)amino]phenyl}amino)methyl]phenoxy}phenoxy)-N-(2-oxotetrahydrofuran-3-yl)butanamide;
2-(2-chloro-5-{4-[((2,4-difluorobenzyl){2-methyl-3-[(methylsulfonyl)amino]phenyl}amino)methyl]phenoxy}phenoxy)-N-[3-(2-oxopyrrolidin-1-yl)propyl]acetamide;
2-(2-chloro-5-{4-[((2,4-difluorobenzyl){2-methyl-3-[(methylsulfonyl)amino]phenyl}amino)methyl]phenoxy}phenoxy)-N-(1,3-thiazol-5-ylmethyl)acetamide; and
2-(2-chloro-5-{4-[((2,4-difluorobenzyl){2-methyl-3-[(methylsulfonyl)amino]phenyl}amino)methyl]phenoxy}phenoxy)-N-(3-morpholin-4-ylpropyl)acetamide.

59. A compound according to claim 40 wherein
B is aryl wherein said aryl is phenyl;
C is aryl wherein said aryl is phenyl;
$L_B$ is —$(CH_2)_mC(O)(CH_2)_n$—;
m and n are each 0;
$L_C$ is —$(CH_2)_pO(CH_2)_q$—;
p is 0;
$R_1$, $R_2$, $R_3$, $R_5$, $X_{A1}$ and $X_{D1}$ are each hydrogen;
$R_4$ is alkyl; and
$R_6$ is alkylsulfonyl.

60. A compound according to claim 59 selected from the group consisting of
N-[3-(benzyl{4-[3-(2-phenylethoxy)benzoyl]benzyl}amino)-2-methylphenyl]methanesulfonamide; and
N-[3-(benzyl{4-[3-(benzyloxy)benzoyl]benzyl}amino)-2-methylphenyl]methanesulfonamide.

61. A compound according to claim 40 wherein
B is aryl wherein said aryl is phenyl;
C is heterocycle;
$L_B$ is —$(CH_2)_mC(O)(CH_2)_n$—;
m and n are each 0;
$L_C$ is —$(CH_2)_pO(CH_2)_q$—;
p is 0;
$R_1$, $R_2$, $R_3$, $R_5$, $X_{A1}$ and $X_{D1}$ are each hydrogen;
$R_4$ is alkyl; and
$R_6$ is alkylsulfonyl.

62. A compound according to claim 61 selected from the group consisting of
N-[3-(benzyl{4-[3-(tetrahydrofuran-2-ylmethoxy)benzoyl]benzyl}amino)-2-methylphenyl]methanesulfonamide;
N-[3-(benzyl{4-[3-(tetrahydrofuran-3-ylmethoxy)benzoyl]benzyl}amino)-2-methylphenyl]methanesulfonamide;
N-{3-[benzyl(4-{3-[2-(2-oxopyrrolidin-1-yl)ethoxy]benzoyl}benzyl)amino]-2-methylphenyl}methanesulfonamide; and
N-{3-[benzyl(4-{3-[2-(4-methyl-1,3-thiazol-5-yl)ethoxy]benzoyl}benzyl)amino]-2-methylphenyl}methanesulfonamide.

63. A compound according to claim 1 of formula (V)

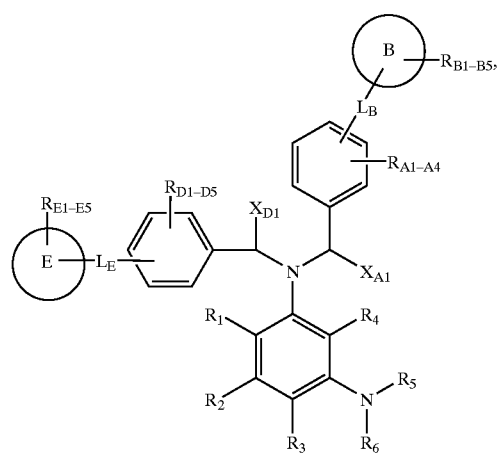

(V)

or a pharmaceutically acceptable salt or prodrug thereof.

64. A compound according to claim 63 wherein
B is aryl wherein said aryl is phenyl;
E is aryl wherein said aryl is phenyl;
$L_B$ is —$(CH_2)_mO(CH_2)_n$—;
m and n are each 0;
$L_E$ is —$(CH_2)_rC(O)(CH_2)_s$—
r and s are each 0;
$R_1$, $R_2$, $R_3$, $R_5$, $X_{A1}$ and $X_{D1}$ are each hydrogen;
$R_4$ is alkyl; and
$R_6$ is alkylsulfonyl.

65. A compound according to claim 64 selected from the group consisting of
(3-{4-[((4-benzoylbenzyl){2-methyl-3-[(methylsulfonyl)amino]phenyl}amino)methyl]phenoxy}phenoxy)acetic acid; and
(5-(4-(((4-benzoylbenzyl)(2-methyl-3-((methylsulfonyl)amino)phenyl)amino)methyl)phenoxy)-2-chlorophenoxy)acetic acid.

66. A pharmaceutical composition comprising a therapeutically effective amount of a compound of claim 1 in combination with a pharmaceutically acceptable carrier.

67. A method of selectively modulating the effects of the glucocorticoid receptor in a mammal comprising administering an effective amount of a compound of claim 1.

68. A method of treating type II diabetes in a mammal comprising administering a therapeutically effective amount of a glucocorticoid receptor antagonist.

69. A method of treating type II diabetes in a mammal comprising administering a therapeutically effective amount of a compound of claim 1.

70. A method of treating symptoms related to type II diabetes wherein said symptoms are selected from the group consisting of hyperglycemia, hyperinsulinemia, inadequate, glucose clearance, obesity, hypertension and high glucocorticoid levels in a mammal comprising administering a therapeutically effective amount of a compound of claim 1.

71. A method of treating diseases associated with an excess or deficiency of glucocorticoids, said diseases selected from the group consisting of diabetes, obesity, Syndrome X, Cushing's Syndrome, Addison's disease, inflammatory diseases such as asthma, rhinitis and arthritis, allergy, autoimmune disease, immunodeficiency, anorexia, cachexia, bone loss or bone frailty, and wound healing comprising administering a therapeutically effective amount of a compound of claim 1.

72. A method of treating a disease, comprising administering a compound of claim 1 in combination with an anti-diabetic agent, wherein said disease is selected from the group consisting of diabetes and Syndrom X.

73. A method according to claim 72, wherein said anti-diabetic agent is selected from the group consisting of insulin, mecasermin, nateglinide, metformin, chlorpropamide, glipizide, glyburide, troglitazone, pioglitazone, rosiglitazone, acarbose, voglibose, miglitol, zopolrestat and repaglinide.

74. A method of treating obesity, comprising administering a compound of claim 1 in combination with an anti-obesity agent.

75. A method according to claim 74, wherein said anti-obesity agent is selected from the group consisting of orlistat, sibutramine, dexfenfluramine, bromocryptine, phentermine, phendimetrazine and mazindol.

* * * * *